United States Patent
Padala

(10) Patent No.: US 12,396,855 B1
(45) Date of Patent: Aug. 26, 2025

(54) SYSTEMS, DEVICES, AND METHODS FOR REDUCING HEART VALVE REGURGITATION

(71) Applicant: Nyra Medical, Inc., Atlanta, GA (US)

(72) Inventor: Sai Muralidhar Padala, Decatur, GA (US)

(73) Assignee: Nyra Medical, Inc., Atlanta, GA (US)

( * ) Notice: Subject to any disclaimer, the term of this patent is extended or adjusted under 35 U.S.C. 154(b) by 0 days.

(21) Appl. No.: 18/796,048

(22) Filed: Aug. 6, 2024

Related U.S. Application Data

(60) Provisional application No. 63/675,682, filed on Jul. 25, 2024.

(51) Int. Cl.
*A61F 2/24* (2006.01)
*A61B 17/00* (2006.01)

(52) U.S. Cl.
CPC .......... *A61F 2/2466* (2013.01); *A61F 2/2418* (2013.01); *A61B 2017/00243* (2013.01)

(58) Field of Classification Search
CPC ................ A61F 2/2466; A61F 2/2418; A61B 2017/00243; A61B 17/12122
See application file for complete search history.

(56) References Cited

U.S. PATENT DOCUMENTS

| | | | |
|---|---|---|---|
| 4,556,060 A | 12/1985 | Perlin | |
| 6,264,691 B1 | 7/2001 | Gabbay | |
| 7,635,329 B2 | 12/2009 | Goldfarb et al. | |
| 8,690,939 B2 | 4/2014 | Miller et al. | |
| 8,758,431 B2 | 6/2014 | Orlov et al. | |
| 8,926,691 B2 | 1/2015 | Chau et al. | |
| 8,932,348 B2 | 1/2015 | Solem et al. | |
| 9,011,468 B2 | 4/2015 | Ketai et al. | |

(Continued)

FOREIGN PATENT DOCUMENTS

| | | |
|---|---|---|
| CN | 115399920 A | 11/2022 |
| JP | 2008514307 A | 5/2008 |
| JP | 2017506973 A | 3/2017 |
| WO | WO-2016042022 A2 | 3/2016 |
| WO | WO-2019023138 A1 | 1/2019 |
| WO | WO-2021011206 A2 | 1/2021 |

(Continued)

OTHER PUBLICATIONS

Agricola et al., "Echocardiographic classification of chronic ischemic mitral regurgitation caused by restricted motion according to tethering pattern" Eur J Echocardiogr. Oct. 2004; 5(5):326-334.

(Continued)

*Primary Examiner* — Dinah Baria
(74) *Attorney, Agent, or Firm* — COOLEY LLP

(57) ABSTRACT

Embodiments described herein relate to an implant delivery system for delivering an implant for reducing heart valve regurgitation. The implant delivery system may include an implant catheter disposed in an inner lumen of a guide catheter. The implant catheter may include one or more hypotubes disposed therein, each hypotube configured to receive an elongate member such as a braided tether. A distal end of the implant catheter may be coupled to an implant holder configured to receive the implant. The implant holder may define one or more channels, each channel configured to receive a portion of a respective elongate member. The elongate members configured to couple the implant to the implant holder and transition the implant between configurations. The implant configured to be disposed around a portion of a leaflet of a heart valve to improve coaptation of the heart valve.

31 Claims, 47 Drawing Sheets

(56) References Cited

U.S. PATENT DOCUMENTS

| | | |
|---|---|---|
| 9,089,422 B2 | 7/2015 | Ryan et al. |
| 9,254,141 B2 | 2/2016 | Morris et al. |
| 9,414,918 B2 | 8/2016 | Chau et al. |
| 9,474,605 B2 | 10/2016 | Rowe et al. |
| 9,510,946 B2 | 12/2016 | Chau et al. |
| 9,510,948 B2 | 12/2016 | Padala |
| 9,592,118 B2 | 3/2017 | Khairkhahan et al. |
| 9,592,121 B1 | 3/2017 | Khairkhahan |
| 9,662,208 B2 | 5/2017 | Padala et al. |
| 9,770,330 B2 | 9/2017 | Maurer et al. |
| 9,867,704 B2 | 1/2018 | Lee et al. |
| 9,907,652 B2 | 3/2018 | Chau et al. |
| 9,913,717 B2 | 3/2018 | Chau et al. |
| 10,123,873 B1 | 11/2018 | Metchik et al. |
| 10,136,993 B1 | 11/2018 | Metchik et al. |
| 10,231,837 B1 | 3/2019 | Metchik et al. |
| 10,517,726 B2 | 12/2019 | Chau et al. |
| 10,646,342 B1 | 5/2020 | Marr et al. |
| 10,779,829 B2 | 9/2020 | Wei |
| 10,799,359 B2 | 10/2020 | Siegel et al. |
| 10,813,760 B2 | 10/2020 | Metchik et al. |
| 10,874,514 B2 | 12/2020 | Dixon et al. |
| 10,905,552 B2 | 2/2021 | Dixon et al. |
| 10,905,554 B2 | 2/2021 | Cao |
| 10,912,646 B2 | 2/2021 | Spence |
| 10,918,483 B2 | 2/2021 | Metchik et al. |
| 10,925,734 B2 | 2/2021 | Delgado et al. |
| 10,932,908 B2 | 3/2021 | Dixon et al. |
| 11,020,229 B2 | 6/2021 | Delgado et al. |
| 11,083,582 B2 | 8/2021 | McCann et al. |
| 11,141,158 B2 | 10/2021 | Ketai et al. |
| 11,259,927 B2 | 3/2022 | Metchik et al. |
| 11,278,409 B2 | 3/2022 | McCann et al. |
| 11,399,940 B2 | 8/2022 | Spence |
| 11,484,331 B2 | 11/2022 | Goldfarb et al. |
| 11,559,401 B2 | 1/2023 | Spence |
| 11,571,305 B2 | 2/2023 | Padala et al. |
| 11,602,431 B2 | 3/2023 | Delgado et al. |
| 11,660,185 B2 | 5/2023 | Chau et al. |
| 11,723,772 B2 | 8/2023 | Dixon et al. |
| 11,730,598 B2 | 8/2023 | Metchik et al. |
| 11,766,330 B2 | 9/2023 | McCann et al. |
| 11,793,629 B2 | 10/2023 | Solem |
| 11,793,642 B2 | 10/2023 | Chau et al. |
| 11,839,545 B2 | 12/2023 | Hauser et al. |
| 11,850,153 B2 | 12/2023 | Delgado et al. |
| 11,911,264 B2 | 2/2024 | Chau et al. |
| 11,918,469 B2 | 3/2024 | Metchik et al. |
| 11,969,346 B2 | 4/2024 | Cao |
| 11,992,199 B2 | 5/2024 | Chen et al. |
| 2003/0153946 A1 | 8/2003 | Kimblad |
| 2004/0093023 A1 | 5/2004 | Allen et al. |
| 2004/0220593 A1 | 11/2004 | Greenhalgh |
| 2005/0159810 A1 | 7/2005 | Filsoufi |
| 2005/0216039 A1 | 9/2005 | Lederman |
| 2006/0241745 A1 | 10/2006 | Solem |
| 2006/0293698 A1 | 12/2006 | Douk |
| 2007/0118151 A1 | 5/2007 | Davidson |
| 2007/0197858 A1 | 8/2007 | Goldfarb et al. |
| 2008/0051807 A1 | 2/2008 | St. Goar et al. |
| 2008/0195126 A1 | 8/2008 | Solem |
| 2009/0043381 A1 | 2/2009 | Macoviak et al. |
| 2009/0276040 A1 | 11/2009 | Rowe et al. |
| 2011/0077733 A1 | 3/2011 | Solem |
| 2012/0197388 A1 | 8/2012 | Khairkhahan et al. |
| 2013/0053950 A1 | 2/2013 | Rowe et al. |
| 2014/0067048 A1 | 3/2014 | Chau et al. |
| 2014/0371766 A1 | 12/2014 | Morris et al. |
| 2015/0119981 A1 | 4/2015 | Khairkhahan et al. |
| 2015/0230919 A1 | 8/2015 | Chau et al. |
| 2015/0366566 A1 | 12/2015 | Kuntz |
| 2015/0366666 A1 | 12/2015 | Khairkhahan et al. |
| 2016/0157862 A1 | 6/2016 | Hernandez et al. |
| 2016/0287387 A1 | 10/2016 | Wei |
| 2016/0317290 A1 | 11/2016 | Chau et al. |
| 2016/0331523 A1 | 11/2016 | Chau et al. |
| 2017/0020521 A1 | 1/2017 | Krone et al. |
| 2017/0056176 A1 | 3/2017 | Rowe et al. |
| 2017/0189186 A1 | 7/2017 | Mohl |
| 2017/0258589 A1 | 9/2017 | Pham et al. |
| 2018/0147054 A1 | 5/2018 | Chau et al. |
| 2018/0161159 A1 | 6/2018 | Lee et al. |
| 2018/0185154 A1 | 7/2018 | Cao |
| 2018/0256318 A1 | 9/2018 | Khairkhahan et al. |
| 2019/0142589 A1 | 5/2019 | Basude |
| 2019/0201191 A1 | 7/2019 | McLean et al. |
| 2019/0282364 A1 | 9/2019 | Khairkhahan et al. |
| 2019/0343623 A1 | 11/2019 | Chau et al. |
| 2019/0343624 A1 | 11/2019 | Chau et al. |
| 2020/0060818 A1 | 2/2020 | Geist et al. |
| 2020/0138569 A1 | 5/2020 | Basude et al. |
| 2020/0205978 A1 | 7/2020 | Padala et al. |
| 2020/0222185 A1 | 7/2020 | Kappetein et al. |
| 2020/0229918 A1 | 7/2020 | Pham et al. |
| 2020/0229919 A1 | 7/2020 | Geist et al. |
| 2020/0268512 A1 | 8/2020 | Mohl |
| 2020/0275974 A1 | 9/2020 | Gifford, III et al. |
| 2020/0289265 A1 | 9/2020 | Gifford, III et al. |
| 2020/0405477 A1 | 12/2020 | Chau et al. |
| 2021/0038376 A1 | 2/2021 | Metchik et al. |
| 2021/0085462 A1 | 3/2021 | Gifford, III et al. |
| 2021/0145582 A1 | 5/2021 | Cao |
| 2021/0154005 A1 | 5/2021 | Metchik et al. |
| 2021/0196462 A1 | 7/2021 | Khairkhahan |
| 2021/0338418 A1 | 11/2021 | Feld |
| 2021/0346023 A1 | 11/2021 | Krone et al. |
| 2021/0353418 A1 | 11/2021 | Mohl |
| 2022/0000621 A1 | 1/2022 | Gifford, III et al. |
| 2022/0008201 A1 | 1/2022 | Passman et al. |
| 2022/0054132 A1 | 2/2022 | Ketai et al. |
| 2022/0079755 A1 | 3/2022 | Zimmerman, III et al. |
| 2022/0096236 A1 | 3/2022 | Guidotti et al. |
| 2022/0160499 A1 | 5/2022 | Miyashiro et al. |
| 2022/0160508 A1 | 5/2022 | Miyashiro et al. |
| 2022/0183839 A1 | 6/2022 | Khairkhahan et al. |
| 2022/0192822 A1 | 6/2022 | McLean et al. |
| 2022/0240920 A1 | 8/2022 | Goldfarb et al. |
| 2022/0346993 A1 | 11/2022 | Srinimukesh et al. |
| 2022/0409235 A1 | 12/2022 | Solem et al. |
| 2022/0409372 A1 | 12/2022 | Khairkhahan et al. |
| 2023/0132907 A1 | 5/2023 | McLean et al. |
| 2023/0138388 A1 | 5/2023 | Padala et al. |
| 2023/0142064 A1 | 5/2023 | Chau et al. |
| 2023/0181313 A1 | 6/2023 | Mohl et al. |
| 2023/0210663 A1 | 7/2023 | Solem et al. |
| 2023/0263624 A1 | 8/2023 | Chau et al. |
| 2023/0270549 A1 | 8/2023 | Guidotti et al. |
| 2023/0329866 A1 | 10/2023 | Spence |
| 2023/0346556 A1 | 11/2023 | Metchik et al. |
| 2023/0380971 A1 | 11/2023 | McCann et al. |
| 2024/0041602 A1 | 2/2024 | Chau et al. |
| 2024/0081988 A1 | 3/2024 | Desai et al. |
| 2024/0081999 A1 | 3/2024 | Metchik et al. |
| 2024/0164898 A1 | 5/2024 | Nir et al. |
| 2024/0245512 A1 | 7/2024 | Padala et al. |
| 2025/0064589 A1 | 2/2025 | Padala |

FOREIGN PATENT DOCUMENTS

| | | |
|---|---|---|
| WO | WO-2022229667 A1 | 11/2022 |
| WO | WO-2022250983 A1 | 12/2022 |
| WO | WO-2023048918 A1 | 3/2023 |
| WO | WO-2023100176 A1 | 6/2023 |
| WO | WO-2023105334 A1 | 6/2023 |
| WO | WO-2023114289 A1 | 6/2023 |
| WO | WO-2024065977 A1 | 4/2024 |
| WO | WO-2024174412 A1 | 8/2024 |

OTHER PUBLICATIONS

Agricola et al., "Ischemic mitral regurgitation: mechanisms and echocardiographic classification" Eur J Echocardiogr. Mar. 2008; 9(2):207-221. doi: 10.1016/j.euje.2007.03.034.

(56) References Cited

OTHER PUBLICATIONS

AHA/ACC Guideline Committee, "2014 AHA/ACC Guideline for the Management of Patients With Valvular Heart Disease: Executive Summary: A Report of the American College of Cardiology/American Heart Association Task Force on Practice Guidelines" Circulation (2014) 129:2440-2492.

Asgar et al., "Secondary mitral regurgitation in heart failure: pathophysiology, prognosis, and therapeutic considerations" J Am Coll Cardiol. Mar. 31, 2015; 65(12):1231-1248.

Baumgartner et al., "Echocardiographic assessment of valve stenosis: EAE/ASE recommendations for clinical practice" Eur J Echocardiogr. Jan. 2009; 10(1):1-25.

Bhudia et al., "Edge-to-edge (Alfieri) mitral repair: results in diverse clinical settings" Ann Thorac Surg. May 2004; 77(5):1598-1606.

Blondheim et al., "Dilated cardiomyopathy with mitral regurgitation: decreased survival despite a low frequency of left ventricular thrombus" Am Heart J. Sep. 1991; 122(3 Pt 1):763-771.

Bloodworth et al., "Ex Vivo Methods for Informing Computational Models of the Mitral Valve" Ann Biomed Eng. Feb. 2017; 45(2):496-507.

Boerlage-Van Dijk et al., "Mitral inflow patterns after MitraClip implantation at rest and during exercise" J Am Soc Echocardiogr. Jan. 2014; 27(1):24-31.e1.

Bonow et al., "2020 Focused Update of the 2017 ACC Expert Consensus Decision Pathway on the Management of Mitral Regurgitation: A Report of the American College of Cardiology Solution Set Oversight Committee" J Am Coll Cardiol. May 5, 2020; 75(17):2236-2270.

Carpentier, "Cardiac valve surgery—the "French correction"" J Thorac Cardiovasc Surg. Sep. 1983; 86(3):323-337.

Chan et al., "Real-world experience of MitraClip for treatment of severe mitral regurgitation" Circ J. (2012); 76(10):2488-2493.

Crick et al., "Anatomy of the pig heart: comparisons with normal human cardiac structure" J Anat. Jul. 1998; 193(Pt 1):105-119.

Dal-Bianco et al., "Anatomy of the mitral valve apparatus: role of 2D and 3D echocardiography" Cardiol Clin. May 2013; 31(2):151-164.

Dal-Bianco et al., "Basic mechanisms of mitral regurgitation" Can J Cardiol. Sep. 2014; 30(9):971-981.

De Bonis et al., "Optimal results immediately after MitraClip therapy or surgical edge-to-edge repair for functional mitral regurgitation: are they really stable at 4 years?" Eur J Cardiothorac Surg. Sep. 2016; 50(3):488-494.

De Varennes et al., "Initial results of posterior leaflet extension for severe type IIIb ischemic mitral regurgitation" Circulation. Jun. 2, 2009; 119(21):2837-2843.

Dziadzko et al., "Causes and mechanisms of isolated mitral regurgitation in the community: clinical context and outcome" Eur Heart J. Jul. 14, 2019; 40(27):2194-2202.

Dziadzko et al., "Outcome and undertreatment of mitral regurgitation: a community cohort study" Lancet. Mar. 10, 2018; 391(10124):960-969.

English translation of Japanese Office Action issued in JP 2020-503766, dated Jul. 29, 2022, 6 pages.

English translation of Japanese Office Action issued in JP2023-109628, mailed May 23, 2024, 5 pages.

Espiritu et al., "Transcatheter Mitral Valve Repair Therapies: Evolution, Status and Challenges" Ann Biomed Eng. Feb. 2017; 45(2):332-359.

Extended European Search Report for European Application No. 24185624.4 mailed Oct. 16, 2024, 9 pages.

Feldman et al., "Assessing the Balance Between Less Mitral Regurgitation and More Residual Transmitral Pressure Gradient After MitraClip" JACC Cardiovasc Interv. May 8, 2017; 10(9):940-941.

Fukui et al., "Prior inferior myocardial infarction has worse early outcomes in patients undergoing coronary artery bypass grafting than prior anterior myocardial infarction" Ann Thorac Surg. Feb. 2009; 87(2):475-480.

Gaasch et al., "Left ventricular response to mitral regurgitation: implications for management" Circulation. Nov. 25, 2008; 118(22):2298-2303.

Garcia et al., "Mechanisms of hemolysis with mitral prosthetic regurgitation. Study using transesophageal echocardiography and fluid dynamic simulation" J Am Coll Cardiol. Feb. 1996; 27(2):399-406.

Goel et al., "Prevalence and outcomes of unoperated patients with severe symptomatic mitral regurgitation and heart failure: comprehensive analysis to determine the potential role of MitraClip for this unmet need" J Am Coll Cardiol. Jan. 21, 2014; 63(2):185-186.

Gogoladze et al., "Analysis of the mitral coaptation zone in normal and functional regurgitant valves" Ann Thorac Surg. Apr. 2010; 89(4):1158-1161.

Goldstein et al., "Two-Year Outcomes of Surgical Treatment of Severe Ischemic Mitral Regurgitation" N Engl J Med. Jan. 28, 2016; 374(4):344-353.

Gorman et al., "Infarct size and location determine development of mitral regurgitation in the sheep model" J Thorac Cardiovasc Surg. Mar. 1998; 115(3):615-622.

Grayburn et al., "Quantitation of mitral regurgitation" Circulation. Oct. 16, 2012; 126(16):2005-2017.

Hadjadj et al., "Echocardiographic Variables Associated with Transvalvular Gradient After a Transcatheter Edge-To-Edge Mitral Valve Repair" J Am Soc Echocardiogr. Jan. 2022; 35(1):86-95.

Harken et al., "The surgical correction of mitral insufficiency" J Thorac Surg. Dec. 1954; 28(6):604-624.

He et al., "Integrated mechanism for functional mitral regurgitation: leaflet restriction versus coapting force: in vitro studies" Circulation. Sep. 16, 1997; 96(6):1826-1834.

Hensey et al., "Transcatheter Mitral Valve Replacement: An Update on Current Techniques, Technologies, and Future Directions" JACC Cardiovasc Interv. Mar. 8, 2021; 14(5):489-500.

Hilberath et al., "Intraoperative evaluation of transmitral pressure gradients after edge-to-edge mitral valve repair" PLoS One. Sep. 2, 2013; 8(9):e73617, 6 pages.

Ikenaga et al., "Mechanisms of mitral regurgitation after percutaneous mitral valve repair with the MitraClip" Eur Heart J Cardiovasc Imaging. Oct. 1, 2020; 21(10):1131-1143.

International Search Report and Written Opinion, issued in connection with International Application No. PCT/US18/43307, dated Oct. 2, 2018. 9 pages.

Itabashi et al., "Different indicators for postprocedural mitral stenosis caused by single- or multiple-clip implantation after percutaneous mitral valve repair" J Cardiol. Apr. 2018; 71(4):336-345.

Ito et al., "Mechanism of atrial functional mitral regurgitation in patients with atrial fibrillation: A study using three-dimensional transesophageal echocardiography" J Cardiol. Dec. 2017; 70(6):584-590.

Johns et al., "Mitral insufficiency: the experimental use of a mobile polyvinyl sponge prosthesis" Ann Surg. Sep. 1954; 140(3):335-341.

Kaewkes et al., "Usefulness of Computed Tomography to Predict Mitral Stenosis After Transcatheter Mitral Valve Edge-to-Edge Repair" Am J Cardiol. Aug. 15, 2021; 153:109-118.

Kalra et al., "Temporal changes in interpapillary muscle dynamics as an active indicator of mitral valve and left ventricular interaction in ischemic mitral regurgitation" J Am Coll Cardiol. Nov. 4, 2014; 64(18):1867-1879.

Kaplan et al., "Three-dimensional echocardiographic assessment of annular shape changes in the normal and regurgitant mitral valve" Am Heart J. Mar. 2000; 139(3):378-387.

Kaul et al., "Mechanism of ischemic mitral regurgitation. An experimental evaluation" Circulation. Nov. 1991; 84(5):2167-2180.

Kimura et al., "The unique mechanism of functional mitral regurgitation in acute myocardial infarction: a prospective dynamic 4D quantitative echocardiographic study" Eur Heart J Cardiovasc Imaging. Apr. 1, 2019; 20(4):396-406.

Kincaid et al., "Anterior leaflet augmentation for ischemic mitral regurgitation" Ann Thorac Surg. Aug. 2004; 78(2):564-568.

Kron et al., "Predicting recurrent mitral regurgitation after mitral valve repair for severe ischemic mitral regurgitation" J Thorac Cardiovasc Surg. Mar. 2015; 149(3):752-761.e1.

(56) References Cited

OTHER PUBLICATIONS

Kumanohoso et al., "Mechanism of higher incidence of ischemic mitral regurgitation in patients with inferior myocardial infarction: quantitative analysis of left ventricular and mitral valve geometry in 103 patients with prior myocardial infarction" J Thorac Cardiovasc Surg. Jan. 2003; 125(1):135-143.

Ladich et al., "Pathological healing response of explanted MitraClip devices" Circulation. Apr. 5, 2011; 123(13):1418-1427.

Lam et al., "Hemolysis after mitral valve repair: mechanisms and treatment" Ann Thorac Surg. Jan. 2004; 77(1):191-195.

Lam et al., "Morphology of the human mitral valve. I. Chordae tendineae: a new classification" Circulation. Mar. 1970; 41(3):449-458.

Lang et al., "Recommendations for cardiac chamber quantification by echocardiography in adults: an update from the American Society of Echocardiography and the European Association of Cardiovascular Imaging" J Am Soc Echocardiogr. Jan. 2015; 28(1):1-39. e14.

Lee et al., "Mechanisms of recurrent functional mitral regurgitation after mitral valve repair in nonischemic dilated cardiomyopathy: importance of distal anterior leaflet tethering" Circulation. May 19, 2009; 119(19):2606-2614.

Levack et al., "Three-dimensional echocardiographic analysis of mitral annular dynamics: implication for annuloplasty selection" Circulation. Sep. 11, 2012; 126(11 Suppl 1):S183-S188.

Lubos et al., "MitraClip therapy in surgical high-risk patients: identification of echocardiographic variables affecting acute procedural outcome" JACC Cardiovasc Interv. Apr. 2014; 7(4):394-402.

Machino-Ohtsuka et al., "Novel Mechanistic Insights Into Atrial Functional Mitral Regurgitation—3-Dimensional Echocardiographic Study" Circ J. Sep. 23, 2016; 80(10):2240-2248.

Mack et al., "3-Year Outcomes of Transcatheter Mitral Valve Repair in Patients With Heart Failure" J Am Coll Cardiol. Mar. 2, 2021; 77(8):1029-1040.

Magne et al., "Ischemic mitral regurgitation: a complex multifaceted disease" Cardiology. (2009) 112(4):244-259.

Magne et al., "Preoperative posterior leaflet angle accurately predicts outcome after restrictive mitral valve annuloplasty for ischemic mitral regurgitation" Circulation. Feb. 13, 2007; 115(6):782-791.

Magne et al., "Restrictive annuloplasty for ischemic mitral regurgitation may induce functional mitral stenosis" J Am Coll Cardiol. Apr. 29, 2008; 51(17):1692-1701.

Maisano et al., "The edge-to-edge technique: a simplified method to correct mitral insufficiency" Eur J Cardiothorac Surg. Mar. 1998; 13(3):240-246.

Mann et al., "Mechanisms and models in heart failure: the biomechanical model and beyond" Circulation. May 31, 2005; 111(21):2837-2849.

Marchena et al., "Respective prevalence of the different carpentier classes of mitral regurgitation: a stepping stone for future therapeutic research and development" J Card Surg. Jul. 2011; 26(4):385-392.

Marzilli et al., "Role of the papillary muscle in opening and closure of the mitral valve" Am J Physiol. Mar. 1980; 238(3):H348-H354.

Mauri et al., "The EVEREST II Trial: design and rationale for a randomized study of the evalve mitraclip system compared with mitral valve surgery for mitral regurgitation" Am Heart J. Jul. 2010; 160(1):23-29.

Mirabel et al., "What are the characteristics of patients with severe, symptomatic, mitral regurgitation who are denied surgery?" Eur Heart J. Jun. 2007; 28(11):1358-1365.

MitraClip G4 Features—Tailored. Optimized. Proven. Accessed Sep. 5, 2024. https://mitraclip.com/physician/mitraclip-procedure/mitraclip-features. 10 pages.

Mitral Valve Repair Center, "Mitral Valve Function", Accessed Apr. 19, 2022. https://www.mitralvalverepair.org/mitral-valve-function, 4 pages.

Mittal et al., "Combined papillary muscle and left ventricular wall dysfunction as a cause of mitral regurgitation. An experimental study" Circulation. Aug. 1971; 44(2):174-180.

Nagaura et al., "Percutaneous Edge-to-Edge Repair for Atrial Functional Mitral Regurgitation: A Real-Time 3-Dimensional Transesophageal Echocardiography Study" JACC Cardiovasc Imaging. Sep. 2019; 12(9):1881-1883.

Nematzadeh et al., "Effects of material properties on mechanical performance of nitinol stent designed for femoral artery: Finite element analysis" Sci. Iran. (2012) 19(6):1564-1571.

Neuss et al., "Elevated Mitral Valve Pressure Gradient After MitraClip Implantation Deteriorates Long-Term Outcome in Patients With Severe Mitral Regurgitation and Severe Heart Failure" JACC Cardiovasc Interv. May 8, 2017; 10(9):931-939.

Nielsen et al., "Edge-to-edge mitral repair: tension on the approximating suture and leaflet deformation during acute ischemic mitral regurgitation in the ovine heart" Circulation. Sep. 18, 2001; 104(12 Suppl 1):I29-35.

Nkomo et al., "Burden of valvular heart diseases: a population-based study" Lancet. Sep. 16, 2006; 368(9540):1005-1011.

Noack et al., "Changes in dynamic mitral valve geometry during percutaneous edge-edge mitral valve repair with the MitraClip system" J Echocardiogr. Jun. 2019; 17(2):84-94.

Non-Final Office Action for U.S. Appl. No. 18/089,127 mailed Aug. 29, 2024, 9 pages.

Non-Final Office Action for U.S. Appl. No. 18/614,081 mailed on Aug. 30, 2024, 11 pages.

Obadia, J-F et al., "Percutaneous Repair or Medical Treatment for Secondary Mitral Regurgitation," New England Journal of Medicine, Dec. 2018, vol. 379, No. 24, pp. 2297-2306.

Odell et al., "Long-term results of the Ivalon baffle mitral valve repair" Ann Thorac Surg. Aug. 1992; 54(2):283-285.

Onishi et al., "Mechanistic features associated with improvement in mitral regurgitation after cardiac resynchronization therapy and their relation to long-term patient outcome" Circ Heart Fail. Jul. 2013; 6(4):685-693.

Onohara et al., "Image-Guided Targeted Mitral Valve Tethering with Chordal Encircling Snares as a Preclinical Model of Secondary Mitral Regurgitation" J Cardiovasc Transl Res. Jun. 2022; 15(3):653-665.

Onohara et al., "Mitral regurgitation worsens cardiac remodeling in ischemic cardiomyopathy in an experimental model" J Thorac Cardiovasc Surg. Sep. 2020; 160(3):e107-e125.

Ooms et al., "Transcatheter Edge-to-Edge Repair in Proportionate Versus Disproportionate Functional Mitral Regurgitation" J Am Soc Echocardiogr. Jan. 2022; 35(1):105-115.e8.

Otsuji et al., "Insights from three-dimensional echocardiography into the mechanism of functional mitral regurgitation: direct in vivo demonstration of altered leaflet tethering geometry" Circulation. Sep. 16, 1997; 96(6):1999-2008.

Otsuji et al., "Restricted diastolic opening of the mitral leaflets in patients with left ventricular dysfunction: evidence for increased valve tethering" J Am Coll Cardiol. Aug. 1998; 32(2):398-404.

Otto et al., "2020 ACC/AHA Guideline for the Management of Patients With Valvular Heart Disease: A Report of the American College of Cardiology/American Heart Association Joint Committee on Clinical Practice Guidelines" J Am Coll Cardiol. Feb. 2, 2021; 77(4):e25-e197.

Padala et al., (Oct. 16, 2016). MitraPlug: Transcatheter leaflet extending for mitral & tricuspid repair [PowerPoint presentation], TCT Conference, Cardiovascular Research Foundation, Washington D.C., 16 pages.

Padala, "The arithmetic of a successful mitral valve repair" J Thorac Cardiovasc Surg. Nov. 2017; 154(5):1638-1640.

Pelton et al., "Optimization of processing and properties of medical grade Nitinol wire" Min Invas Ther & Allied Technol (2000) 9(1) 107-118.

Pibarot et al., "MITRA-FR vs. COAPT: lessons from two trials with diametrically opposed results" Eur Heart J Cardiovasc Imaging. Jun. 1, 2019; 20(6):620-624.

Ranganathan et al., "Morphology of the human mitral valve. II. The value leaflets" Circulation. Mar. 1970; 41(3):459-467.

(56) References Cited

OTHER PUBLICATIONS

Rassi et al., "Differing mechanisms of exercise flow augmentation at the mitral and aortic valves" Circulation. Mar. 1988; 77(3):543-551.

Reid et al., "Geometric differences of the mitral valve apparatus in atrial and ventricular functional mitral regurgitation" J Cardiovasc Comput Tomogr. Sep.-Oct. 2022; 16(5):431-441.

Rogers et al., "Early experience with Millipede IRIS transcatheter mitral annuloplasty" Ann Cardiothorac Surg. Nov. 2018; 7(6):780-786.

Rossi et al., "Independent prognostic value of functional mitral regurgitation in patients with heart failure. A quantitative analysis of 1256 patients with ischaemic and non-ischaemic dilated cardiomyopathy" Heart. Oct. 2011; 97(20):1675-1680.

Rumel et al., "The correction of mitral insufficiency with a transvalvular polyvinyl formalinized plastic (ivalon) sponge prosthesis; a preliminary report" Dis Chest. Apr. 1958; 33(4):401-413.

Search Report, issued in EP Application No. 18837757.6, dated Mar. 31, 2021. 8 pages.

Shah et al., "Percutaneous Mitral Valve Interventions (Repair): Current Indications and Future Perspectives" Front Cardiovasc Med. Jul. 2019 12:6:88. 18 pages.

Shi et al., "A Swine Model of Percutaneous Intracoronary Ethanol Induced Acute Myocardial Infarction and Ischemic Mitral Regurgitation" J Cardiovasc Transl Res. Aug. 2017; 10(4):391-400.

Sielicka et al., "Pathological Remodeling of Mitral Valve Leaflets from Unphysiologic Leaflet Mechanics after Undersized Mitral Annuloplasty to Repair Ischemic Mitral Regurgitation" J Am Heart Assoc. Nov. 6, 2018; 7(21):e009777. 18 pages.

Silbiger, "A novel mechanism by which MitraClip implantation may favorably alter the natural history of left ventricular remodeling in patients with mitral regurgitation: proposed role of the ventricular-valvular loop" J Am Soc Echocardiogr. Feb. 2013; 26(2):217-219.

Silbiger, "Does left atrial enlargement contribute to mitral leaflet tethering in patients with functional mitral regurgitation? Proposed role of atriogenic leaflet tethering" Echocardiography. Nov. 2014; 31(10):1310-1311.

Silbiger, "Mechanistic insights into atrial functional mitral regurgitation: Far more complicated than just left atrial remodeling" Echocardiography. Jan. 2019; 36(1):164-169.

Silbiger, "Mechanistic insights into ischemic mitral regurgitation: echocardiographic and surgical implications" J Am Soc Echocardiogr. Jul. 2011; 24(7):707-719.

Silverman et al., "The mitral complex. Interaction of the anatomy, physiology, and pathology of the mitral annulus, mitral valve leaflets, chordae tendineae, and papillary muscles" Am Heart J. Sep. 1968; 76(3):399-418.

Sorajja et al., "Outcomes With Transcatheter Mitral Valve Repair in the United States: An STS/ACC TVT Registry Report" J Am Coll Cardiol. Nov. 7, 2017; 70(19):2315-2327.

Stone et al., "Transcatheter Mitral-Valve Repair in Patients with Heart Failure" N Engl J Med. Dec. 13, 2018; 379(24):2307-2318.

Sturla et al., "In vitro and in silico approaches to quantify the effects of the Mitraclip® system on mitral valve function" J Biomech. Jan. 5, 2017; 50:83-92.

Suresh, "Development of a Transcatheter Cardiac Leaflet Enhancer to Treat Functional Mitral Regurgitation" Dissertation May 2022, Georgia Institute of Technology, Emory University, 332 pages.

Sutton et al., "Left ventricular remodeling after myocardial infarction: pathophysiology and therapy" Circulation. Jun. 27, 2000; 101(25):2981-2988.

Szerlip et al. "2-Year Outcomes for Transcatheter Repair in Patients With Mitral Regurgitation From the CLASP Study" JACC Cardiovasc Interv. Jul. 26, 2021; 14(14):1538-1548.

Templeton et al., "Experimental Reconstruction of Cardiac Valves by Venous and Pericardial Grafts" Ann Surg. Feb. 1949; 129(2):161-176.

Utsunomiya et al., "Comparison of mitral valve geometrical effect of percutaneous edge-to-edge repair between central and eccentric functional mitral regurgitation: clinical implications" Eur Heart J Cardiovasc Imaging. Apr. 1, 2019; 20(4):455-466.

Utsunomiya et al., "Effect of Percutaneous Edge-to-Edge Repair on Mitral Valve Area and Its Association With Pulmonary Hypertension and Outcomes" Am J Cardiol. Aug. 15, 2017; 120(4):662-669.

Van Der Merwe et al., "Mitral Valve Replacement—Current and Future Perspectives" Open J Cardiovasc Surg. Jul. 13, 2017: 9:1179065217719023. 6 pages.

Van Rosendael et al., "New insights on Carpentier I mitral regurgitation from multidetector row computed tomography" Am J Cardiol. Sep. 1, 2014; 114(5):763-768.

Vokonas et al., "Dynamic geometry of the left ventricle in mitral regurgitation" Circulation. Oct. 1973; 48(4):786-796.

Votta et al., "3-D computational analysis of the stress distribution on the leaflets after edge-to-edge repair of mitral regurgitation" J Heart Valve Dis. Nov. 2002; 11(6):810-822.

Yoshida et al., "Impact of Percutaneous Edge-to-Edge Repair in Patients With Atrial Functional Mitral Regurgitation" Circ J. Jun. 25, 2021; 85(7):1001-1010.

Zahr et al., "Mitral Valve Repair with More Natural Physiologic Functionality of the Mitral Valve (Half-Moon)" Oregon Health & Science University (2021), TVT, 15 pages.

Zeng et al., "Asymmetric versus symmetric tethering patterns in ischemic mitral regurgitation: geometric differences from three-dimensional transesophageal echocardiography" J Am Soc Echocardiogr. Apr. 2014; 27(4):367-375.

Zhan-Moodie et al., "Papillary Muscle Approximation Reduces Systolic Tethering Forces and Improves Mitral Valve Closure in the Repair of Functional Mitral Regurgitation" JTCVS Open. Sep. 2021; 7:91-104.

Zoghbi et al., "Recommendations for Noninvasive Evaluation of Native Valvular Regurgitation: A Report from the American Society of Echocardiography Developed in Collaboration with the Society for Cardiovascular Magnetic Resonance" J Am Soc Echocardiogr. Apr. 2017; 30(4):303-371.

International Search Report and Written Opinion for International Application No. PCT/US2024/043651 mailed Jan. 21, 2025, 18 pages.

Invitation to Pay Additional fees for International Application No. PCT/US2024/043651, mailed Oct. 31, 2024, 3 pages.

Non-Final Office Action for U.S. Appl. No. 18/782,496 mailed Feb. 24, 2025, 12 pages.

Non-Final Office Action for U.S. Appl. No. 18/782,496 mailed Nov. 13, 2024, 9 pages.

Notice of Allowance for U.S. Appl. No. 18/089,127 mailed on Mar. 26, 2025, 7 pages.

Notice of Allowance for U.S. Appl. No. 18/614,081 mailed Jan. 2, 2025, 8 pages.

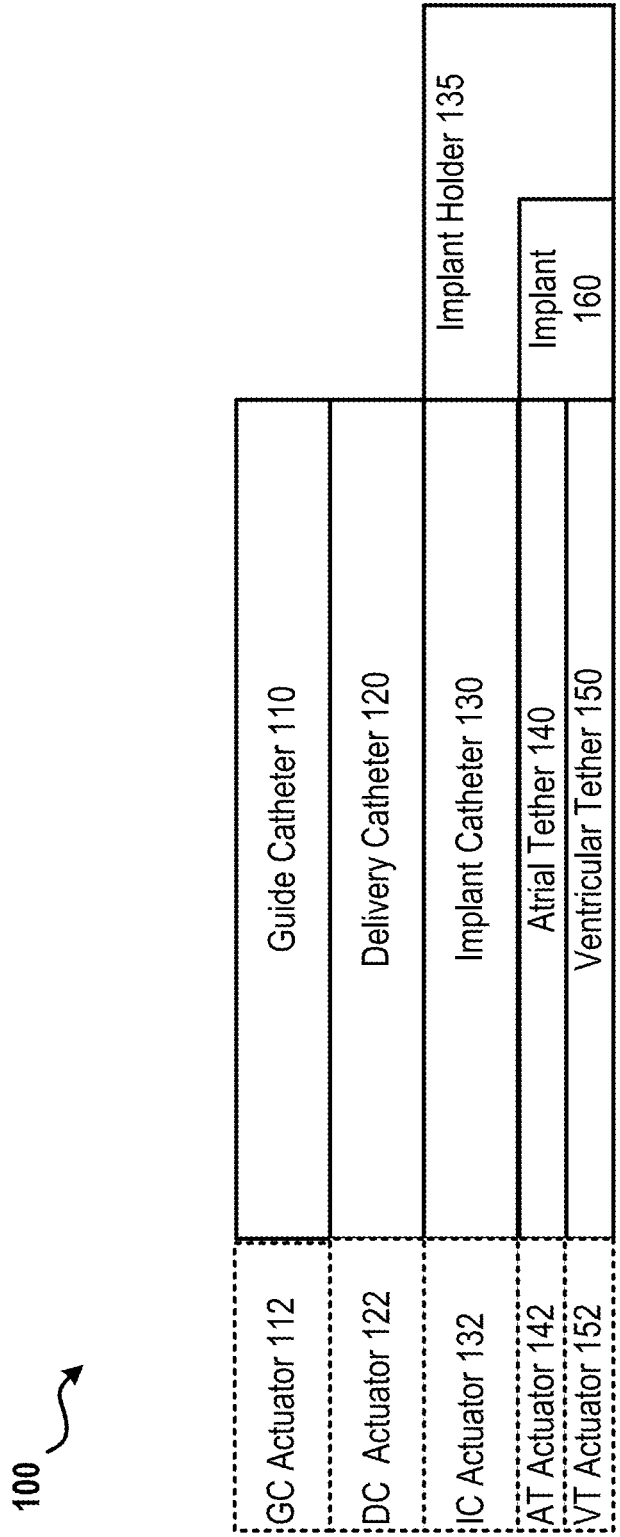

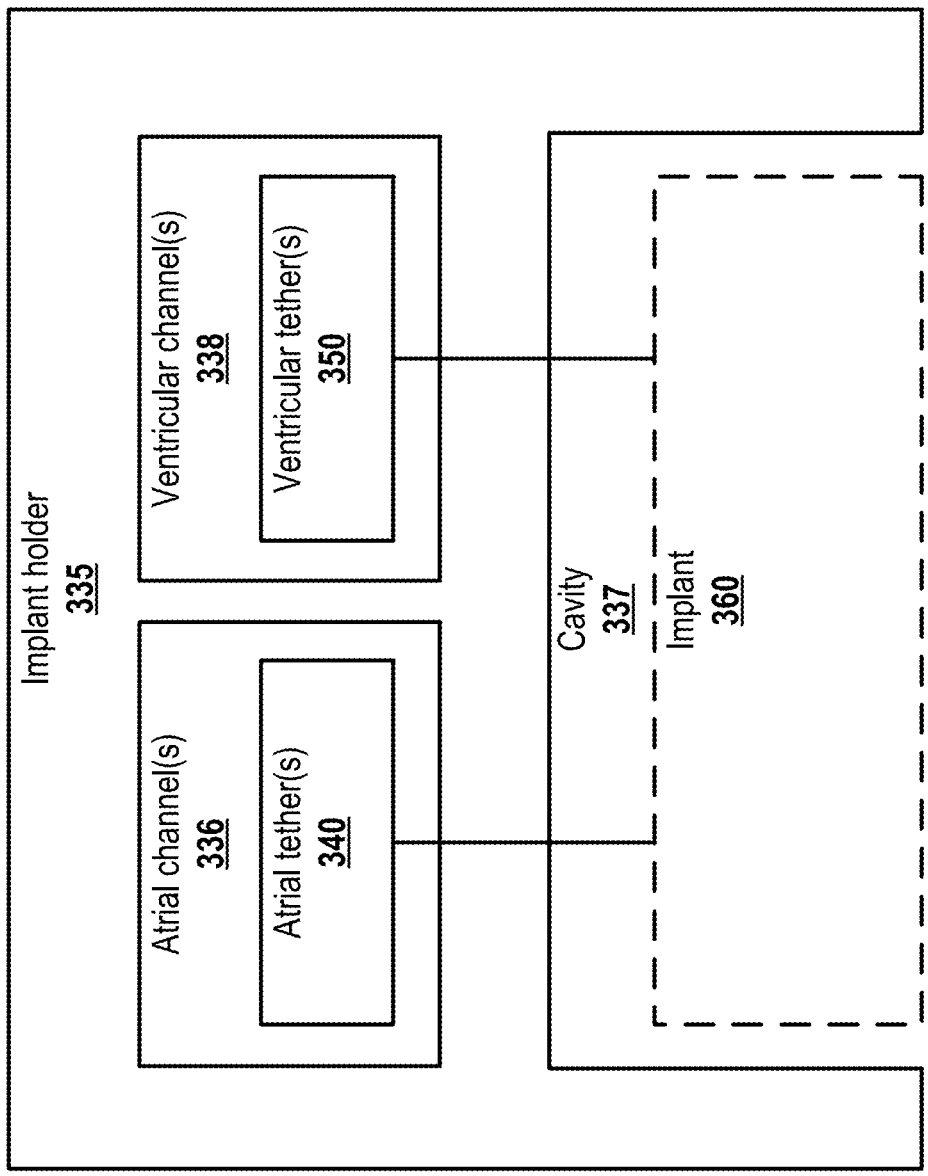

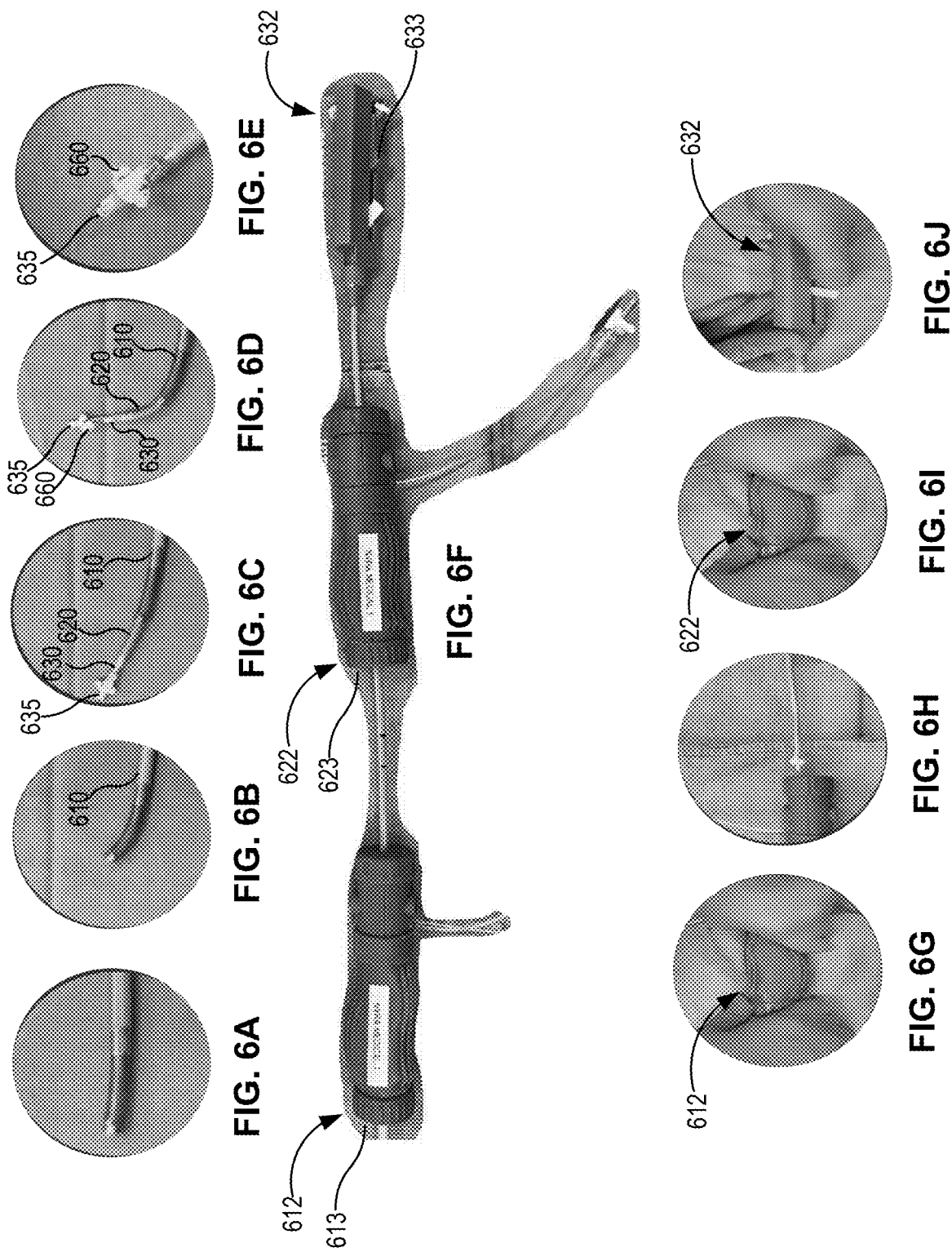

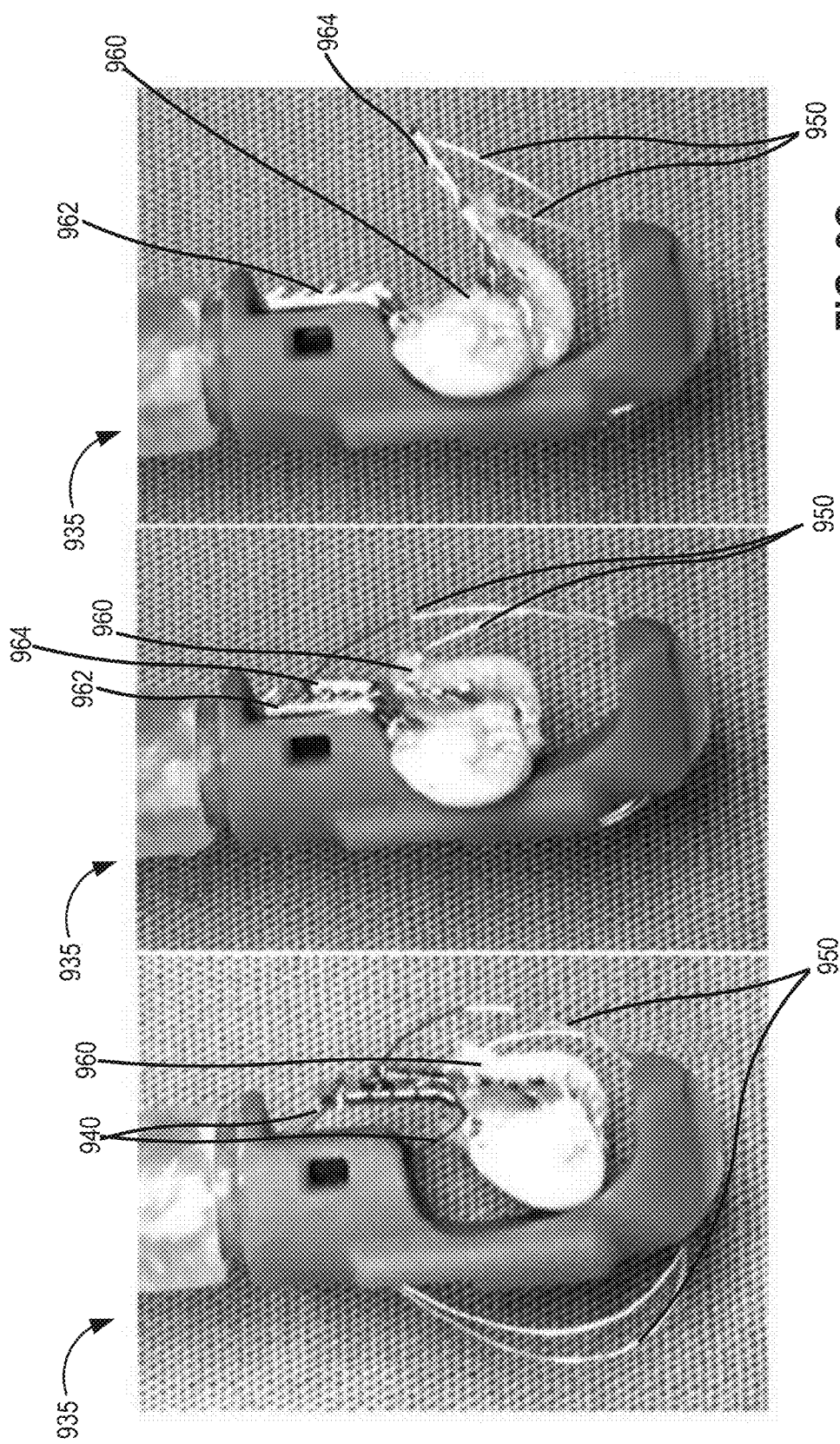

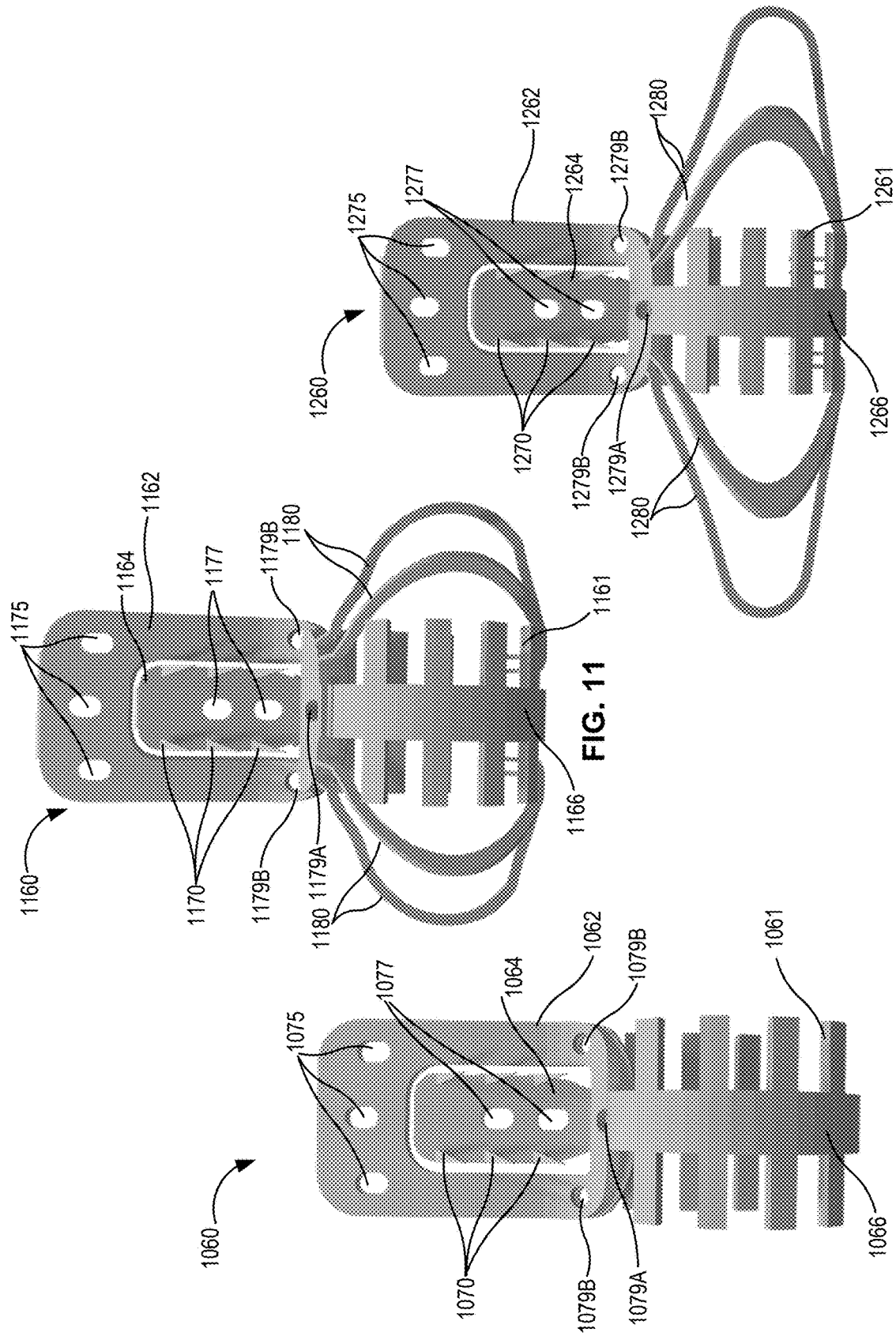

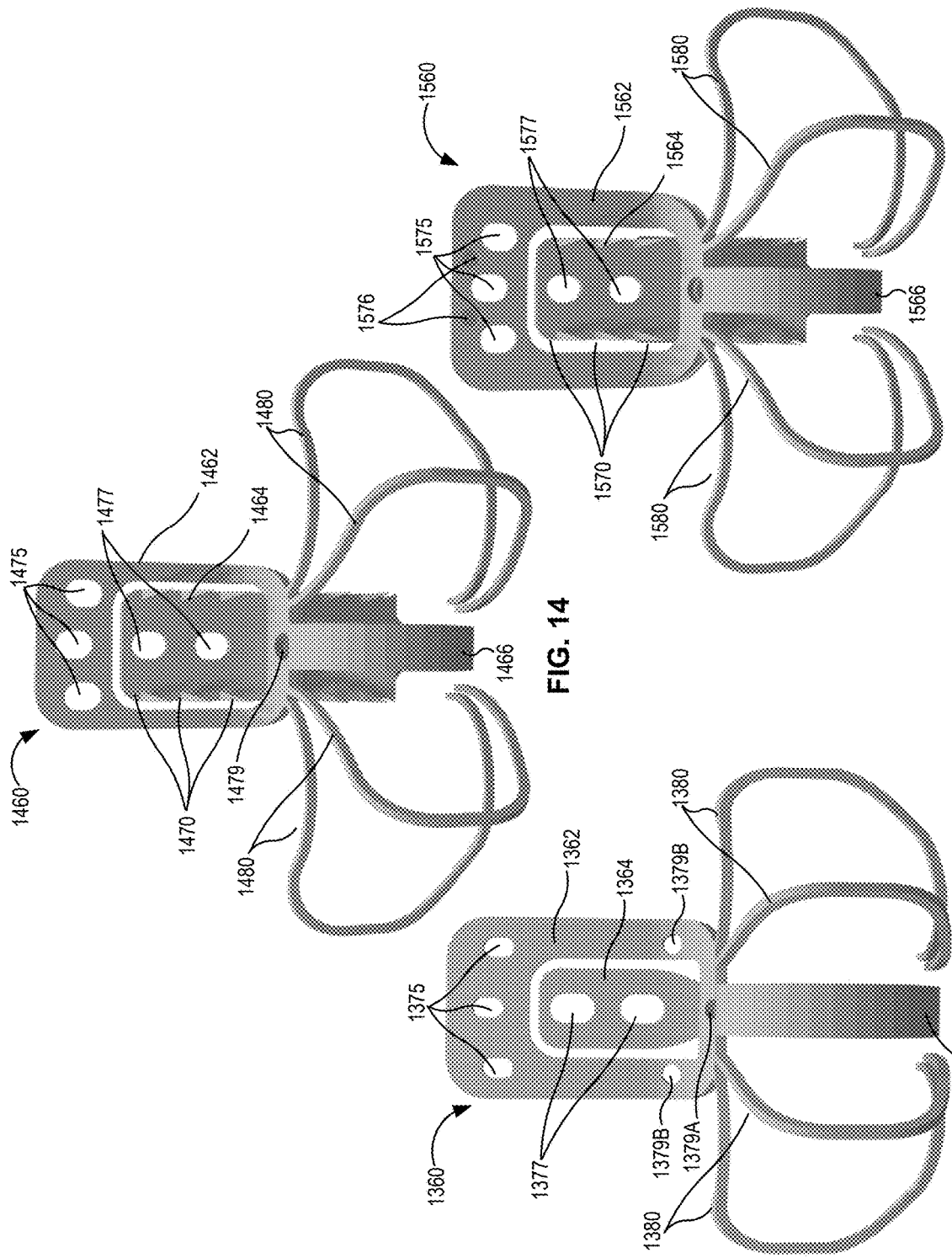

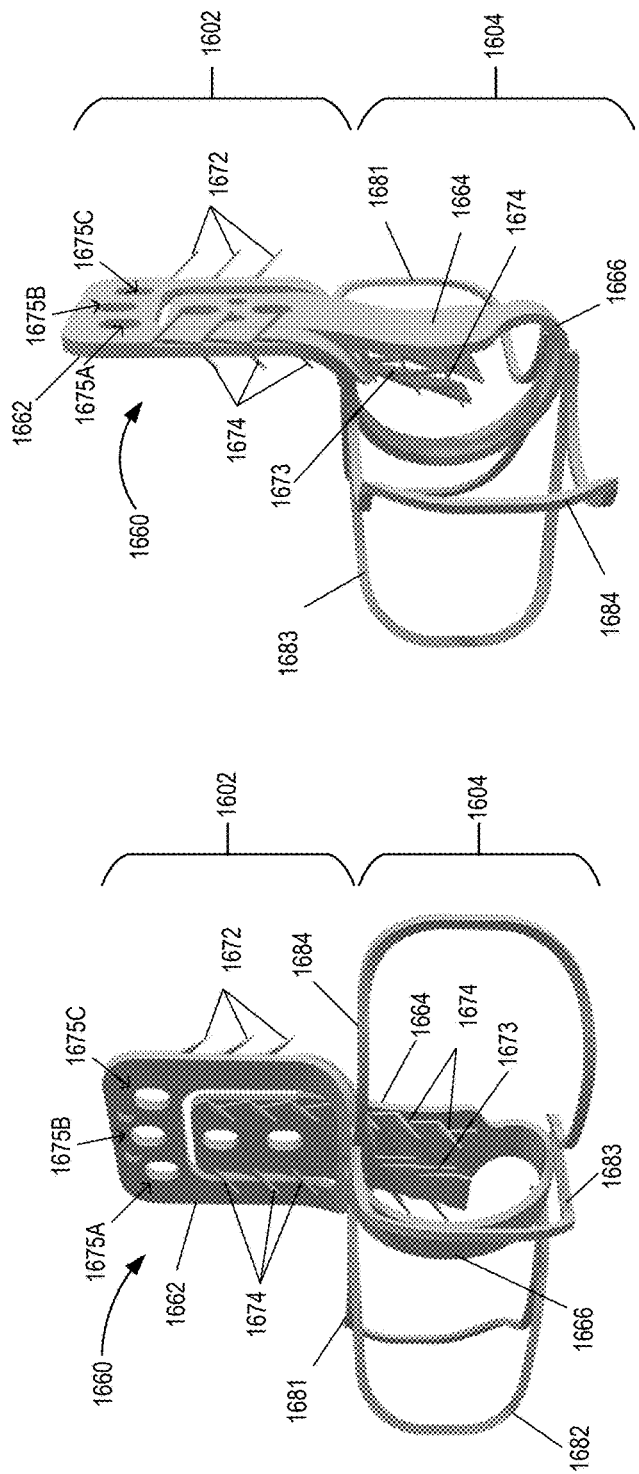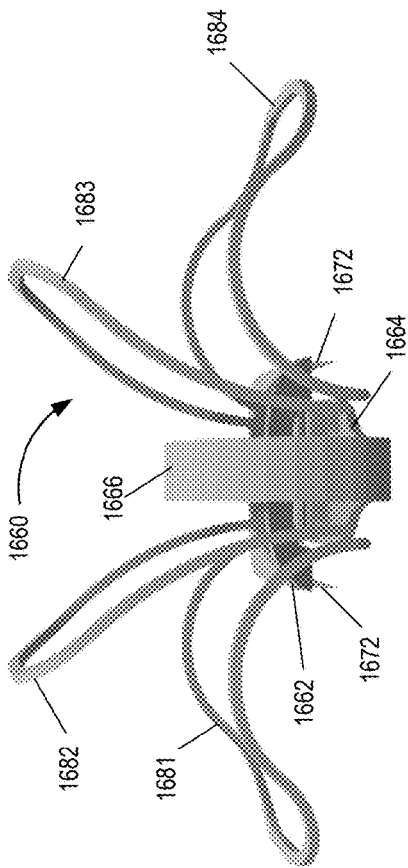

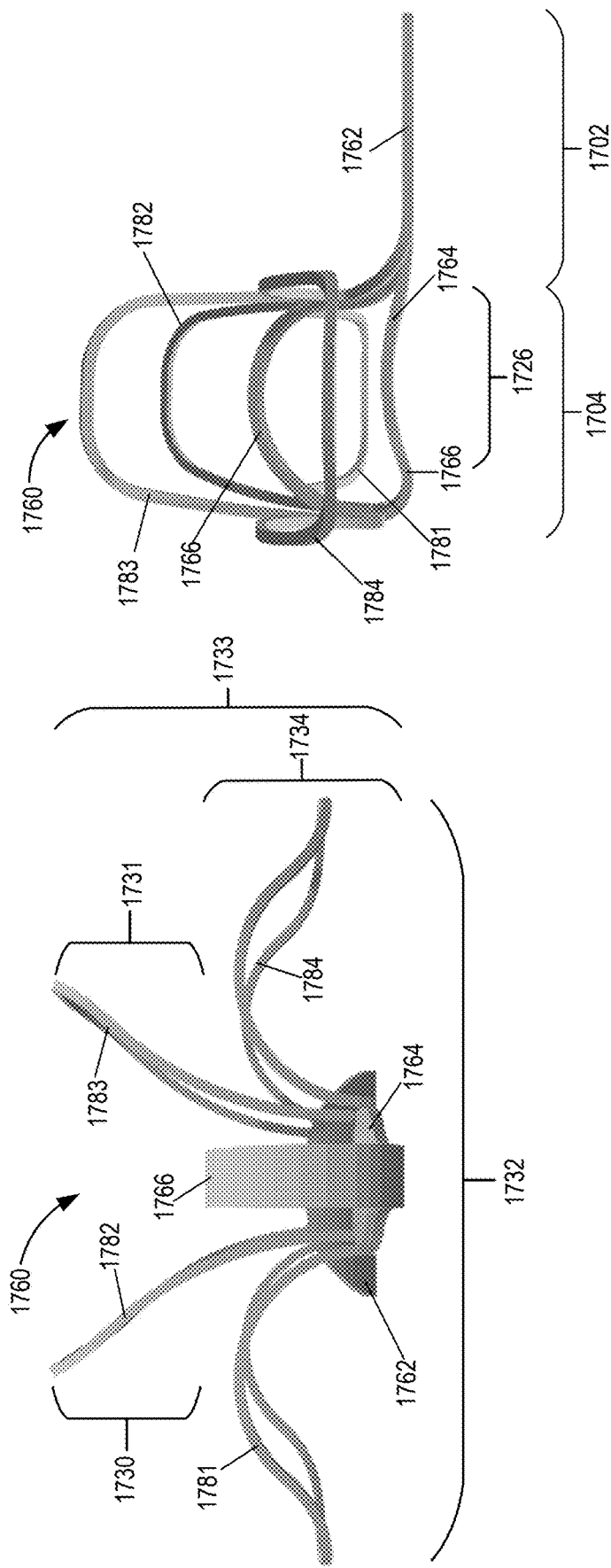

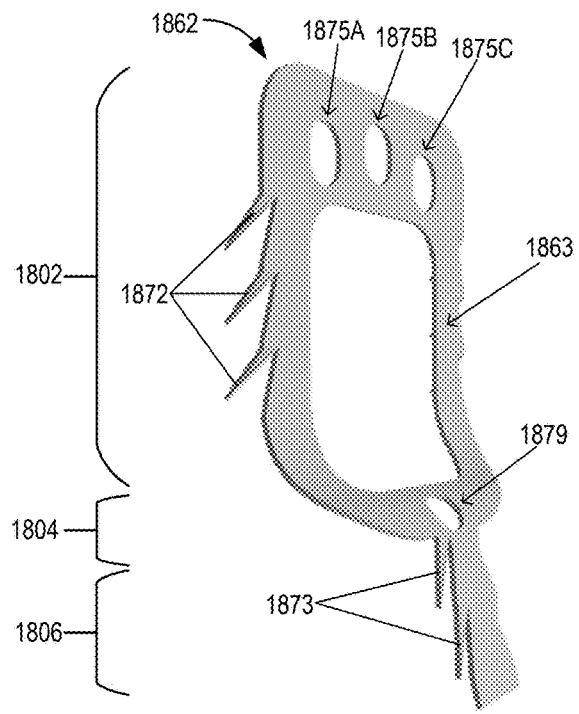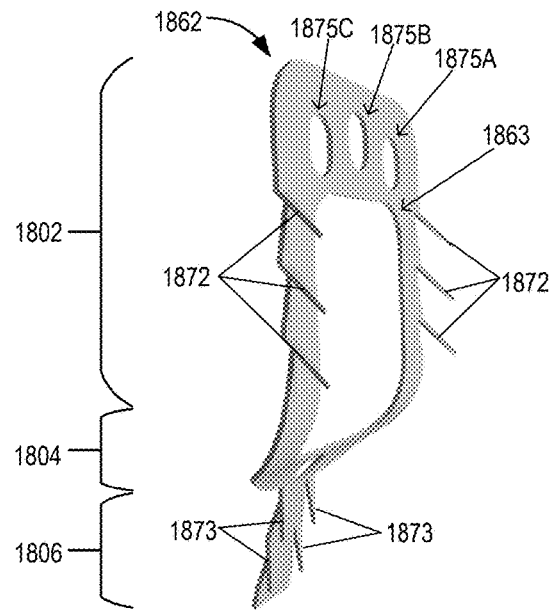
FIG. 18A  FIG. 18B
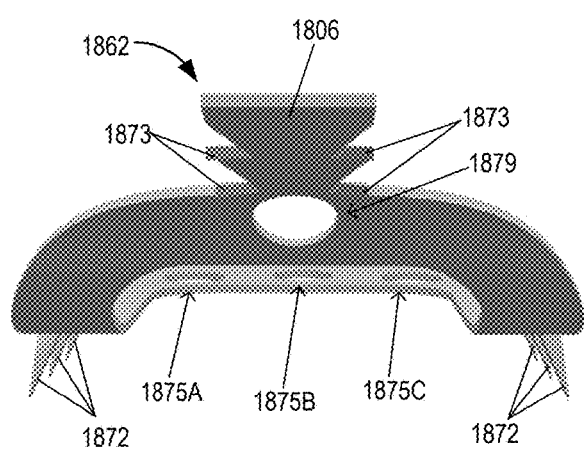
FIG. 18C

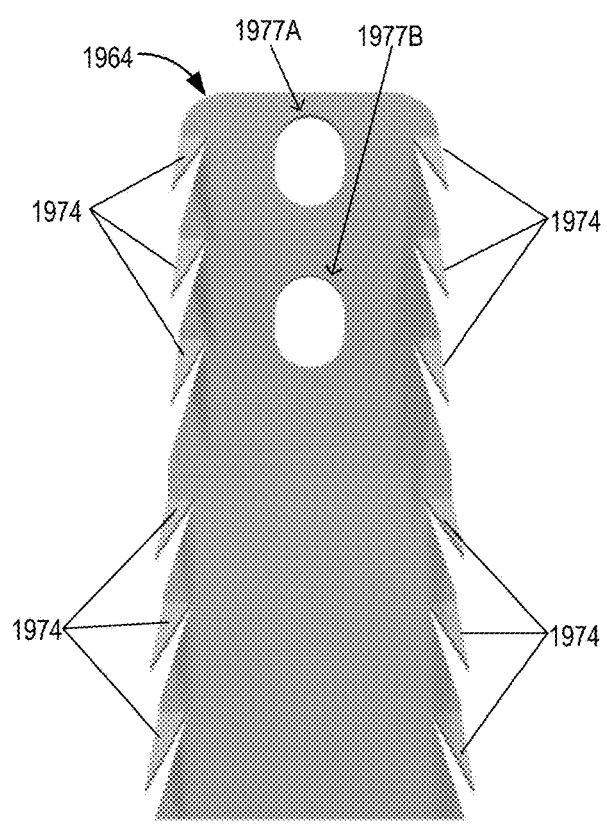
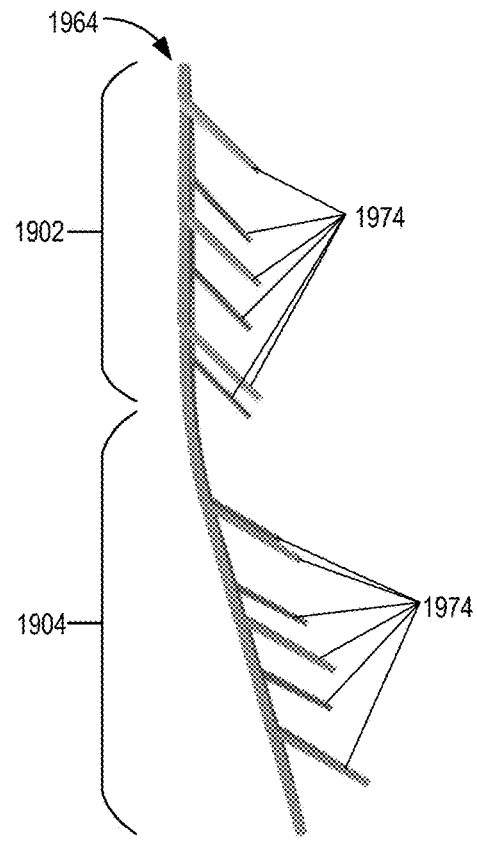
FIG. 19A
FIG. 19B
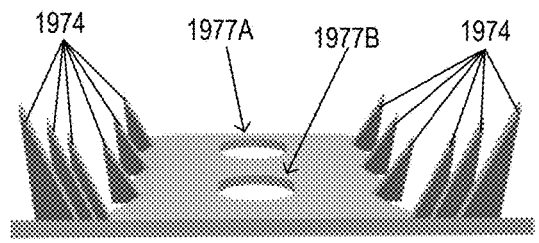
FIG. 19C

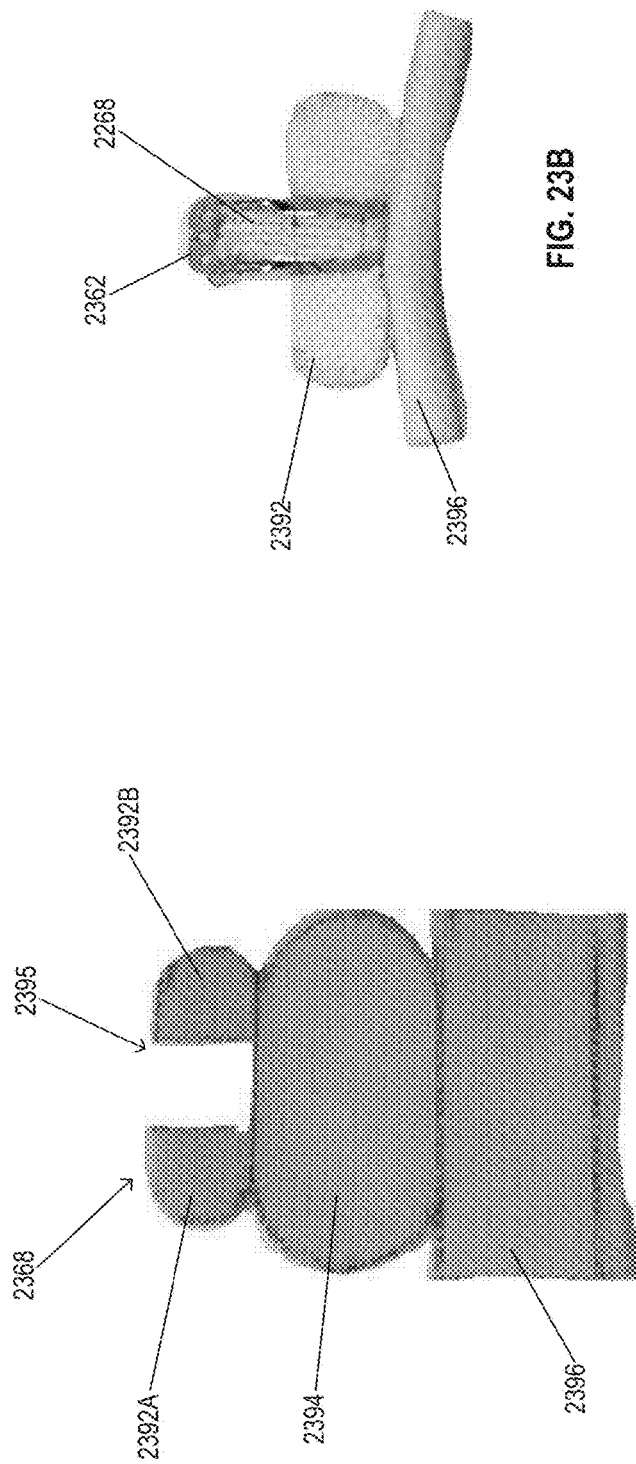
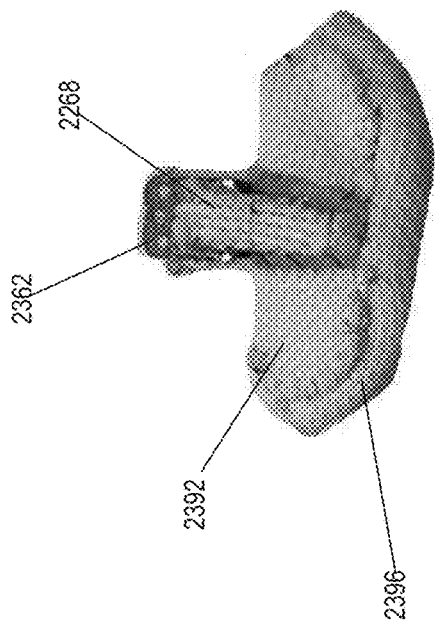

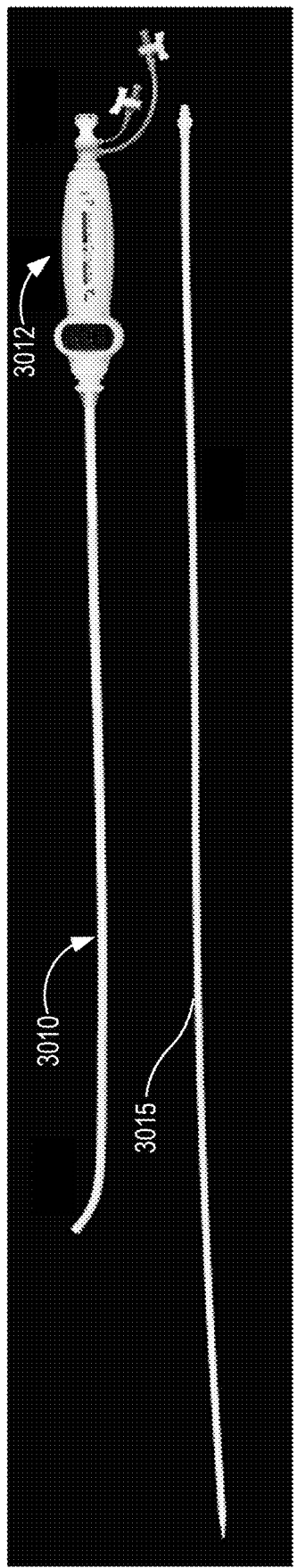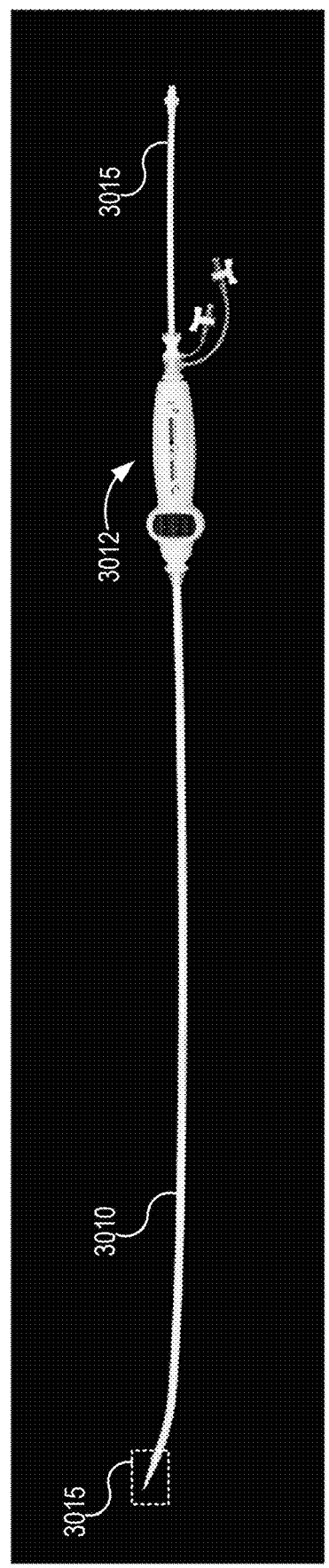
FIG. 30A
FIG. 30B

FIG. 32A
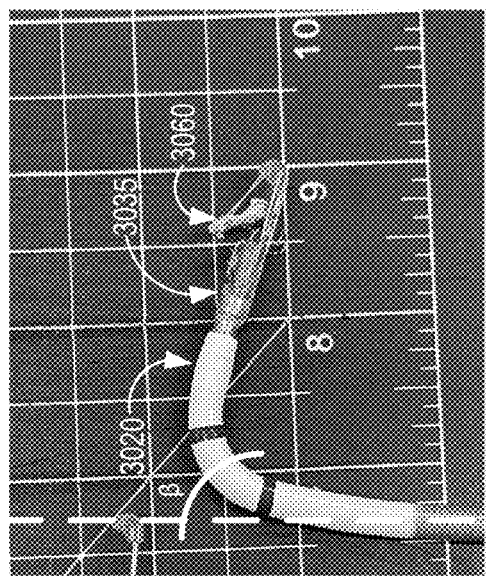
FIG. 32D
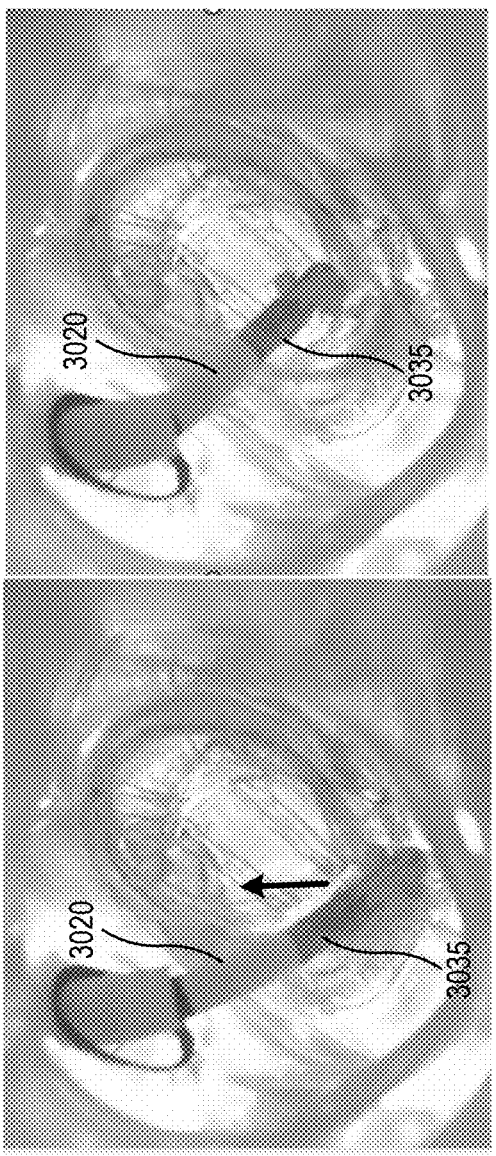
FIG. 32C
FIG. 32B

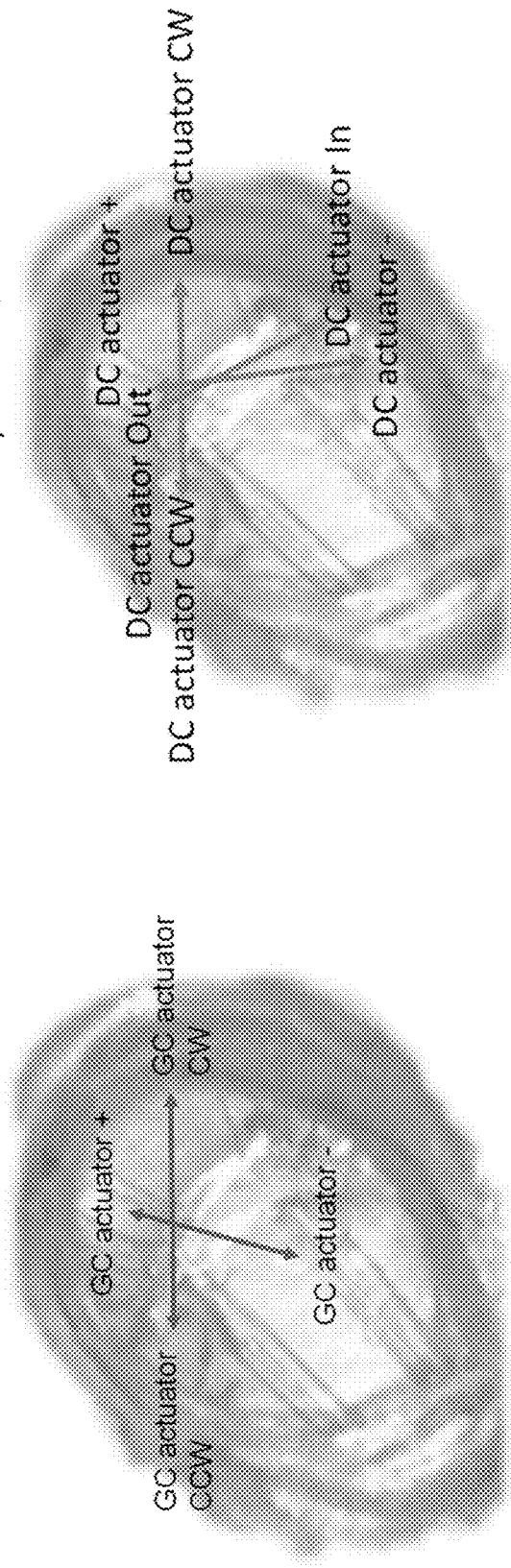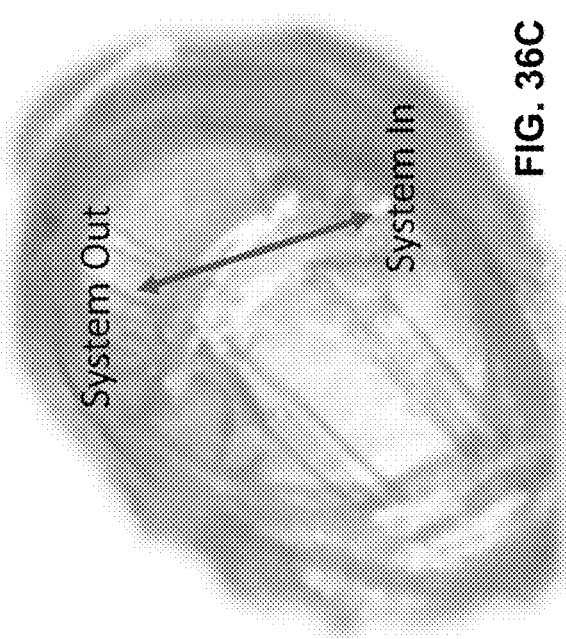
FIG. 36B
FIG. 36C
FIG. 36A

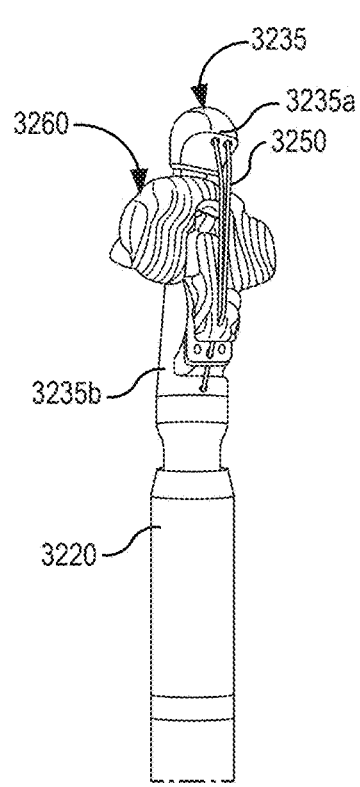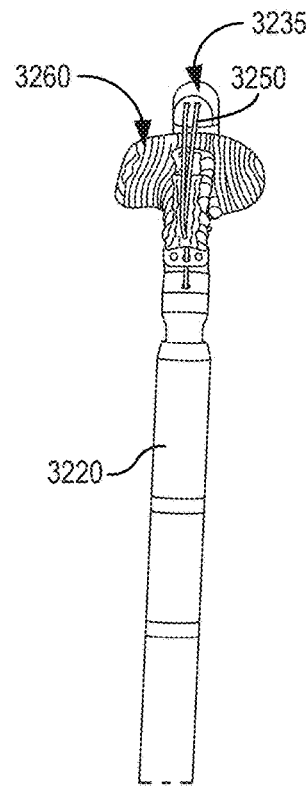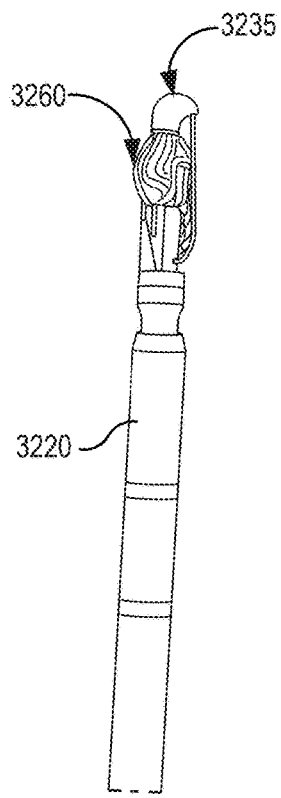
FIG. 41A  FIG. 41B  FIG. 41C
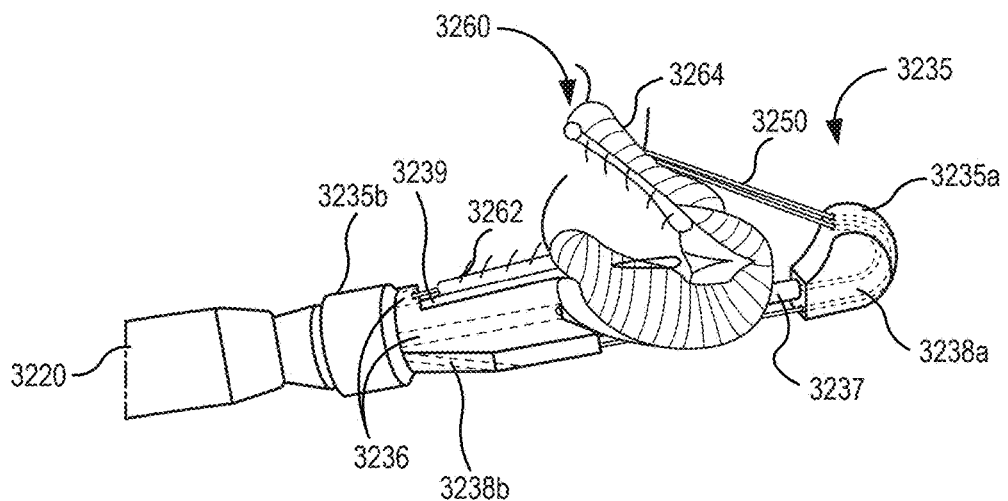
FIG. 41D

FIG. 42A
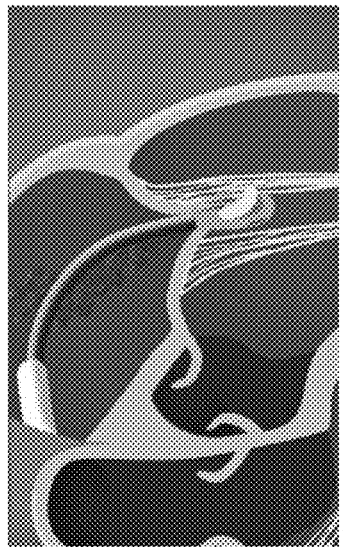
FIG. 42B
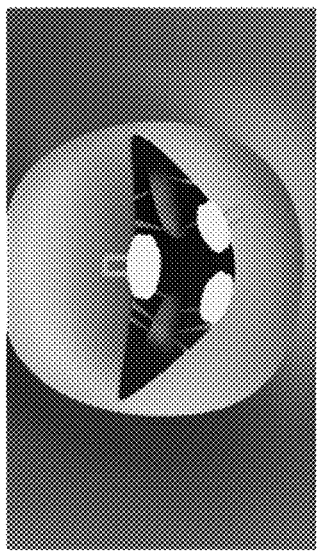
FIG. 42C
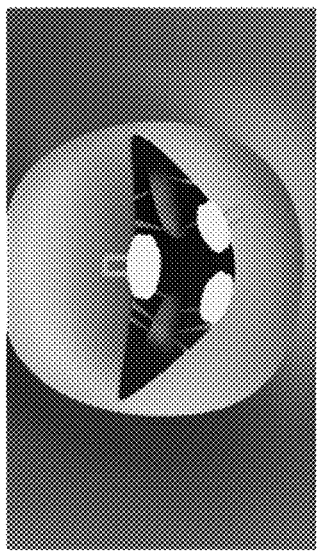
FIG. 42D
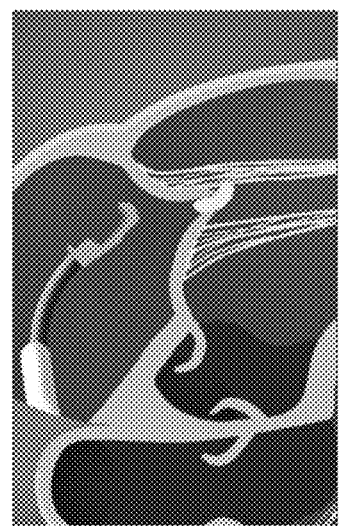
FIG. 42E
FIG. 42F

4800

Cut a pre-determined design of an implant body from a substantially flat sheet of material
4810

↓

Reduce sharpness of at least one edge of the implant body
4820

↓

Set the implant body into a pre-determined configuration
4830

↓

Set each of a first plate and a second plate into a pre-determined configuration
4840

↓

Attach the first plate to a first arm of the implant body
4850

↓

Attach the second plate to a second arm of the implant body
4860

↓

Attach at least one visualization marker to the first arm
4870

↓

Attach at least one visualization marker to the second arm
4880

↓

Attach at least one cover to the implant body
4890

FIG. 46

SYSTEMS, DEVICES, AND METHODS FOR REDUCING HEART VALVE REGURGITATION

CROSS REFERENCE TO RELATED APPLICATIONS

This application claims priority to and the benefit of U.S. Provisional Application No. 63/675,682, filed Jul. 25, 2024, entitled "Systems, Devices, and Methods for Reducing Heart Valve Regurgitation", the contents of which are hereby incorporated by reference herein in its entirety.

TECHNICAL FIELD

Embodiments described herein relate to an implant and an implant delivery system for reducing heart valve regurgitation. In particular, embodiments described herein relate to a transcatheter delivery system for delivering an implant to the mitral heart valve.

BACKGROUND

Heart valve regurgitation, particularly functional mitral regurgitation (FMR), is a common heart valve lesion seen in heart failure (HF) patients and it has been shown to worsen the progression of heart failure and increase the mortality of patients. Most heart failure patients are too high-risk for surgeries due to their poor health conditions. Minimally invasive transcatheter approaches exist for delivering implants to the heart valves (e.g., the mitral valve); however, current implant technologies fail to adequately treat FMR and can disturb the native valve dynamics resulting in poor long-term durability.

BRIEF DESCRIPTION OF THE DRAWINGS

FIGS. 2A-2C are schematic diagrams of an implant delivery system for reducing heart valve regurgitation during different stages of delivery of the implant, according to embodiments.

FIG. 3 is a schematic block diagram of an implant holder of an implant delivery system, according to embodiments.

FIGS. 6A-6E show images of steerability of catheters of an implant delivery system and FIGS. 6F-6J show images of proximal control mechanisms of the implant delivery system configured to steer the catheters, according to embodiments.

FIGS. 9A-9C show images of an implant holder of an implant delivery system including an implant coupled thereto, according to embodiments.

FIGS. 10-15 depict implants for treating heart valve regurgitation, according to various embodiments.

FIGS. 16A-16C illustrate a front perspective view (FIG. 16A), a back perspective view (FIG. 16B), and a bottom view (FIG. 16C) of an implant, according to an embodiment.

FIG. 17F illustrates a bottom view of the implant of FIG. 17A. FIG. 17G illustrates a side view of the implant of FIG. 17A.

FIGS. 18A-18C illustrate a front perspective view, a back perspective view, and a bottom view, respectively, of a first plate of an implant, according to an embodiment.

FIGS. 19A-19C illustrate a front view, a side view, and a bottom view of a second plate of an implant, according to an embodiment.

FIG. 23A illustrates a top view of a cover in a flat configuration, according to embodiments. FIGS. 23B-23C illustrate a front view of the cover coupled to the implant, according to embodiments.

FIGS. 30A-30B show the handle assembly of FIG. 29 including a guide catheter actuator coupled to a guide catheter and a dilator configured to be disposed through a lumen of the guide catheter, according to embodiments.

FIG. 32A shows a first actuation of a delivery catheter actuator, according to embodiments.

FIGS. 32B-32D show a distal end of the delivery catheter in response to the first actuation of the delivery catheter actuator, according to embodiments.

FIGS. 36A-36C show steerability maps of a distal end of the implant delivery system in response to actuation of the guide catheter actuator, the delivery catheter actuator, and the entire handle assembly, respectively, according to embodiments.

FIGS. 41A-41D shows an implant holder including a proximal portion and a distal portion joined by a connector therebetween, according to embodiments.

FIGS. 42A-42F illustrate a method for delivery an implant to a heart valve using an implant delivery system to treat heart valve regurgitation, according to embodiments.

FIG. 46 is a flow chart for an example method of manufacture an implant for treating heart valve regurgitation, according to embodiments.

DETAILED DESCRIPTION

Figure 1A:
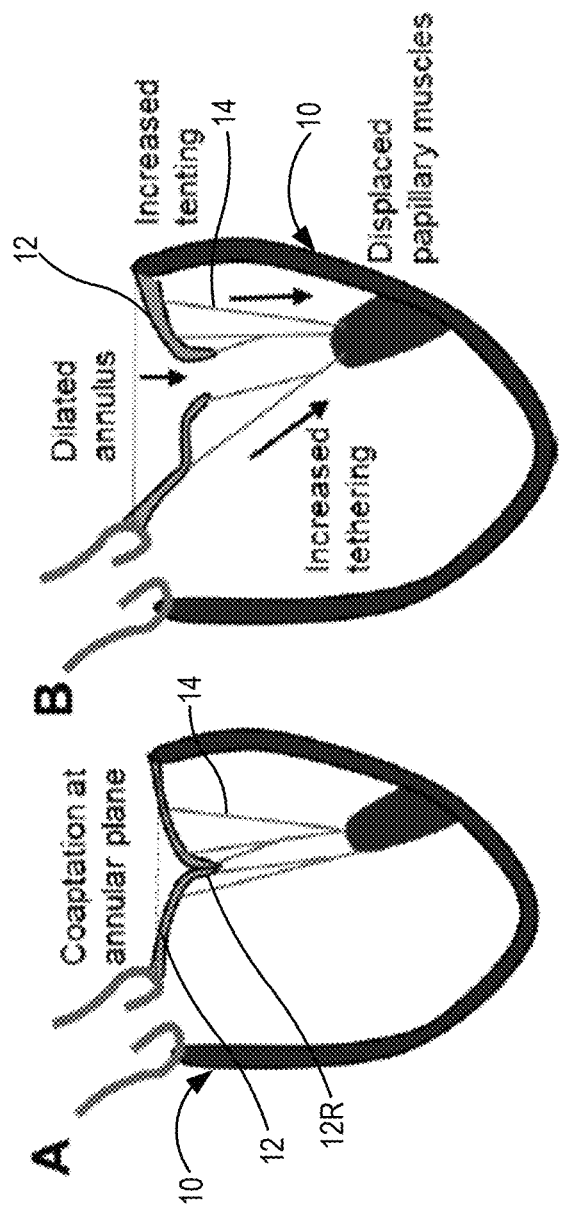
FIG. 1A is a diagram illustrating coaptation at an annular plane of a heart valve (left) and dilation of the annulus and the ventricular cavity that deforms the heart valve and that results in heart valve regurgitation.

Heart valve regurgitation has been shown to worsen the progression of heart failure (HF) and increase the mortality rate of patients. The first line of treatment for HF patients with heart valve regurgitation, such as mitral valve regurgitation, is guideline directed medical therapy (GDMT). Medical therapy targets the hemodynamics or left ventricular (LV) remodeling, rather than the valve itself, in an attempt to improve LV geometry which in turn would have secondary effect on mitral regurgitation. Cardiac resynchronization therapy (CRT) is also used to treat mitral regurgitation in patients with prolonged QRS. CRT helps with synchronizing the LV contraction thereby increasing its systolic function, which in turn increases the LV closing force. FMR can also often be treated by either surgical repair or replacement of the valve when patients undergo concomitant coronary bypass surgery. However, most HF patients are deemed as too high-risk for surgeries due to their poor health condition. Therefore, minimally invasive transcatheter technologies to repair or replace the valve are in need for such patients. Current technologies fail to adequately treat FMR and disturb the native valve dynamics resulting in poor long-term durability.

In contrast, embodiments described herein augment the valve leaflet at the regurgitant site using a light-weight implant to provide leaflet extension and cover the regurgitant gap in systole; and the implant can move along with the leaflet in diastole to allow unrestricted inflow. In some embodiments, the implant can focally augment the native leaflet when attached. A steerable implant delivery system may be used for transcatheter deployment of the implant under image guidance. The implant described herein overcomes the anatomical constraints for implant interventions for heart valve regurgitation, thereby helping with expanding the patient population who can be treated significantly. The embodiments described herein can use a single leaflet capture approach, so the risk of developing functional stenosis or capturing short leaflets or restricting the possibility of future interventions on the same valve is eliminated.

Disclosed herein are devices, systems, and methods for reducing heart valve regurgitation. Generally, the devices (e.g., implants) described herein may be configured to couple to a heart valve such that the heart valve may be altered to treat a patient's cardiac condition, such as heart valve regurgitation. The devices described herein generally comprise implantable devices configured to couple to cardiac tissue, such as one or more of a valve leaflet, chordae tendineae, and an annulus of a heart valve, to reduce or eliminate heart valve regurgitation. The devices may comprise an attachment section and a coaptation section. The attachment section may be configured to couple the implant to tissue, and the coaptation section may be configured (e.g., alone or in combination with the attachment section) to enhance and/or alter one or more physical characteristics of the heart valve. Physical characteristics may include, but are not limited to, leaflet length, leaflet height, leaflet width, leaflet thickness, leaflet curvature, leaflet stiffness, leaflet shape, leaflet strength, and a combination thereof. In this manner, when implanted, the implant may enhance and/or alter one or more physical characteristics that may affect the movement, deformation, and/or stretch of the leaflet. The altered physical characteristics may affect a portion of the heart valve or, in some variations, the entire heart valve. The altered physical characteristics may be useful in treating (e.g., partially or completely correcting) a cardiac condition, such as heart valve regurgitation (e.g., functional mitral regurgitation (FMR), tricuspid valve regurgitation, aortic valve regurgitation, pulmonary valve regurgitation).

In some variations, the one or more altered physical characteristics of the heart valve may reduce or eliminate a gap between leaflets, thereby reducing or eliminating valve regurgitation. For example, the devices described herein may alter one or more physical characteristics of a valve in a manner that increases a coaptation surface area for the valve leaflets. That is, the devices described herein may couple to a leaflet of a valve such that a length, thickness, and/or width of that leaflet is modified (e.g., increased). The modified length, width, and/or thickness of the leaflet may provide for a modified coaptation surface (e.g., increased coaptation surface area) that decreases or eliminates regurgitation. For instance, the devices described herein may protrude or otherwise extend from a surface of a heart valve leaflet such that another leaflet may coapt onto a portion of the device during systole, which may re-establish unidirectional blood flow through the valve. In some embodiments, the devices described herein may couple to the valve such that leaflet movement is modified in a manner that reduces or eliminates regurgitation.

The devices described herein may provide many benefits. For example, the devices may be configured to capture a single leaflet, which may preserve a valve orifice, as opposed to an edge-to-edge approach. In some embodiments, the single leaflet may be captured while the associated valve may be open (e.g., during diastole). Additionally, the devices may be configured to move with the heart valve during diastole and accordingly diastolic flow may not be impeded and thus the devices may avoid inducing functional stenosis. In a further example, the devices may be used in combination with valve replacement (e.g., transcatheter mitral valve replacement). That is, the devices may be coupled to the same valve that may undergo valve replacement without removing the coupled devices and/or requiring additional techniques or technologies to accommodate the coupled devices, and/or modifying the anatomy of the valve favorably (i.e. increase leaflet dimension) to enable transcatheter mitral valve replacement. Furthermore, the one or more physical characteristics of the heart valve to be altered may be specifically selected based on characteristics (e.g., anatomy, severity of condition to be treated, etc.) of a specific patient. For example, a patient's leaflet thickness may require enhancement so the devices described herein may alter the leaflet thickness without affecting a leaflet width. In a further example, the patient's leaflet thickness and width may require enhancement, such that the devices may facilitate both enhancements. In this way, the devices may be used in a wide range of patients, including patients with relatively small heart valves, relatively older patients, and/or patients with relatively calcified mitral annuluses.

In addition, the devices described herein may be deformable such that the devices may non-destructively (e.g., atraumatically) affect the structure or function of the heart valve and/or may receive a portion of the heart valve (e.g., a leaflet) via coaptation. For example, the devices may releasably attach to heart valve tissue (e.g., native leaflets, chordae tendineae) via a compressive force and/or friction force that may not damage the tissue. The compressive force may be applied by an attachment section comprising a first segment or arm and a second segment or arm of the implant. In some configurations, at least a portion of each of the first and second segments or arms may be coplanar with one another, which may assist in maintaining the position of the device relative to the heart valve. The central member may define a portion of a coaptation section, and the coaptation section may further include one or more support members. The support members may extend from the first segment or arm and may assist in defining a volume within the coaptation section. At least a portion of the coaptation section (e.g., at least a portion of the central member, one or more support members or a portion thereof) may be deflectable and/or deformable upon contact by a native leaflet. For example, one or more support members may deflect and/or deform relative to one or more additional support members. By virtue of the deflection and/or deformation of one or more of the support members (e.g., two, three, four, or more), the coaptation section volume at least partially defined by the support members may change (e.g., may decrease) upon contact by a native leaflet, and may be restored to its pre-contact volume upon loss of contact with the native leaflet.

Moreover, the devices described herein may be adjustable such that a physician may change the configuration and/or position of the devices during the procedure without detrimentally affecting the structure or function of the heart valve. For example, the devices may be configured to transition between a first configuration (e.g., an implanted configuration) and a second configuration (e.g., an open configuration) multiple times, and may avoid damaging tissue while applied to the heart valve (including during reapplication or application several times) during any such transition between the configurations. In this way, the devices may be positioned and repositioned until the devices are placed in an optimal orientation on the heart valve such that the effectiveness (as measured by, for example, a reduction in regurgitation) of the devices is maximized. To further aid in the positioning of the devices, the devices may also be directly or indirectly visualized by a physician during the procedure, such that the physician may determine the position and configuration of specific portions of the devices. Accordingly, the adjustability and visibility of the devices may reduce or eliminate the need for subsequent surgical procedures that may otherwise be required to adjust the position(s) of the devices. In some variations, multiple devices may each be releasably attached to heart valve tissue simultaneously such that the effects of each device may be combined to optimally reduce heart valve regurgitation. The devices may further enable tissue encapsulation such that the devices may be permanently integrated into the heart valve. The tissue encapsulation may provide additional thickness to the coaptation section, which may increase the efficacy of the devices. The efficacy may continue to increase as the thickness of the tissue increases over time. In this way, the efficacy and permanence of the devices described herein may result in patients reducing or eliminating heart valve regurgitation, the use of anti-coagulants, and/or avoiding risks associated with tissue maladaptation.

The systems described herein may include an implant delivery system configured to advance an implant attached thereto within a patient. The implant delivery system may comprise a handle coupled to one or more catheters, with each catheter comprising one or more lumens. One or more elongate members (e.g., wires, sutures, tubes) may be routed through the one or more lumens of the catheter. In some variations, the elongate member may comprise a tube comprising a lumen therethrough, and one or more tubes may be routed through the one or more lumens of the catheter. One or more additional elongate members (e.g., wires, sutures) may be advanced through the one or more tubes. The elongate member(s) may be operatively coupled to the first segment or arm of the implant and/or the second segment or arm of the implant, such that the first and second segments or arms may be moved relative to each other. In some variations, the elongate member may be operatively coupled to the first segment or arm and/or the second segment or arm via a direct attachment between the elongate member and the first segment or arm and/or the second segment or arm, while in other variations the elongate member may be operatively coupled to the first segment or arm and/or the second segment or arm via an indirect connection. For example, in some variations, coupling via an indirect connection may include coupling the elongate member to the first segment or arm and/or the second segment or arm via a looped elongate member (e.g., suture loop) attached to the first segment or arm or the second segment or arm to which the elongate member couples. Accordingly, the delivery device may facilitate positioning the implant adjacent to a target heart valve location (e.g., native leaflet, annulus, chordae tendineae), release the first and/or second segments or arms to couple the implant to the heart valve, and optionally reapply a force to the first and/or second segment or arm to decouple the implant from the heart valve to facilitate removal, retrieval, and/or repositioning of the implant.

FIG. 1A is a diagram illustrating coaptation at an annular plane of a heart valve (e.g., the mitral valve (MV)) on the left and dilation of the annulus that results in heart valve regurgitation on the right. The mitral valve is the bicuspid atrio-ventricular valve located between left ventricle (LV) 10 and left atrium (LA) of the heart. The valve has two leaflets, the anterior leaflet and the posterior leaflet 12, the base of these leaflets attached to a fibrous structure between LV 10 and LA called annulus 12. The MV annulus is saddle shaped with high points/peaks at anterior and a posterior portion and low points at the lateral and medial commissure. The chordae tendinae (hereinafter, "chords") 14 are string-like structures that connect the leaflets 12 to the papillary muscles and the LV 10. The chords 14 originate from the tip of the papillary muscles and insert into the ventricular side of both anterior leaflet (AL) and posterior leaflet (PL). Mitral regurgitation (MR) occurs when the valve leaflets 12 fail to coapt during systole resulting in backflow of blood through the gap formed between the leaflets. This backflow of blood engorges the pulmonary veins causing shortness of breath, and also causes volume overload in the LV 10 and is one of the significant contributors of heart failure (HF). Functional mitral regurgitation can be broadly classified into atriogenic or atrial FMR and ventricular FMR based on the underlying pathology.

In FMR, this physiological leaflet motion is perturbed and thus the coaptation seal is inadequate. The dilated annulus draws the leaflets 12 away from each other in diastole, and a larger distance needs to be traversed by the leaflets 12 before they coapt in systole. The dyskinetic and enlarged LV tethers both marginal and strut chordae, and both the anterior and posterior leaflets, resulting in inadequate deformation of the leaflets to enable the verticalization of the leaflet edges to form a coaptation shelf in systole. As shown, in a normal mitral valve, the rough zone 12R of the leaflet edges 12 verticalize and form the coaptation shelf or seal in systole. In the abnormal mitral valve shown on the right, displacement of papillary muscles and dilation of annulus results in an increased chordal tension preventing the leaflet edges 12 to verticalize and forming a coaptation shelf or seal.

Figure 1B:
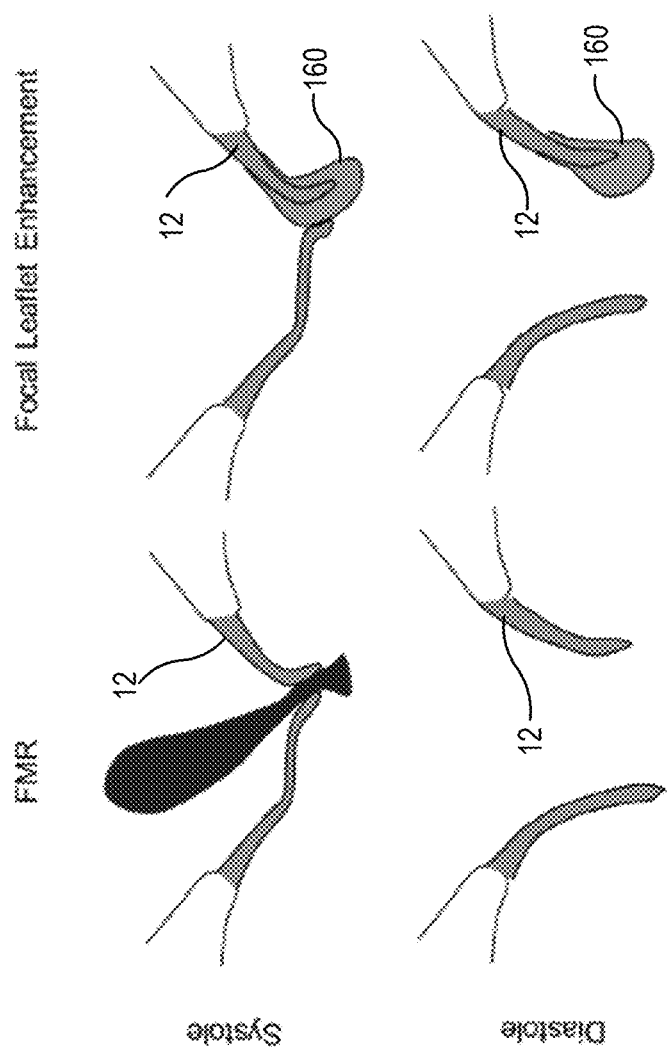
FIG. 1B is a diagram illustrating mitral regurgitation during systole (left) and treatment of the heart valve regurgitation using an implant (right).

FIG. 1B is a diagram illustrating mitral regurgitation during systole (left) and treatment of the heart valve regurgitation using an implant 160 (right). As shown on the right, an implant 160 may be atraumatically attached to the edge of one of the leaflets 12 at the regurgitant site to provide the vertical shelf needed for coaptation. This implant 160 protrudes off the leaflet 12 surface to focally increase the length and width at the leaflet edge 12, which can potentially provide enough leaflet 12 reserve and also reduce the extent of motion of opposing leaflet needed to get into coaptation. The protrusion of the implant can be appropriately sized based on the regurgitant jet dimensions and characteristics such that this focal augmentation using the implant fits the regurgitant gap in systole but would not interfere with the opening of the valve during diastole to avoid the risk of stenosis. The protrusion of the implant can be appropriately oversized based on the regurgitant jet dimensions and characteristics such that this focal augmentation using the implant may be larger than the regurgitant gap in systole to achieve a large reserve of coaptation, but does not interfere with the opening of the valve during diastole to avoid the risk of stenosis.

Figure 2B:
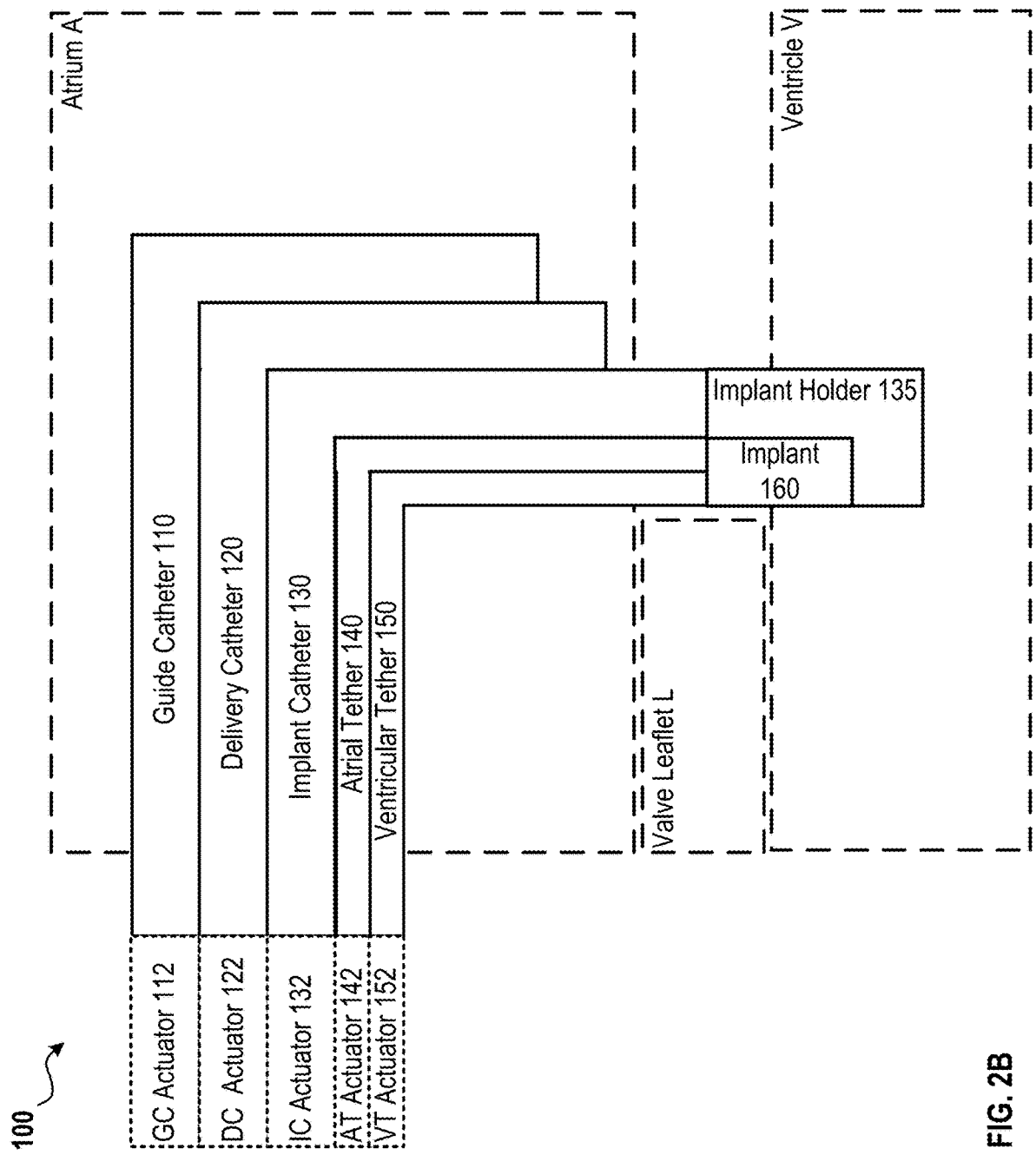
Figure 2C:
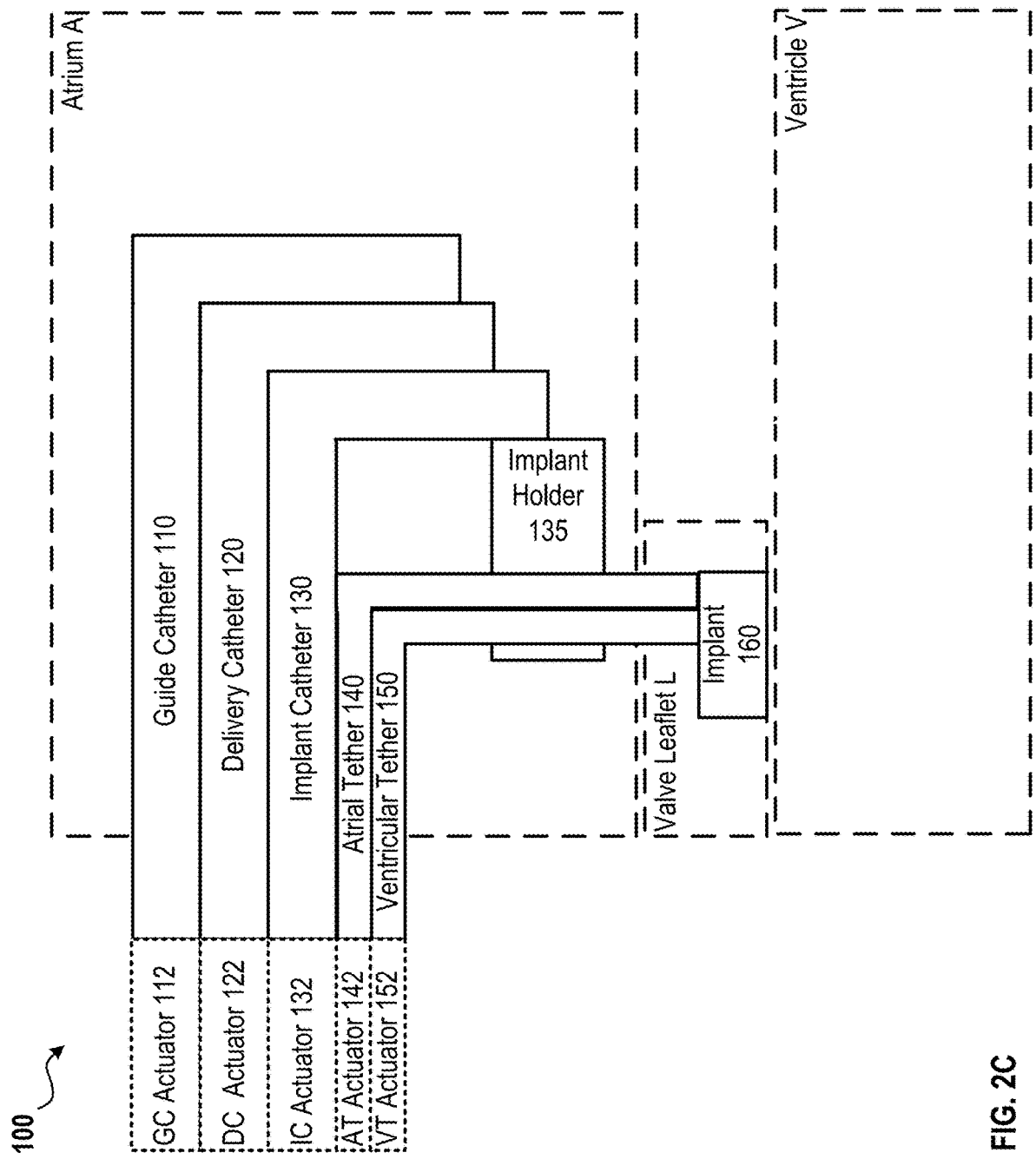

FIGS. 2A-2C are schematic diagrams of an implant delivery system 100 for reducing heart valve regurgitation during different stages of delivering an implant 160, according to embodiments. The implant delivery system 100 may include one or more catheters and a handle assembly coupled to a proximal end of the one or more catheters. In some embodiments, the implant delivery system 100 may include an implant catheter (IC) 130 extending alongside or through an inner lumen of a delivery catheter (DC) 120. The delivery catheter 120 may extend alongside or through an inner lumen of a guide catheter (GC) 110. A distal end of the implant catheter 130 may be coupled to an implant holder 135 including a cavity, space, or opening configured to receive the implant 160.

At least one of the implant catheter 130, the delivery catheter 120, or the guide catheter 110 may be steerable (e.g., may articulate in one or more planes) to navigate the implant delivery system 100 to a leaflet of the heart valve such that the implant 160 can be secured to the leaflet. In some embodiments, the delivery catheter 120 and the guide catheter 110 may be steerable to position the implant 160 near a heart valve of the patient. In some embodiments, the implant catheter 130 may not be steerable. For example, a stiffness of the implant catheter 130 may be less than that of the delivery catheter 120 such that a portion of the implant catheter 130 disposed in the delivery catheter 120 bends or flexes with the delivery catheter 120. As shown in FIG. 2B, the implant catheter 130, the delivery catheter 120, and the guide catheter 110 may be configured to navigate the implant holder 135 through a left atrium LA of the patient, past the valve leaflet L, and at least partially into the left ventricle LV such that the implant 160 can be secured to the leaflet of the mitral valve.

In some embodiments, the guide catheter 110 may be capable of bending to an angle from the longitudinal axis of up to 90 degrees, 100 degrees, 120 degrees, 135 degrees, 145 degrees, 150 degrees along one plane (e.g., a first plane). In some embodiments, the delivery catheter 120 may be configured to bend along one or more planes (e.g., along the first plane and a second plane perpendicular to the first plane). In some embodiments, the delivery catheter 120 may be configured to bend to an angle from the longitudinal axis of up to about 110 degrees, 120 degrees, 130 degrees, 140 degrees, 150 degrees, 160 degrees 170 degrees, 180 degrees, 190 degrees along the first plane. In some embodiments, the delivery catheter 120 may be configured to bend to an angle from the longitudinal axis of up to about 30 degrees, 40 degrees, 45 degrees, 50 degrees, 55 degrees, 60 degrees along the second plane. In some embodiments, the guide catheter 110 can be bent to an angle of up to about 135 degrees, to access the left atrium. In some embodiments, the delivery catheter 120 can be bent to an angle of up to about 120 degrees, to help to point the implant 160 towards the valve and get access to different valve segments. In some embodiments, the implant catheter may not be steerable. In some embodiments, the implant catheter 130 may be configured to translate linearly (e.g., proximally and distally) relative to the delivery catheter 120 for positioning of the implant 160 near or on the leaflet. In some embodiments, the implant catheter 130 may be configured to translate linearly a distance of up to about 3 cm, 4 cm, 5 cm, 6 cm, 7 cm, 8 cm, 9 cm, 10 cm, inclusive of all ranges and subranges therebetween.

In some embodiments, the delivery catheter 120 may be configured to rotate (e.g., between about 180 degrees to about 360 degrees) about its own longitudinal axis. In some embodiments, the implant catheter 130 may be configured to rotate about its own longitudinal axis. This rotation enables deployment on either the anterior or posterior leaflet of the heart valve. In some embodiments, the catheters 110, 120, 130 (or a portion thereof) may be formed from any suitable material such as, Nylon, Polyethylene, Nylon/Polyethylene, Pebax®, etc. In some embodiments, the catheters 110, 120, 130 may be extruded. In some embodiments, the catheters (e.g., the steerable catheters 120, 130) may be extruded with a metal ring along a length of the catheter (e.g., at a distal end) and one or more pull wires coupled to the ring. In some embodiments, the catheters (e.g., the steerable catheters 120, 130) may include two pull wires coupled to the ring with a predetermined degree of separation therebetween (e.g., about 180 degrees) such that tension to each of the pull wires articulates the catheter along one plane. In some embodiments, the catheters 110, 120, 130 may include any number of pull wires spaced at any interval around the circumference of the ring. In some embodiments, the catheters 110, 120, 130 may include 1 pull wire, 2 pull wires, 3 pull wires, 4 pull wires, 5 pull wires, 6 pull wires, 7 pull wires, 8 pull wires. The pull wires may run along a length of the respective catheter (e.g., the steerable catheters 120, 130) and be anchored to an actuator on the proximal end of the implant delivery system 100 (e.g., a GC actuator 112, a DC actuator 122, and/or an IC actuator 132 described in further detail below). In some embodiments, the actuator may be any suitable actuator such as, for example, rack and pinion, gear system, knob, slider etc. In some embodiments, the actuators may allow the user to steer the catheters 120, 130.

In some embodiments, at least one of the catheters 110, 120, 130 may include a port (e.g., a flushing port) connected to the inner lumen of the catheters 110, 120, 130. The port may introduce fluid to reduce frictional contact between the catheters 110, 120, 130 and/or to remove air or prevent air from entering the patients' circulation. In some embodiments, a valve (e.g., a hemostatic valve) may be included in the handle assembly proximal to the port to close the proximal end of the catheters 110, 120, 130 and prevent leakage of blood.

In some embodiments, the catheters 110, 120, 130 have varying stiffness or hardness along their length. For example, the catheters 110, 120, 130 may include harder material at the proximal end transitioning to softer material at the distal end to allow bending of the softer portion while keeping the harder portion in place. In some embodiments, the stiffness or hardness may be measured using the Shore durometer scale with "D" referring to an index of the Shore durometer scale. In some embodiments, a stiffness of the guide catheter 130 may transition from about 45D to about 80D at a proximal end to about 15D to about 35 D at a distal end. In some embodiments, a stiffness of the delivery catheter 120 may transition from about 45D to about 80D at a proximal end to about 15D to about 35 D at a distal end. In some embodiments, a stiffness of the implant catheter may be less than 35 D. In some embodiments, a stiffness of the implant catheter may be less than 25 D. In some embodiments, the catheters 110, 120, 130 may have a column strength to be introduced and advanced into the vasculature, while also having flexibility to be articulated through the geometry of the heart. In some embodiments, a bending length (e.g., a length of a bending portion of the catheter configured to bend or a length of a steerable portion) of the guide catheter 110 may be in a range of about 10 mm to about 140 mm, inclusive of all ranges and subranges therebetween. In some embodiments, the bending length of the guide catheter 110 may be in a range of about 30 mm to about 110 mm, inclusive of all ranges and subranges therebetween. In some embodiments, the bending length of the guide catheter 110 may be about 100 mm. In some embodiments, a bending length of the delivery catheter 120 may be in a range of about 10 mm to about 90 mm, inclusive of all ranges and subranges therebetween. In some embodiments, the bending length of the delivery catheter 120 may be about 55 mm. In some embodiments, the bending length of the delivery catheter may be about 37 mm.

In some embodiments, the guide catheter 110 and/or the delivery catheter 120 may include a bendable portion (e.g., a shape-set section) configured to bend a predetermined angle from the longitudinal axis. In some embodiments, the bendable portion may include a different material than the rest of the guide catheter 110 and/or delivery catheter 120. In some embodiments, the guide catheter 110 and/or the delivery catheter 120 may have a constant hardness aside from the bendable portion. In some embodiments, the bendable portion may bend to an angle of about 10 degrees, about 20 degrees, about 30 degrees, about 40 degrees, about 50 degrees, inclusive of all ranges and subranges therebetween. In some embodiments, the predetermined angle may correspond to shape of the heart. For example, the bendable portion may be configured to bend to a 20 degree angle to maintain the distal end of the implant delivery system in the left atrium (e.g., by hooking the atrium) and stabilize the distal end of the implant delivery system. In some embodiments, the guide catheter 110 may include or be coupled to one or more valves. For example, the guide catheter may be coupled to a hemostatic valve for flushing bodily fluid (e.g., blood) from the lumen of the guide catheter 110. In some embodiments, the delivery catheter. In some embodiments, the implant delivery system 100 may be configured to receive a dilator. The dilator may define a central lumen configured to accommodate a guide wire. The dilator may have a tapered distal end that forms a point. In some embodiments, a proximal portion of the tapered distal end may have a diameter corresponding to the diameter of the guide catheter 110 such that the dilator may expand tissue in preparation for the guide catheter 110 to be disposed therethrough.

In some embodiments, the implant delivery system may only include two steerable catheters, and the implant holder may be coupled directly to one of the steerable catheters (e.g., a two-catheter delivery system). The guide catheter 610 may include a proximal portion that is of a hardness between about 60D to 65D (e.g., 63D), a middle portion of hardness between about 50D to 60 D (e.g., 55D), and a distal portion of hardness between about 20D to 30D (e.g., 25D). In some embodiments, the guide catheter 610 may gradually transition between hardness levels. The delivery catheter 620 may include a proximal portion having a hardness between 60D to 65D (e.g., 63D) and a distal portion having a hardness between 30D to 40D (e.g., 35D).

In some embodiments, the catheters 110, 120, 130 may be visible on fluoroscopy and echocardiography to aid in navigation of the implant delivery system 100. In some embodiments, a distal tip of the guide catheter 110 may include a radio-opaque marker such as a ring including radio-opaque material. In some embodiments, a sleeve of the delivery catheter 120 may include a radio-opaque marker disposed at or near a distal tip of the delivery catheter 120. In some embodiments, the implant holder 135 may include a radio-opaque marker at its distal tip. In some embodiments, one or more radio-opaque markers may be disposed at a predetermined distance from a distal end of the guide catheter 110. For example, the predetermined distance from the distal end of the guide catheter may be about 2.5 mm, about 5 mm, about 7.5 mm, about 9 mm, about 10.5 mm, about 13 mm, about 14.5 mm, about 17 mm, about 18.5 mm, about 20 mm. In some embodiments, one or more radio-opaque markers may be disposed at a predetermined distance from a distal end of the delivery system. For example, the predetermined distance from the distal end of the delivery catheter 120 may be about 2.5 mm, about 5 mm, about 7.5 mm, about 9 mm, about 10.5 mm, about 13 mm, about 14.5 mm, about 17 mm, about 18.5 mm, about 20 mm. In some embodiments, the delivery catheter 110 may include two radio-opaque markers disposed thereon: a first radio-opaque marker disposed about 5 mm from the distal end and a second radio-opaque marker disposed about 20 mm from the distal end.

In some embodiments, the proximal end of the implant delivery system 100 may include a handle assembly. The handle assembly may include one or more actuators (e.g., a button, a lever, a trigger, a linear slider, a knob, a wheel, or the like) configured to control a configuration of the implant 160 and/or an articulation of the catheters 110, 120, 130. In some embodiments, the handle assembly may include a GC actuator 112 coupled to the guide catheter 110 (e.g., and one or more pull wires) and configured to articulate the guide catheter 110 during navigation of the implant delivery system 100 and/or delivery of the implant 160. In some embodiments, the handle assembly may include a DC actuator 122 coupled to the delivery catheter 110 (e.g., and one or more pull wires) and configured to articulate the delivery catheter 120 during navigation of the implant delivery system 100 and/or delivery of the implant 160. In some embodiments, the handle assembly may include an IC actuator 132 coupled to the implant catheter 130 and configured to articulate the implant catheter 130 during navigation of the implant delivery system 100 and/or to move the implant catheter 130 linearly (e.g., proximally and/or distally) relative to the steerable catheters 120, 130. In some embodiments, the three catheters 110, 120, 130 may work together to accommodate the geometry of the vasculature and the heart to deliver the implant 160 to a target heart valve.

In some embodiments, the implant 160 may include a central member coupled to a first segment or arm and a second segment or arm. In some embodiments, the implant 160 may further include one or more support members, one or more positioning openings, and/or one or more friction elements. The implant 160 may be configured to move between one or more configurations including a delivery configuration, an open configuration, a closed configuration, and an implanted configuration. For example, the implant 160 may move from the delivery configuration in which the first arm and the second arm are substantially coplanar and the one or more support members are in a partially or completely extended shape (e.g., an elongated state) and/or in a partially or completely collapsed shape (e.g., a compressed state), to an open configuration in which the first arm and the second arm are separated from one another. The implant 160 may move between the open configuration and an implanted configuration in which the first arm and the second arm are disposed around the leaflet and apply a clamping force to the leaflet. In some embodiments, the implant 160 may be in a closed configuration in which each of the first arm and second arm are substantially coplanar with one another. In this way, the implant 160 in the open configuration can be positioned around a portion of a leaflet of the heart valve, and the implant 160 in the implanted configuration can apply the clamping force on the leaflet to secure the implant 160 to the leaflet. In some embodiments, the implant 160 may include a cover disposed around the central member to prevent damage to the leaflet tissue and/or to promote tissue growth. The implant 160 is described in further detail with respect to FIG. 4 and FIGS. 10-29F.

In some embodiments, the implant catheter 130 may be coupled to the implant holder 160 such that there is no rotational movement therebetween. For example, the implant catheter 130 may be welded to the implant holder 160. In some embodiments, the implant catheter 130 may define one or more lumens extending therethrough. In some embodiments, one or more elongate members (e.g., wires, sutures, tethers, braids, etc.) may extend through the one or more lumens of the implant catheter 130 from a proximal end to a distal end of the implant catheter 130.

In some embodiments, the implant catheter 130 may define a main lumen, and include a pattern cut on one side thereof (e.g., via laser cutting) to improve flexibility while maintaining torque-ability (e.g., maintaining a column strength of the implant catheter 130 for rotation). In some embodiments, the main lumen of the implant catheter 130 may be formed from a metal (e.g., stainless steel), alloy (e.g., Nitinol), or a combination thereof. In some embodiments, the main lumen may include one or more hypotubes extending therethrough. In some embodiments, four hypotubes may be disposed inside the main lumen of the implant catheter 130. Each hypotube may define a lumen in which a portion of an elongate member may be disposed. In some embodiments, the hypotubes may be formed from a material to prevent deformation of or friction with the one or more elongate members. In some embodiments, the hypotubes may include a metal or metal alloy such as stainless steel, Nitinol or a polymer such as Nylon, Polyethylene, Polyurethane, Polyimide, etc. In some embodiments, the one or more hypotubes may include a polymer such as polyamide. In some embodiments, the one or more hypotubes may be braided polyamide tubes. In some embodiments, the one or more hypotubes may be configured to move within the main lumen of the implant catheter 130. In some embodiments, the one or more elongate members may be formed from electropolished Nitinol or a polymer such as Teflon, Polyethylene, Kevlar etc. Additionally or alternatively, the elongate members (e.g., the atrial 142 and ventricular tethers 152) may include a braided suture including a polymer. In some embodiments, the elongate members may be configured to have a stretchability below a predetermined threshold. Therefore, when a force is applied to the elongate member (e.g., the elongate member is actuated), the elongate member may impart a substantially equal force on the implant (e.g., without absorbing force by stretching). In some embodiments, the one or more elongate members may include a coating configured to reduce or limit friction between the elongate member and the lumen of the hypotubes and/or delivery catheter 130. In some embodiments, the hypotubes may have a diameter corresponding to that of the elongate members. For example, in some embodiments, the hypotubes may each have an inner diameter in a range between about 0.010 inches and about 0.015 inches, inclusive of all ranges and subranges therebetween. In some embodiments, the hypotubes may have an outer diameter in a range between about 0.015 inches to about 0.021 inches, inclusive of all ranges and subranges therebetween. In some embodiments, the hypotubes may have an inner diameter of 0.012 inches. In some embodiments, the hypotube may have an outer diameter of 0.018 inches.

In some embodiments, the one or more elongate members may include an atrial tether (AT) 140 and a ventricular tether (VT) 150. In some embodiments, the atrial tether 140 and the ventricular tether 150 may each form a loop removably couplable to a portion of the implant 160 (e.g., be disposed through one or more openings defined by the implant 160). In some embodiments, the implant (e.g., the atrial arm and the ventricular arm) may include suture loops coupled thereto. In some embodiments, the atrial tether 140 and ventricular tether 150 may be coupleable to the one or more suture loops on the implant 160. In some embodiments, the atrial tether 140 and the ventricular tether 150 may extend through at least a portion of the implant holder 135 and may secure the implant 160 in the cavity of the implant holder 135. Each of the atrial tether 140 and the ventricular tether 150 may include a first end and a second end coupled to the proximal end of the implant delivery system 100 such that each form a loop (e.g., about 0.005 inches in diameter) at the distal end of the implant delivery system 100. For example, a portion of the atrial tether 140 and the ventricular tether 150 may run along the length of the implant catheter 130 inside each hypotube, with their first and second ends anchored on the handle. In some embodiments, the second end of the atrial tether 140 and/or the second end the ventricular tether 150 may not be coupled to the handle and may instead be coupled to a portion of the tether 140, 150 distal to the handle.

In some embodiments, the handle assembly may further include an AT actuator 142 coupled to the atrial tether 140 and a VT actuator 152 coupled to the ventricular tether 150. The AT actuator 142 and the VT actuator 152 may be configured to control a configuration of the atrial tether 140 and the ventricular tether 150 (e.g., apply/release tension the tethers, decouple the tethers from the implant 160, etc.). In some embodiments, the AT actuator 142 and the VT actuator 152 may each include linear sliders coupled to the atrial tether 140 and the ventricular tether 150, respectively, such that when each of the AT actuator 142 and the VT actuator 152 are moved proximally, tension is applied to the atrial tether 140 and the ventricular tether 150, respectively.

In some embodiments, the atrial tether 140 and the ventricular tether 150 may be configured to manipulate the implant 160 into different configurations when tension is applied to the atrial tether 140 and/or the ventricular tether 150 (e.g., via the AT actuator 142 and/or the VT actuator). For example, the atrial tether 140 may be operatively coupled to the first segment or arm of the implant 160 (e.g., the atrial arm) and the ventricular tether 150 may be operatively coupled to the second segment or arm of the implant 160 (e.g., the ventricular arm). In this way, the physician may manipulate the AT actuator 142 and/or the VT actuator 152 (e.g., pull a trigger, move the linear slider proximally, rotate a knob in a first direction) to retract the atrial tether 140 and/or ventricular tether 150, which may pull the first and second segments of the implant 160 apart from one another. In some embodiments, the AT actuator 142 may be actuated or maintained in position such that the first segment or arm (e.g., the atrial arm) of the implant 160 is stabilized. When the atrial arm of the implant 160 is stabilized, the VT actuator 152 may be actuated to tension the ventricular tether 150 such that the second segment or arm of the implant 160 (e.g., the ventricular arm) is moved away from the first segment or arm. This may be performed by the physician when the implant 160 is within the patient and adjacent the target heart valve location (e.g., native leaflet, annulus, chordae tendineae), such that the implant 160 may surround the valve tissue. The physician may release the VT actuator (e.g., stop pulling the trigger, move the linear slider distally, rotate a knob in a second direction) to release the ventricular tether 150, which may cause the first and second segments or arms of the implant 160 to move towards one another and couple the first and/or second segments or arms to the heart valve tissue.

In some embodiments, a distance an actuator (e.g., the AT actuator 142 and/or the VT actuator 152) travels or moves may correspond to a degree the implant 160 opens (e.g., an angle between the first segment or arm and the second segment or arm). In embodiments where the actuator is a linear slider, a distance a linear slider moves corresponds to the degree the implant 160 opens. In some embodiments, a maximum length the linear slider travels may be in a range between about 5 mm to about 50 mm, inclusive of all ranges and subranges therebetween. In some embodiments, the maximum length the linear slider travels may be about 15 mm. In some embodiments, about 5 mm of linear motion may correspond to about a 45 degree increment of opening between the segments or arms of the implant 160.

In some embodiments, the actuator (e.g., the AT actuator 142 and/or the VT actuator 152) may include a rotatable actuator (e.g., a knob) to control tension applied to the atrial tether(s) 140 and/or ventricular tether(s) 150, and therefore control a degree the implant 160 opens. In some embodiments, the AT actuator 142 may include a linear slider and a locking mechanism. In some embodiments, the AT actuator 142 may be tensioned to secure the atrial tether 140 in a desired position, and once the atrial arm is in the desired position, the locking mechanism may be activated (e.g., pulled, pushed, rotated, etc.) to lock the atrial tether 140 with the tension corresponding to the desired position of the atrial arm. In some embodiments, the VT actuator 152 may include a knob, and a degree of rotation of the knob may control an amount of tension applied tot the ventricular tether 150, and therefore, a degree to which the implant 160 opens. In embodiments where the actuator is a knob, a degree of rotation of a knob may correspond to the degree the implant 160 opens. In some embodiments, 180 degrees of rotation of the VT actuator 152 may correspond to about a 45 degree increment of opening between the segments or arms of the implant 160. In some embodiments the actuator may be hybrid, translating a rotary knob motion to a linear translational motion.

In some embodiments, the proximal end of the implant delivery system 100 may include one or more stopping members for precise control over articulation of the implant 160. In some embodiments, the stopping members may be disposed at a predetermined position along a length of the sliding path of the AT actuator 142 and/or the VT actuator 152 such that the implant 160 may only be opened or closed a predetermined amount and/or to indicate to the user (e.g., tactically) a degree the implant 160 has opened and/or closed. The stopping members may be protrusions, grooves, indents, detents, openings, slots, or the like configured to engage the actuators to prevent movement past the predetermined amount. For example, in some embodiments, a portion of the AT actuator 142 and/or a portion of the VT actuator 152 may have a shape complimentary to the sliding path on the proximal end of the implant delivery system 100 to indicate to the user a degree with which the implant 160 has been opened or closed. In some embodiments, the stopping members may at least temporarily stop or prevent movement of the AT actuator 142 and/or VT actuator 152. In some embodiments, the stopping members may be disposed along the length of the sliding path to indicate the inter-arm angle of the implant 160 is 0 degrees, 45 degrees, 90 degrees, and/or 120 degrees.

In some embodiments, the distal end of the implant delivery system 100 may be navigated near the heart valve such that the implant catheter 130 is oriented substantially perpendicular to the annular plane of the heart valve (e.g., mitral valve). In some embodiments, the second arm of the implant (e.g., the ventricular arm) may be opened (e.g., by tensioning the ventricular tether 150), and the distal end of the delivery system may be visualized (e.g., via echocardiography). In some embodiments, the implant holder 135 may be oriented (e.g., rotated) to align the ventricular arm with the desired leaflet capture location. For example, the ventricular arm may be positioned near a portion of the leaflet that is not achieving coaptation. In some embodiments, after visualization, one or more locations of the implant 160 may be demarcated (e.g., by the user) on the echocardiogram. For example, the following markers may be annotated and/or considered: (1) a first marker can correspond to a proximal end of the atrial arm, (2) a second marker can correspond to a proximal end of the ventricular arm, and (3) third marker can correspond to a distal end of the ventricular arm. In some embodiments, the implant catheter 130 may be advanced towards the heart valve until the proximal end of the atrial arm aligns with an edge of the leaflet. In some embodiments, once the proximal end of the atrial arm aligns with the edge of the leaflet, a location at which the implant catheter 130 protrudes from the delivery catheter 120 can be demarcated on the implant catheter 130. At this location, the implant is entirely below the leaflet edge (e.g., and positioned in the ventricle V).

Once the implant 160 is positioned below the leaflet edge, the ventricular arm can be opened away from the atrial arm. For example, tension can be applied to the ventricular tether 150 to open the ventricular arm (e.g., approximately to 90 degrees). For example, the VT actuator 152 may be actuated to open the ventricular arm. In some embodiments, while the ventricular arm is opened, the implant catheter 130 may be biased towards the leaflet. With the ventricular arm open, the implant catheter 130 may be retracted proximally. In some embodiments, the implant catheter 130 may be retracted proximally until the second marker location (e.g., to assess a degree to which the implant 160 covers the opening of the heart valve). The implant catheter 130 may be retracted further proximally to the third marker on the implant catheter 130. Once retracted to the third marker, the ventricular arm may be closed a predetermined amount. For example, the VT actuator 152 may be actuated to loosen the ventricular tether 150 such that the ventricular arm closes to 45 degrees (i.e., 45 degrees between the atrial and ventricular arm). Closing the arm to 45 degrees can restrain the leaflet from opening beyond the ventricular arm. In some embodiments, the atrial arm can then be loosened from the implant holder 135 to move the atrial arm towards the leaflet. For example, the AT actuator 142 may be actuated to loosen the atrial tether 140 such that the atrial arm moves towards the leaflet. Moving the atrial arm towards the leaflet can cause the implant 160 to move with the leaflet such that the position of the protrusion of the implant 160 off of the leaflet (e.g., the location of augmentation) becomes clear. If the position of the implant 160 is not satisfactory (e.g., does not prevent valve regurgitation), tension to the atrial arm can be applied, and then tension onto the ventricular arm can be applied to open the implant 160 and repeat the previously described steps after steering to a new location.

Once the implant 160 is in the desired position, tension may be applied to the atrial arm to move the atrial arm towards the implant holder 135, and then the ventricular tether 150 may be decoupled from the ventricular arm. The atrial arm tether can be decoupled after the ventricular arm tether is decoupled to release the implant 160 away from the implant holder 135.

As shown in FIG. 2C, once the implant 160 is clamped onto a portion of the valve leaflet L, the atrial tether 140 and/or the ventricular tether 150 can be manipulated (e.g., loosened, de-tensioned) to move the implant 160 away from the cavity of the implant holder 135 such that the physician can monitor the placement of the implant 160 without detaching the implant 160 from the implant delivery system 100. This allows for real time assessment of regurgitation correction; it allows the implant to go into coaptation freely without complete disengagement of the implant 160 from the implant delivery system 100. If adjustments need to be made, the tethers can be tensioned to transition the implant 160 towards its open configuration sufficient to release the implant 160 from the valve leaflet L and pull the implant back into the cavity of the implant holder 135, and the implant 160 can be repositioned using the tethers 140, 150. Once the placement of the implant 160 is confirmed by determining sufficient coaptation of the heart valve with the implant 160, the atrial tether 140 and the ventricular tether 150 can be decoupled from the implant 160, and the implant delivery system 100 can be navigated out of the heart, leaving the implant 160 attached to the valve leaflet L. For complete disengagement of the implant 160 from the implant catheter 130, anchors can be removed or otherwise disengaged to release the tethers 140, 150, and the wire loops can be pulled out by the user. For example, one end of the tether can be released from the proximal end of the delivery system, and second end of the tether can be pulled proximally until the first end is pulled through the arm of the implant.

In some embodiments, the implant delivery system 100 may include a snare in the handle assembly and/or positioned along the catheters 110, 120, 130 (e.g., the implant catheter 130). In some embodiments, a portion of the atrial tether(s) 140 and/or a portion of the ventricular tether(s) 150 may be coupled to the snare. For example, a first end of each of the atrial tether(s) 140 and ventricular tether(s) 150 may be coupled to the snare. Once the implant 160 has been attached to the leaflet and positioning of the implant 160 has been confirmed, the snare may be configured to cut, sever, clip, etc. the first end of each of the atrial tether(s) 140 and the ventricular tether(s) 150 so that the tethers 140, 150 can be pulled out of the proximal end of the system 100. In some embodiments, a cutting portion of the snare may be positioned near a distal end of the implant delivery system 100 such that a distance to pull the tethers 140, 150 to remove them is reduced. The snare positioned near a distal end of the implant delivery system 100 may reduce likelihood that the tethers 140, 150 get stuck in the lumen of the implant catheter 130.

FIG. 3 is a schematic block diagram of an implant holder 335 of an implant delivery system, according to embodiments. In some embodiments, the implant holder 335 may include a proximal portion, a central portion, and a distal portion. The proximal portion may include a first cross-sectional area, the central portion may include a second cross-sectional area, and the distal portion may include a third cross-sectional area. The second cross-sectional area may be smaller than the first and second cross-sectional areas such that the central portion forms a cavity 337. The implant holder 335 may define the cavity 337 in the central portion configured to receive at least a portion of an implant 360 during navigation and delivery of the implant 360 onto the heart valve. In some embodiments, the distal portion of the implant holder 335 may form an atraumatic tip (e.g., blunt, rounded, etc.) to prevent damage to the tissue during delivery of the implant 360. In some embodiments, the implant holder 335 may have a straight distal tip to increase the moment length. In some embodiments, the implant holder 335 may define one or more atrial channels 336 and one or more ventricular channels 338. The atrial channel(s) 336 and the ventricular channel(s) 338 may extend along a portion of a length of the implant holder 335. In some embodiments, the implant holder 335 may include two atrial channels (e.g., a first atrial channel and a second atrial channel) and two ventricular channels 338 (e.g., a first ventricular channel and a second ventricular channel). In some embodiments, the atrial channel(s) 336 each define an opening near a proximal end of the implant holder 335 and the ventricular channel(s) 338 define an opening near a distal end of the implant holder 335. One or more atrial tethers 340 may extend through the atrial channel(s) 336, and one or more ventricular tethers 350 may extend through the ventricular channel(s) 338. In some embodiments, a first portion of an atrial tether 340 may extend through the first atrial channel and a second portion of the atrial tether 340 may extend through the second atrial channel such that a loop is formed between an opening of the first atrial channel and an opening of the second atrial channel. In some embodiments, a first portion of an ventricular tether 350 may extend through the first ventricular channel and a second portion of the ventricular tether 350 may extend through the second ventricular channel such that a loop is formed between an opening of the first ventricular channel and an opening of the second ventricular channel.

In some embodiments, a loop of the atrial tether 340 may be disposed through a first portion of the implant 360 (e.g., an opening defined by the atrial arm of the implant 360) to couple the atrial arm to the atrial tether 340. For example, a first end of the atrial tether 340 may fixed to the proximal end, and the second end of the atrial tether may be disposed through the opening of the implant 360 and fed through the implant catheter to the proximal end of the implant catheter. The atrial tether 340 may be configured to stabilize a position of the implant 360 relative to the implant holder 335. The first atrial channel and the second atrial channel may have unequal lengths such that each atrial channel 336 defines an opening at different locations of the implant holder 335. The length of each atrial channel 336 may correspond to a respective predetermined region of the atrial arm of the implant 360 such that the atrial tether 340 couples to the atrial arm of the implant 360 at its respective predetermined region. The atrial tether 340 may couple to the atrial arm at the predetermined regions may stabilize the implant 360 relative to the implant holder 335 (e.g., prevent sliding or displacement of the implant 360). For example, the first atrial channel may define a first opening and the second atrial channel may define a second opening distal to the first opening such that the atrial tether 340 extends from the second opening, through the atrial arm of the implant 360, and into the first opening or vice versa. The first opening and the second opening may correspond to locations along the atrial arm of the implant 360.

In some embodiments, the ventricular tether 350 may be disposed through a second portion of the implant 360 (e.g., an opening defined by the ventricular arm of the implant) to couple the ventricular arm of the implant 360 to the ventricular tether 350. The ventricular tether 350 may be coupled to the implant 360 in a similar manner as the atrial tether 340. In some embodiments, the ventricular channels 338 may be configured such that the ventricular tether(s) 350 extend partially outside of the implant holder 335. The implant holder 335 may include two sets of ventricular channel(s) 338. A first set of ventricular channel(s) 338 in the proximal portion of the implant holder 335 and a second set of ventricular channel(s) 338 in the distal portion of the implant holder. The first set of ventricular channels may define a first set of openings in the proximal portion of the implant holder 335 and the second set of ventricular channels may define a second set of openings at the distal portion of the implant holder 335. The second set of openings may include two openings on a backside of the implant holder 335 and two openings on a frontside of the implant holder 335. The ventricular tether(s) 350 may be configured to (i) extend through a ventricular channel from the first set of ventricular channel(s) 338, (ii) exit the back side of the implant holder 335 and extend outside of the implant holder 335, (iii) extend back into a backside of the implant holder 335 at the distal end, (iv) exit a front side of the implant holder 335 at the distal end, and (v) loop through the ventricular arm of the implant 360. The implant 360 may be transitioned from a closed configuration to an open configuration in response to tension applied to the ventricular tether 350 (e.g., by actuating the ends of the ventricular tether proximally), thereby pulling the ventricular arm away from the atrial arm of the implant 360. The implant 360 may be transitioned from the open configuration back to the closed configuration by releasing tension from (e.g., introducing slack to) the ventricular tether 350 (e.g., actuating the ends of the ventricular tether distally). In some embodiments, the implant 360 may be loosened from the cavity 337 by releasing tension from (e.g., introducing slack to) the atrial tether 340 (e.g., actuating the ends of the at least one atrial tether distally). In some embodiments, tension may also be released from the ventricular tether 350 after tension is released from the atrial tether 340 to loosen (e.g., further loosen) the implant 360 from the cavity 337. The implant catheter may be withdrawn proximally such that effectiveness of the implant 360 clamped onto the leaflet of the heart valve in reducing heart valve regurgitation can be visualized (e.g., via imaging). In some embodiments, tensioning the atrial tether 340 can tighten or pull the implant 360 against the implant holder 335, releasing tension on the atrial tether 340 allows the distal end of the delivery system to be moved away from the implant 360, and re-tensioning the atrial tether 340 can re-tighten or pull the implant 360 against the implant holder 335.

In some embodiments, a first atrial channel may define an opening (e.g., the first opening) on the implant holder 335 configured to align with a proximal edge of the first arm or segment of the implant 360 when the implant 360 is coupled to the implant holder. In some embodiments, a second atrial channel may define an opening (e.g., the second opening) on the implant holder 335 configured to align with a location of a distal edge of the first arm or segment (e.g., where the central member begins) when the implant 360 is coupled to the implant holder 335. In this way, the first arm or segment of the implant 360 may be secured to the implant holder 335 at two points along its length. In some embodiments, a first atrial tether may extend through the first atrial channel and a second atrial tether may extend through the second atrial channel. In some embodiments, the first atrial tether may couple to the first segment or arm of the implant 360 at a first location, and the second atrial tether may couple to the first segment or arm of the implant 360 at a second location distal to the first location. In some embodiments, one atrial tether may extend through both the first and second atrial channels, and a first portion of the atrial tether may couple to the implant 360 at the first location and a second portion of the atrial tether may couple to the implant 360 at the second location.

In some embodiments, a total length of the implant holder 335 (e.g., a distance between a proximal end and a distal tip of the implant holder 335) may be in a range of about 15 mm to about 45 mm, inclusive of all ranges and subranges therebetween. In some embodiments, the total length of the implant holder 335 may be about 21 mm. In some embodiments, a distal portion of the implant holder 335 from a distal end of the implant 360 in the closed configuration to a distal tip of the implant holder 335 may have a length corresponding to a moment arm for articulating the implant 360. In some embodiments, the distal portion of the implant holder 335 may be straight. In some embodiments, the distal portion of the implant holder 335 may form a curve. In some embodiments, the distal portion of the implant holder 335 may form a dome shape. The curved or dome shape distal portion may act as a fulcrum when the ventricular tether(s) 350 is tensioned to open the arm. For example, at least a portion of the second set of ventricular channel(s) 338 in the distal end of the implant holder 335 may act as a fulcrum for the ventricular tether(s). In some embodiments, increased length of the distal portion may increase the moment arm to enable the implant 360 to transition between the open and closed configurations more easily (e.g., with less tensile force acting on the tethers). In some embodiments, the length of the distal portion of the implant holder 335 may be about 3 mm, 4 mm, 5 mm, 6 mm, 7 mm, 8 mm, 9 mm, or about 10 mm, inclusive of all ranges and subranges therebetween. In some embodiments, a length of the implant holder 335 may be at least 2 mm longer, at least 3 mm longer, at least 4 mm longer, at least 5 mm longer, at least 6 mm longer, at least 7 mm longer than a length of the implant 360 to ensure a desired moment arm to facilitate articulation and/or to open the ventricular arm of the implant 360 to an angle that is greater than 90 degrees without the distal portion of the implant holder 335 obstructing the ventricular arm from such motion. In some embodiments, the implant holder 335 may be at least 5 mm longer than a length of the implant 360. The distal tip should be longer than the implant to increase the moment arm for easy articulation. However, the distal tip should not be so long that it is incapable of navigating through curved paths of the delivery system. Therefore, the distal tip should have a length shorter than a bend length of the guide catheter (as described with respect to FIGS. 1A-1B).

In some embodiments, a shape of the cavity 337 may correspond to dimensions of the implant 360. For example, the cavity 337 may define a radius of curvature at least that of a radius of curvature of the implant 360 including the cover. In some embodiments, the implant 360 may sit in the cavity 337 to reduce catching of the implant 360 on nearby tissue during navigation of the implant holder 335 through the vasculature and the heart. In some embodiments, a profile of the implant holder 335 may be in a range of about 5 mm to about 6.5 mm, inclusive of all ranges and subranges therebetween. In some embodiments, the implant holder 335 may be substantially cylindrical. In some embodiments, diameter of the implant holder 335 may be in a range of about 4 mm to about 10 mm, inclusive of all ranges and subranges therebetween.

In some embodiments, the implant holder 335 may include a proximal engagement surface (e.g., a flat portion) on which the first segment or arm (e.g., the atrial arm) of the implant 360 may be secured. For example, when the atrial tether(s) 340 are tensioned, at least a portion of the atrial arm of the implant 360 may be configured to abut at least a portion of the proximal engagement surface of the implant holder 335 to help secure a position of the implant 360 relative to the implant holder 335. In some embodiments, the proximal engagement surface may be in a plane parallel to a plane through a longitudinal axis of the implant holder 335. In some embodiments, the proximal engagement surface may be slanted (e.g., not parallel to a plane through the longitudinal axis of the implant holder 335). In some embodiments, a length of the proximal engagement surface may correspond to a length of the first segment or arm of the implant 360. For example, the length of the engagement surface may be in a range of about 4 mm to about 10 mm, inclusive of all ranges and subranges therebetween. In some embodiments, the slanted proximal portion may reduce the overall profile of the implant holder 335. In some embodiments, the implant holder 335 may be formed from a rigid biocompatible material (e.g., a material similar to that of the catheters 110, 120, 130).

Figure 4:
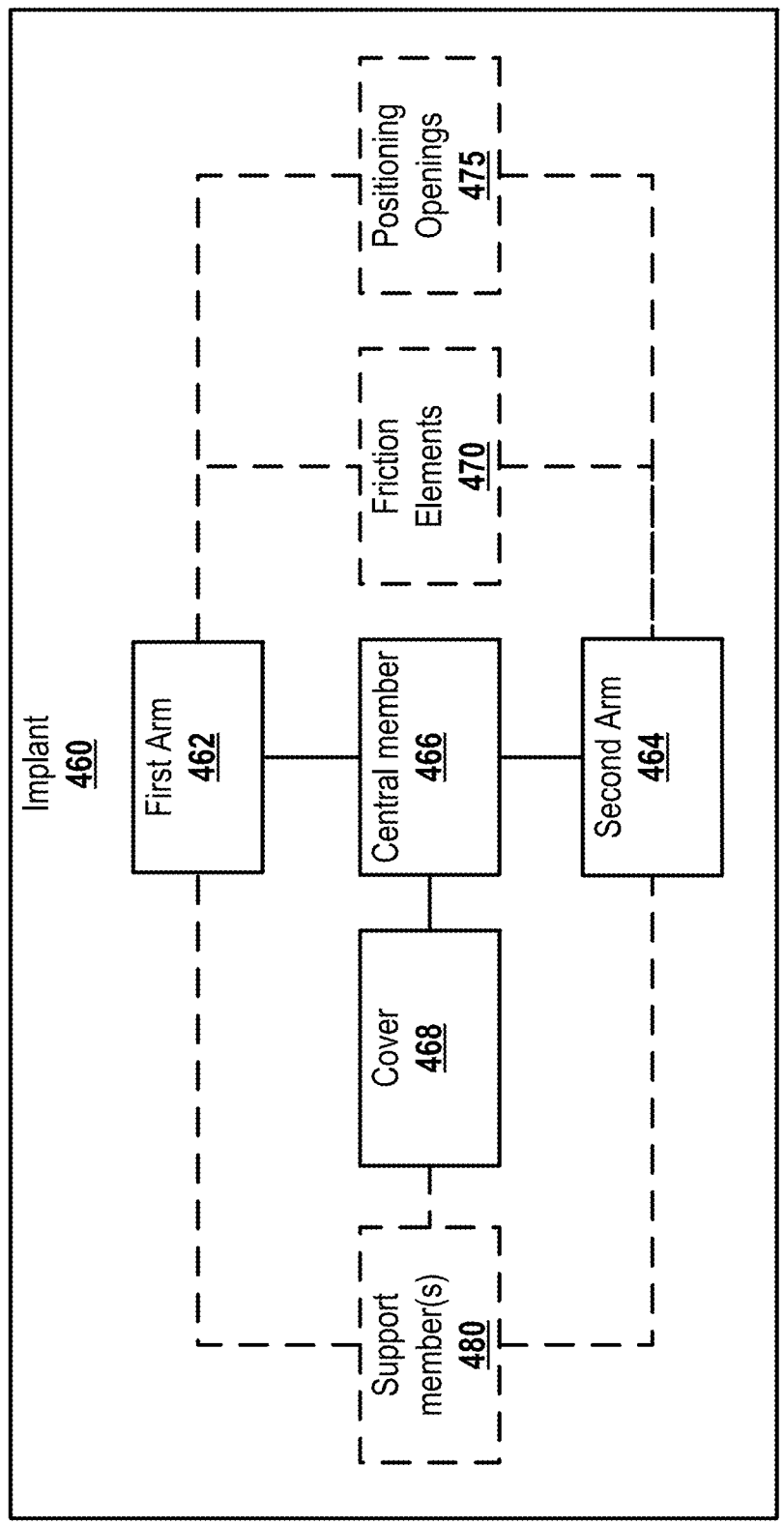
FIG. 4 is a schematic diagram of an implant for reducing heart valve regurgitation, according to embodiments.

FIG. 4 is a schematic diagram of an implant 460 configured to be implanted on a leaflet of a heart valve to reduce heart valve regurgitation, according to embodiments. In some embodiments, the implant 460 may have a coaptation section comprising a 3-dimensional shape and an attachment section configured to couple the device to a heart valve (e.g., mitral, tricuspid, pulmonic, aortic) at a treatment site thereof. The treatment site may correspond to a portion of the heart valve that contributes to a cardiac condition, such as heart valve regurgitation during systole. For example, the treatment site may be located along the anterior leaflet of the mitral valve (e.g., A1, A2, A3), posterior leaflet of the mitral valve (e.g., P1, P2, P3), chordae tendineae of the mitral valve, anterior leaflet (i.e., cusp) of the tricuspid valve, posterior leaflet (i.e., cusp) of the tricuspid valve, septal leaflet (i.e., cusp) of the tricuspid valve, chordae tendineae of the tricuspid valve, left coronary leaflet (i.e., cusp) of the aortic valve, right coronary leaflet (i.e., cusp) of the aortic valve, non-coronary leaflet (i.e., cusp) of the aortic valve, left leaflet (i.e., cusp) of the pulmonary valve, right leaflet (i.e., cusp) of the pulmonary valve, or anterior leaflet (i.e., cusp) of the pulmonary valve.

The implant 460 may be coupled to heart valve tissue at the treatment site (e.g., a first native leaflet) in a manner that reduces or eliminates regurgitation. For example, the implant 460 may be coupled to the heart valve tissue such that a gap between the two native leaflets of the heart valve is reduced or eliminated. In one variation, the implant 460 may be coupled to the heart valve tissue such that the coaptation section of the implant 460 may be coaptated by a second native leaflet. For example, in some variations in which the coaptation section of the implant 460 provides a coaptation surface for the second native leaflet, the treatment site may be referred to as P3-A3, in that the device may be coupled to the P3 portion of the posterior leaflet of the mitral valve and may be coaptated by the A3 region of the anterior leaflet of the mitral valve. In a further example, the implant 460 may be coupled to the A3 portion of the posterior leaflet of the mitral valve and may be coaptated by the P3 region of the anterior leaflet of the mitral valve. In some variations, the implant 460 may be coupled to a leaflet having a gap or cleft, such that the coaptation section of the device may cover the gap or cleft of the leaflet while enabling coaptation of an opposing leaflet onto the coaptation section. In some variations, multiple implants 460 may be coupled to the leaflet having a gap, such that they are adjacent to each other on the same leaflet, opposing each other on different leaflets, or a combination thereof.

The treatment site may correspond to portions of the heart valve associated with injury, disease, geometric distortion, and/or poor leaflet mobility and may be determined by a physician using clinical data, such as blood pressure, heart rate, audio signals, images generated by non-invasive techniques (e.g., MRI, CT, ultrasound, fluoroscopy), images generated by invasive techniques (e.g., intracardiac echocardiography, transesophageal echocardiography), or a combination thereof. For example, a physician may use a measurement of leaflet mobility to determine the treatment site, such as excursion angle. Excursion angle may correspond to the magnitude of leaflet movement between diastole and systole. In some variations, the excursion angle may be between about 5 degrees to about 75 degrees, about 5 degrees to about 60 degrees, about 5 degrees to about 45 degrees, or about 5 degrees to about 25 degrees. For example, in some variations, the excursion angle may be about 5 degrees, about 15 degrees, about 25 degrees, or about 45 degrees, or less than about 25 degrees. In this way, the implant 460 may be advanced to the heart valve and coupled to the treatment site to reduce or eliminate heart valve regurgitation (e.g. reduce or close a gap between leaflets), despite the reduced excursion angles of the leaflets.

The implant 460 may include one or more sections configured to couple to one or more portions of a heart valve, such that the implant may reduce or eliminate heart valve regurgitation. In some embodiments, the attachment section may be configured to releasably engage heart valve tissue and may advantageously enable the implant to be securely coupled to the heart valve tissue and, if so desired by a physician, decoupled from the heart valve tissue, either for removal or for repositioning at another treatment site of the heart valve. In some variations, the length of the leaflet coupled (e.g., grasped) by the implant 460 may be adjusted, such that the attachment section may grasp more or less of the leaflet. In this way, the physician may optimize the effectiveness of the implant by repositioning (e.g., one or more times) at a treatment site associated with the greatest reduction in heart valve regurgitation (e.g., reducing a gap between the posterior and anterior leaflets of the mitral valve).

The attachment section of the implant 460 may include two segments (e.g., planar segments) or arms configured to couple to portions of a heart valve thereby coupling the implant 460 to one or more of a native leaflet, and chordae tendineae. For example, the attachment section may comprise a first segment or arm 462 and at least a portion of a second segment or arm 464. The first and second segments or arms 462, 464 may be biased towards one another such that the first and second segments or arms 462, 464 hold (e.g., compress) heart valve tissue (e.g., posterior or anterior leaflet of the mitral valve) received therebetween. In some variations, the first and second segments or arms 462, 464 may be biased towards one another such that the first and second segments or arms 462, 464 are at least partially, and in some variations, fully coplanar in a delivery configuration or a closed configuration (e.g., a resting position). The first and second segments or arms 462, 464 may be configured to securely attach to the heart valve, such that the implant 460 may not come loose after implantation. The attachment section may define a distal portion of the device (relative to the physician during implantation).

The attachment section may further comprise one or more friction elements 470 configured to apply a friction force to heart valve tissue. The one or more friction elements 470 may extend from at least one of the first and second segments or arms 462, 464 to assist in preventing unintentional movement and/or removal of the implant 460 during and/or after implantation. The friction force resulting from the friction elements 470 may be mitigated by a physician during the implantation process (e.g., during removal and/or repositioning if so desired) by, for example, separating the first and second segments or arms 462, 464 and/or pulling the first and second segments or arms 462, 464 upwards first and then away from heart valve tissue to disengage the friction elements 470 from the heart valve tissue. In this way, the implant 460 may remain securely coupled to heart valve tissue during normal cardiac events (e.g., heart beating under nominal conditions, which may include strenuous exercise associated with high heart rates) while providing flexibility to the physician to position and reposition the implant 460 one or more times (e.g., two, three, four or more times) during implantation.

The coaptation section of the implant 460 may be configured (alone or in combination with the attachment section) to enhance and/or alter a physical characteristic of the native leaflet (e.g., a first native leaflet). In some variations, the coaptation section may be configured to provide a coaptation surface for another native leaflet of the heart valve (e.g., a second native leaflet). For example, the coaptation section may be configured to provide a contact surface for non-destructively receiving the second native leaflet during systole, which may reduce or eliminate heart valve regurgitation (e.g. reduce or close a gap between leaflets). At least a portion of the coaptation section may deflect upon coaptation by the native leaflet. In some embodiments, the coaptation section may be configured to receive a portion of the first native leaflet therein (i.e., the leaflet to which the attachment section is coupled). Put differently, the coaptation section may define a volume, and a portion of the first native leaflet may be positioned within the volume when the device is coupled to the first native leaflet.

The coaptation section may comprise a central member 466 from which the first and second segments or arms 462, 464 may each extend. The first segment or arm 462 may extend from a first portion of the central member 466 and the second segment or arm 464 may extend from a second, different portion of the central member 466. In some embodiments, the first and second segments or arms 462, 464 may extend from opposite ends of the central member 466. The central member 466 may be shaped (e.g., curved) to bias or assist in biasing the first and second segments or arms 462, 464 towards one another. The biasing force provided by the central member 466 may be sufficient to maintain the first and second segments or arms 462, 464 in place when coupled to heart valve tissue. The biasing force may be overcome by applying a force to at least one of the segments or arms 462, 464, such as by the elongate members or tethers of an implant delivery system (e.g., the atrial tether 140 and/or ventricular tether 150), such that the first and second segments or arms 462, 464 may be separated from one another. In this way, the implant 460 may be opened to receive heart valve tissue and/or may be removed from heart valve tissue (e.g., for repositioning). Additionally, the change in a curvature and/or shape of the central member 466 may enable the first and second segments or arms 462, 464 to be separated from one another.

The coaptation section may further comprise one or more support members 480 configured to provide a surface for coaptation by a native leaflet, such as by supporting a cover 468. The one or more support members 480 supporting the cover 468 may be referred to as a first portion of the coaptation section. The coaptation section may further comprise a second portion extending from a proximal end of the first portion. The second portion may be devoid of support members 480. In some embodiments, the support members 480 may extend from the central member 466. In some embodiments, the support members 480 may extend from the first segment or arm 462 and may be configured to elastically deform with each interaction with the opposing leaflet, which may contribute to the durability and effectiveness of the implant 460. For example, mechanical stress concentrations may be reduced by extending the support members 480 from the first segment or arm 462, which may increase the durability of the implant 460. The support members 480 may extend from the first segment or arm 462 to define a larger volume of the coaptation section relative to a variation in which the support members 480 extend from the central member 466. For example, a radius of curvature of the support members 480 extending from the first segment or arm 462 may be greater than a radius of curvature of support members 480 extending from the central member 466. The larger radius of curvature may allow the implant 460 absorb a force (e.g., via coaptation) from the native leaflet without being damaged, loosening from the first native leaflet, and/or damaging any part of the native leaflet.

The support members 480 may comprise a free end such that the support members 480 may move (e.g., deflect, extend, contract) relative to other portions of the implant 460. For example, the support members 480 may deflect when a leaflet applies a force to the coaptation section (e.g., during systole) and elastically return to their previous configuration when the leaflet is not applying the force to the coaptation section (e.g., during diastole). The movement facilitated by the free ends may advantageously minimize mechanical stresses at the connection point between the support members 480 and the first segment or arm 462. Minimizing such mechanical stresses may allow the support members to deflect, bend, or otherwise move without breaking upon coaptation by another portion of the heart valve, which may facilitate complete closure of a heart valve and/or reduce the size of a fluid flow path (e.g., by reducing a gap between two native leaflets). Implants partially attached to chordae tendineae may behave similarly.

The coaptation section may define a volume configured to receive a portion of a native leaflet upon coaptation and/or surround a portion of a native leaflet (e.g., the native leaflet coupled by the attachment section). In some variations, the volume of the coaptation section may be determined by a total width and a total height of the outer portions of two or more support members 480 and a coaptation section length associated with a portion of the second segment or arm 464 and/or a portion of the central member 466. Accordingly, the total width, total height, and coaptation section length may be used to determine the coaptation section volume. The coaptation section may form a bulbous shape. In some embodiments, a maximum length of the coaptation section (e.g., a maximum length along a longitudinal axis of the coaptation section) may be shorter than a maximum width of the coaptation section (e.g., a maximum length along a transverse axis of the coaptation section). A height of the coaptation section may be defined as a distance from a first surface of the cover 468 contacting the leaflet to a second surface of the cover 468 facing away from the leaflet. The maximum length and maximum width of the coaptation section and/or a ratio of the maximum length to maximum width may each be modified by modifying the shape of the support members 480. The coaptation section may taper (e.g., a cross-sectional area may decrease) along the longitudinal axis and/or along the transverse axis. For example, the length, the width, and/or the height of the coaptation section may decrease toward the outer edges of the implant 460 such that the coaptation section forms an oval shape, a football shape, an almond shape, or the like. Along the longitudinal axis, the coaptation section may be flush with the leaflet surface, reach a peak (e.g., increase in height from the leaflet surface), and then taper back toward the leaflet surface. In some embodiments, a volume captured between the native leaflet surface and the surface defined by the cover 468 disposed over the support member 480 may be symmetric (or substantially symmetric) along the longitudinal axis.

The implant 460 may be at least partially covered by the cover 468. In some embodiments, any portion of the implant 460 may include one or more materials configured to elastically deflect. For example, the implant 460, including the first and/or second segments or arms 462, 464, may include any suitable material such as, for example, a metal (e.g., nitinol, titanium, aluminum, gold, silver, alloys thereof) or a polymer (e.g., polypropylene, polyvinyl chloride, polyethylene, polyurethane). In some embodiments, the implant 460 may include Nitinol with austenite finish temperature below room temperature. This means the implant 460 may remain in its set form at room temperature and/or body temperature, and the implant 460 may be restored to its set shape after deformation when the deformation force is released. The implant 460 may be configured to withstand strain up to about 3%, about 4%, about 5%, about 6%, about 7%, about 8%, about 9%, about 10%, about 11%, about 12%, about 13%, about 14%, about 15%, about 16%, about 17%, about 18%, about 19%, about 20%. In some embodiments, the implant 460 may be configured to withstand strain up to about 10%.

In some embodiments, the cover 468 may include any suitable material such as, for example, a fabric (e.g., textile) or a polymer (e.g., polyester, polytetrafluoroethylene (PTFE)). In some embodiments, the cover 468 may include, for example, a polyester fabric, a knitted polyester, a woven polyester, PTFE, or a combination thereof. In some embodiments, the cover 468 may include two different materials. The fabric may be further reinforced with a metallic wire along its boundary or part of the boundary, so as to provide it a shape that is distinct from the shape that the implant provides. The attachment section and the coaptation section of the implant may be covered in distinct materials and using distinct methods. The attachment section may be covered to enhance visibility of clinical imaging modalities during implantation and be optimized to have a thickness that enables partial protrusion of the teeth/friction elements from the fabric. The coaptation section may be covered to provide a smooth surface for coaptation of the opposing native leaflet, to avoid wear and tear with repeated coaptation with opposing leaflet, and/or to be hemocompatible and allow tissue growth and endothelialization. In some embodiments, the material of the first and/or second arms 462, 464 and/or the material of the cover 468 may be selected to optimize (e.g., minimize) the weight of the implant 460, which may prevent the implant 460 from pulling on portions of the heart valve due to the force of gravity, which in turn could reduce the effectiveness of the implant in reducing heart valve regurgitation. Accordingly, in some embodiments, the implant 460 may have a weight of about 50 mg to about 500 mg, about 100 mg to about 150 mg, or about 130 mg to about 140 mg, including about 100 mg, about 110 mg, about 120 mg, about 130 mg, about 140 mg, or about 150 mg. In some embodiments, the body of the implant 460 (e.g., the arms 462, 464 and central member 466) may be formed from a single sheet of metal or metal alloy. Therefore, no tiny parts or complex assemblies may be required to assemble the implant 460. In some embodiments, the body of the implant may be formed from a first sheet of metal or metal alloy, and the friction elements 470 may be formed separately from a second sheet of metal or metal alloy thinner than the first sheet and welded onto the body. In some embodiments, the friction elements 470 may be welded onto the body with weld seems along specific regions of the implant 460. Therefore, a thickness of the body may be larger than a thickness of the friction elements 470. For example, the first sheet (and therefore the body of the implant 460) may have a thickness of about 250 µm and the second sheet (and therefore the friction elements 470) may have a thickness of about 100 µm. In some embodiments, a total length of the implant (e.g., along a longitudinal axis of the implant 460) may be about 8 mm, about 9 mm about 10 mm, about 11 mm, about 12 mm, about 13 mm, about 14 mm, about 15 mm, about 16 mm, about 17 mm, about 18 mm, inclusive of all ranges and subranges therebetween. In some embodiments, the implant 460 may be manufactured in a 10 mm, a 12 mm, and a 16 mm size.

In some embodiments, the cover 468 (e.g., the material of the cover 468) may promote tissue encapsulation of the implant 460. For example, the cover 468 may enable permanent integration of the implant 460 into the native leaflet within 30-60 days of implantation. Patients thus can be weaned off anticoagulants and survive a life free of bleeding. In some embodiments, a gap between yarns of the fabric of the cover 468 (e.g., a knitted polyester) may impact the incorporation rate. In some embodiments, a diameter of the yarn may impact the incorporation rate. So, in some implementations, the cover 468 may define gaps within fabric configured to increase and/or optimize the incorporation rate, and/or a diameter of the fabric or yarn may be selected or configured to increase and/or optimize the incorporation rate.

a. Segments or Arms

As described herein, the implant 460 includes first and second segments or arms 462, 464 configured to facilitate coupling to heart valve tissue by applying a force thereto (e.g., compressing tissue therebetween). Accordingly, the shape of the first and/or second segments or arms 462, 464 may be configured to provide a distributed compressive force to heart valve tissue while minimizing stress concentrations during deployment, implantation, and/or removal methods described herein with respect to FIGS. 29A-29F, 30A-30D, and 31-33. The first and second segments or arms 462, 464 may be configured to couple different sides of the same native leaflet. For example, the first segment or arm 462 may be configured to couple a first side of a first native leaflet (e.g., an atrial side) and the second segment or arm 464 may be configured to couple a second side of the first native leaflet (e.g., a ventricular side).

In some embodiments, the first and second segments or arms 462, 464 may each include one or more sections configured to non-destructively couple heart valve tissue. For example, the first and second segments or arms 462, 464 may each include a planar section and a curved section. More specifically, the first segment or arm 462 may include a first planar section and a first curved section and the second segment or arm 464 may include a second planar section and a second curved section. The planar sections of the first and/or second segments or arms 462, 464 may be configured to contact heart valve tissue without causing damage to the heart valve tissue. In some variations, the first and second planar sections may be substantially coplanar when the implant 460 is in the delivery configuration or closed configuration. For example, the first segment or arm 462 may have a greater maximum width than the second segment or arm 464 and may define an opening sufficient to receive the second segment or arm 464 such that the first and second segments or arms 462, 464 may be coplanar. In some embodiments, the second segment or arm 464 may be disposed at least partially through the opening defined by the first segment or arm 462 such that the leaflet is compressed at multiple areas to provide a better grip on the leaflet. For example, the first segment or arm 462 may push the leaflet toward the second segment or arm 464 such that when the leaflet is disposed the first and segment arms or segments 462, 464, the leaflet forms a wave-like shape, which can prevent displacement or sliding of the implant 460.

The first and second curved sections may extend from the first and second planar sections of the first and second segments or arms 462, 464, respectively. The first and second curved sections may each be configured to provide a biasing force to the first and second planar sections, respectively. More specifically, the first curved section may provide a biasing force to the first planar section when the first planar section may be in contact with heart valve tissue, such that the first planar section may not unintentionally separate from the heart valve tissue. Similarly, the second curved section may provide a biasing force to the second planar section when the second planar section is in contact with heart valve tissue, such that the second planar section may not unintentionally separate from the heart valve tissue. While described above as each comprising a planar and a curved section, it should be appreciated that the first and/or second segment or arm may each be entirely planar or entirely curved.

The size (e.g., length, width) of the first and second segments or arms 462, 464 may be determined based on a variety of factors, including but not limited to a patient's height, age, gender, valve to be treated, valve anatomy, and severity of the cardiac condition. Accordingly, the implant 460 may be manufactured in a variety of sizes, such that a physician may pre-select the implant 460 based on patient specific factors, such as those mentioned above. Pre-selecting the implant 460 may increase the effectiveness of the implant 460 by more closely matching the size of the implant 460 to the particular patient's characteristics. In some variations, the first segment or arm 462 may comprise a first length of about 1 mm to about 10 mm, about 2 mm to about 9 mm, about 3 mm to about 8 mm, or about 4 mm to about 7 mm, including about 1 mm, about 2 mm, about 3 mm, about 4 mm, about 5 mm, about 6 mm, about 7 mm, about 8 mm, about 9 mm, or about 10 mm. The second segment or arm may comprise a second length of about 1 mm to about 10 mm, about 2 mm to about 9 mm, about 3 mm to about 8 mm, or about 4 mm to about 7 mm, including about 1 mm, about 2 mm, about 3 mm, about 4 mm, about 5 mm, about 6 mm, about 7 mm, about 8 mm, about 9 mm, or about 10 mm.

In some embodiments, the implant 460 may occupy about 4%, about 5%, about 6%, about 7%, about 8%, about 9%, about 10%, about 11%, about 12%, about 13%, about 14%, about 15% of the total leaflet surface area of the heart valve. In some embodiments, the implant 460 may occupy about 5% to about 10% of the total leaflet surface area. In some embodiments, when attached to the leaflet, the implant 460 occupies 8% of the total leaflet surface area and is not expected to restrict flow across the valve in diastole.

In some variations, the first segment or arm 462 may comprise a length different than a length of the second segment or arm 464. The different lengths may correspond to the surface area of the native leaflet surfaces to which the respective segments or arms may couple. Accordingly, the length of the first segment or arm 462 may be about 1% to about 75%, about 5% to about 60%, about 5% to about 50%, or about 5% to about 25% greater than the length of the second segment or arm 464. For example, in some variations, the length of the first segment or arm 462 may be about 1%, about 5%, about 25%, or about 50% greater than the length of the second segment or arm 464. The relative lengths of the first segment or arm 462 to the second segment or arm 464 may define a ratio. In some variations, the ratio of lengths may be about 1.01 to about 1.75, about 1.05 to about 1.6, about 1.05 to about 1.5, or about 1.05 to about 1.25. For example, in some variations, the ratio of lengths may be about 1.01, about 1.05, about 1.25, or about 1.5.

In addition to the lengths of the first and second segments or arms 462, 464, the widths of each segment or arm 462, 464 may be configured to distribute the compressive force. In some variations, the width of the first and/or second segment or arm 462, 464 may vary along its length. In some variations, varying the width of the first and/or second segment or arm 462, 464 may reduce mechanical stresses and/or avoid stress concentration "hot-spots" during or after implanting the device. For example, each of the first arm and/or second arm 462, 464 may transition from a first width to a second width at any point along the longitudinal dimension first arm and/or the second arm 462, 464, such as about ¼, about ⅓, about ½, about ⅔, or about ¾ from the distal edge of the first arm and/or the second segment or arm 462, 464. In some embodiments, a maximum width of the first segment or arm 462 may be about 1 mm to about 10 mm, about 2 mm to about 8 mm, about 3 mm to about 7 mm, and about 4 mm to about 6 mm, including about 1 mm, about 2 mm, about 3 mm, about 4 mm, about 5 mm, about 6 mm, about 7 mm, and about 8 mm. In some variations, a maximum width of the second segment or arm 464 may be about 1 mm to about 8 mm, about 2 mm to about 8 mm, or about 3 mm to about 5 mm, including about 1 mm, about 2 mm, about 3 mm, about 4 mm, or about 5 mm. In some embodiments, the first segment or arm 462 may have a greater maximum width than the second segment or arm 464 such that the first segment or arm 462 may define an opening sufficient to receive the second segment or arm 464. Accordingly, in some variations, a maximum width of the first segment or arm 462 may be about 1.01 to about 2, about 1.05 to about 1.75, or about 1.05 to about 1.5 times greater than a maximum width of the second segment or arm 464. For example, in some variations, the maximum width of the first segment or arm 462 may be about 1.05, about 1.25, about 1.5, or about 1.75 times greater than the maximum width of the second segment or arm 464.

The first and second segments or arms may each include any shape suitable for attaching to heart valve tissue and retaining the position of the implant relative to the anatomy. For example, the shape of the first and/or section segment or arm 462, 464 may be square, rectangular, circular, trapezoidal, ovular, triangular, combinations thereof, or the like. In some variations, it may be advantageous to avoid use of sharp corner that could inadvertently damage tissue and accordingly, in some embodiments, one or more ends or edges of the first and/or second segments or arms 462, 464 may be rounded. For example, in some variations, the first and/or second segments or arms 462, 464 may have a square or rectangular shape with rounded corners. The first and second segments or arms 462, 464 may also have any suitable cross-sectional shape, including, for example be a square, a circle, a trapezoid, a triangle, or combinations thereof.

b. Friction Elements

In some variations, the first and/or second segments or arms 462, 464 may be configured to apply a friction force. The friction force may be configured to maintain the implant 460 at the intended treatment site without slipping or otherwise moving. For example, each of the first and second segments or arms 462, 464 may comprise one or more (e.g. a plurality of) friction elements 470 configured to apply a friction force to non-destructively engage heart valve tissue. The friction elements 470 may include, but are not limited to, tines, teeth, prongs, hooks, bumps (e.g., rounded bumps), surface roughening, or the like. The friction elements 470 may be positioned on or otherwise carried by any portion of a tissue-facing surface of the first and/or second segments or arms 462, 464. More specifically, the friction elements 470 may be positioned along one or more edges of one or more of the first and second segments or arms 462, 464, along a central axis of a tissue-facing surface 462, 464, and/or or between one or more edges and the central axis.

In some embodiments, the friction elements 470 may be arranged along a longitudinal dimension of one or more of the first and/or second segments or arms 462, 464. The longitudinal arrangement may be collinear or, in some variations, may include one or more offsets. The friction elements 470 may be uniformly spaced along the tissue-facing surface (e.g., along an edge of the tissue-facing surface of the first and/or second segment or arm 462, 464) or may be non-uniformly spaced. In some embodiments, the friction elements 470 may be formed integrally with the first and/or second segment or arm 462, 464. Alternatively and/or additionally, the friction elements 470 may be formed separately from the first and/or second segment or arm 462, 464 and may be attached thereto (e.g., via a plate or other structural element on which the friction elements 470 are formed). The friction elements 470 may have a cross-sectional shape, such as a triangle, a circle, or a rectangle, etc. In some embodiments, the friction elements 470 may all have the same size and shape. In some embodiments, one or more friction elements 470 may have a first size and/or shape and one or more other friction elements 470 may have a different size and/or shape. Similarly, the first and/or second segments or arms 462, 464 may comprise the same or different types of friction elements 470. For example, one or more friction elements 470 on the first and/or second segment or arm 462, 464 may be of a first type (e.g., tines) and one or more friction elements on the first and/or second segment or arm 462, 464 may be of a second type (e.g., hooks). In some variations, all of the friction elements 470 on the first segment or arm 462 may be of a first size, shape, and/or type, and all of the friction elements 470 on the second segment or arm 464 may be of a second, different, size, shape and/or type. In some embodiments, an angle at which the friction elements 470 extend from the first and/or segment or arms 462, 464 may vary based on a location of the implant 460. For example, the friction elements 470 have equivalent shapes and sizes but may be bent to different angles based on their respective location on the implant 460, described in further detail in FIGS. 16A-16C.

In some embodiments, the friction elements 470 may include one or more surface roughening features. For example, each of the first and second segments or arms 462, 464 may comprise a plurality of protrusions configured to increase a friction coefficient between the tissue-facing surface of the respective segment or arm 462, 464 and heart valve tissue. In some embodiments, each protrusion may be rounded. In some embodiments, each protrusion may be pointed (e.g., tines). The plurality of protrusions may be arranged in one or more lines, which may form a grid. In some variations, the plurality of protrusions may be arranged randomly or may be arranged in one or more lines, which may extend along the longitudinal and/or lateral dimension of the respective segment or arm 462, 464. The plurality of protrusions may be combined with any other configuration of friction elements 470 described herein.

The friction elements 470 may extend from a tissue-facing surface of the first and/or second segment or arm 462, 464 and may form an angle therewith. For example, in some embodiments, the angle between one or more friction element 470 and the tissue-facing surface of the first and/or second segment or arm 462, 464 at a base of or otherwise adjacent to the friction element 470 may be about 5 degrees to about 90 degrees, about 10 degrees to about 75 degrees, about 15 degrees to about 60 degrees, or about 40 degrees to about 50 degrees, inclusive of all ranges and subranges therebetween. For example, in some variations, the angle may be about 5 degrees, about 15 degrees, about 30 degrees, about 45 degrees, or about 60 degrees, inclusive of all ranges and subranges therebetween. In some embodiments, all of the friction elements 470 may extend from the tissue-facing surface of the respective arm 462, 464 on which they are positioned at the same angle. In other embodiments, some friction elements 470 on the first and/or second segment or arm 462, 464 may extend at different angles than other friction elements 470 on that same segment or arm or on the opposing segment or arm.

The implant 460 may include any suitable number of friction elements 470 to maintain a position of the implant 460 relative to patient anatomy while the implant 460 is implanted. For example, each of the first and second segment or arm 462, 464 may include 1 to 20, 2 to 15, or 3 to 10 friction elements 470, inclusive of all ranges and subranges therebetween. In some embodiments, the first and/or second segment or arm 462, 464 may include between about 6 and 12 friction elements.

In some embodiments, a first set (e.g., 2 or more such as 3, 4, 5, 6, 7, 8, 9, 10, or more) of friction elements 470 may be positioned along one or more edges of a tissue-facing surface of a first portion of the first segment or arm 462 and a second set of friction elements 470 may be positioned along one or more edges of the tissue-facing surface of a second portion of the first segment or arm 462. The first set of friction elements 470 may define a first angle relative to the tissue-facing surface of the first portion of the first segment or arm 462 and the second set of friction elements 470 may define a second angle relative to the tissue-facing surface of the second portion of the first segment or arm 462. Similarly, a third set of friction elements 470 may extend along one or more edges of a tissue-facing surface of the second segment or arm 464, and may define a third angle relative to the tissue-facing surface of the second segment or arm 464. When the implant 460 is in a closed configuration (e.g., when the first and second segments or arms 462, 464 may be coplanar), the first and/or second sets of friction elements 470 may extend beyond the second segment or arm 464 and/or the third set of friction elements 470 may extend beyond the first segment or arm 462. That is, the first and/or second sets of friction elements 470 on the first segment or arm 462 may not be coplanar with the second segment or arm 464, and the third set of friction elements 470 on the second segment or arm 464 may not be coplanar with the first segment or arm 462.

The first, second, and/or third angles defined by each respective set of friction elements 470 may determine the friction force. For example, increasing one or more of the first, second, and third angles may increase the friction force, and decreasing one or more of the first, second, and third angles may decrease the friction force. In this way, the friction force may be adjusted via manipulation of the first, second, and/or third angles, where the manipulation may occur during the manufacturing phase and/or by a physician prior to performing the surgical procedure described herein. The first angle may be about 0 degrees to about 90 degrees, about 10 degrees to about 60 degrees, or about 20 degrees to about 45 degrees, including about 30 degrees, inclusive of all ranges and subranges therebetween. The second angle may be about 0 degrees to about 90 degrees, about 10 degrees to about 60 degrees, or about 20 degrees to about 45 degrees, including about 15 degrees, inclusive of all ranges and subranges therebetween. The third angle may be about 0 degrees to about 90 degrees, about 10 degrees to about 60 degrees, or about 20 degrees to about 45 degrees, including about 40 degrees, inclusive of all ranges and subranges therebetween.

The one or more sets of friction elements 470 may comprise a height sufficient to couple heart valve tissue. In some variations, the height of the one or more sets of friction elements 470 may be about 10 microns to about 100 microns, 25 microns to about 75 microns, or about 30 microns to about 60 microns, inclusive of all ranges and subranges therebetween. For example, in some variations, the height of the one or more sets of friction elements 470 may be about 10 microns, about 25 microns, about 35 microns, about 45 microns, or about 75 microns. The height of one set of friction elements 470 may be the same or different as any other set of friction elements 470, which may facilitate optimizing the friction force applied by the implant 460.

In some embodiments, the friction elements 470 may be formed by creating slots in the first and/or second segment or arm 462, 464 or by creating slots in a structure from which the friction elements are formed (e.g., a plate). In some embodiments, the first and/or second segments or arms 462, 464, or the plate from which the friction elements 470 are formed, may include a plurality of slots. Each slot may be adjacent to a respective friction element 470 and may define a length corresponding to a height of the friction element 470. The slots may facilitate forming (e.g., bending) the friction element 470 to the desired angle that corresponds to a desired friction force. That is, each slot may separate an edge of a friction element 470 from a tissue-facing surface of the segment or arm 462, 464. In some embodiments, one or more, including all, slots may terminate in a circular portion. It may be advantageous to utilize a slot with a circular portion as the circular portion may reduce mechanical stresses associated with forming (e.g., bending) the friction elements. Additionally, in some variations, the circular portion may prevent cracks from propagating from the slot.

c. Central Member

As previously described, the implant 460 may include the central member 466 positioned between the first segment or arm 462 and the second segment or arm 464. The central member 466 may be configured to provide a biasing force to one or more of the first and second segments or arms 462, 464, such that the first and second segments or arms 462, 464 may be biased towards one another. The biasing force may be sufficient to maintain coupling of the first and second segments or arms to the heart valve tissue. In some embodiments, the central member 466 may be curved. For example, the central member 466 may form an arc between the first segment or arm 462 and the second segment or arm 464. Accordingly, the biasing force may be at least partially based on the configuration (e.g., length, a radius of curvature, and/or thickness) of the central member. Therefore, the configuration of the central member 466 may facilitate movement of the second segment or arm 464 towards or away from the first segment or arm 462 and may define the extent to which the first and second segments or arms 462, 464 may separate.

A length of the central member 466 may correspond to the compressive force applied by the first and second segments or arms 462, 464 according to a moment of force (e.g., force multiplied by distance). In some variations, the length of the central member 466 may be about 1 mm to about 10 mm, about 2 mm to about 9 mm, about 3 mm to about 8 mm, or about 4 mm to about 7 mm, including about 1 mm, about 2 mm, about 3 mm, about 4 mm, about 5 mm, about 6 mm, about 7 mm, about 8 mm, about 9 mm, or about 10 mm, inclusive of all ranges and subranges therebetween.

A thickness of the central member 466 may be configured to allow the movement of the first and second segments or arms 462, 464 relative to one another without inelastically deforming or fracturing. In some embodiments, the thickness of the central member 466 may vary along its length. For example, a thickness of a section adjacent to the second segment or arm 464 may be greater than other sections of the central member 466. The thicker section of the central member 466 may correspond to a thicker section of the second segment or arm 464. The thicker sections of the central member 466 and/or second segment or arm 464 may facilitate deflection of the second segment or arm 464 relative to the first segment or arm 462 while reducing excessive force or fracturing of the central member 466. In some embodiments, the thickness of the central member 466 may be between about 50 microns to about 500 microns, about 100 microns to about 300 microns, or about 200 microns to about 300 microns. In some embodiments, the thickness may be about 50 microns, about 100 microns, about 200 microns, about 250 microns, about 300 microns, or about 400 microns.

A width of the central member 466 may be configured such that the mechanical stresses associated with adjusting the central member 466 (e.g., during transitions between configurations) may be minimized. In some embodiments, the width of the central member 466 may be less than the width of one or more of the first and second segments or arms 462, 464. The width of the central member 466 may be about 1 mm to about 10 mm, about 2 mm to about 7 mm, or about 2 mm to about 5 mm. For example, in some variations, the width of the central member 466 may be about 1 mm, about 2 mm, about 3 mm, about 4 mm, or about 5 mm. In some embodiments, a radius of curvature of the central member 466 may be in a range of about 2 mm to about 10 mm or beyond. In some embodiments, the radius of curvature of the central member 466 may be about 4 mm.

The biasing force generated by the central member 466 may correspond to a compressive force applied by the first and/or second segments or arms 462, 464 to heart valve tissue. The compressive force may not be so great as to damage the heart valve tissue. In some embodiments, the compressive force may be characterized by the amount of force required to separate the first and second segments or arms 462, 464. In some embodiments, the biasing force may be about 100 mN to about 1000 mN, about 150 mN to about 600 mN, or about 200 mN to about 450 mN, including about 150 mN, about 200 mN, about 250 mN, about 300 mN, about 350 mN, about 400 mN, about 450 mN, about 500 mN, about 550 mN, or about 600 mN. The force applied by the first and second segments or arms 462, 464 may be configured to counter a force generated by the transmitral systolic pressure gradient on the mitral valve.

d. Support Members

The implant 460 may include one or more support members 480 configured to absorb impingement (e.g., via coaptation) from one or more portions of a heart valve and, in some cases, provide support for the cover 468 that may cover the support members 480 or otherwise be coupled thereto. Accordingly, the support members 480 may each have a radius of curvature to facilitate supporting the cover 468 and/or forming an appropriate coaptation surface for a native leaflet. The radii of curvature may allow the support members 480 and/or cover 468 to deflect such as, for example, upon impingement (e.g., coaptation) by another portion of the heart valve. In some embodiments, the support members 480 may deflect (e.g., bend and/or extend) in one or more directions such that the support members 480 are in an elongated configuration (e.g., in a delivery configuration). Each support member 480 may have a plurality of sections, where each section may have a different shape and/or radius of curvature. In some variations, each section may be linear. In some embodiments, one or more sections of each support member 480 may be linear and one or more sections may be curved. In some embodiments, each section of the support members 480 may be curved. For example, one or more support members 480 may have one or more of a convex section and a concave section. In some embodiments, one or more of the support members 480 may have a section with a radius of curvature greater than the radius of curvature of the central member 466. The radius of curvature of one support member 480 may be different than any other radius of curvature of another support member 480. Additionally, or alternatively, one or more of the support members 480 may include a free end, as described previously. The free ends of the support members 480 may allow the support members 480 to extend or contract even further. In some embodiments, the free ends of the support members 480 may each include an atraumatic distal tip such that the support members 480 may avoid damaging or otherwise traumatizing heart valve tissue. In some embodiments, the free end of each of the support members 480 may be coplanar with a proximal surface of the central member 466.

In some embodiments, at least one of the support members 480, such as a first support member, may be configured to contact a first native leaflet (i.e., the leaflet to which the attachment section is coupled) while at least one other support member 480, such as a second support member, may be configured to avoid contact with the first native leaflet. The second support member may be configured to contact a second native leaflet (e.g., via coaptation). At least one cover (e.g., cover 468) may be coupled to the coaptation section. The cover 468 may be a flexible (e.g., stretchable, malleable) material configured to move with the support members 480, such that the cover 468 may deflect when a leaflet applies a force to the coaptation section. In this way, a heart valve may be altered such that complete closure may be achieved, which may facilitate durably correcting heart valve regurgitation.

The support members 480 may include one or more dimensions configured to provide the flexibility described herein. For example, each support member 480 may comprise a length, which may, in some embodiments, may determine the volume of the coaptation section. Each support member 480 may have the same length, or a different length, as any of the other support members 480. In some embodiments, a length of the support members 480 may be about 1 mm to about 20 mm, about 3 mm to about 15 mm, or about 5 mm to about 12 mm, including about 3 mm, about 5 mm, about 7 mm, about 9 mm, about 11 mm, or about 13 mm. Each support member may have a width, which may be determined to minimize a stress concentration during deflection. In some embodiments, the width may be about 10 microns to about 500 microns, about 50 microns to about 250 microns, or about 100 microns to about 200 microns, including about 50 microns, about 100 microns, or about 150 microns.

The number of support members 480 may be determined by the treatment site and/or the size of the heart valve. In some embodiments, the number of support members 480 may alternatively or additionally be determined by a size (e.g., an area) of the cover 468. For example, the number of support members 480 may be increased to accommodate a larger cover 468, which may facilitate treating relatively severe heart valve regurgitation associated with a relatively large gap between valve leaflets. In some instances, it may be advantageous to have an even number of support members 480 as this may assist in evenly distributing the mass of the implant 460 when coupled to heart valve tissue. In some embodiments, the implant 460 may include between 2 and 10, 2 and 9, 2 and 8, 2 and 7, 2 and 6, 2 and 5, 2 and 4, and 2 and 3 support members 480. In some embodiments, the implant 460 may include 4 support members 480.

In embodiment with an even number of support members 480, the support members 480 may be symmetric (e.g., mirrored) about the central member 466. That is, there may be the same number of support members 480 on either side of the central member 466 and symmetric pairs of support members 480 may have the same dimensions (e.g., length, width) and/or shape (e.g., radius or radii of curvature). For example, there may be a first and second support member on a first side of the central member 466 and third and fourth support members on a second side of the central member 466, where the third support member may be symmetric to the second support member about the central member 466 and the fourth support member may be symmetric to the first support member about the central member. In some embodiments, the support members 480 need not be symmetric, which may facilitate customizing the coaptation section to optimize treatment for a given patient.

In some embodiments, the support members 480 may attach to the central member 466 and/or the first or second arm 462, 464 and are free at their distal end. Therefore, when the implant 460 is compressed into the implant catheter of the implant delivery system (e.g., in the compressed configuration), the support members 480 compress inwards, but also elongate longitudinally to accommodate that compression. When the implant 460 is advanced out of the implant catheter, the support members 480 may transition to their baseline configuration or state (e.g., an expanded configuration), longitudinal elongation may be decreased. In other words, when the support members 480 are in the compressed configuration (e.g., when the implant 460 is in a delivery configuration), a transverse protrusion length of the support members 480 is reduced, and when the support members 480 are in the expanded configuration (e.g., when the implant 460 is in the open configuration and/or the implanted configuration), the transverse protrusion length is increased (e.g., restored to a base condition).

e. Openings

The implant 460 may define one or more openings configured to receive one or more segments or arms 462, 464, as described herein. For example, the first segment or arm 462 may define an intermediate opening configured to receive the second segment or arm 464. The intermediate opening may be configured to receive at least a portion of the second segment or arm 464 when the portion of the second segment or arm 464 is at least partially coplanar with at least a portion of the first segment or arm 462. Accordingly, in some embodiments, the intermediate opening may comprise a size and/or shape corresponding to a portion of the second segment or arm 464. The intermediate opening may comprise a length and a width. The length of the intermediate opening may be about 1 mm to about 10 mm, about 2 mm to about 8 mm, or about 3 mm to about 6 mm. For example, in some variations, the length of the intermediate opening may be about 1 mm, about 3 mm, about 4 mm, about 5 mm, or about 6 mm. The width of the intermediate opening may be about 1 mm to about 10 mm, about 2 mm to about 8 mm, about 2 mm to about 6 mm, or about 2.5 mm to about 5.5 mm. For example, in some embodiments, the width of the intermediate opening may be about 1 mm, about 2 mm, about 3 mm, about 4 mm, about 5 mm, or about 6 mm. In some variations, the length and/or width of the intermediate opening may maintain a gap between the first segment or arm 462 and second segment or arm 464, such that a cover 468 may be routed through the gap while allowing the segments or arms 462, 464 to freely move relative to each other. The intermediate opening may be positioned at a midline of the lateral (e.g., width) dimension of the first segment or arm. In some embodiments, the intermediate opening may be positioned at any point along the lateral dimension of the first segment or arm.

The implant 460 may further define one or more openings (e.g., positioning openings) 475 configured to facilitate adjusting the position of each of the first and second segments or arms 462, 464 (e.g., opening and/or closing the implant 460). The one or more openings 475 may be configured to receive one or more elongate members (e.g., the atrial tether 140 and/or the ventricular tether 150) to assist in adjusting the position of one or more of the first and second segments or arms 462, 464. As described previously, an implant delivery system (e.g., implant delivery system 100) may be used to assist in opening and/or closing the implant 460. The one or more elongate members (e.g., wires, sutures, etc.) of the implant delivery systems may be disposed through one or more of the positioning openings 475 of each of the first and second segments or arms 462, 464. For example, a first suture or tether (e.g., the atrial tether 140) may be routed through one or more positioning openings 475 (e.g., suture holes) of the first segment or arm 462 and back through an implant catheter of the implant delivery system, such that both ends of the first suture or tether are controllable by the implant delivery system. Additionally, the second suture or tether may be disposed through one or more positioning openings 475 of the second segment or arm 464 and back into the implant catheter of the implant delivery system, such that the ends of both the first and second sutures or tethers are controllable by the implant delivery system. In some embodiments, the first suture or tether may be disposed through one or more positioning openings 475 of the first and/or second segment or arm 462, 464 and subsequently tied (e.g., to itself or a portion of the catheter) to form a first loop, and the second suture or tether may be disposed through the first loop and back into the implant catheter of the implant delivery system to form a second loop, wherein the first loop may be smaller than the second loop.

Accordingly, the one or more positioning openings may comprise a size and/or shape corresponding to one or more elongate members (e.g., the atrial tether 140 and/or the ventricular tether 150). For example, the shape of the positioning opening 475 may be a circle, oval, rectangle, or combination thereof. The shape may be determined to reduce friction between the segment or arm 462, 464 and the elongate member. The size of the positioning opening 475 may correspond to a diameter of the elongate member. In some variations, the size may correspond to multiple elongate members routed through the same positioning opening 475. The width and length dimensions of each positioning opening 475 may be the same or may be different, and may depend on the number of elongate members routed therethrough.

The plurality of positioning openings 475 of the first and/or second segments or arms 462, 464 may be arranged to facilitate application of a pre-determined force profile to the first and/or second segments or arms 462, 464 via the elongate member(s). For example, a plurality of positioning openings 475 may be arranged collinearly across a width of the first and/or second segment or arm 462, 464, such that an elongate member may apply a force evenly across the first and/or second segment or arm 462, 464. In some embodiments, the plurality of positioning openings 475 may not be arranged collinearly such that one or more positioning openings 475 are offset from at least one other positioning opening 475. The offset may reduce a friction force between an elongate member and the positioning opening(s) 475, such as when the elongate member may be routed through more than one positioning opening 475. In some embodiments, the plurality of positioning openings 475 may be arranged along a longitudinal dimension of one or more of the first and/or second segments or arms 462, 464. The longitudinal arrangement may be collinear or, in some embodiments, may include one or more offsets. The arrangement may be determined to evenly distribute the force applied by one or more elongate members routed through the plurality of positioning openings 475 and/or may reduce a friction force between the elongate member and the positioning openings 475. In some embodiments, the longitudinal arrangement may be centered with respect to the width of one or more of the first and/or second segment or arms 462, 464, which may further facilitate even distribution of the force applied by the one or more elongate members.

In some embodiments, each of the first and second segments or arms 462, 464 may include a number of positioning openings 475 determined by the size and/or shape of the respective segment or arm 462, 464. For example, each of the first and second segments or arms 462, 464 may include 1, 2, 3, 4, 5, 6, 7, 8, 9, or 10 positioning openings 475 configured to receive an elongate member. In some embodiments, the first and/or second segments or arms 462, 464 may include openings used during manufacturing to hold a portion of the implant 460 with a shape setting fixture. These openings may not be used in the function of the implant 460. In some embodiments, the first and second segments or arms 462, 464 may include the same number and/or configuration of positioning openings 475. In some embodiments, the first and second segments or arms 462, 464 may include different numbers and/or configurations of positioning openings 475. For example, the number of positioning openings 475 of the first segment or arm 462 may not be equivalent to the number of positioning openings 475 of the second segment or arm 464, which may be determined by the size of each segment or arm 462, 464 and/or the amount of force required to separate the segments or arms 462, 464 from one another. That is, the number of positioning openings 475 may be increased if a greater force is required to separate the segments or arms 462, 464 and/or more elongate members are required to apply the necessary separation force to avoid breaking the one or more elongate members. In some embodiments, the first segment or arm 462 may include four positioning openings 475 and the second segment or arm 464 may include two positioning openings 475.

Utilizing the one or more elongate members, the physician may manipulate the configuration of the segments or arms 462, 464 such that the segments or arms 462, 464 may be separated prior to receiving and/or coupling to heart valve tissue, released to couple to heart valve tissue, and optionally reseparated to reposition the implant 460. In some embodiments, the first and second segments or arms 462, 464 of the implant 460 may be coplanar in a closed configuration, a delivery configuration, and/or an implanted configuration. The physician may apply tension to the one or more elongate members via the implant delivery system, which may apply a force to the first and second segments or arms 462, 464 sufficient to overcome the biasing force provided by the central member 466 and thus separate the first and second segments or arms 462, 464 to the open configuration. The separation of the first and second segments or arms 462, 464 in the open configuration may define a separation angle relative to the closed configuration (e.g., coplanar). The separation angle may be about 1 degrees to about 180 degrees, about 10 degrees to about 150 degrees, or about 15 degrees to about 120 degrees. The separation angle may correspond, at a minimum, to an uncompressed thickness of the targeted heart valve tissue (e.g., at the treatment site). The separation angle may determine a separation distance between portions of the first and second segments or arms 462, 464. For example, the separation distance may be defined by the maximum distance between the distal end of the first segment or arm 462 relative to the distal end of the second segment or arm 464. In some embodiments, the separation distance may be about 1 mm to about 20 mm, about 5 mm to about 18 mm, or about 10 mm to about 15 mm. For example, in some variations, the separation distance may be about 1 mm, about 5 mm, about 15 mm, about 17 mm, or about 20 mm.

The physician may also reduce tension in the one or more elongate members via the implant delivery system 100, which may allow the biasing force to bring the first and second segments or arms 462, 464 towards one another to an implanted configuration. The implanted configuration may correspond to the first and/or second segments or arms 462, 464 being coupled to heart valve tissue. Accordingly, the implanted configuration may correspond to a compressed thickness of the targeted heart valve tissue. Depending on the thickness of the compressed heart valve tissue the first and second segments or arms 462, 464 may not be coplanar relative to each other in the implanted configuration. In some embodiments, the first and second segments or arms 462, 464 may be partially or fully coplanar relative to each other in the implanted configuration.

The implant 460 described herein may further include one or more visualization openings configured to receive visualization markers, which may assist with visualization of the implant 460 (e.g., the position and/or configuration) before, during, and/or after implantation. The implant 460 may define one or more visualization openings in any location, such as in one or more of the first segment or arm 462, the second segment or arm 464, and the central member 466. For example, the first and/or second segment or arm 462, 464 may each include one or more visualization openings configured to receive a visualization marker (e.g., a radiopaque marker). In some embodiments, the visualization openings of the first and/or second segment or arm 462, 464 may be located in a distal portion thereof, such that the separation distance between the first arm 462 and the second segment or arm 464 may be determined. When coupled to the first and/or second segments or arms 462, 464, the visualization markers may be indirectly visible to the physician while the implant 460 is within the patient. In some embodiments, the visualization markers may be directly visible, e.g., via fluoroscopy, echocardiography, and/or other imaging modality. In this way, the position of the first and second segments or arms 462, 464 relative to each other may be determined via the radiopaque markers attached thereto, which may be used to determine the configuration of the implant 460 (e.g., delivery, closed, open, or implanted). Additionally, if the segments or arms 462, 464 are separated (e.g., in the open configuration), the visualization markers may be used to determine the separation distance between the segments or arms 462, 464.

The visualization openings described herein may include dimensions corresponding to the shape and size of the visualization markers. A visualization opening may have the same shape and size, or a or different shape and size, as any of the other visualization openings. In some embodiments, the openings and associated visualization markers may have any shape, such as a circle, an oval, a triangle, a rectangle, a square, or a trapezoid. For example, a substantially circular opening may correspond to a substantially circular radiopaque marker. The visualization openings may comprise a diameter or length. The diameter or length may correspond to a diameter or width of the visualization marker. The diameter or length of the visualization opening may be about 250 microns to about 2 microns, about 500 microns to about 1.5 mm, or about 500 microns to about 1 mm. For example, in some variations, the diameter or length may be about 250 microns, about 500 microns, about 750 microns, or about 1 mm. In some embodiments, the visualization opening may extend through the thickness of segments or arms 462, 464 described herein (i.e., are through holes).

In some embodiments, a first visualization opening or a first set of visualization openings defined by the first arm or segment 462 may have a different shape and/or orientation than a second visualization opening or second set of visualization openings defined by the second arm or segment 464. For example, a first visualization opening on the first arm or segment 462 may be elongated vertically (e.g., an oval, slit, or rectangle, that is longer along the longitudinal axis of the first arm or segment 462) and a second visualization opening on the second arm or segment 464 may be elongated horizontally (e.g., an oval, slit, or rectangle that is longer along the transverse axis of the second arm or segment 464). When the first arm or segment 462 and the second arm or segment 464 are coplanar, the first visualization opening and second visualization opening form a "+" shape. When the first arm or segment 462 and the second arm or segment 464 are not coplanar, the first and second visualization markers form a series of horizontal and vertical shapes.

In some embodiments, each of the first and second segments or arms 462, 464 may comprise 0 to 20 visualization openings, such as 0, 1, 2, 3, 4, 5, 6, 7, 8, 9, 10, 15, or 20 visualization openings configured to receive a visualization marker. The number of visualization openings of the first segment or arm 462 may not be equivalent to the number of visualization openings of the second segment or arm 464. For example, the number of visualization openings of each segment or arm 462, 464 may be determined by the size of each segment or arm 462, 464. For example, the number of visualization openings of the first segment or arm 462 may be greater than may be the number of visualization openings of the second segment or arm 464 because of the larger surface area of the first segment or arm 462 relative to the second segment or arm 464. In some embodiments, the number of visualization openings of a segment or arm 462, 464 may be increased if a surface area thereof, is increased to enable a physician to identify the position of the larger segment or arm 462, 464. In some embodiments, one or more visualization markers may be coupled to the first and/or second segments or arms 462, 464 without being received in a corresponding visualization opening, which may facilitate coupling additional visualization markers to the device after the initial assembly of the implant 460.

f. Plates

The implants 460 may further include one or more plates configured to couple to the implant 460 (e.g., the first segment or arm 462 and/or the second segment or arm 464). The one or more plates may be coupled to the implant 460 such that the plates remain fixedly attached to the implant 460 during the initial implant process and any subsequent repositioning. For example, a first plate may be coupled to the first segment or arm 462 and a second plate may be coupled to the second segment or arm 464. The first plate may comprise a shape corresponding to at least a portion of the first segment or arm 462 and/or the second plate may comprise a shape corresponding to at least a portion of the second segment or arm 464. Accordingly, in some embodiments, each of the first and second plates may comprise one or more of a planar section and a curved section. The curved sections of the first and second plates may be shaped to match the curved sections of the first and second segments or arms 462, 464 described previously. The one or more plates may be further configured to releasably couple to heart valve tissue, which may facilitate repositioning the implant 460. The one or more plates may include any of the friction elements 470 described above in detail and in any of the configurations described herein.

The one or more plates may further include one or more openings (e.g., positional openings 475) configured to receive one or more elongate members, which may facilitate opening and/or closing the implant 460. For example, the first plate may comprise one or more positioning openings 475 with a similar size and position as the one or more positioning openings 475 of the first segment or arm 462. Additionally, or alternatively, the second plate may comprise one or more positioning openings 475 with a similar size and position as the one or more positioning openings 475 of the second segment or arm 464. In this way, one or more elongate members may be routed through the positioning openings of at least one of the first plate, first segment or arm 462, second plate, and/or second segment or arm 464. In some embodiments, the first and/or second plates may each include one or more visualization openings configured to receive a visualization marker. In some embodiments, the first and/or second plates may not include one or more visualization openings, such that the first and/or second plates may cover one side of the visualization openings of the respective first and second segments or arms 462, 464 and thus provide a mounting surface (e.g., backstop). In this way, a visualization marker received within one of the visualization opening of the first and/or second segments or arms 462, 464 may be securely mounted to the first or second plates.

Alternatively or additionally, the implant may include one or more attachments, couplers, loops, and/or the like, coupled to the first segment or arm 462 and/or the second segment or arm 464. For example, the implant may include one or more suture loops through one or more (e.g., two) positional openings in the atrial arm, and one or more suture loops through one or more (e.g., two) positional openings in the ventricular arm. In some embodiments, the atrial tether and the ventricular tether may be configured to couple to the suture loops in addition to or instead of the positional openings 475. For example, the atrial tether and/or ventricular tether may be routed through the one or more suture loops and coupled to the proximal end of the implant delivery system. In some embodiments, the atrial tether may be routed through one or more suture loops on the atrial arm. In some embodiments, the ventricular tether may be routed through one or more suture loops on the ventricular arm. In some embodiments, the suture loop may only be on one of the segments or arms of the implant 460 to provide less friction or resistance when releasing and/or withdrawing the tethers. In some embodiments, coupling the tethers to suture loops on the implant 460 may provide a larger moment arm than coupling the tethers directly to the implant. In some embodiments, the tethers routed through the suture loops may be easier to decouple from the implant 460. In some embodiments, coupling the tethers to the suture loops may also cause less deformation of the tethers than when the tethers are directly coupled to the implant 460. In some embodiments, the suture loops may remain on the implant 460 permanently. In some embodiments the suture be removed from the implant after implantation.

The first and second plates described herein may be coupled to the first and second segments or arms 462, 464, respectively. For example, in some embodiments, the first and second plates may be fixedly attached (e.g., permanently) to the first and second segments or arms 462, 464, respectively, such that the implant 460 may maintain its structural integrity before, during, and after the implantation process. The first and second plates may be coupled to the first and second segments or arms 462, 464 via any suitable fastening technique, such as, for example, via welding, adhesives, and/or mechanical fasteners (e.g., screws, bolts). The means of coupling may be at least partially dependent upon the material of the plates and/or segments or arms 462, 464.

In some embodiments, the plates and segments or arms 462, 464 may each be manufactured using metal (e.g., stainless steel, nitinol) such that the first plate may be welded to the first segment or arm 462, and the second plate may similarly be welded to the second segment or arm 464. In some embodiments, the plates and arms may each be manufactured using a plastic such that the plates may be coupled to the respective segments or arms 462, 464 using a polyurethane adhesive, which may be non-toxic to humans and thus suitable for a medical device. The first and second plates may each have a thickness between about 50 microns to about 500 microns, about 50 microns to about 300 microns, about 50 microns to 200 microns, or about 75 microns to about 125 microns. For example, in some variations, the first and second plates may each have a thickness of about 50 microns, about 75 microns, about 100 microns, about 200 microns, or about 250 microns.

g. Visualization Markers

The implant 460 may be implanted within a patient without direct visualization of the implant 460, which may reduce the number of components associated with the surgical procedure, facilitate a minimally invasive procedure, and/or reduce a size of the implant 460 and/or the delivery system. For example, the implant 460 may be implanted within the patient using visualization via X-ray, CT, or similar medical imaging means. In some embodiments, the implant 460 may include one or more visualization markers (e.g., one or more a radiopaque markers) configured to allow a user to indirectly visualize the implant 460 and thereby determine a position of one or more elements of the implant 460. As described above, the implant 460 may define one or more visualization openings configured to receive one or more visualization markers. In some embodiments, the first and second plates may be configured to provide a mounting surface for one or more visualization markers. In this way, the precise position of implant 460 may be determined relative to a heart valve. Furthermore, the position of the first and second segments or arms 462, 464 relative to each other may also be determined via the visualization markers attached thereto. Therefore, it may be possible to determine whether the first and second segments or arms 462, 464 are coplanar (e.g., in a closed configuration) or if they are separated (e.g., in an open configuration) and, if so, the distance by which the segments or arms 462, 464 are separated.

The visualization markers described herein may comprise dimensions corresponding to the shape and size of the visualization openings receiving them. In some embodiments, a width of the visualization marker may be about 250 microns to about 2 mm, about 500 microns to about 1.5 mm, or about 500 microns to about 1 mm. For example, in some variations, the width may be about 250 microns, about 500 microns, about 750 microns, or about 1 mm. A height of the visualization marker may be about 50 microns to about 300 microns, about 100 microns to about 300 microns, or about 150 microns to about 300 microns. In embodiments in which a visualization opening extends through the segment or arm 462, 464, the height of the visualization marker may be about 200 microns to about 300 microns, including about 250 microns.

The visualization markers may be coupled to the implant 460 such that the visualization markers remain fixedly attached to the implant 460 for the entire duration that the implant remains within the patient. For example, the visualization markers may be coupled to the arm(s) 462, 464 and/or plate(s) using welding, adhesives, and/or mechanical fasteners (e.g., screws, bolts). The means of coupling may be at least partially dependent upon the material of the visualization markers, plates, and/or arms. In some embodiments, the visualization markers may be manufactured from gold, platinum, iridium, tantalum, or other radiopaque material. In some embodiments, the visualization markers (e.g., radiopaque marker) may include platinum and may be welded to an implant 460 made from nitinol.

While described above as received within a visualization opening, in some embodiments, one or more visualization markers may be coupled to a surface of the first and/or second segment or arm 462, 464, or the central member 466, without the use of an opening. Moreover, in some instances, a visualization marker may be in the form of a visual marker on the surface of the implant 460 (e.g., first and/or second segment or arm 462, 464, central member 466) that is intended to be viewed with an endoscope without the use of radiology.

h. Covers

The implant 460 may include one or more covers 468 configured to couple to and in some instances surround at least a portion of the implant 460. In some embodiments, the cover 468 may extend along at least a portion of the attachment section and coaptation section of the implant 460. For example, the cover 468 may cover at least a portion of each of the first and/or second segments or arms 462, 464. In some embodiments, the cover 468 may cover each of the first and second segments or arms 462, 464 except for the plurality of positioning openings 475 and/or friction elements 470 thereof. The cover 468 may cover the central member 466 and/or may cover the support members 480. When used to cover the support members 480, the cover 468 may be configured to alter one or more physical characteristics of heart valve tissue, such as a thickness, length, width, curvature, and/or stiffness thereof. The cover 468 may also assist in providing a malleable coaptation surface for receiving heart valve tissue and may, in combination with the support members 480, advantageously provide a coaptation surface for heart valve tissue. The cover 468 may also provide a surface upon which native tissue may grow, which may facilitate improved outcomes and/or further reduce heart valve regurgitation as native tissue naturally connects portions of the heart valve after the implanting process. Additionally or alternatively, the cover 468 may operate as a flexible extension of the implant 460 such that a greater surface area of heart valve tissue (e.g., a second native leaflet) may contact the implant 460 and/or a larger gap between the native leaflets may be filled. In these embodiments, the cover 468 may further reduce the precision required by physician during the implanting process because the cover may increase the overall size of the implant 460.

The cover 468 may be made from a material with sufficient pliability to match the movements of the attachment and/or coaptation sections without tearing, breaking, or otherwise being damaged. As described above, the material of the cover 468 may facilitate native heart valve tissue growth. Accordingly, in some embodiments, the cover 468 may comprise one or more of a fabric (e.g., textile) and a polymer (e.g., polyester, polytetrafluoroethylene). Additionally, or alternatively, the cover 468 may be woven, braided, and/or layered using one or more materials. The material and texture of the cover 468 may be determined based on biocompatibility with heart valve tissue and/or durability. The cover 468 may be coupled to the implant 460 using any suitable technique, such as, for example, sutures, ties, knots, adhesives, and/or elastic bands.

In some embodiments, the cover 468 may include three portions, such as a first portion configured to couple to the support members 480, a second portion configured to extend therefrom, and a third portion configured to couple to the attachment section (e.g., at least a portion of the first and second segment or arms 462, 464). The portions may be integrally formed or may be separate from one another. For example, the first and second portions may be integrally formed (e.g., a first cover) and the third portion may be formed separately (e.g., a second cover), such that the first and second covers may be coupled to the implant 460 during assembly.

In another example, the cover 468 may include a first portion configured to couple to the plurality of support members 480 of the coaptation section, with one or more (e.g., all) of the support members 480 supporting the cover 468. The cover 468 may further include a second portion that may extend from a proximal end of the first portion, such that the second portion may not be in direct contact with or otherwise covering the implant body (e.g., the second portion may be devoid of support members 480). Accordingly, the second portion may increase one or more dimensions of the implant 460 (e.g., of the coaptation section) and may provide additional volume to the implant body by defining a 3-dimensional shape. In some embodiments, the first portion may be coupled to the second portion along a distal edge of the second portion and/or along a width of the second portion. The second portion may be rolled and/or folded (e.g., accordion fold), and may be curved along a lateral dimension (e.g., width) of the implant 460. For example, in some embodiments, the second portion may be or may include a cylindrical cuff that may be formed from rolled material (e.g., cover material such as fabric) and secured (e.g., using a mechanical fastener such as a suture, adhesive, and/or the like) such that it retains a rolled configuration when in use. In these embodiments, the second portion may provide a flexible and/or unrollable extension that may be configured to increase the size of the implant 460. The third portion may be configured to couple to the attachment section, such that the third portion covers at least a part of the first and second segments or arms 462, 464. The third portion may cover the friction elements 470 of the first and/or second segments or arms 462, 464. In some embodiments, some or all of the friction elements 470 of the first and/or second segments or arms 462, 464 may extend through (e.g., pierce) the cover 468 such that the friction elements 470 may directly engage native leaflet tissue.

Figure 5A:
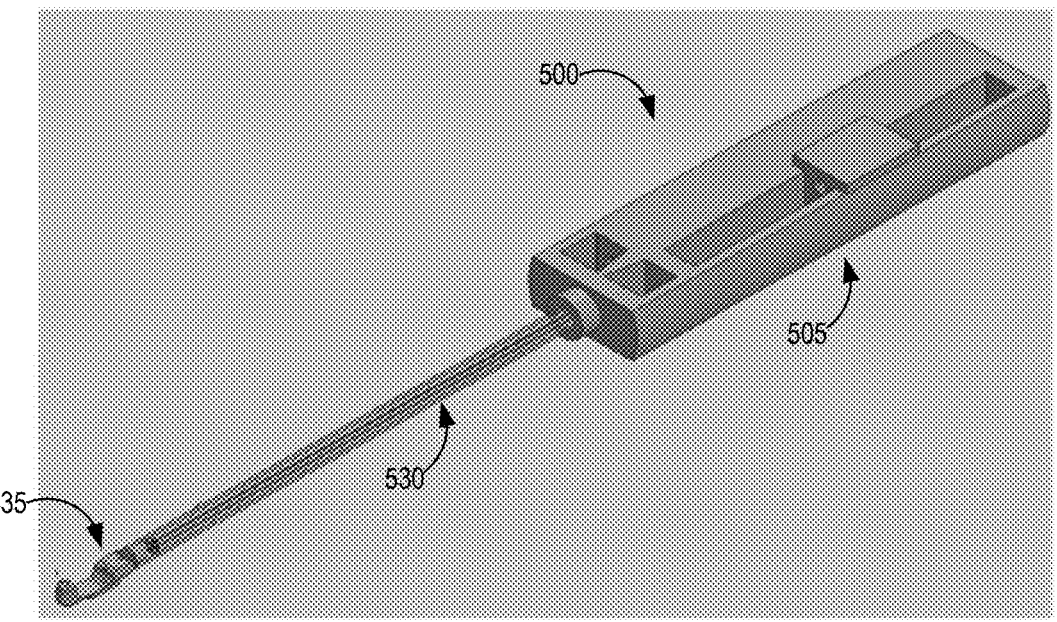
FIG. 5A is an illustration of an implant delivery system including a multi-lumen implant catheter and an implant holder, according to embodiments.
Figure 5B:
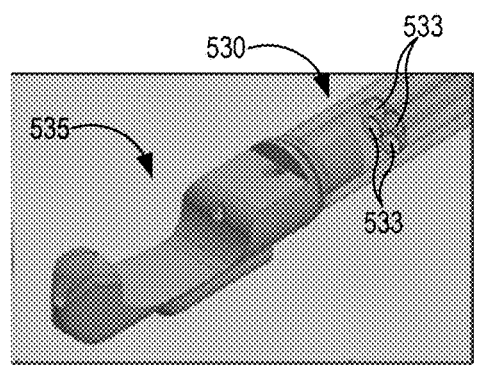
FIG. 5B shows a close up of a distal end of the implant delivery system, according to embodiments.

FIG. 5A is an illustration of a short catheter implant delivery system 500 including a handle assembly 505, an implant catheter 530, and an implant holder 535, according to embodiments. FIG. 5B shows a close up of a distal end of the implant delivery system 500, according to embodiments. As shown, the implant catheter 530 includes four hypotubes extending therethrough. Each hypotube may define a lumen 533 configured to receive an elongate member (e.g., the tethers not shown) that extends therethrough. Each tether extends along the length of the implant catheter 530 inside each lumen 533 of a respective hypotube with at least one end or portion of the tether anchored (e.g., removably anchored) to the handle assembly 505. The implant holder 535 is coupled to a distal end of the implant catheter 530 and includes four channels, each channel configured to receive a respective portion of a tether. For example, each tether may extend from a distal end of a respective hypotube and through a respective channel in the implant holder 535 such that each tether can be coupled to a portion of an implant disposed in the implant holder 535. Although not shown, in some embodiments, a first tether (e.g., the atrial tether) may be configured to couple to the first arm (e.g., atrial arm) of the implant and a second tether (e.g., the ventricular tether) may be configured to couple to the second arm (e.g., ventricular arm) of the implant.

Figure 5C:
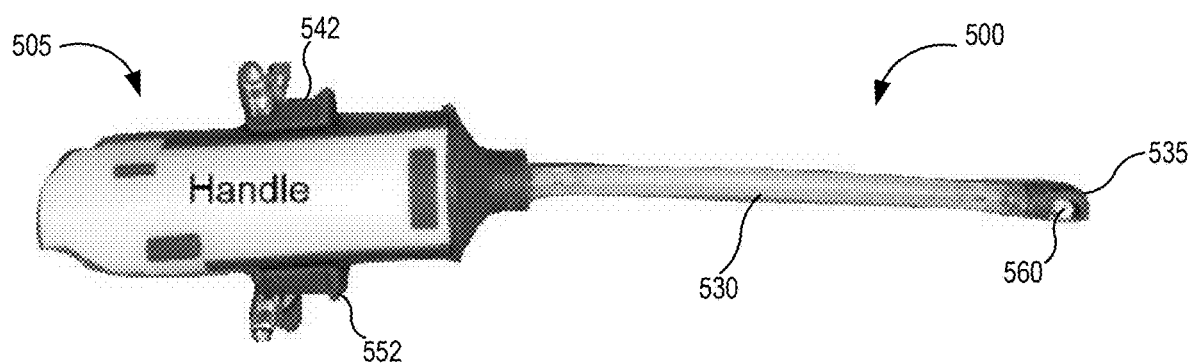
FIG. 5C is an image of the implant delivery system including a handle assembly, an implant catheter, and an implant holder, according to embodiments.

FIG. 5C shows the handle assembly of the short catheter implant delivery system 500. As shown, the handle assembly 505 includes an AT actuator 542 and a VT actuator 552. The AT actuator 542 is configured to be coupled to the atrial tether (not shown) and the VT actuator 552 is configured to be coupled to the ventricular tether (not shown). The AT actuator 542 and the VT actuator 552 may be configured to move linearly along the length of the handle assembly 505 in response to being manipulated by a user to apply tension and/or to introduce slack to the tethers in order to control a configuration of the implant 560. For example, to dispose the implant 560 around a portion of a heart valve, the AT actuator 542 may be moved proximally to tension the atrial tether such that the first arm of the implant 560 is stabilized in the implant holder 535. Then, the VT actuator 552 may be moved proximally to tension the ventricular tether, thereby transitioning the implant 560 to the open configuration in which the second arm (not shown) of the implant 560 is moved away from the first arm (not shown) of the implant 560. Once the implant 560 is positioned to clamp a portion of the heart valve tissue, the VT actuator 552 can be moved distally to transition the implant 560 to the implanted configuration in which the first arm and the second arm exert a clamping force on the heart valve tissue. In order to confirm a position of the implant 560 relative to the heart valve, the AT actuator 542 and the VT actuator 552 can be moved distally to introduce slack to the atrial and ventricular tethers such that the distal end of the implant delivery system can be moved away from the implant 560 without unclamping the implant 560 from the heart valve tissue. This partial disengagement allows for the implant 560 position to be inspected after initial deployment. Moving the AT actuator 542 and the VT actuator 552 proximally can enable repositioning of the implant 560 if desired. For complete disengagement of the implant 560 from the implant holder 535, the atrial and ventricular tethers can be removed (e.g., cut, unlooped, decoupled, etc.) and pulled out of the proximal end of the implant delivery system (e.g., by a user). The implant delivery system 500, the implant holder 535, and the implant 560 may be structurally and/or functionally similar to the implant delivery system 100, the implant holder 135, 335, and the implant 160, 360, 460; and therefore, certain aspects of the delivery system 500, the implant holder 535, and the implant 560 are not described in further detail herein with respect to FIGS. 5A-5C.

FIGS. 6A-6J show images of proximal control mechanisms for each catheter of an implant delivery system. The proximal control mechanisms may be separate or may be included in one handle assembly. As shown in FIGS. 6A-6J, the implant delivery system may include a guide catheter 610 coupled to a guide catheter (GC) actuator 612, a delivery catheter 620 coupled to a delivery catheter (DC) actuator 622, and an implant catheter 630 coupled to an implant catheter (IC) actuator 632. A distal end of the implant catheter 630 is coupled to an implant holder 635, and the implant holder 635 is configured to receive an implant 660. The delivery catheter 630 and the guide catheter 610 may be steerable via the DC actuator 622 and the GC actuator 612, respectively. In some embodiments, the catheters 610, 620, 630 may have varying thickness along their length. For example, the catheters 610, 620, 630 may be more rigid at a proximal end and less rigid at a distal end such that a portion of the catheter 610, 620, 630 that is less rigid may be bent while the more rigid portion of the catheter 610, 620, 630 remains straight and stabilizes the delivery system. In some embodiments, the guide catheter 610 and the delivery catheter 620 may each have a proximal portion having a first hardness, a middle portion having a second hardness lower than the first hardness, and a distal portion having a third hardness smaller than the second hardness. The delivery catheter 620 and the guide catheter 630 may each include a weld ring at a distal end thereof and two articulating members (e.g., pull wires) including a first end coupled to the weld ring and a second end coupled to a proximal control mechanism. In some embodiments, the articulating members may be coupled to the weld ring 180 degrees apart. In some embodiments, the DC actuator 622 and/or the GC actuator 612 may each include a rack and pinion assembly. The gears on each rack and pinion assembly may be calibrated to enable precise steering of each catheter independently. The user may turn a knob 613 on the GC actuator 612 to steer the guide catheter 610. The user may turn a knob 623 on the DC actuator 622 to steer the delivery catheter 620. Each of the catheters 610, 620, 630 may include a flushing port connected to an inner lumen thereof to help reduce frictional contact between the catheter shafts and to prevent air from moving into the patient's circulation.

In some embodiments, the guide catheter 610 may be a 24Fr catheter, the delivery catheter 620 may be a 16Fr catheter, and the implant catheter 620 may be a 12Fr catheter. In some embodiments, a maximum angle the delivery catheter 620 may be steered is larger than a maximum angle the guide catheter 610 may be steered. In some embodiments, a length of the steerable portion of the delivery catheter 620 may be smaller than a length of the steerable portion of the guide catheter 610. In some embodiments, the guide catheter 610 may be steered up to an angle between about 0 degrees to about 150 degrees from the longitudinal axis of the catheter 610, inclusive of all ranges and subranges therebetween. In some embodiments a length of the steerable portion of the guide catheter 610 may be in a range of about 30 mm to about 80 mm, inclusive of all ranges and subranges therebetween. In some embodiments, the delivery catheter 620 may be steered up to an angle between about 0 degrees and about 150 degrees, inclusive of all ranges and subranges therebetween. In some embodiments, a length of the steerable portion of the delivery catheter 620 may be in a range of about 20 mm to about 70 mm, inclusive of all ranges and subranges therebetween.

The implant catheter 630 can be moved linearly (e.g., in a proximal and distal direction) within the delivery catheter 620 via a linear slider 633 on the IC actuator 632. The implant catheter 630 may have a stiffness or hardness of 35D. The implant catheter 630 may be configured for pushability and torquability such that the implant catheter 640 may can extend linear out of the delivery catheter 620 even when the delivery catheter 620 is in a curved configuration. Therefore, the trajectory of the implant 660 may be independent of the curvature of the implant catheter 630, which may allow precise positioning and leaflet capture. The implant catheter 630 may include a plurality of hypotubes (e.g., 4 hypotubes) extending therethrough. Each hypotube may include an elongate member (e.g., the atrial and/or ventricular tethers) extending therethrough. As shown, the IC actuator 632 may further include one or more actuators each coupled to an elongate member to control tension of the elongate members. The one or more actuators may be any suitable actuator such as, for example, a knob, rotating screw, button, slider, etc. In some embodiments, the IC actuator 632 may include a first rotational screw configured to control tension on the atrial tether and a second rotational screw configured to control tension on the ventricular tether. Rotation of the rotating screws in a first direction may apply tension to the tethers and rotation of the rotating screws in a second direction may release tension from the tethers. The implant catheters 610, 620, 630, the implant holder 635, and the implant 660 may be structurally and/or functionally similar to the implant catheters 110, 120, 130, the implant holder 135, 335, and the implant 160, 360, 460; and therefore, certain aspects of the implant catheters 610, 620, 630, the implant holder 635, and the implant 660 are not described in further detail herein with respect to FIGS. 6A-6J.

Figures 7A, 7B, 7C:
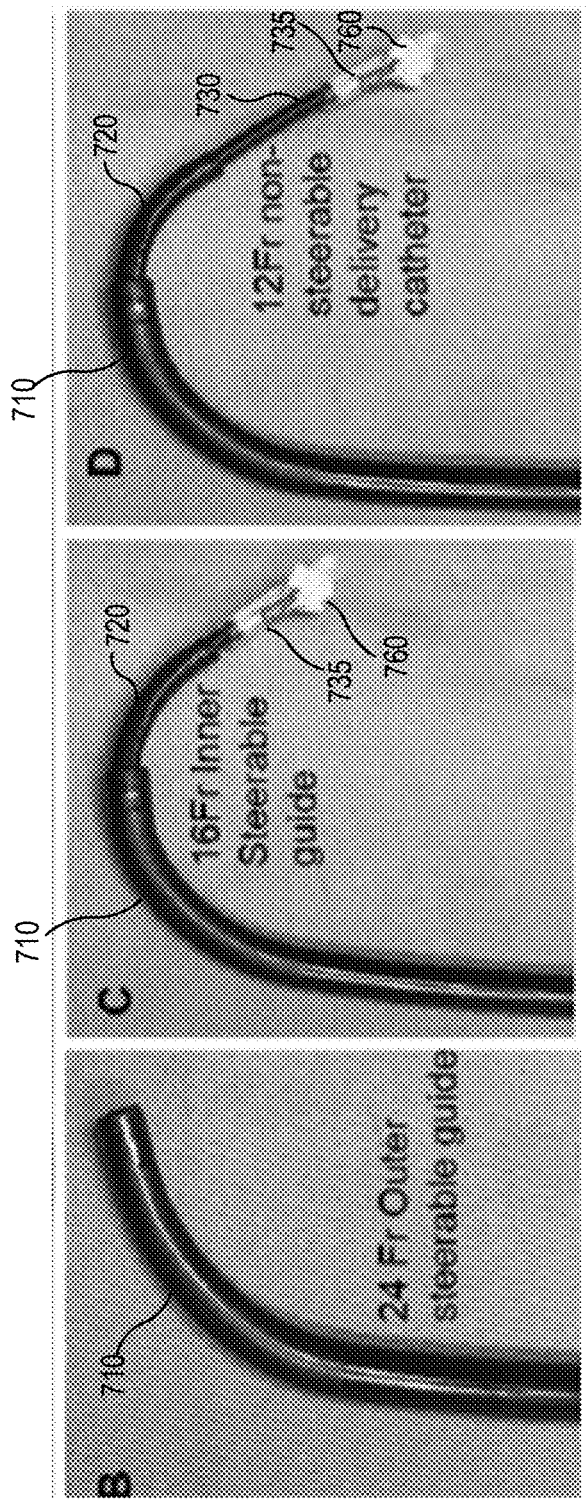
FIGS. 7A-7C shows steerability of an implant delivery system including three catheters, according to embodiments.

FIGS. 7A-7C shows steerability of a three-catheter system of an implant delivery system, according to embodiments. As shown, the implant delivery system includes a guide catheter 710, a delivery catheter 720, and an implant catheter 730. The implant catheter 730 is coupled to an implant holder 735 holding an implant 760. The guide catheter 710 is steerable, the delivery catheter 720 is steerable, and the implant catheter 730 may be non-steerable. However, the implant catheter 730 may be translated linearly relative to the delivery catheter 720 and guide catheter 710 and rotated about its own longitudinal axis. In some embodiments, the implant catheter 730 may be torqued (e.g., rotated about its longitudinal axis). In some embodiments, the guide catheter 710 is steerable in one plane and configured to achieve a curvature corresponding to a path of access to the left atrium by crossing the septum. Although not shown, the delivery catheter 720 may have biplane steerability (e.g., steerability in two planes). The three-catheter system, enables the user to achieve a compound curve at a distal end of the delivery system that may be in more than one plane(s). In some embodiments, the three-catheter system may achieve an angle at the distal end up to about 180 degrees, about 175 degrees, about 170 degrees, about 165 degrees, about 160 degrees, about 155 degrees, about 150 degrees, inclusive of all ranges and subranges therebetween. The implant catheters 710, 720, 730, the implant holder 735, and the implant 760 may be structurally and/or functionally similar to the implant catheters 110, 120, 130, 530, 630 the implant holder 135, 335, 535, 635 and the implant 160, 360, 460, 560, 660; and therefore, certain aspects of the implant catheters 710, 720, 730, the implant holder 735, and the implant 760 are not described in further detail herein with respect to FIGS. 7A-7C.

Figure 8:
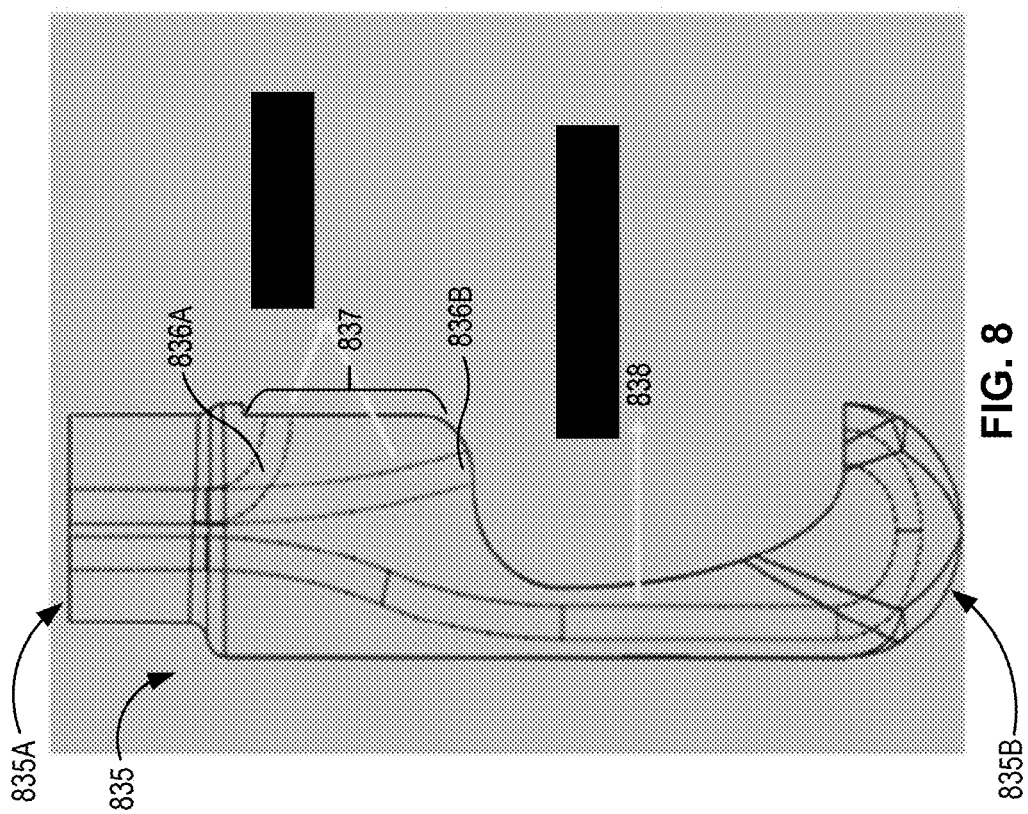
FIG. 8 is a diagram of an implant holder of an implant delivery system, according to embodiments.

FIG. 8 is a diagram of an implant holder 835 of an implant delivery system, according to embodiments. The implant holder 835 includes a proximal end 835A configured to couple to a distal end of an implant catheter (not shown) of the delivery system. The implant holder 835 has a curved distal end 835B. The curved distal end 835B may be atraumatic to prevent damage to tissue during delivery of the implant. The implant holder 835 may further define a cavity configured to receive a first portion the implant (not shown in FIG. 8) and a proximal engagement surface (e.g., a flat portion 837) configured to receive a second portion of the implant. The implant holder 835 includes a pair of atrial channels 836A, 836B and a pair of ventricular channels 838 (only one ventricular channel 838 is shown in FIG. 8 because the other channel sits directly behind the shown channel in side view). Each channel may be configured to receive an elongate member (e.g., a tether) to couple the implant to the implant holder 835 and transition the implant between configurations. A first atrial channel 836A may define a first opening at a proximal end of the flat portion 837 of the implant holder 835. A second atrial channel 836B may define a second opening at a proximal end of the cavity of the implant holder 835. The first opening and the second opening may correspond to positional openings on the first arm of the implant when the implant is coupled to the implant holder 835. The ventricular channels 838 may define a third and fourth opening, respectively, at a distal end of the implant holder 835. The implant holder 835 may be structurally and/or functionally similar to the implant holder 135, 335, 535, 635, 735; and therefore, certain details of the implant holder 835 are not described herein with respect to FIG. 8.

FIGS. 9A-9C show images of an implant holder 935 of an implant delivery system including an implant 960 coupled thereto, according to embodiments. As shown, the implant holder 935 includes a proximal end coupled to an implant catheter and a curved distal end. The implant holder 935 defines a cavity in which a first portion of the implant 960 (e.g., the central portion and a first portion of the second arm) is disposed and an engagement surface (e.g., a flat portion, a surface feature etc.) in which a second portion of the implant 960 (e.g., the first arm 962 and a second portion of the second arm) may be disposed. In some embodiments, the engagement surface may be a flat portion of the implant holder 935. In some embodiments, the engagement surface may be curved or shaped corresponding to a portion of the implant 960. In some embodiments, the engagement surface may include one or more surface features to help engage the portion of the implant 960. The atrial tether 940 is configured to extend through a first atrial channel defining a first opening at a proximal end of the flat portion, through a positional opening on the first arm 962 of the implant 960, and into a second atrial channel defining a second opening at a proximal end of the cavity. The ventricular tether 950 may be configured to extend through a first ventricular channel defining a third opening at the distal end of the implant holder 935, through a positional opening on the second arm 964 of the implant 960, and into a second ventricular channel defining a fourth opening at the distal end of the implant holder 935 adjacent to the third opening.

As shown in FIG. 9B, the atrial tether 940 can be tensioned such that the first arm 962 of the implant abuts the engagement surface of the implant holder 935. Tensioning the atrial tether 940 stabilizes the first arm of the implant 960 such that the first arm 962 is held in place when a force is applied to the second arm 964 of the implant 960. When the ventricular tether 950 is tensioned, the second arm 964 of the implant is moved away from the first arm 962 of the implant 960, thereby transitioning the implant 960 to the open configuration, as shown in FIG. 9C. The implant holder 935 and implant 960 may be structurally and/or functionally similar to the implant holder 135, 335, 535, 635, 735, 835 and implant 160, 360, 460, 560, 660; and therefore, certain details of the implant holder 935 are not described herein with respect to FIGS. 9A-9C.

FIGS. 10-15 depict implants 1060, 1160, 1260, 1360, 1460, 1560 for treating heart valve regurgitation, according to various embodiments. As shown in FIG. 10, an implant 1060 includes a first arm 1062, a second arm 1064, and a central portion 1066. The first arm 1062 may include three positional openings 1075 configured to receive one or more atrial tethers to couple the first arm 1062 to an implant holder. Although not shown, the first arm may further include one or more friction elements configured to secure the first arm 1062 relative to tissue of the heart valve when the implant 1060 is implanted. The second arm 1064 may also include two positional openings 1077 configured to receive one or more ventricular tethers to couple the second arm 1064 to the implant holder. The first arm may further include positional openings 1079A, 1079B on a proximal end thereof. Positional opening 1079A may be centrally located on the proximal end of the first arm 1062, and positional openings 1079B may be on opposing sides of the proximal end of the first arm 1062. The second arm 1064 may further include one or more frictional elements 1070 to secure the implant 1060 to the heart tissue. The central portion 1066 may include one or more horizontal struts 1061 disposed along the length of the central portion 1066. In some embodiments, a cover may be disposed over the central portion 1066 and a portion of the second arm 1064. The implant 1060 may be formed from a material including Nitinol such that the implant 1060 can deform between configurations (e.g., delivery configuration, open configuration, closed configuration, implanted configuration, etc.). The implant 1060 may be structurally and/or functionally similar to any of the implants described herein, and therefore, certain aspects of the implant 1060 are not described in detail with respect to FIG. 10.

Similarly to the implant 1060 of FIG. 10, FIG. 11 shows an implant 1160 including a first arm 1162 including three positional openings 1175, a second arm 1164 including two positional openings 1177, and a central portion 1166. The first arm may include additional positional openings 1179A, 1179B on a proximal end thereof. The first and second arm may include one or more frictional elements 1170 configured to secure the implant 1160 to the heart tissue. The central portion 1166 includes horizontal struts 1161 disposed along its length. In contrast to the implant 1060 of FIG. 10, implant 1160 includes four support members 1180 welded to the implant frame. For example, a first support member and a second support member may be disposed on a first side of the central portion 1166 and a third support member and a fourth support member may be disposed on a second side of the central portion 1166 opposite the first side. Each support member may include a first end that may be welded to the proximal end of the first arm and a second end that may be welded to a proximal end of the central portion 1166. In some embodiments, a cover can be mounted over the support members 1180.

The implant 1260 of FIG. 12 may also include a first arm 1262 and a second arm 1264 including positional openings 1275, 1277 and friction elements 1270; a central member 1266 including horizontal struts 1261; and four support members 1280. The first arm 1262 may include additional positional openings 1279A, 1279B on a proximal end thereof. The implant 1260 may differ from the implant 1160 of FIG. 11, in that the support members 1280 of implant 1260 may be integrated into the implant frame (rather than welded) and may extend further away from the central member 1266 such that the implant 1260 has a larger maximum width. FIG. 13 shows an implant 1360 including a first arm 1362 and a second arm 1364 including positional openings 1375, 1377; a central member 1366; and four support members 1380. The implant 1360 may include additional positional openings 1379A, 1379B on a proximal end of the first arm 1362. The implant 1360 may differ from the implant 1260 of FIG. 12 in that the central member 1366 does not include horizontal struts, a thickness of the support members 1380 is reduced, and/or an overall radius of curvature of the support members 1380 is larger than that of implant 1260. Furthermore, each support member 1380 may include a free end (e.g., a free proximal end) that is not coupled to the implant frame. Although not shown, in some embodiments, the implant 1360 may optionally include friction elements on the first arm 1362 and/or the second arm 1364. In some embodiments, the implant 1360 may not include friction elements.

FIG. 14 shows an implant 1460 including a first arm 1462 and a second arm 1464 including positional openings 1475, 1477 and friction elements 1470; a central member 1466; and four support members 1480. The implant 1460 may differ from the implant 1360 of FIG. 13 in that a width of the second arm 1464 (e.g., the ventricular arm) is increased and a width of an opening defined by the first arm (e.g., the atrial arm) is increased to accommodate the second arm 1464. Therefore, a width of the sides of the first arm 1462 that frame the second arm 1464 is decreased accordingly. Additionally, the positional openings located on opposing sides of the proximal end of the first arm (e.g., 1379B) are removed. Therefore, implant 1460 may only include one positional opening 1479 on the proximal end of the first arm 1462.

FIG. 15 shows an implant 1560 including a first arm 1562 and a second arm 1564 including positional openings 1575, 1577 and friction elements 1570; a central member 1566; and four support members 1580. The implant 1560 may differ from the implant 1460 of FIG. 14 in that a width of the first arm 1562 (e.g., the atrial arm) is larger than a width of the first arm 1462. Additionally, the second arm 1564 has been modified to have two portions having two different widths. A first portion of the second arm 1564 that biases into the opening of the first arm 1562 has a first width, and a second portion of the second arm 1564 that is not disposed in the opening of the first arm 1562 has a second width larger than the first width. Implant 1560 further includes openings 1576 disposed at a distal end of the first arm 1562 and configured to receive radio-opaque markers. The implant 1560 may further include openings on the second arm 1564 configured to receive radio-opaque markers. These radio-opaque openings may enable the user to locate the implant 1560 by imaging during implantation of the implant 1560. The implant design will be described in further detail with respect to FIGS. 16A-16C.

FIGS. 16A-16C illustrate a front perspective view (FIG. 16A), a back perspective view (FIG. 16B), and a bottom view (FIG. 16C) of an implant 1660, according to an embodiment. The implant 1660 may comprise an attachment section 1602 and a coaptation section 1604. The attachment section 1602 may include a first segment or arm 1662 and a first portion of a second segment or arm 1664. The coaptation section 1604 may include a second portion of the second segment or arm 1664 and a central member 1666. The first arm 1662 may extend from a first end of the central member 1666 and the second arm 1664 may extend from a second end of the central member 1666. As shown, at least a portion of each of the first arm 1662 and second arm 1664 may be coplanar when in the closed configuration and/or implanted configuration. In some embodiments, this coplanarity may facilitate securely coupling the implant 1660 to the heart valve tissue. Additionally, as depicted, the first arm 1662 and the second arm 1664 may each have a plurality of friction elements 1672, 1673, 1674a, 1674b extending therefrom. The friction elements 1672, 1673, 1674a, 1674b may be configured to apply a friction force to the heart valve tissue. The friction elements 1672 and 1673 of the first arm 1662 may be coupled to or integrally formed with a tissue-facing surface of the first arm 1662. Similarly, the friction elements 1674a, 1674b of the second arm 1664 may be coupled to or integrally formed with a tissue-facing surface of the second arm 1664. Accordingly, the friction elements 1672, 1673, 1674a, 1674b may be configured to non-destructively engage heart valve tissue when heart valve tissue is received between the first and second arms 1662, 1664. For example, a flat portion of the first arm 1662 and the second arm 1664 may be coplanar in a plane while the friction elements 1672 may extend or protrude beyond the plane. Therefore, when the first arm 1662 and the second arm 1664 are coplanar and clamped around the leaflet, the friction elements 1672 may at least partially extend into the leaflet tissue. As shown, the friction elements 1672, 1673 may extend beyond the second arm 1664 and/or the friction elements 1674 may extend beyond the first arm 1662 when the implant may be in the closed configuration. That is, the friction elements 1672, 1673 of the first arm 1662 may not be coplanar with second arm 1644 and the friction elements 1674 may not be coplanar with the first arm 1662.

In some embodiments, the friction elements 1674a, 1672 in the attachment section 1602 may have an angle with a surface of the respective arm or segment 1662, 1664 than the friction elements 1674b, 1673 in the coaptation section 1604. For example, the friction elements 1672 may form a first angle with a surface of the first segment or arm 1662 and the friction elements 1674a may form a second angle from a surface of the second segment or arm 1662. In some embodiments, the first angle and the second angle may be equivalent. In some embodiments, the friction elements 1674b may form a third angle with the surface of the first segment or arm 1662 and the friction elements 1673 may form a fourth angle with the surface of the second segment or arm 1664. In some embodiments, the third angle and the fourth angle may be equivalent. The first angle and the second angle may be greater than the third angle and the fourth angle such that the friction elements 1674b and 1673 do interfere with one another when the implant 1660 is in the closed configuration.

Extending from the first arm 1662 may be a plurality of support members, such as a first support member 1681, a second support member 1682, a third support member 1683, and a fourth support member 1684. The plurality of support members 1681, 1682, 1683, 1684 may be configured to elastically deflect, including during the delivery process and/or coaptation by a native leaflet. One or more of the support members 1681, 1682, 1683, 1684, including all of the support members, may extend from the first arm 1662 to a free end, which may further facilitate the deformability of each of the support members 1681, 1682, 1683, 1684. In some variations, the free end of each of the supporting members 1681, 1682, 1683, 1684 may be positioned relative to the central member 1666 to facilitate delivery, coaptation, and/or contacting heart valve tissue. For example, when the implant 1660 is in a closed configuration, for example, the free end of each of the support members 1681, 1682, 1683, 1684 may be coplanar with a proximal surface of the central member 1666. The coplanarity of the free ends of the support members 1681, 1682, 1683, 1684 with a proximal surface of the central member 1666 may maximize the volume defined by coaptation section 1604. In some instances, a first support member may mirror or otherwise have corresponding and opposite shapes as a second support member. For example, in some embodiments, a first support member on a first side of the central member may mirror a second support member on a second side of the central member. As shown, the first support member 1681 and the second support member 1682 may be mirrored counterparts to the third support member 1683 and the fourth support member 1684. When implanted, the support members 1681, 1682, 1683, 1684 may deform or otherwise flex independently, such that the support members 1681, 1682, 1683, 1684 need not maintain a mirrored configuration. In some embodiments, the implant 1660 may further include one or more positional openings 1675A, 1675B, 1675C defined by the first arm or segment 1662, as described in further detail with respect to FIG. 25-26.

FIGS. 17A-17G show different views of an implant 1760 for treating heart valve regurgitation in a closed configuration, according to an embodiment. The closed configuration may correspond to a pre-set configuration formed by the manufacturing process, and the implant 1760 may be manufactured from a material (e.g., nitinol) capable of returning to the pre-set configuration after deforming during, for example, a delivery process. The pre-set configuration of the implant 1760 may facilitate the biasing forces described herein. The implant 1760 may comprise an attachment section 1702 and a coaptation section 1704, as previously described. The attachment section 1702 may include a first segment or arm 1762 and a first portion of a second segment or arm 1764, such as a planar section 1724. The coaptation section 1704 may include a second portion of the second segment or arm 1764, such as a curved section 1726, and a central member 1766.

Figure 17A:
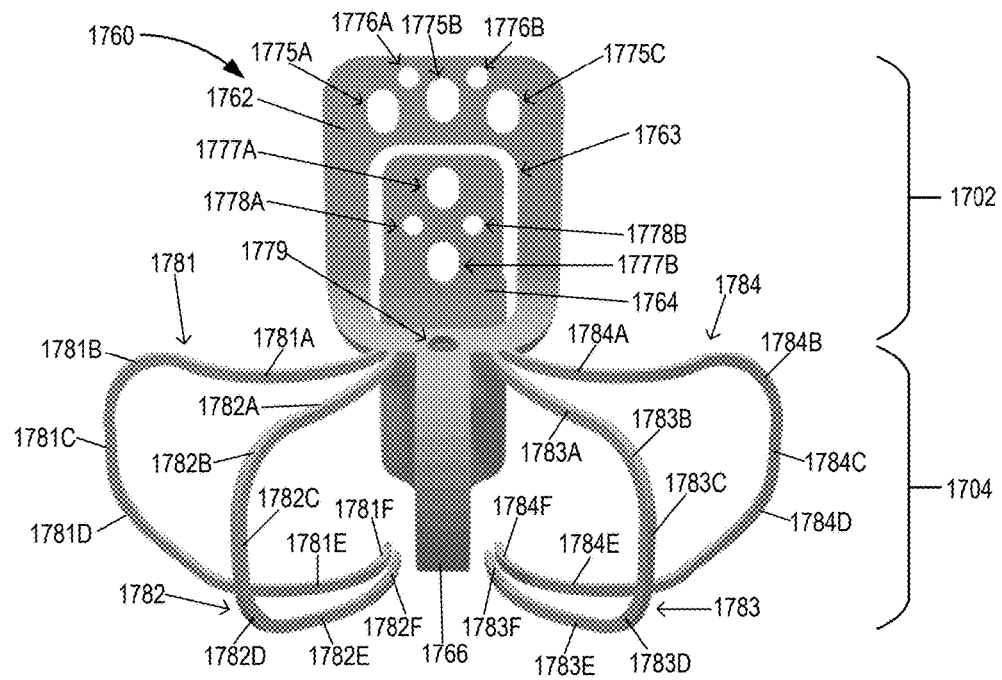
FIG. 17A illustrates a front view of an implant, according to an embodiment.
Figure 17B:
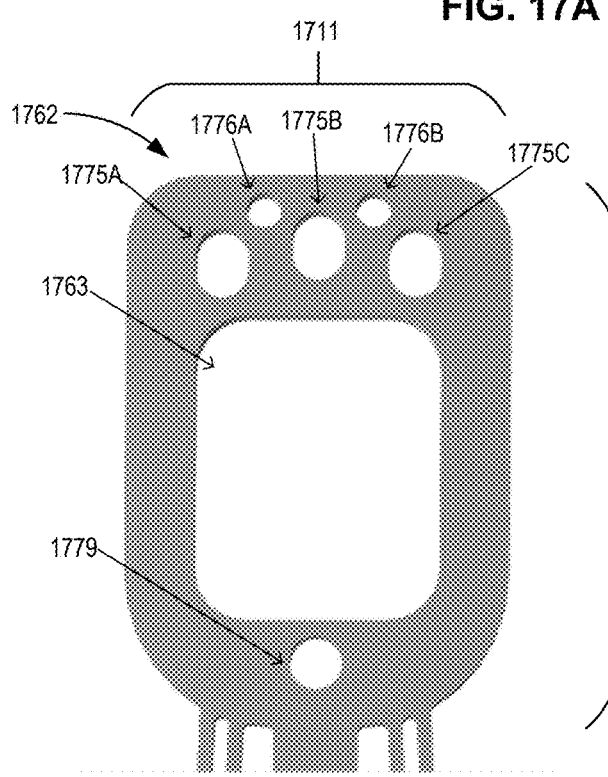
FIG. 17B illustrates a front view of a first arm of the implant of FIG. 17A, according to an embodiment.
Figure 17C:
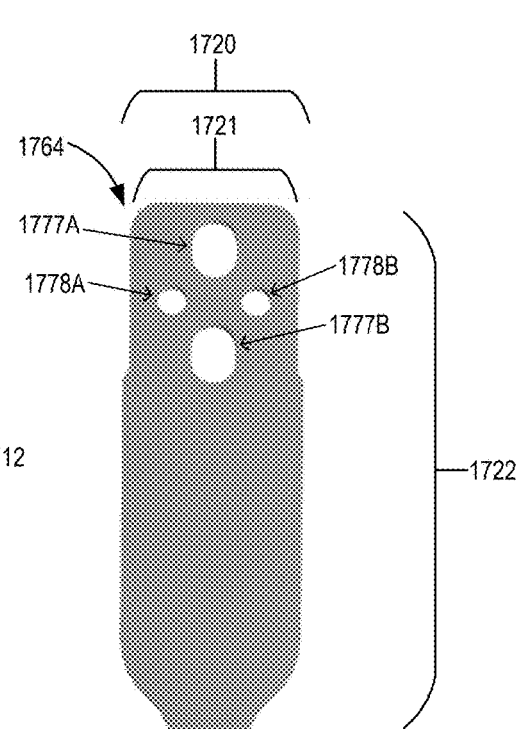
FIG. 17C illustrates a front view of a second arm of the implant body of FIG. 17A, according to an embodiment.
Figure 17D:
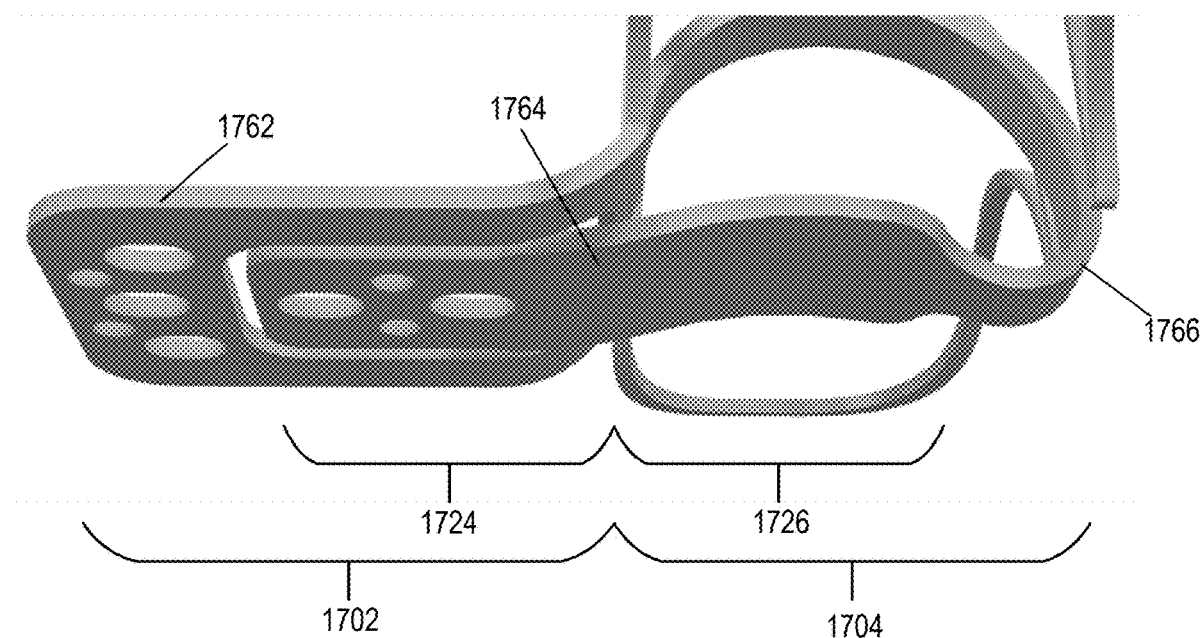
FIG. 17D illustrates a back perspective view of the implant of FIG. 17A, according to an embodiment.
Figure 17E:
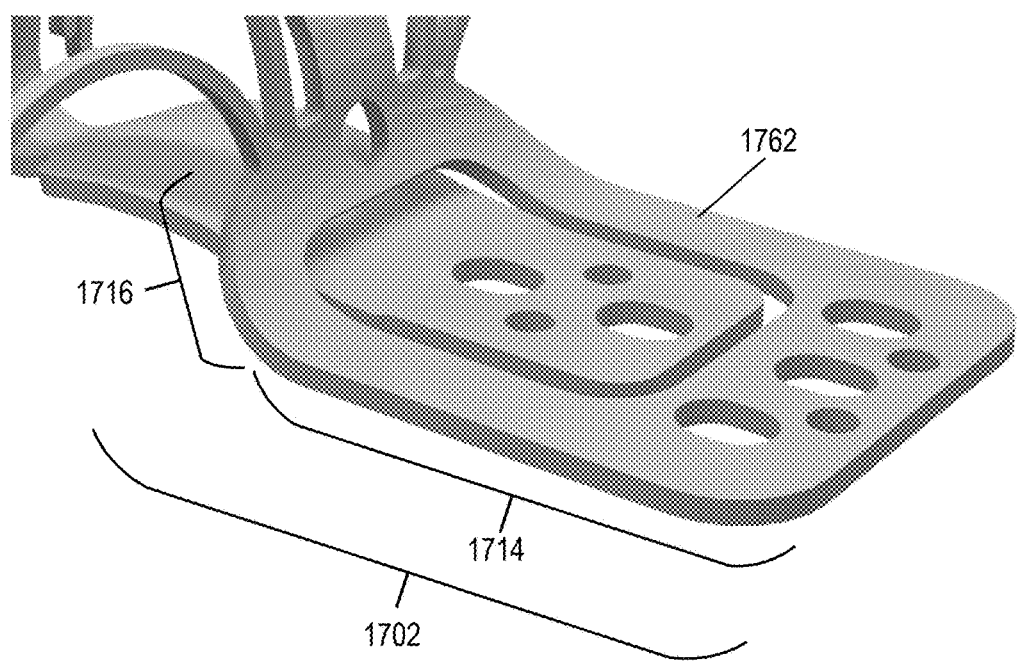
FIG. 17E illustrates a front perspective view of the implant of FIG. 17A, according to an embodiment.

The attachment section 1702 may comprise a length between about 1 mm to about 15 mm, about 2 mm to about 12, about 4 mm to about 10 mm, or about 5 mm to about 7 mm. For example, in some variations, the length of the attachment section 202 may be about 4 mm, about 5 mm, about 6 mm, about 6.5 mm, about 7 mm, or about 10 mm. The coaptation section 1704 may comprise a length between about 1 mm to about 15 mm, about 2 mm to about 12, about 4 mm to about 10 mm, or about 5 mm to about 7 mm. For example, in some variations, the length of the coaptation section 1704 may be about 4 mm, about 5 mm, about 6 mm, about 6.5 mm, about 7 mm, or about 10 mm. A ratio of the length of the attachment section 1702 to the length of coaptation section 1704 may be between about 1:1 to about 1.5:1. In some variations, each of the first and second segments or arms 1762, 1764 may comprise one or more of a planar section and a curved section. As illustrated in FIG. 17E, the first arm 1762 may comprise a planar section 1714 and a curved section 1716. The curved section 1716 may extend from the central member 1766. In some variations, the attachment section 1702 may comprise the planar section 1714 and the curved section 1716. Similarly, the second arm 1764 may comprise a planar section 1724 and the curved section 1726, as shown in FIG. 17D. The curved section 1726 may extend from the central member 1766.

As illustrated, the first arm 1762 may comprise a size greater than the second arm 1764, which may allow the second arm 1764 to interpose the first arm 1762. For example, the second arm 1764 may be received within an intermediate opening 1763 defined by the first arm 1762. The intermediate opening 1763 may be sized such that a gap may form between the first arm 1762 and second arm 1764. The gap may facilitate extending a cover (not shown) through the opening 1763 and between the first arm 1762 and second arm 1764. Accordingly, the first arm 1762 may comprise a width 1711 and a length 1712. In some variations, the width 1711 may be between about 2 mm to about 10 mm, about 2 mm to about 9 mm, about 4 mm to about 8 mm, or about 4 mm to about 7 mm. For example, in some variations, the width 1711 may be about 2 mm, about 4 mm, about 5 mm, about 5.5 mm, about 6 mm, or about 7 mm. The length 1712 may be between about 2 mm to about 12 mm, about 3 mm about 11 mm, about 5 mm to about 10 mm, or about 6 mm to about 8 mm. For example, in some variations, the length 1712 may be about 4 mm, about 5 mm, about 6 mm, about 7 mm, or about 8 mm. In comparison, the second arm 1764 may comprise a first width 1720, a second width 1721, and a length 1722. As described previously, the second arm 1764 may comprise a varying width to reduce mechanical stresses associated with coupling heart valve tissue. The first width 1720 may be greater than the second width 1721. Each of the first width 1720 and second width 1721 may be less than the width 1711 of the first arm 1762. The transition from the first width 1720 to the second width 1721 may occur at any point along the longitudinal dimension (e.g., length) of the second segment or arm 1764, such as about ⅓ from the distal edge of the second segment or arm 1764.

In some variations, the transition between widths 1720, 1721 may be gradual such that stress concentrations may be reduced. In some variations, the first width 1720 may be between about 0.25 mm to about 8 mm, about 1 mm to about 5 mm, about 2 mm to about 4 mm, or about 2.5 mm to about 3.5 mm. For example, in some variations, the first width 1720 may be about 2 mm, about 2.5 mm, about 3 mm, or about 3.5 mm. In some variations, the second width 1721 may be between about 1 mm to about 5 mm, about 2 mm to about 4 mm, about 2.5 mm to about 3.5 mm, or about 2.5 mm to about 3 mm. For example, in some variations, the second width 1721 may be about 2 mm, about 2.5 mm, about 2.75 mm, or about 3 mm. The length 1722 may be less than the length 1712. In some variations, the length 1722 may be between about 2 mm to about 12 mm, about 3 mm to about 12 mm, about 5 mm to about 10 mm, or about 6 mm to about 8 mm. For example, in some variations, the length 1722 may be about 5 mm, about 6 mm, about 7 mm, or about 8 mm.

The first arm 1762 may define a plurality of openings in a distal portion of the first arm 1762, which may be configured to receive one or more elongate members (e.g., sutures) and/or visualization markers (e.g., radiopaque markers). As shown, the first arm 1762 may comprise a plurality of positioning openings (e.g., suture holes) 1775A, 1775B, 1775C that may each be configured to receive an elongate member. In the variation shown, the positioning openings 1775A and 1775C may be arranged collinearly and the positioning opening 1775B may be slightly offset therefrom. The slight offset of positioning opening 1775B may allow an elongate member to be routed through each of the positioning openings 1175A-1775C in a looped configuration such that a number of contact points between the suture is limited, which may reduce a friction force associated with the suture contacting itself. Defined in a proximal portion (e.g., the curved section 1716) of the first arm 1762 may be a positioning opening 1779, which may be configured to receive an elongate member in a similar fashion to the positioning openings 1775A-1775C. The positioning openings 1775B and 1779 may be colinear with the longitudinal axis of the first arm 1762 and may be centered with respect to the width of the first arm 1762. The placement of the positioning openings 1775A-1775C, 1779 may allow for applying an even force to the first arm 1762 via the suture(s) routed therethrough. In some variations, a single elongate member may be routed through each of the positioning openings 1775A-1775C, 1779, which may allow a user to manipulate the entire first arm 1762. In further variations, a first elongate member may be routed through each of the positioning openings 1775A-1775C and a second elongate member may be routed through the positioning opening 1779. In such a variation, a user (e.g., physician) may control the proximal and distal portions of the first arm 1762 separately, which may allow the user to adjust the position of the first arm 1762 with increased precision relative to the variation using a single elongate member. The plurality of openings defined in the distal portion of the first arm 1762 may include a plurality of visualization openings, such as the visualization openings 1776A, 1776B. The visualization openings 1776A, 1776B may each be configured to receive a visualization marker (e.g., radiopaque marker). As described previously, the visualization markers received within the visualization openings 1776A, 1776B may be indirectly visible to the physician while the implant is within the patient.

Similar to the first arm 1762, the second arm 1764 may define a plurality of openings in a distal portion of the second arm 1764, which may be configured to receive one or more elongate members and/or visualization markers. In turn, the openings defined by the second arm 1764 may facilitate opening, closing, and/or locating the second arm 1764. As shown, a plurality of positioning openings (e.g., suture holes) may be defined in a distal portion of the second arm 1764. The plurality of positioning openings may include the positioning openings 1777A, 1777B. The positioning openings 1777A, 1777B may be collinear relative to each other and may also be collinear with the longitudinal axis of the second arm 1764 and/or central member 1766. The collinear configuration of the positioning openings 1777A, 1777B may facilitate routing an elongate member through each of the positioning openings 1777A, 1777B. In this way, the elongate member may form a loop such that the elongate member may, for example, be routed back through the delivery device. Further defined in the distal portion of the second arm 1764 may be a plurality of visualization openings, such as visualization openings 1778A, 1778B. The visualization openings 1778A may each be configured to receive a visualization marker (e.g., radiopaque marker) and may be colinear with a transverse axis of the second arm 1764.

The first arm 1762 may comprise a plurality of support members 1781, 1782, 1783, 1784 extending from a curved portion of the first arm 1762. The central member 1766 may separate a first support member 1781 and a second support member 1782 from a third support member 1783 and a fourth support member 1784. As shown, each of the plurality of support members 1781-1784 may comprise a plurality of curves. For example, the first support member 1781 may comprise a first section 1781A that is connected to a second section 1781B, which may be connected to a third section 1781C. The first section 1781A may comprise a first radius of curvature forming a convex shape. The second section 1781B may comprise a second radius of curvature that may form a concave shape. The first radius of curvature may be greater than the second radius of curvature. The third section 1781C may extend along a plane parallel to a plane defined by the first arm 1762. Extending from the third section 1781C may be a fourth section 1781D, which may comprise a curve with a third radius of curvature. A fifth section 1781E may extend from the fourth section 1781D. A sixth section 1781F may extend from the fifth section 1781E, and the sixth section 1781F may comprise a curve with a fourth radius of curvature. The sixth section 1781F may define a free distal end of the support member 1781. The free distal end of the sixth section 1781F may be curved towards the central member 1766. The free distal end of the support members 1781 may be dulled such that it may not pierce heart valve tissue. Accordingly, as described and illustrated, the support members 1781 may comprise a concave and convex configuration. In some variations, the fourth support member 1784 may be symmetric to the first support member 1781 about the central member 1766. The fourth support member 1784 may include a first section 1784A, a second section 1784B, a third section 1784C, a fourth section 1784D, a fifth section 1784E, and a sixth section 1784F that are similar to those of the first support member 1781. The first support member 1781 and fourth support member 1784 may together define a total width 1732 of the implant 1760. In some variations, the total width 1732 may be between about 10 mm to about 20 mm, about 12 mm to about 20 mm, about 13 mm to about 18 mm, about 14 mm to about 17 mm, or about 15 mm to about 16 mm. For example, in some variations, the total width 1732 may be about 12 mm, about 14 mm, about 15 mm, about 15.5 mm, about 15.8 mm, about 16 mm, or about 17 mm. The second support member 1782 and/or third support member 1783 may define a total height 1733 of the implant 1760. In some variations, the total height 1733 may be between about 3 mm to about 12 mm, about 4 mm to about 9 mm, about 5 mm to about 8, or about 6 mm to about 8 mm. For example, in some variations, the total height 1733 may be about 4 mm, about 5 mm, about 6 mm, about 7 mm, about 7.2 mm, about 7.5 mm, or about 8 mm. The total width 1732, total height 1733, and length of the coaptation section 1704 may be used (e.g., multiplied together) to determine a total volume of the coaptation section.

As further illustrated, the second support member 1782 may comprise a plurality of sections 1782A, 1782B, 1782C, 1782D. A first section 1782A may comprise a first radius of curvature than may be less than the first radius of curvature of the first section 1782A of the first support member 1782. Extending from the first section 1782A may be a second section 1782B that may comprise a curve with a second radius of curvature. A third section 1782C may extend from the second section 1782B and may connect to a fourth section 1782D. The third section 1782C may be configured to avoid contacting heart valve tissue. The fourth section 1782D may comprise a curve with a third radius of curvature. The third radius of curvature may be similar (e.g., substantially equivalent) to the second radius of curvature of the second section 1782B. A fifth section 1782E may extend from the fourth section 1782D. A sixth section 1782F may extend from the fifth section 1782E, and, similar to the description of 1782F above, may comprise a curve with a fourth radius of curvature and may define a free distal end of the support member 1782. The free distal end of the support member 1782 may be curved towards the central member 1766 and/or curved section 1726. In some variations, the third support member 1783 may be symmetric to the second support member 1782 about the central member 1766. In some embodiments, the third support member 1783 may include a first section 1783A, a second section 1783B, a third section 1783C, a fourth section 1783D, a fifth section 1783E, and a sixth section 1783F similar to those of the second support member 1782. The second support member 1782 may define an apex distance 1730 corresponding to the distance between the apex of the support member 1782 and the apex of the central member 1766. The apex of the central member 1766 may determine a central member height 1734, relative to a plane defined by the planar section 1714 of the first segment or arm 1762. The central member height 1734 may be between about 1 mm to about 7 mm, about 2 mm to about 6 mm, or about 3 mm to about 5 mm. For example, in some variations, the central member height 1734 may be about 3 mm, about 4 mm, or about 5 mm. Accordingly, the apex distance 1730 may be between about 1 mm to about 6 mm, about 2 mm to about 5 mm, or about 2.5 mm to about 3.5 mm. For example, in some variations, the apex distance 1730 may be about 1 mm, about 2 mm, about 3 mm, about 4 mm, or about 5 mm. Similarly, the third support member 1783 may define an apex distance 1731 corresponding to the distance between the apex of the support member 1783 and the apex of the central member 1766. The apex distance 1731 may be the same as the apex distance 1730. In some variations, the apex distances 1730, 1731 may be different, such as during deflection of one or more support members during coaptation by a native leaflet. Accordingly, the apex distance 1731 may be between about 1 mm to about 6 mm, about 2 mm to about 5 mm, or about 2.5 mm to about 3.5 mm. For example, in some variations, the apex distance 1730 may be about 1 mm, about 2 mm, about 3 mm, about 4 mm, or about 5 mm.

FIGS. 18A-18C illustrate a front perspective view, a back perspective view, and a bottom view, respectively, of a first plate configured to be coupled to a bottom surface of a first arm of an implant, according to an embodiment. The first plate 1862 may comprise a planar section 1802, a curved section 1804, a plate extension 1806, an intermediate opening 1863, a plurality of positioning openings 1875A-1875C, 1879, and friction elements 1872, 1873. The planar section 1802 and the curved section 1804 may each comprise shapes corresponding to the respective sections of the first arm described herein. The planar section 1802 may define one or more openings, such as positioning openings 1875A-1875C, and the curved section 1804 may also define one or more openings, such as positioning opening 1879. As described above, the positioning openings 1875A-1875C, 1879 of the first plate 1862 may correspond to positioning openings of the first arm such that an elongate member may be routed through one or more the positioning openings 1875A-1875C, 1879 to facilitate opening and/or closing the implant. Interposing each of the planar section 1802 and curved section 1804 may be the intermediate opening 1863. The intermediate opening 1863 may comprise a size and shape corresponding to the size and shape of the second arm (not shown) such that the second arm may be received therein. For example, the opening 1863 may be sized such that the second arm may pass through the opening 1863 without contacting the first plate 1862.

Extending from the curved section 1804 may be the plate extension 1806, which may be configured to contact heart valve tissue and/or apply a compressive force thereto. While the planar section 1802 and curved section 1804 may contact the first arm, the plate extension 1806 may not contact the first arm (e.g., the plate extension 1806 may extend away from the first arm). The plate extension 1806 may advantageously apply a compressive force due to the protruding configuration of the plate extension 1806. The plate extension 1806 may comprise a smaller width than the planar section 1802 and/or curved section 1804, which may contribute to the elastic deformability of the plate extension 1806. In some variations, the width of the plate extension 1806 may be such that the plate extension 1806 may be positioned between (e.g., not in contact with) friction elements of the second segment or arm or second plate. Accordingly, the width of the plate extension 1806 may be between about 0.5 mm to about 3 mm, about 0.5 mm about 2 mm, about 1 mm to about 2 mm, or about 1 mm to about 1.5 mm. For example, in some variations, the width of the plate extension 306 may be about 0.5 mm, about 1 mm, about 1.2 mm, or about 1.5 mm.

The plates may comprise friction elements which, as described previously, may be configured to apply a friction force to heart valve tissue. As shown, the first plate 1862 may comprise a first set of friction elements 1872 along two edges of the planar section 1802 and a second set of friction elements 1873 along two edges of the plate extension 1806. The first set of friction elements 1872 may define a first angle relative to a tissue-facing surface of the planar section 1802 and the second set of friction elements 1873 may define a second angle relative to a tissue-facing surface of the plate extension 1806. The first and second angles may not be the same, which may facilitate easier disengagement of the friction elements 1872, 1873 from tissue such that the implant as described herein may be non-destructively removed from a first position of a heart valve (e.g., a first native valve leaflet) and moved to a second position of the heart valve. In further variations, the first and second angles may be the same, which may facilitate faster and/or easier manufacturing.

FIGS. 19A-19C illustrate a front view, a side view, and a bottom view of a second plate 1964 configured to be coupled to a top surface of a second arm of an implant, according to an embodiment. The second plate 1964 may comprise a planar section 1902, a curved section 1904, a plurality of positioning openings 1977A, 1977B, and a plurality of friction elements 1974. The planar section 1902 and the curved section 1904 may each comprise shapes corresponding to the second arm described herein. Similar to the first plate 1862, the second plate 1964 may define one or more openings, such as positioning openings 1977A, 1977B. The positioning openings 1977A, 1977B may correspond to positioning openings of the second arm such that an elongate member may be routed through one or more the positioning openings 1977A, 1977B to facilitate opening and/or closing the implant. The plurality of friction elements 1974 may define a third angle relative to a tissue-facing surface of the second plate 1964. The third angle may be the same or different as either the first angle or second angle associated with the plurality of friction elements 1872, 1873. Any of the first, second, or third angles may be adjusted during the manufacturing phase or by a physician prior to inserting the implant into the patient.

Figure 20E:
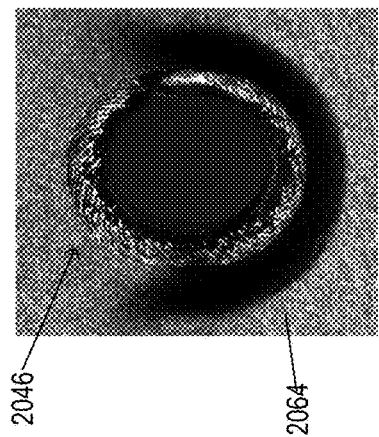
FIGS. 20B-20E show edges of the implant where one or more plates are welded to the implant, according to embodiments.
Figure 20B:
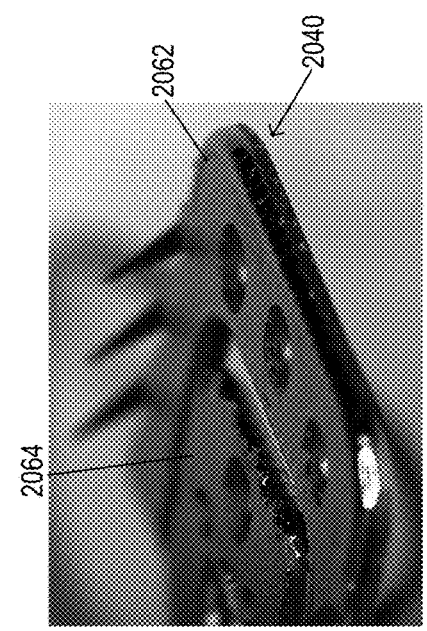
Figure 20D:
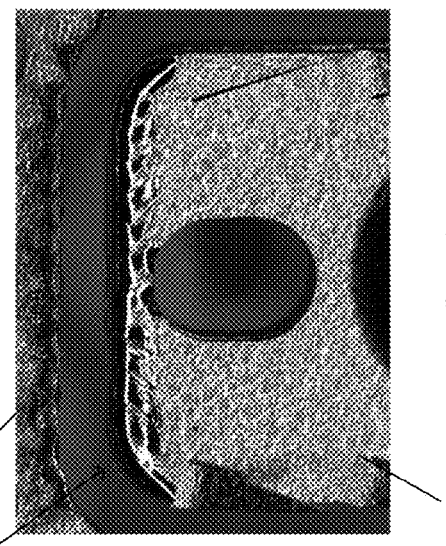
Figure 20A:
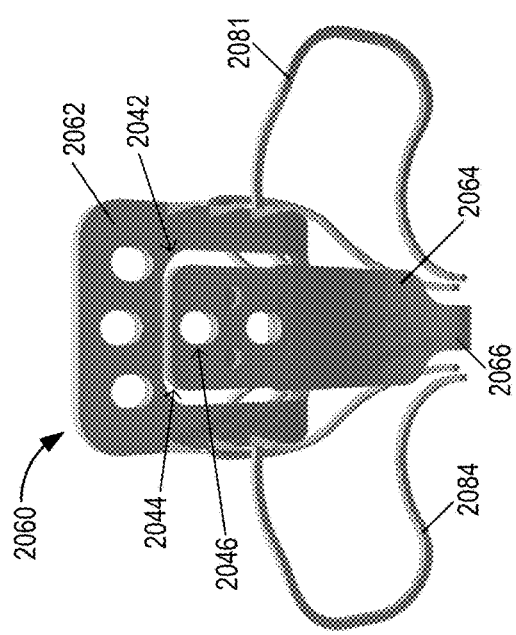
FIG. 20A illustrate a top perspective view of an implant, according to an embodiment.
Figure 20C:
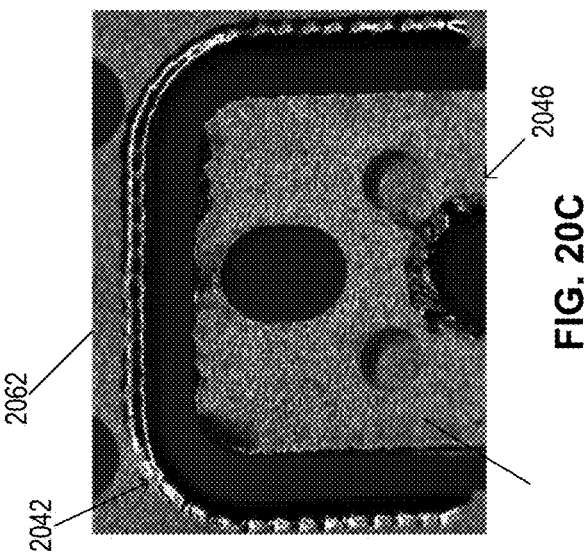

FIG. 20A illustrate an exemplary embodiment of coupling the first plate to the first arm and the second plate to the second arm. The illustrated implant 2060 may be made of a metal (e.g., nitinol) so the components may be well-suited for welding. As illustrated, the first plate may be coupled to the first arm via a plurality of welds, such as along a first seam 2040 and a second seam 2042. The first seam 2040 may extend along a portion of an outer perimeter of each of the first arm and first plate, and the second seam 2042 may extend along a portion of an inner perimeter of each of the first arm and first plate. The length of the weld seams 2040, 2042 may be sufficient to withstand any forces associated with the surgical procedure, implanting process, and/or cardiac events described herein. Accordingly, the length of the weld seam 2040 may be between about 2 mm to about 15 mm, about 4 mm to about 12 mm, or about 5 mm to about 8 mm. For example, in some variations, the length of the weld seam 2040 may be about 2 mm, about 4 mm, about 5 mm, about 6 mm, about 7 mm, or about 8 mm. The length of the weld seam 2042 may be between about 3 mm to about 15 mm, about 4 mm to about 13 mm, about 5 mm to about 12 mm, or about 6 mm to about 10 mm. For example, in some variations, the length of the weld seam 2042 may be about 4 mm, about 6 mm, about 8 mm, about 10 mm, or about 12 mm. Additionally or alternatively, the second plate may be coupled to the second arm via a plurality of welds, such as along a third seam 2044 and a fourth seam 2046. The third seam 2044 may extend along a portion of an outer perimeter of each of the second plate and the second arm, and the fourth seam 2046 may extend along the entirety of a perimeter of an opening (e.g., a suture hole) defined by each of the second arm and the second plate. Accordingly, the length of the weld seam 2044 may be between about 3 mm to about 15 mm, about 4 mm to about 12 mm, or about 5 mm to about 10 mm. For example, in some variations, the length of the weld seam 2044 may be about 4 mm, about 6 mm, about 8 mm, or about 10 mm. The length of the weld seam 2046 may be between about 0.5 mm to about 5 mm, about 1 mm to about 5 mm, or about 1 mm to about 3 mm. For example, in some variations, the length of the weld seam 2046 may be about 0.5 mm, about 1 mm, about 2 mm, about 3 mm, or about 5 mm.

Figure 21A:
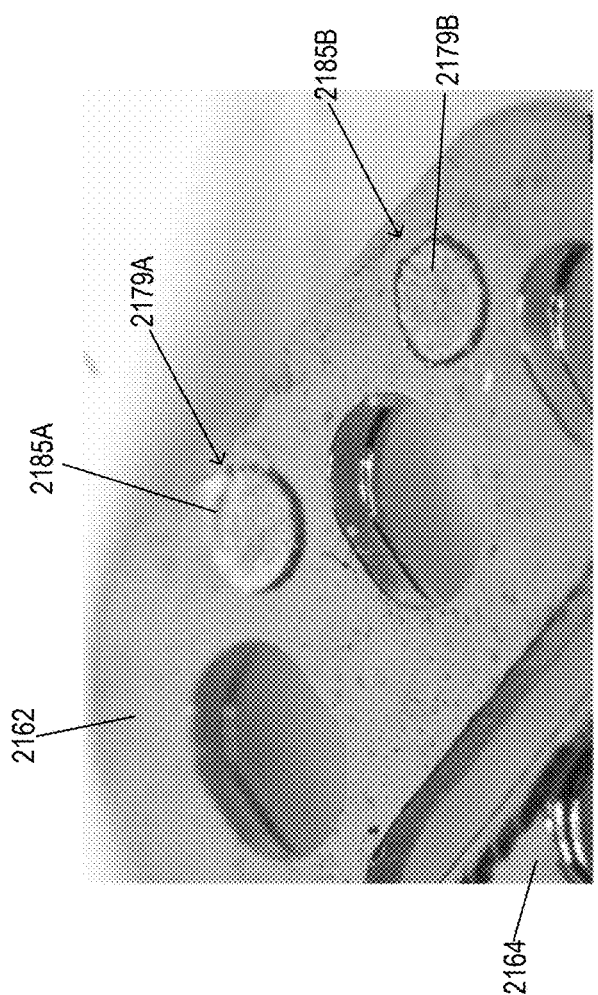
FIGS. 21A-21B illustrate a portion of a first arm showing visualization markers received within an implant, according to embodiments.
Figure 21B:
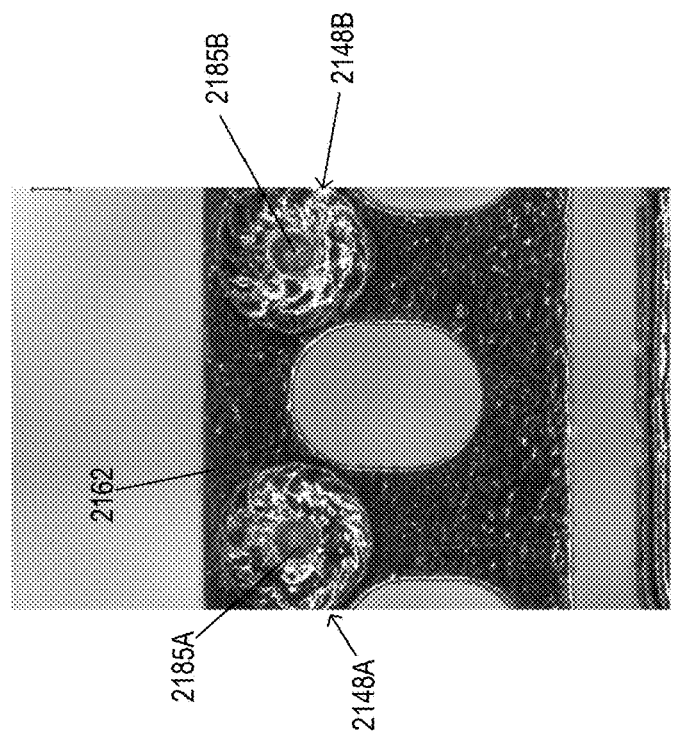

FIGS. 21A-21B illustrate an exemplary variation of visualization markers (e.g., radiopaque markers) received within visualization openings (e.g., radiopaque openings) of a first arm 2162. The first arm 2162 may comprise a first visualization opening 2179A configured to receive a first visualization marker 2185A and a second visualization opening 2179B configured to receive a second visualization marker 2185B. The visualization openings 2179A, 2179B may comprise substantially circular shapes and the visualization markers 2185A, 2185B may be similarly shaped. In some variations, the visualization markers 2185A, 2185B may comprise a diameter slightly less than the diameter of the respective visualization openings 2179A, 2179B such that the visualization markers 2185A, 2185B may utilize friction (e.g., via a friction fit) to fixedly couple to the respective visualization openings 2179A, 2179B. In other variations, the visualization markers 2185A, 2185B may comprise a diameter smaller than the respective visualization opening 2179A, 2179B such that a friction fit technique may not be possible, so an adhesive may be placed under, around, and/or on top of the visualization marker 2185A, 2185B to fixedly couple the radiopaque marker to the radiopaque opening. In either instance, the visualization markers 2185A, 2185B may be securely fastened in place using, for example, an adhesive and/or welding. The visualization markers 2185A, 2185B shown may be manufactured from a metal (e.g., platinum) and thus may be welded into place along a first marker seam 2148A and a second marker seam 2148B. The length of the marker seams 2148A, 2148B may correspond to the entire circumference of the respective visualization openings 2179A, 2179B. In some variations, the length of marker seams may correspond to only a portion of the circumference of the respective visualization openings (e.g., via spot welding). visualization markers may be coupled to visualization openings of the second arm in a similar fashion.

Figure 22A:
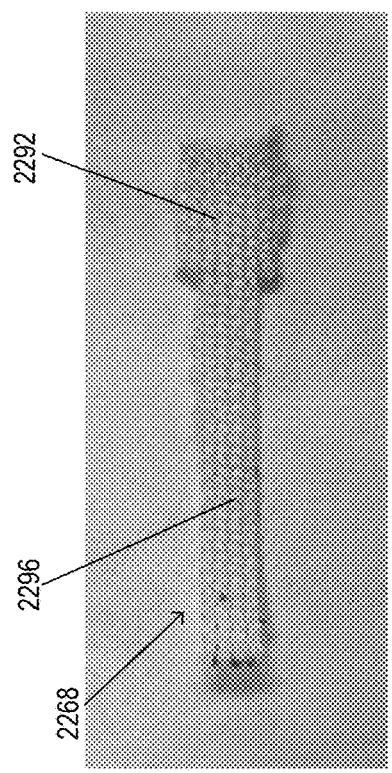
FIGS. 22A-22C illustrate a cover for an implant for treating heart valve regurgitation, according to embodiments.
Figure 22C:
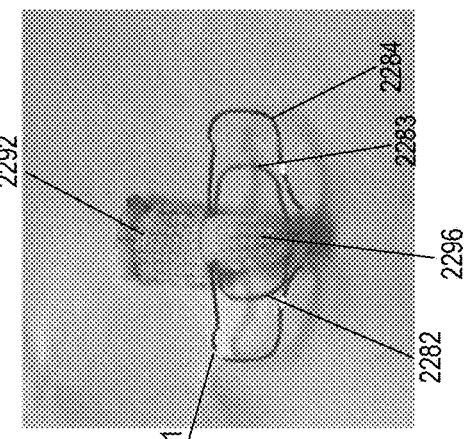
Figure 22B:
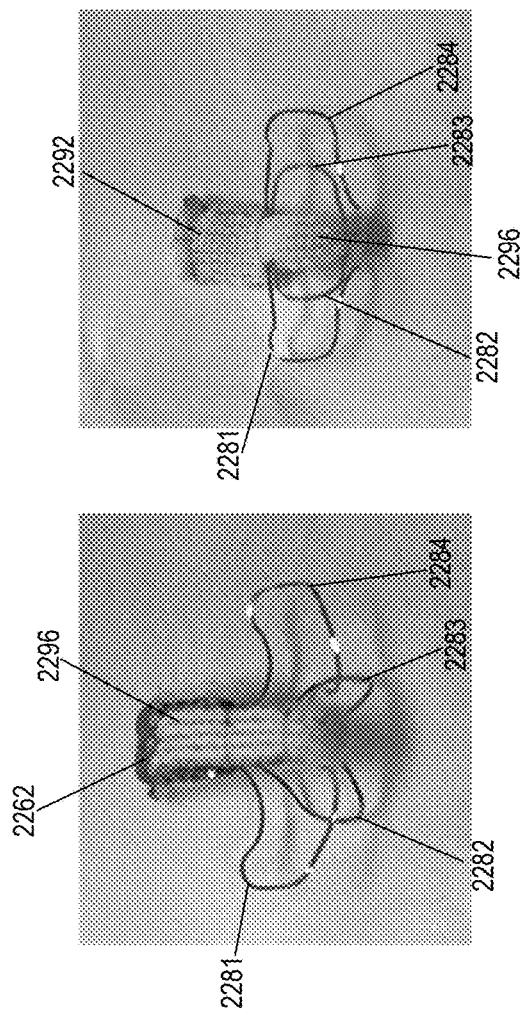

FIG. 22A illustrate a cover for an implant for treating heart valve regurgitation, according to embodiments. The cover 2268 may be configured to cover portions of an attachment section, such as portions of the first arm, central member, and second arm described herein. For example, the cover 2268 may comprise a first section 2292 configured to cover portions of the first arm, and a second section 2296 configured to cover portions of the central member and the second arm. As shown, the first section 2292 may comprise a greater width than the second section 2296, which may correspond to the greater width of the first arm relative to the second arm and/or central member. As also shown, the second section 2296 may comprise a greater length than the first section 2292, which may correspond to the combined lengths of portions of the central member and the second arm relative to the length of the first arm. FIGS. 22B-22C illustrate alternative views of the cover 2268 coupled to an implant. As shown, the section 2296 may cover a majority of the second arm and the central member and may extend through an opening defined by the first arm 2262. The section 2292 may cover a majority of the first arm, while leaving the support members 2281, 2282, 2283, 2284 extending from the first arm uncovered. The sections 2292, 2296 may similarly leave uncovered friction elements extending from each of the first and second arms. The cover 2268 may be securely coupled to the implant via a plurality of sutures along a perimeter of the cover 2268.

Figure 24:
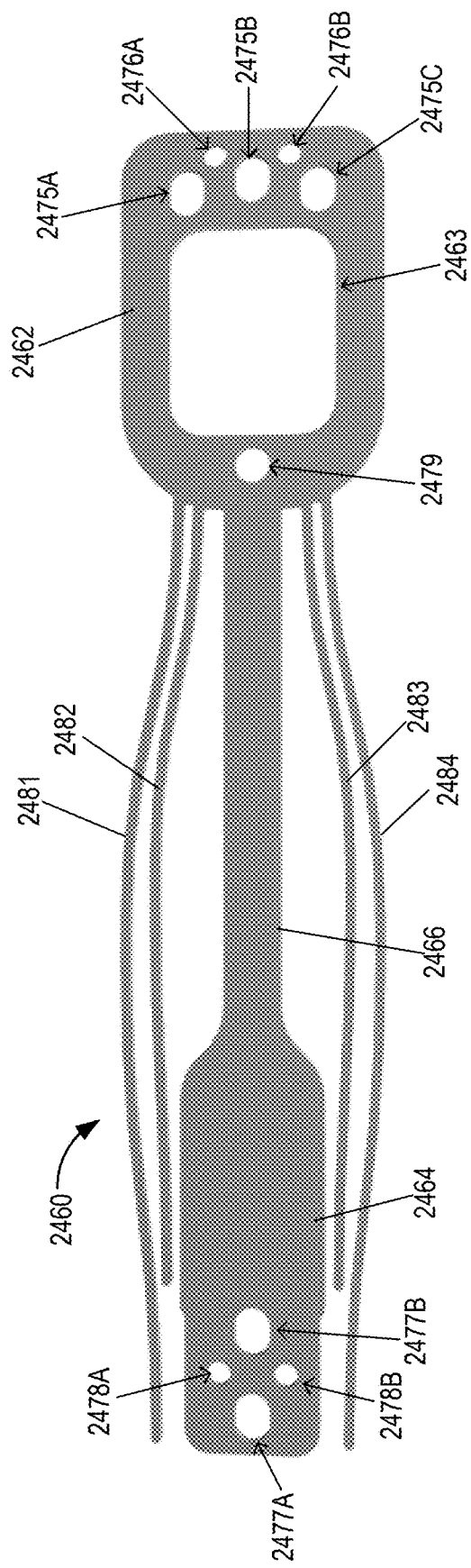
FIG. 24 illustrates a front view of the implant shown in FIGS. 17A-17G in a substantially flat configuration, according to embodiments.

FIG. 23A illustrates a top view of a cover in a flat configuration, according to embodiments. FIGS. 23B-23C illustrate a front view of the cover coupled to the implant, according to embodiments. As illustrated, the cover 2368 may be used in combination with the cover 2268 shown in FIGS. 22A-22C. The cover 2368 may be configured to cover portions of the support members and extend beyond the implant. For example, the cover 2368 may comprise a first section 2392A and a second section 2392B that together define a channel 2395. The first section 2392A may be configured to cover a portion of support members on a first side of the central member, and the second section 2392B may be configured to cover a portion of support members on a second side of the central member. The channel 2395 may be configured to receive the central member, which may already be covered by the cover 2268. The cover 2368 may further comprise a third section 2394, which may be configured to cover another portion of the support members on both sides of the central member. In this way, the third section 2394 may be coupled to each of the first section 2392A and second section 2392B such that the support members are covered therebetween. The cover 2368 may further comprise a fourth section 2396, which may be initially formed as a rectangle before being rolled up into a cylinder and partially attached to other portions of the cover 2368. For example, the fourth section 2396 may be coupled to the third section 2394 via one or more sutures and/or adhesives. In this way, the fourth section 2396 may extend beyond the implant body, which may increase the surface area of the coaptation section to provide a larger surface area for coaptation. The increased surface for coaptation may facilitate use of the implant described in a patient with a clinical condition (e.g., heart valve regurgitation) associated with a relatively large gap between leaflets FIG. 24 illustrates a front view of the implant shown in FIGS. 17A-17G in a substantially flat configuration, according to embodiments. The flat configuration of the implant body may be achieved via cutting the outline of the implant from a flat sheet of material. As shown, the implant body 2460 shown in a flat configuration may include a first arm 2462, a central member 2466, and a second arm 2464. The first arm 2462 may extend from, or may be otherwise coupled to, a first end of the central member 2466 and the second arm 2464 may extend from, or may be otherwise coupled to, a second end of the central member 2466 that is opposite the first end. The first arm 2462 may define a plurality of openings in a distal portion of the first arm 2462, such as positioning openings 2475A, 2475B, 2475C that are each configured to receive an elongate members (e.g., suture), similar to the description for FIG. 17A-17G. The plurality of openings in the distal portion of the first arm 2462 may also include a plurality of visualization openings, such as visualization openings 2476A, 2476B. As described previously in reference to FIG. 17A-17G, the visualization openings 2476A, 2476B may each be configured to receive a visualization marker. Further defined by the first arm 2462 may be an intermediate opening 2463, which may be configured to receive a portion of the second arm 2464. The central opening 2463 may be further configured to receive a portion of a cover, such as the cover 2268, 2368 described previously. Defined in a proximal portion of the first arm 2462 may be a positioning opening 2479, which may be configured to receive an elongate member in a similar fashion to the positioning openings 2475A-2475C.

Extending from the first arm 2462 may be a plurality of support members, such as the support members 2481, 2482, 2483, 2484. The support members 2481, 2482 may be separated from the support members 2483, 2484 by the central member 2466. In some variations, the support members 2481, 2482 may be symmetric to the support members 2483, 2484 about a longitudinal axis of the first arm 2462 and/or the central member 2466. Accordingly, the support members 2481, 2484 may each comprise a first length and the support members 2482, 2483 may each comprise a second length. The first length may be greater than the second length. The support members 2481-2484 may comprise a thickness equivalent to the rest of the implant body and may each comprise a width of about 100 microns to about 200 microns, such as about 150 microns. The width may facilitate the flexibility of the support members described herein by reducing mechanical stresses generated at the connection points between the support members and the first arm 2462.

Similar to the descriptions provided in reference to FIG. 17A-17G, the second arm 2464 may comprise a plurality of openings to facilitate opening, closing, and/or locating the second arm 2464. As shown, a plurality of positioning openings may be defined in a distal portion (relative to a physician during implanting when the implant body may be in a closed configuration) of the second arm 2464. The plurality of positioning openings may include the positioning openings 2477A, 2477B. Further defined in the distal portion of the second arm 2464 may be a plurality of radiopaque openings, such as visualization openings 2478A, 2478B. The visualization openings 2478A, 2478B may each be configured to receive a visualization marker, similar to the descriptions provided previously.

Figure 26:
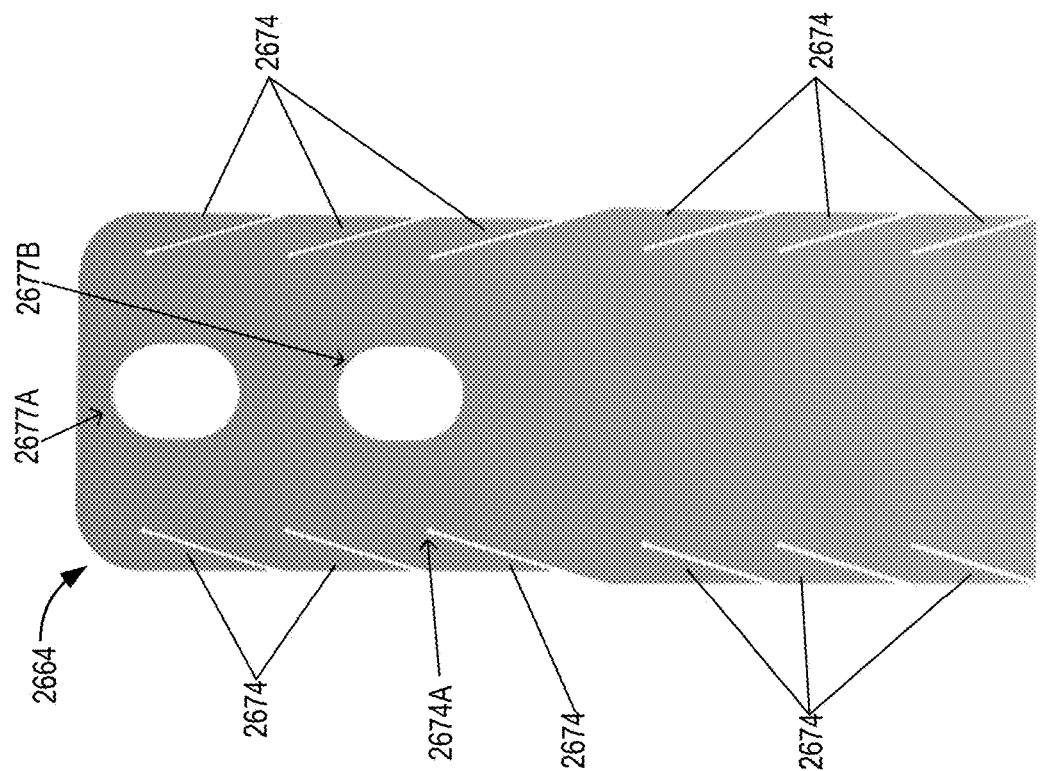
FIG. 26 illustrates a front view of a variation of the second plate shown in FIGS. 19A-19C in a substantially flat configuration, according to embodiments.
Figure 25:
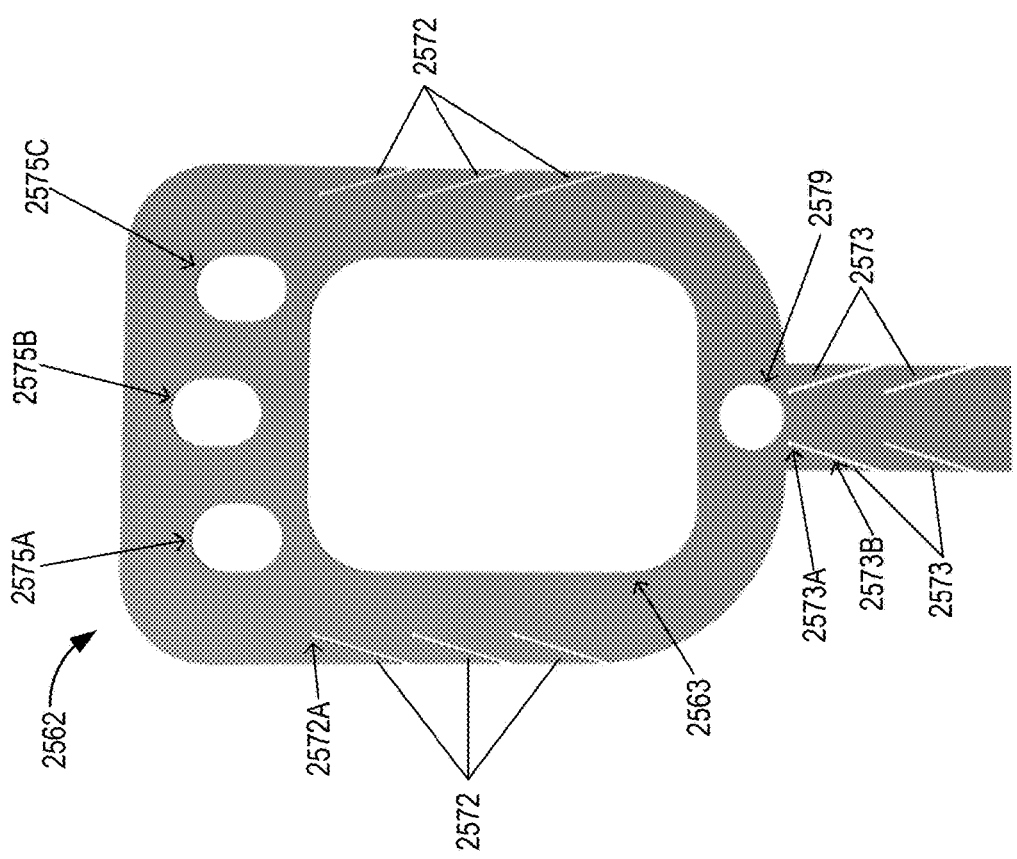
FIG. 25 illustrates a front view of a variation of the first plate shown in FIGS. 18A-18C in a substantially flat configuration, according to embodiments.

FIGS. 25 and 26 illustrate exemplary variations of a first plate 2562 in a flat configuration and a second plate 2564 in a flat configuration, respectively, configured to couple to the body described herein. The first plate 2562 may be manipulated into the configuration shown in FIGS. 18A-18C. Accordingly, the description of the positioning openings 2575A, 2575B, 2575C, 2579 correspond to the positioning openings 1875A, 1875B, 1875C, 1879. The plate 1862 may further comprise a plurality of slots 2572 that may each be adjacent to a friction element 1872, 1873 (not shown). Each slot 2572 may define a length corresponding to a height of the friction element 1872, 1873 and may facilitate bending the friction element 1872, 1873 (shown in FIGS. 18A-18C) to the desired angle that corresponds to a desired friction force. Each slot 2572 may terminate in a circular portion 2572A. The circular portion 2572A may be configured to reduce mechanical stresses associated with bending the friction elements 1872 (shown in FIGS. 18A-18C). The second plate 2664 may be manipulated into the configuration shown in FIGS. 19A-19C. The second plate 2664 may comprise a plurality of positioning openings 2677A, 2677B, which may correspond to the positioning openings 1977A, 1977B. The second plate 2664 may further comprise a slot 2674 and a circular portion 2674A that function similarly to the slot 2572 and circular portion 2572A, respectively, described in reference to the first plate 2562 of FIG. 25. The plates 2562, 2664 may then be coupled to the implant body as described previously in reference to FIGS. 20A-20E.

Figure 27B:
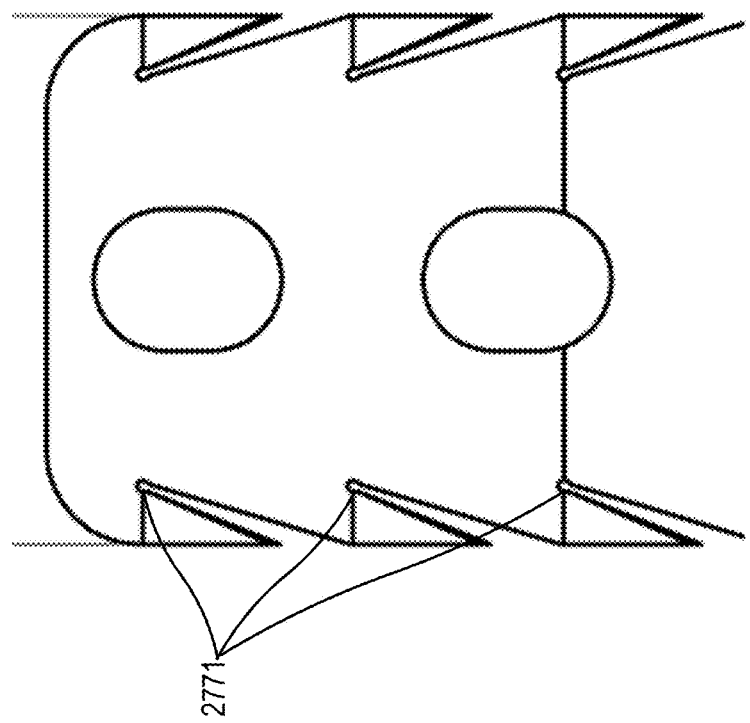
FIGS. 27A-27B are front views of an implant for treating heart valve regurgitation, according to an embodiment.
Figure 27A:
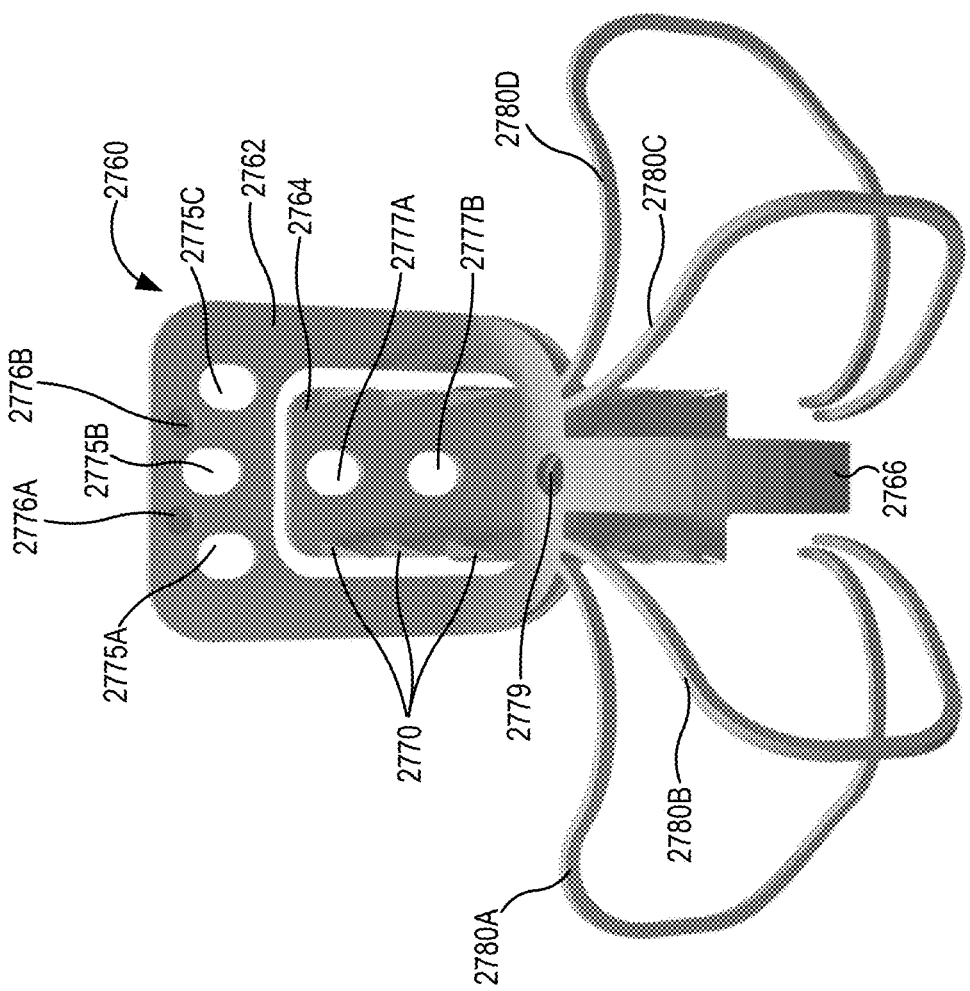

FIG. 27A is a front view of an implant 2760, according to an embodiment. The implant 2760 may include an attachment section and a coaptation section as previously described herein. The attachment section may include a first segment or arm 2762 and a first portion of a second segment or arm 2764. The coaptation section may include a second portion of the second segment or arm 2764 and a central member 2766. The first arm 2762 may include one or more positional openings 2775A, 2775B, 2775C (e.g., three positional openings) disposed at a distal end thereof, and the second arm 2764 may include one or more positional openings 2777A, 2777B (e.g., two positional openings) disposed at a distal end thereof. The first arm 2762 may further include one or more visual marker openings 2776A, 2776B, as previously described herein, disposed distal to the positional openings 2775A, 2775B, 2775C. Each of the first arm 2762 and the second arm 2764 may further include friction elements 2770, as previously described herein. The first arm may further include a proximal positional opening 2779. The implant may further include a first support member 2780A, a second support member 2780B, a third support member 2780C, and a fourth support member 2780D. The implant 2760 may be structurally and/or functionally similar to any of the implants described herein (e.g., implant 460, implant 1660, etc.), and therefore certain details of the implant 2760 are not described in further detail with respect to FIGS. 27A-27B. The implant 2760 may be similar to the implants 1560 and 1660 of FIGS. 15-16; however, the implant 2760 may include a tear drop shape 2771 at the end of each tine or friction element 2770 to reduce stress concentration when they are bent into shape, as shown in FIG. 27B.

Figure 28:
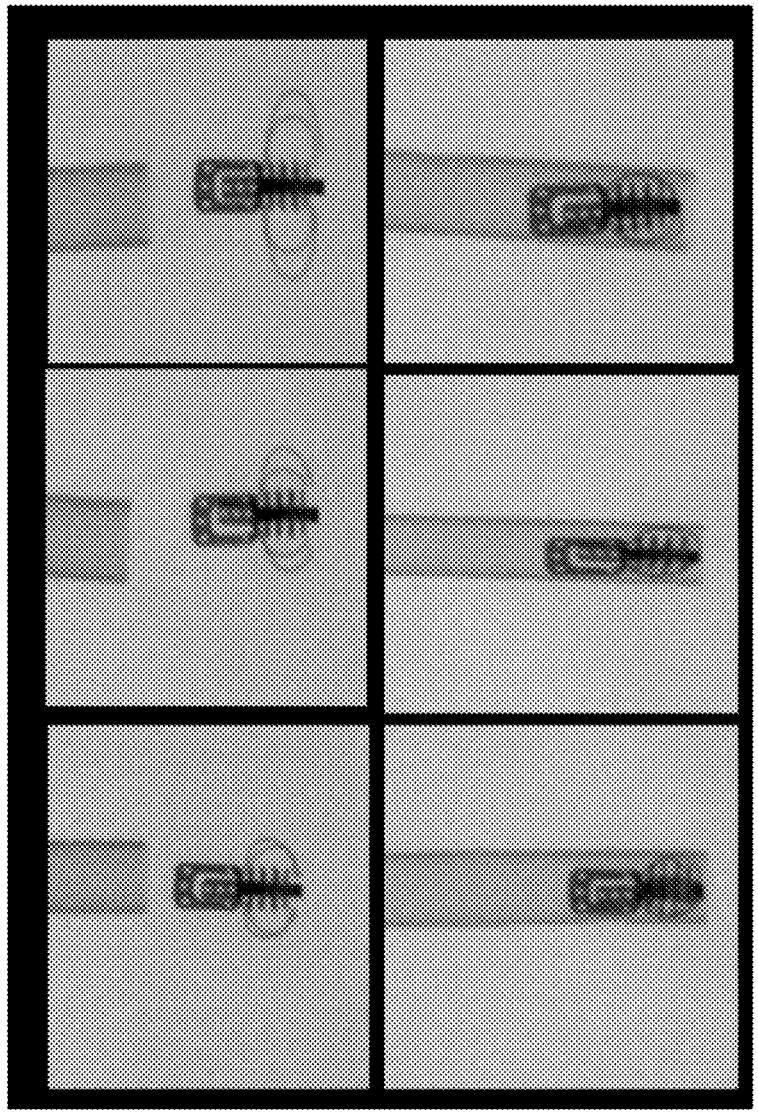
FIG. 28 are images of different size implants in a delivery configuration (bottom row) and a deployed configuration (top row).

FIG. 28 are images of various implant sizes (e.g., 10 mm on left, 12 mm in center, and 16 mm on right) in a delivery configuration (bottom row) and a deployed configuration (top row). The implant in the delivery configuration is in a constrained state, in which the support members of the implant are elongated such that the implant fits in the inner lumen of the implant catheter. In some embodiments, in the constrained state, the support members of the implant are configured to fold across one another to decrease the overall width of (or cross-sectional area of) the implant such that the implant fits in the inner lumen of the implant catheter. The free ends of the support members may enable the support members to fold across one another to transition the implant to the constrained state. In some embodiments, the support members of the implant may elongate in the constrained state to decrease the overall width of the implant. When the implant is deployed (e.g., advanced out of the implant catheter), the implant catheter no longer constrains the implant, and the implant returns to its relaxed state in which the support members expand away from the central member of the implant. While in FIG. 28, the implant is shown directly in the implant catheter, it should be appreciated that the implant can be coupled to an implant holder and transition between the constrained state and the relaxed state while coupled to the implant holder. Additionally, the implant may include a cover disposed over the support members and configured to conform with the support members as the implant transitions between the constrained and relaxed states.

Figure 29:
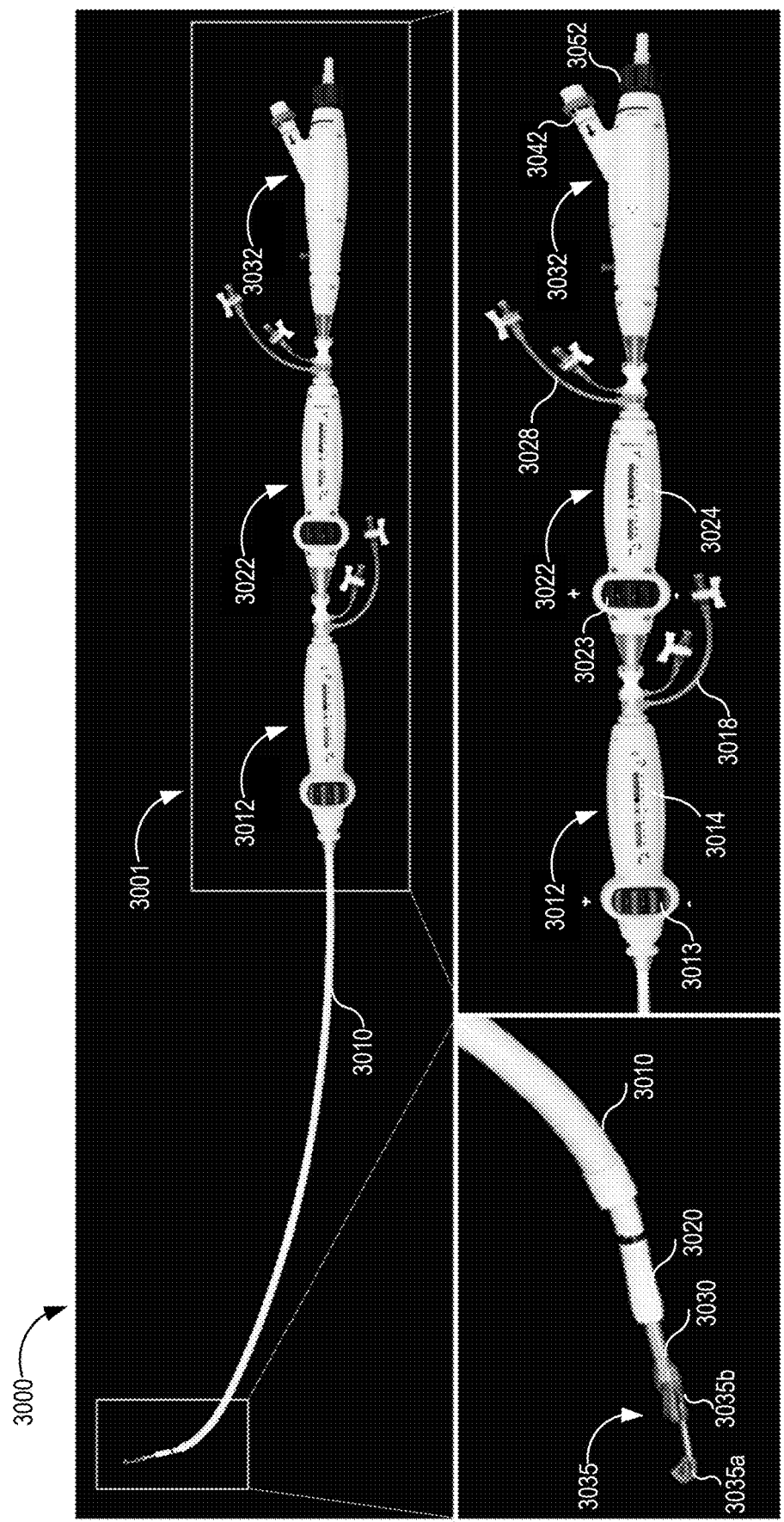
FIG. 29 shows an implant delivery system including a handle assembly coupled to a proximal end of a catheter system and an implant holder coupled to distal end of the catheter system, according to embodiments.

FIG. 29 shows an implant delivery system 3000 including a handle assembly 3001 coupled to a proximal end of a catheter system (e.g., a guide catheter 3010, a delivery catheter 3020, and an implant catheter 3030) and an implant holder 3035 coupled to distal end of the catheter system, according to embodiments. The catheter system may include a guide catheter 3010 coupled to a GC actuator 3012, a delivery catheter 3020 coupled to a DC actuator 3022, and an implant catheter 3030 coupled to an IC actuator 3032. As shown, the handle assembly 3001 includes the GC actuator 3012 including a GC knob 3013 configured to control a degree of bending at a distal end of the guide catheter 3010, and a GC indicator 3014 configured to show a magnitude of the degree of bending at the distal end of the guide catheter 3010. The GC actuator 3012 may be coupled to a guide catheter (GC) flushing port 3018. The GC flushing port 3018 may be in fluid communication with a lumen of the guide catheter 3010 such that bodily fluid (e.g., blood) may be flushed from the lumen of the guide catheter 3010 during implantation. The handle assembly 3001 may further include the DC actuator 3022 including a DC knob 3023 configured to control a degree of bending at a distal end of the delivery catheter 3020, and a DC indicator 3024 configured to show a magnitude of the degree of bending at the distal end of the delivery catheter 3020. The DC actuator 3022 may be coupled to a DC flushing port 3028. The DC flushing port 3028 may be in fluid communication with a lumen of the delivery catheter 3020 such that bodily fluid (e.g., blood) may be flushed from the lumen of the delivery catheter 3020 during implantation.

The distal end of the implant catheter 3030 may be coupled to the implant holder 3035 including a distal portion 3035a and a proximal portion 3035b joined by a connector, further described in FIGS. 40-42D. The implant holder 3035 may be configured to receive an implant between the distal portion 3035a and the proximal portion 3035b. The GC knob 3013 and the DC knob 3023 may be configured to rotate in a clockwise and counterclockwise, as described in further detail with respect to FIGS. 31A-31C and FIGS. 32A-32D, respectively. The handle assembly 3001 further includes the IC actuator 3032 including an atrial tether (AT) actuator 3042 and a ventricular tether (VT) actuator 3052, described further in FIGS. 37A-37B. The GC actuator 3012, the DC actuator 3022, and the IC actuator 3032 may be structurally and/or functionally similar to any of the GC actuator 112, 612, the DC actuator 122, 622, and the IC actuator 132, 632 previously described, and therefore certain details are not described in further detail herein.

FIGS. 30A-30B show the handle assembly 3001 including the GC actuator 3012 coupled to the guide catheter and a dilator 3015 configured to be disposed through a lumen of the guide catheter 3010, according to embodiments. As shown, the dilator 3015 is configured to extend through the GC actuator 3012 such that a proximal portion of the dilator 3015 extends beyond a proximal end of the GC actuator 3012. In some embodiments, the dilator may define a lumen configured to receive a guidewire therethrough. A distal portion of the dilator 3015 may include a tapered end, and a proximal portion of the dilator 3015 may have a diameter substantially equal to (or slightly smaller than) a diameter of the guide catheter 3010 and a distal end of the dilator 3015 may taper to a point such that the dilator 3015 creates an opening in the tissue corresponding to the diameter of the guide catheter 3010. The dilator 3015 may aid in insertion of the guide catheter 3010 during the procedure.

Figure 31C:
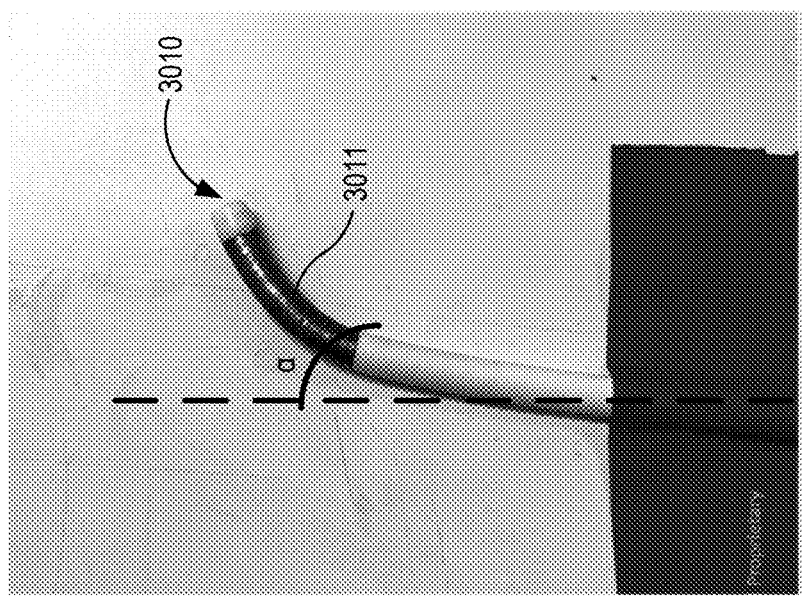
FIGS. 31B-31C show a distal end of the guide catheter including a bendable section configured to bend in response to actuation of the guide catheter actuator, according to embodiments.
Figure 31B:
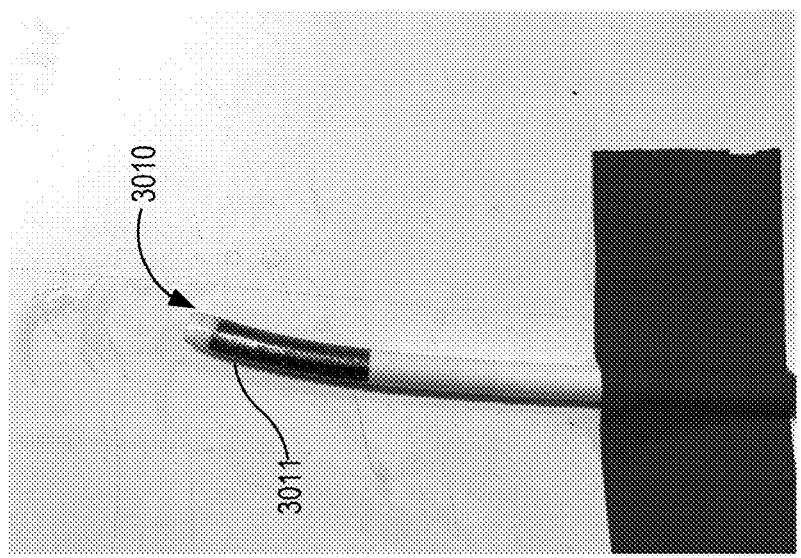
Figure 31A:
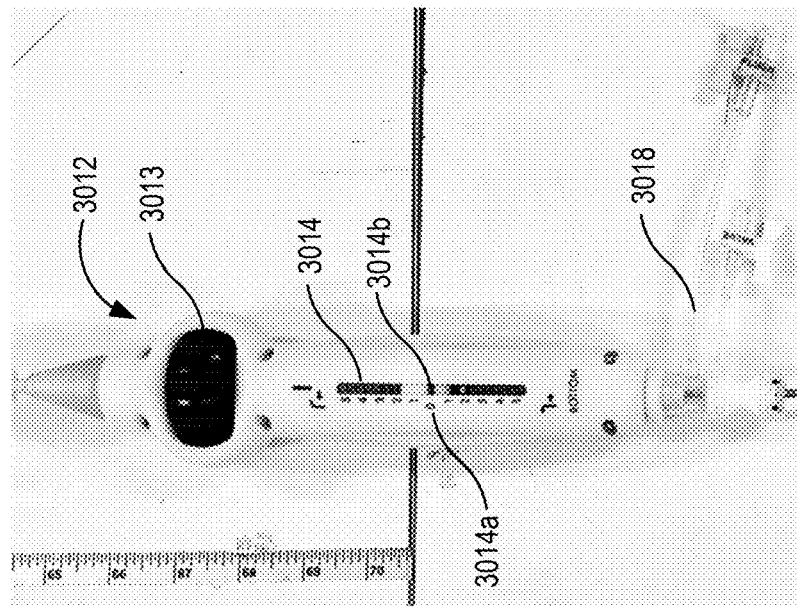
FIG. 31A shows a close-up view of the guide catheter actuator, according to embodiments.

FIG. 31A shows a close-up view of the GC actuator 3012 including the GC knob 3013, the GC indicator 3014, and the GC flushing port 3018. Rotating the GC knob 3013 clockwise may bend a distal portion 3011 of the guide catheter 3010 (e.g., in the bending portion) in a first direction (e.g., toward the flushing port 3018) along a first plane, and rotating the GC knob 3013 counterclockwise may bend the distal portion of the guide catheter 3010 in a second direction (e.g., away from the flushing port 3018) opposite the first direction along the first plane. The clockwise and counterclockwise direction may correspond to when a user is positioned at a proximal end of the implant delivery system and facing toward the distal end of the implant delivery system. In some embodiments, a degree of rotation of the GC knob 3013 may bend the distal portion of the guide catheter 3010 to an angle α from the longitudinal axis. In some embodiments, a ratio of the degree of rotation of the GC knob 3013 to the angle α of the distal portion of the guide catheter 3010 from the longitudinal axis (e.g., the bending angle) may be referred to as a first ratio. In some embodiments, the first ratio is about 10:1, inclusive of all ranges and subranges therebetween. In some embodiments, the GC knob 3013 may turn a screw that in turn causes the distal end of the guide catheter 3010 to bend. In some embodiments, the first ratio of the rotation between the GC knob 3013 and the bending angle of the guide catheter 3010 is defined by a pitch of the screw that is turned by the GC knob 3013.

In some embodiments, the GC indicator 3014 may indicate the magnitude of bending at the distal portion 3011 of the guide catheter 3010. The GC indicator 3014 may include a plurality of indicia 3014a (e.g., numbers, symbols, colors, diagrams, etc.) and a movable indicator 3014b. For example, the GC indicator 3014 may include numerical indicia between −5 to +5 (e.g., −5, −4, −3, −2, −1, 0, +1, +2, +3, +4, +5) and the movable indicator 3014b may be configured to indicate to a user one of the indicia between −5 to +5 as the user rotates the GC knob 3013. In some embodiments, each of the indicia may correspond to 10 degrees of rotation of the GC knob 3013, and therefore, an angle α of 1 degree of bending of the distal portion 3011 of the guide catheter 3010. While the indicia are shown between −5 to +5, it should be appreciated that any numerical range may be used to indicate the magnitude. In some embodiments, the GC scale 3014 may indicate the magnitude of bending in higher or lower resolution. In some embodiments, an entirety of the GC actuator 3012 may be configured to rotate clockwise and/or counterclockwise about the catheter system. Rotating the entire GC actuator 3012 clockwise may move the distal portion of the guide catheter 3010 in a third direction along a second plane substantially orthogonal to the first plane. Rotating the entirety of the GC actuator 3012 counterclockwise may move the distal portion of the guide catheter 3010 in a fourth direction opposite the third direction along the second plane.

FIG. 32A shows a first actuation of the DC actuator 3022, according to embodiments. In some embodiments, the first actuation of the DC actuator 3022 may include rotation of the DC knob 2023. In some embodiments, rotating the DC knob 3023 clockwise may bend a distal portion of the delivery catheter 3020 in a fifth direction along a third plane, as shown in FIGS. 32B-32D. In some embodiments, rotating the DC knob 3023 counterclockwise may bend the distal portion of the delivery catheter 3020 in the sixth direction opposite the fifth direction along the third plane. In some embodiments, the first plane and the third plane may be substantially equal. In some embodiments, the fifth direction may be substantially equal to the first direction, and the sixth direction may be substantially equal to the second direction. In some embodiments, a degree of rotation of the DC knob 3023 may correspond to an angle R the delivery catheter 3020 bends from the longitudinal axis of the delivery catheter 3020. In some embodiments, a ratio of the degree of rotation of the DC knob 3023 and the angle R may referred to as a second ratio. In some embodiments, the second ratio may be about 5:1, inclusive of all ranges and subranges therebetween. In some embodiments, the first ratio may be greater than the second ratio meaning that the precision for controlling the guide catheter 3010 may be courser than a precision for controlling the delivery catheter 3020. This is because, in some implementations and use cases, control over the guide catheter 3010 does not need to be as precise as control over the delivery catheter 3020 to allow the user to steer distal end into the desired configuration. In some embodiments, the DC knob 3023 may turn a screw that in turn causes the distal end of the delivery catheter 3020 to bend. In some embodiments, the second ratio of the rotation between the DC knob 3023 and the bending angle of the delivery catheter 3020 is driven by a pitch of the screw that is turned by the DC knob 3023. In some embodiments, a number of turns of the DC knob 3023 (or the GC knob 3013) may depend on a tension on the atrial and/or ventricular tethers and/or a pitch of the screw. In some embodiments, the DC actuator 3022 may include a DC scale. In some embodiments, the DC scale may be structurally and/or functionally similar to the GC scale 3014, and therefore, details of the DC scale are not described herein.

Figure 33A:
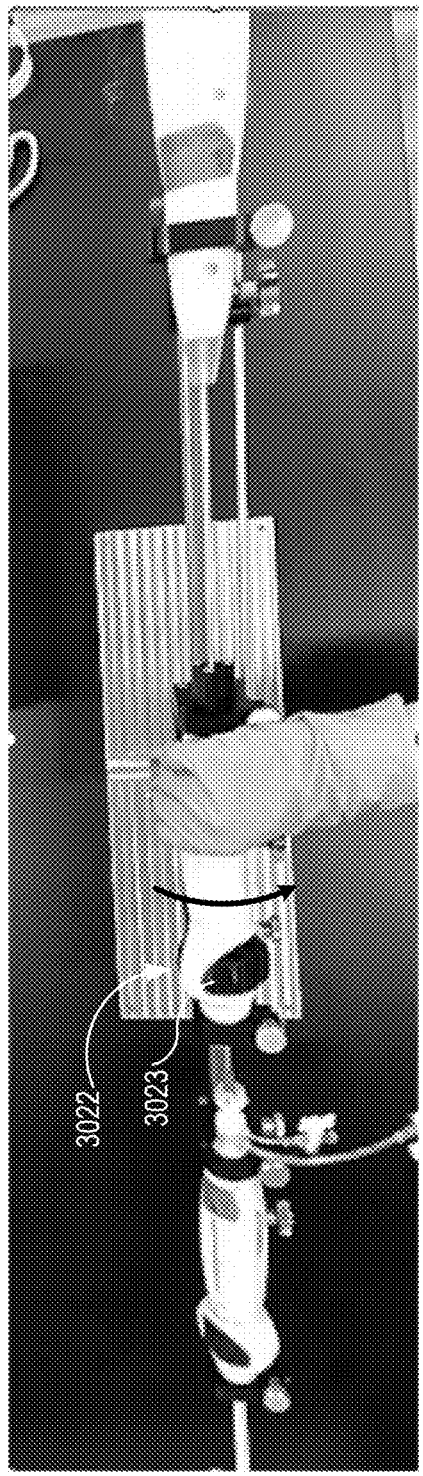
FIG. 33A shows a second actuation of the delivery catheter actuator of FIG. 32A, according to embodiments.
Figure 33C:
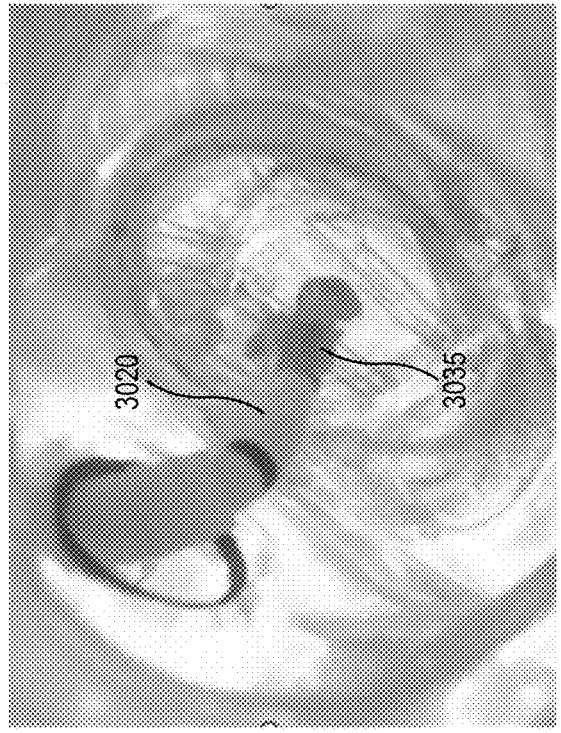
FIGS. 33B-33C show the distal end of the delivery catheter in response to the second actuation, according to embodiments.
Figure 33B:
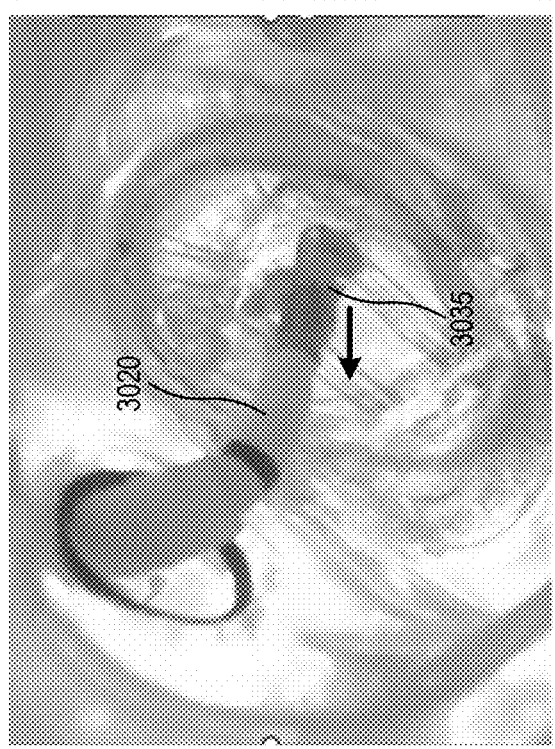

In some embodiments, an entirety of the DC actuator 3022 may be configured to rotate clockwise and/or counterclockwise about the catheter system, as shown in FIG. 33A. Rotating the entire DC actuator 3022 clockwise may move the distal portion of the delivery catheter 3020 in a seventh direction along a fourth plane substantially orthogonal to the third plane. Rotating the entirety of the DC actuator 3022 counterclockwise may move the distal portion of the delivery catheter 3020 in an eighth direction opposite the seventh direction along the fourth plane, as shown in FIGS. 33B-33C. In some embodiments, the second plane and the fourth plane may be substantially equal. In some embodiments, the seventh direction may be substantially equal to the third direction, and the eighth direction may be substantially equal to the fourth direction.

Figure 34A:
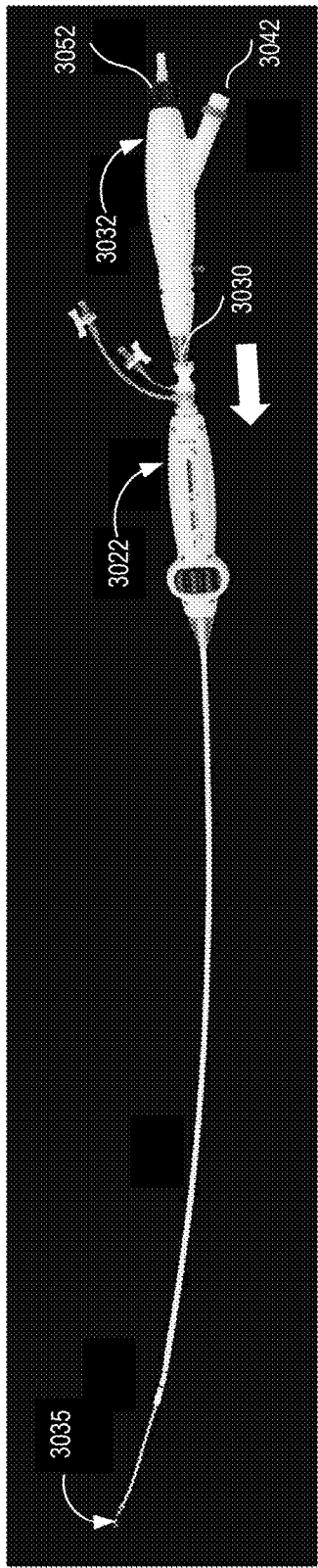
FIGS. 34A and 34C show translation of the delivery catheter actuator relative to an implant catheter actuator, according to embodiments.
Figure 34B:
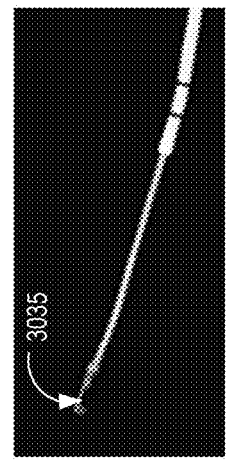
FIGS. 34B and 34D show the distal end of the implant catheter and the delivery catheter in response to the translation, according to embodiments.
Figure 34C:
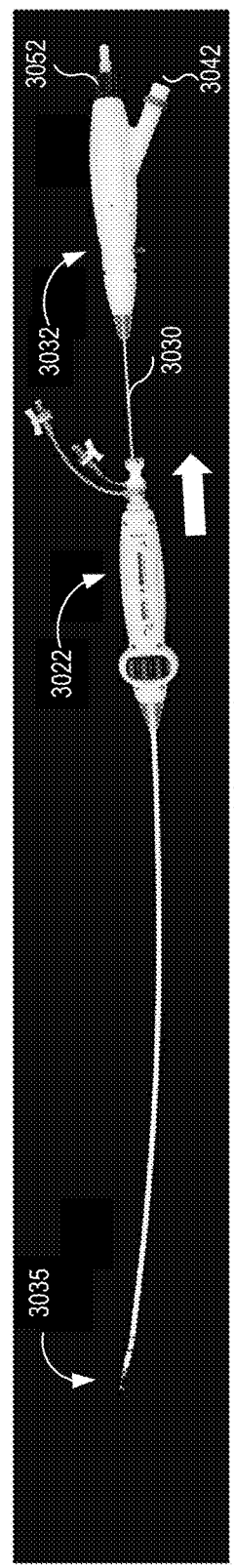
Figure 34D:
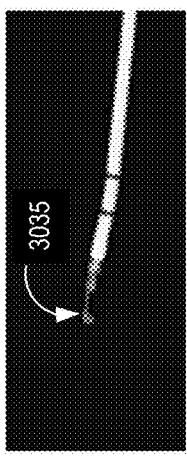

In some embodiments, the IC actuator 3032 and the DC actuator 3022 may be configured to move relative to one another in a proximal/distal direction to transition a distal end of the implant holder 3035 between a retracted configuration and an extended configuration. In some embodiments, distal movement of the IC actuator 3032 may move the implant holder 3035 distally, proximal movement of the IC actuator 3032 may move the retract the implant holder 3035. Alternatively or additionally, proximal movement of the DC actuator 3022 may extend the implant holder 3035, as shown in FIGS. 34A-34B, and distal movement of the DC actuator 3022 may retract the implant holder 3035, as shown in FIGS. 34C-34D. In some embodiments, the DC actuator 3022 may be moved linearly in a distal/proximal direction to extend and/or retract the delivery catheter 3020.

Figure 35A:
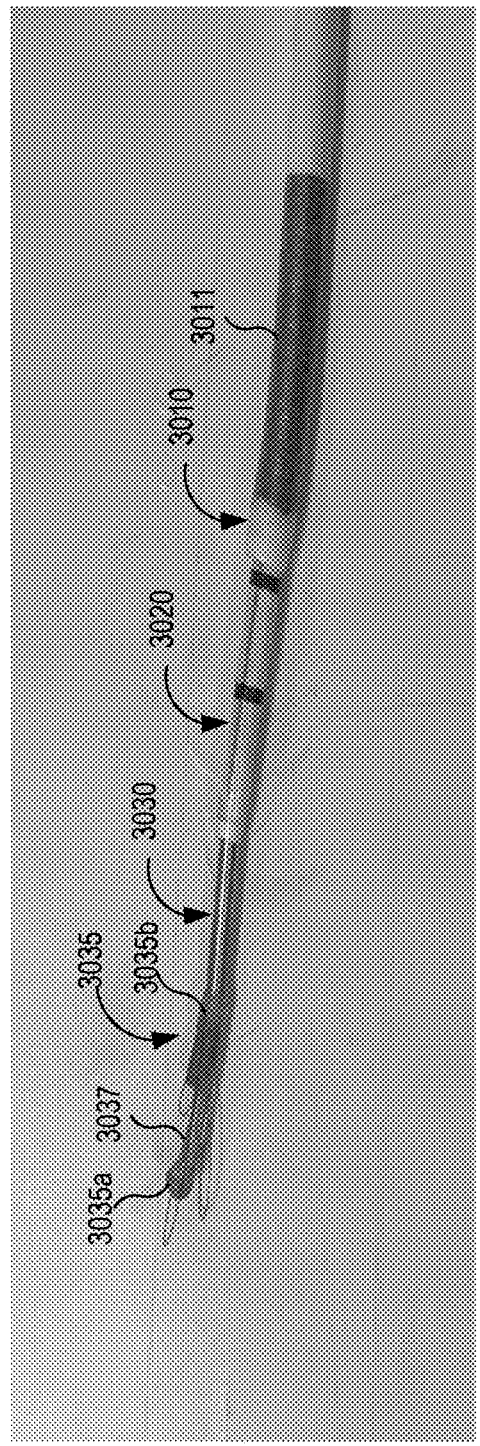
FIGS. 35A-35B show the implant catheter and the delivery catheter in an extended configuration and a retracted configuration, respectively, according to embodiments.
Figure 35B:
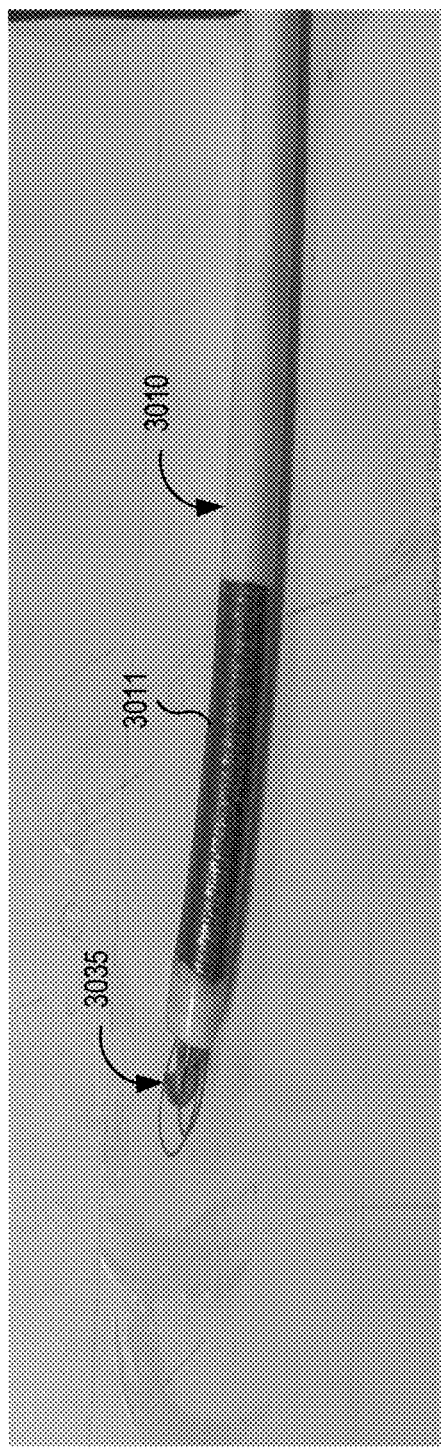

FIG. 35A shows a distal end of the catheter system in an extended configuration in which the delivery catheter 3020 extends distally from the guide catheter 3010, and the implant catheter 3030 extends distally from the delivery catheter 3020 to expose the implant holder 3035. FIG. 35B shows the distal end of the catheter system in a retracted configuration in which the delivery catheter 3020 is retracted into the lumen of the guide catheter 3010, and the implant catheter 3030 is retracted into a lumen of the delivery catheter 3020 such that the implant holder 3035 is at least partially covered by the guide catheter 3010. In some embodiments, the handle assembly 3001 may be configured to move proximally and/or distally (e.g., by a user via a handle assembly holder). The entire catheter system may move proximally in response to the handle assembly 3001 moving proximally. The entire catheter system may move distally in response to the handle assembly 3001 moving distally.

FIGS. 36A-36C show steerability maps of distal end of the implant delivery system relative to a mitral heart valve in response to actuation of the guide catheter actuator, the delivery catheter actuator, and the entire handle assembly, respectively. As shown in FIG. 36A, GC actuator + indicates clockwise rotation of the GC knob (e.g., GC knob 3013), GC actuator − indicates counterclockwise rotation of the GC knob, GC actuator CW indicates clockwise rotation of the entire GC actuator (e.g., GC actuator 3012) about the longitudinal axis of the device, and GC actuator CCW indicates counterclockwise rotation of the entire GC actuator about the longitudinal axis of the device. As described in FIGS. 31A-31B, the clockwise and counterclockwise direction correspond to when a user is positioned at a proximal end of the implant delivery system and facing toward the distal end of the implant delivery system. As shown, rotation of the GC knob causes the distal end of the guide catheter to move along a first axis and rotation of the entirety of the GC actuator causes the distal end of the guide catheter to move along a second axis substantially orthogonal to the first axis. As shown, clockwise rotation of the GC knob causes the distal end of the implant delivery system to move posteriorly in the heart and counterclockwise rotation of the GC knob causes the distal end of the implant delivery system to move anteriorly in the heart. Clockwise rotation of the entire GC actuator causes the distal end of the implant delivery system to move laterally within the heart and counterclockwise rotation of the entire GC actuator causes the distal end to move medially within the heart.

As shown in FIG. 36B, DC actuator + indicates clockwise rotation of the DC knob (e.g., DC knob 3213), DC actuator − indicates counterclockwise rotation of the DC knob, DC actuator CW indicates clockwise rotation of an entirety of the DC actuator (e.g., DC actuator 3212) about the longitudinal axis of the device, and DC actuator CCW indicates counterclockwise rotation of the entire DC actuator about the longitudinal axis of the device. As shown, the DC actuator can control movement of the distal end of the DC catheter along three axes. In some embodiments, clockwise rotation of the DC knob may move the distal end of the implant delivery system posteriorly in the heart, counterclockwise rotation of the DC knob should move the distal end of the implant delivery system anteriorly in the heart. Clockwise rotation of the entire DC actuator causes the distal end of the implant delivery system to move laterally within the heart and counterclockwise rotation of the entire DC actuator causes the distal end to move medially within the heart. Additionally, the entire DC actuator may be moved proximally and distally (e.g., linearly). Moving the entire DC actuator distally results in the delivery catheter moving out of the guide catheter lumen. Moving the entire DC actuator proximally results in the distal end of the delivery catheter system into the lumen of the guide catheter.

In some embodiments, when the DC actuator knob is neutral (e.g., at "0", or not rotated clockwise or counterclockwise), the distal end of the delivery catheter may be parallel to the mitral valve annulus. In some embodiments, when the DC actuator knob is rotated about 45 degrees clockwise, the distal end of the delivery catheter may extend toward a lateral commissure. In some embodiments, when the DC actuator knob is rotated about 90 degrees clockwise, the distal end of the delivery catheter may extend toward a medial commissure.

As shown in FIG. 36C, the implant delivery system can be moved proximally and/or distally. In some embodiments, moving the implant delivery system distally results in the distal end of the implant delivery system moving anterior-lateral. Moving the entire DC actuator proximally results in the implant delivery system moving posterior-medial.

Figure 37B:
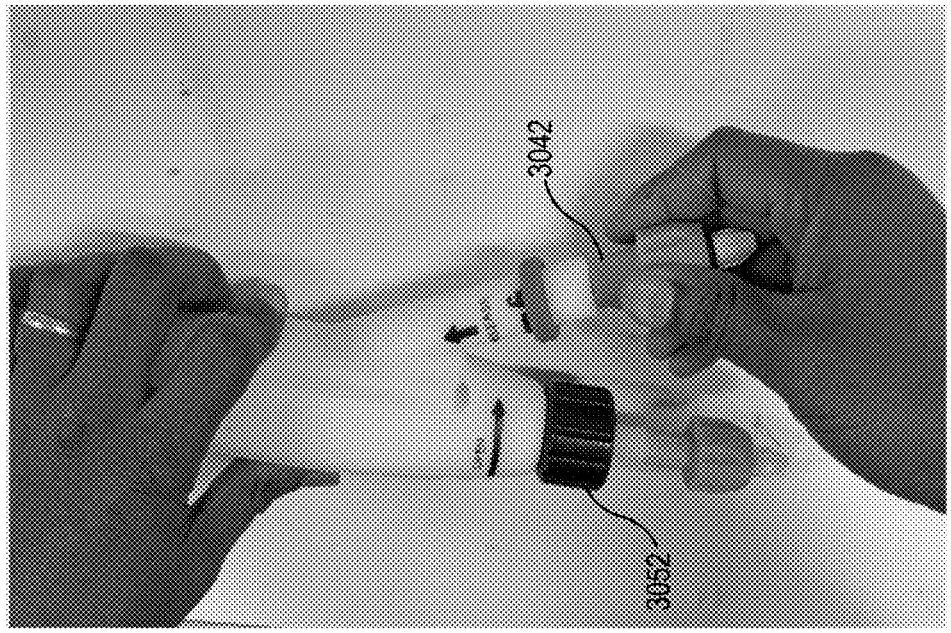
FIGS. 37A-37B show actuation of an atrial tether actuator, according to embodiments.
Figure 37A:
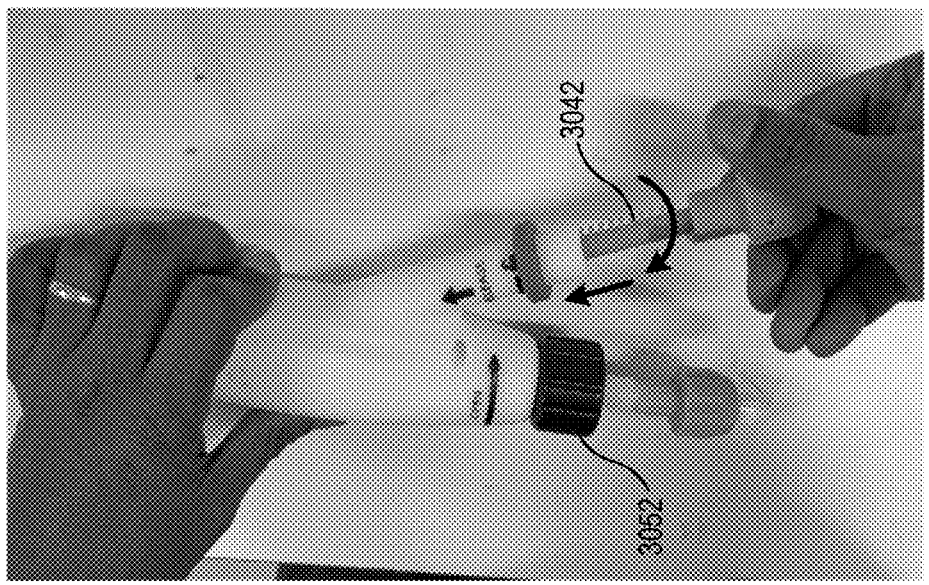

FIGS. 37A-37B show actuation of an AT actuator 3042, according to embodiments. The AT actuator 3042 of the IC actuator 3030 may include a linear slider and/or a rotating actuator. In some embodiments, the AT actuator 3042 may include a locking mechanism configured to lock a linear position of the AT actuator 3042, thereby locking an amount of tension applied on the atrial tether and a position of the atrial arm. In some embodiments, rotating the AT actuator 3042 may lock and/or unlock the locking mechanism such that the AT actuator 3042 can be moved proximally and/or distally. For example, the AT actuator 3042 may be configured to rotate inward (e.g., counter-clockwise or towards a centerline of the delivery system) and then move linearly in (e.g., about 5 mm to about 50 mm). In some embodiments, the AT actuator 3042 may be locked at any position by rotating the AT actuator 3042 outward (e.g., clockwise). In some embodiments, the AT actuator 3042 can be locked in the most proximal position.

In some embodiments, when the AT actuator 3042 is moved distally, tension is released on the atrial tether, and therefore the atrial arm of the implant. Releasing the tension on the atrial arm may allow the atrial arm to drop onto a portion of the leaflet that is disposed between the atrial arm and the ventricular arm (e.g., to clamp the leaflet). Further rotation inwards or distal movement of the AT actuator 3042 can introduce additional slack into the atrial tether, allowing the implant holder to be moved away from the implant when the implant is in its deployed state on the leaflet. When the AT actuator 3042 is rotated outwards (e.g., clockwise) and/or moved proximally the atrial tether, and therefore the atrial arm of the implant, may be tensioned such that the atrial arm of the implant is moved towards the implant holder (e.g., securing the atrial arm to an engagement surface of the implant holder). For example, when preparing open the ventricular arm, the AT actuator 3402 may be moved proximally to tension the atrial tether and secure the atrial arm to the implant holder. As another example, the AT actuator 3042 may be moved proximally to tension the atrial tether and secure the atrial arm to the implant holder before the ventricular tether is decoupled from the ventricular arm.

Figure 38B:
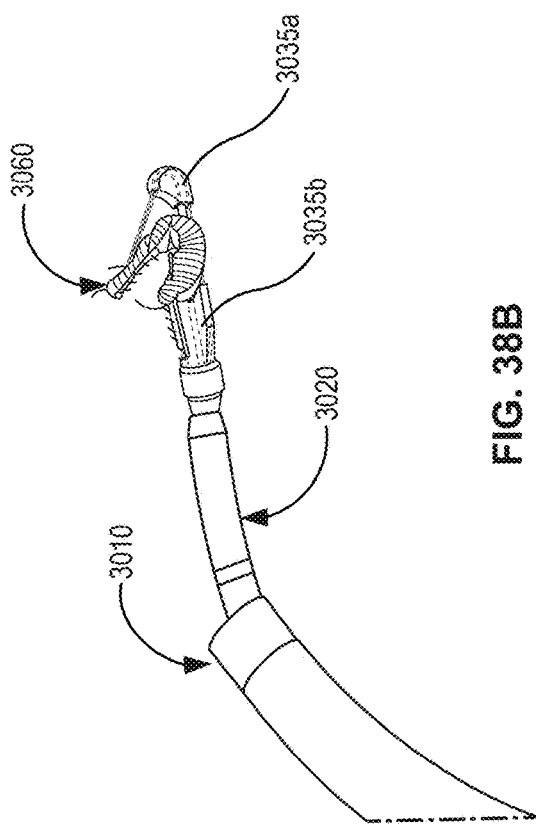
FIGS. 38A-38C show actuation of a ventricular tether actuator to open a ventricular arm of the implant away from an atrial arm of the implant, according to embodiments.
Figure 38C:
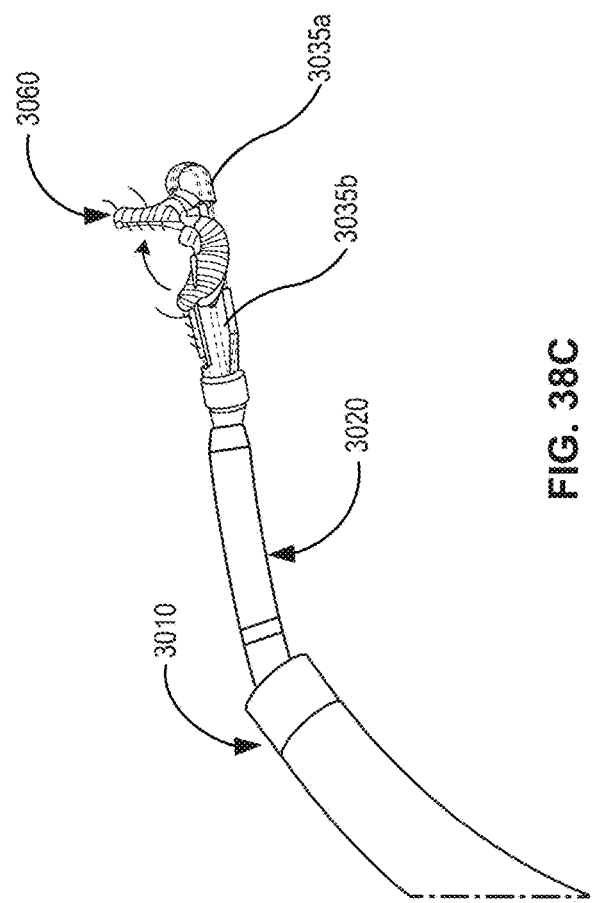
Figure 38A:
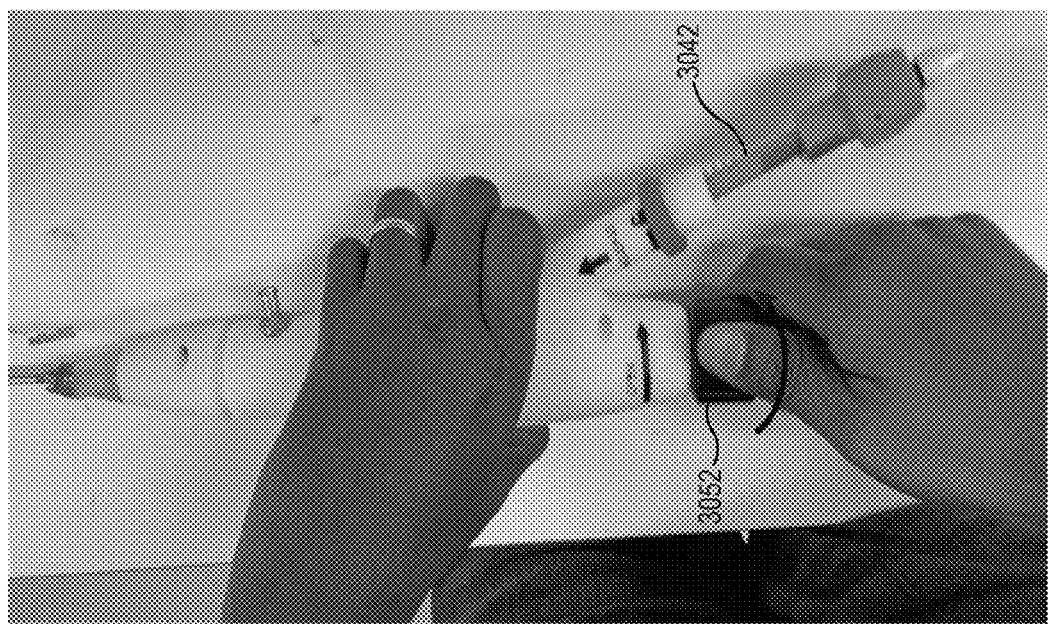

FIGS. 38A-38C show actuation of a ventricular tether (VT) actuator 3052 to open a ventricular arm of the implant away from an atrial arm of the implant, according to embodiments. The VT actuator 3052 may include a linear slider and/or a rotating actuator. The AT actuator 3042 and the VT actuator 3052 may allow the user to deliver the implant to the leaflet with precise control. For example, to deliver the leaflet, the following steps can be completed. In some embodiments, the VT actuator 3052 may include a rotating actuator configured to apply tension and/or reduce tension in the ventricular tether in response to rotation. For example, the VT actuator 3052 may be configured to apply tension to the ventricular tether in response to rotation of the VT actuator 3052 in a first direction (e.g., clockwise) to move the ventricular arm away from the atrial arm and open the implant. In some embodiments, the VT actuator 3052 may reduce tension to the ventricular tether in response to rotation of the VT actuator 3052 in a second direction (e.g., counterclockwise) to move the ventricular arm toward the atrial arm and close the implant. In some embodiments, a degree of rotation of the VT actuator 3052 may correspond to a distance the ventricular arm opens.

Figure 39A:
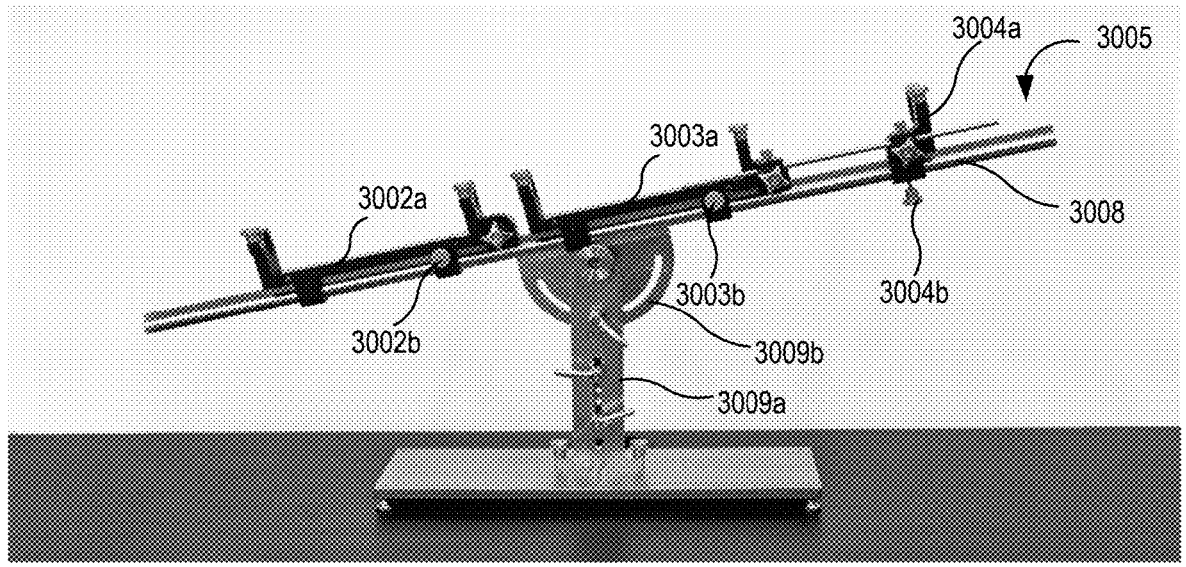
FIGS. 39A-39B show a handle assembly holder to help a user control the handle assembly, according to embodiments.
Figure 39B:
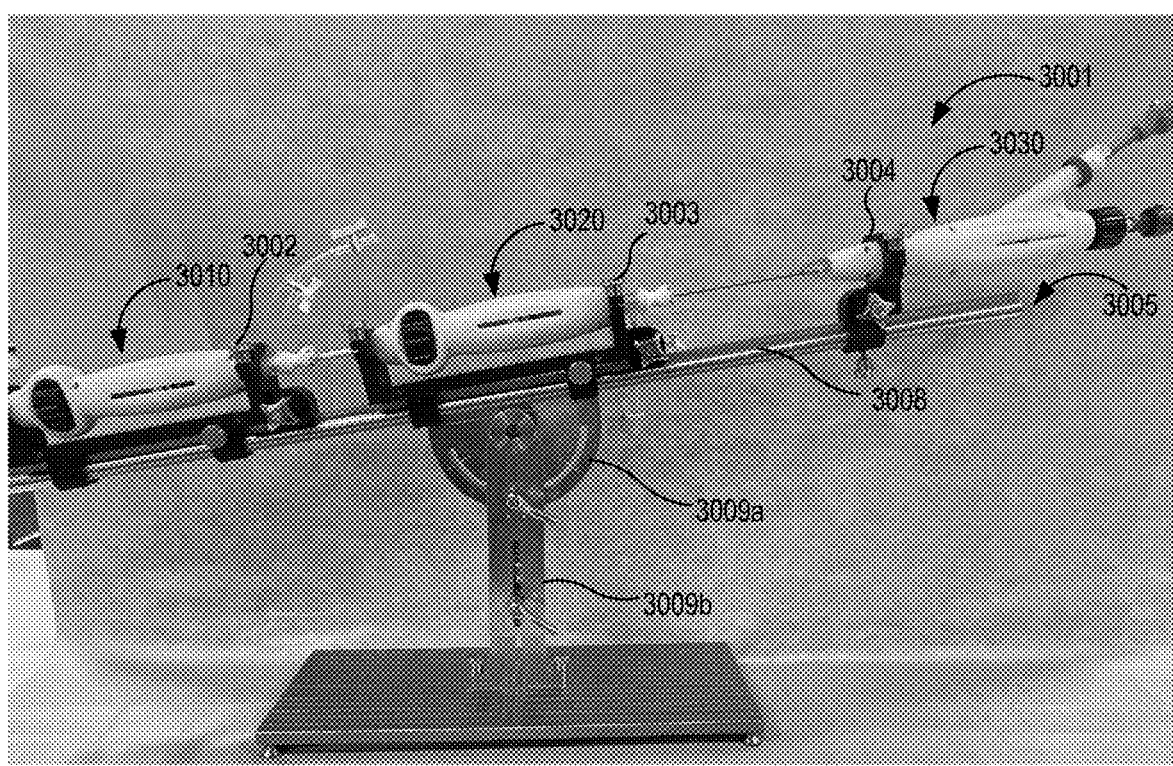

FIGS. 39A-39B show a handle assembly holder 3005 to help a user control the handle assembly 3001, according to embodiments. As shown, the handle assembly holder 3005 includes a base 3009a and a moveable portion 3009 coupled to a support axis 3008. The movable portion 3009 may be configured to adjust an orientation of the support axis 3008 relative to a surface on which the base 3009 is disposed (e.g., a table). The support axis 3008 may be configured to hold the handle assembly 3001 of the implant delivery system such that the implant delivery system is disposed at the predetermined angle relative to the table. In some embodiments, the support axis 3008 may include a first control mechanism 3002a configured to hold and/or control a position of the GC actuator 3010, a second control mechanism 3003a configured hold and/or control a position of the DC actuator 3020, and a third control mechanism 3004a configured to hold and/or control a position of the IC actuator 3030. In some embodiments, the control mechanisms 3002a, 3003a, 3004a may be configured to move along a longitudinal axis of the support axis 3008 (e.g., distally and/or proximally). In some embodiments, the control mechanism 3002a, 3003a, 3004a may move along the support axis 3008 independently, such that the GC actuator 3010, the DC actuator 3020, and the IC actuator 3030 can be moved distally and/or proximally independent from one another. In some embodiments, the first control mechanism 3002a may include a first actuator 3002b (e.g., a knob, a slider), configured to receive an input from a user to move the first control mechanism 3002a. Similarly, the second control mechanism 3003a may include a second actuator 3003b (e.g., a knob, a slider), and the third control mechanism 3004a may include a third actuator 3004b (e.g., a knob, a slider). In some embodiments, the first, second, and third control mechanisms 3002a, 3003a, 3004a, may include a lock configured to lock a position of the control mechanisms 3002a, 3003a, 3004a, and therefore the GC actuator 3010, DC actuator 3020m and IC actuator 3030 in place.

Figure 40:
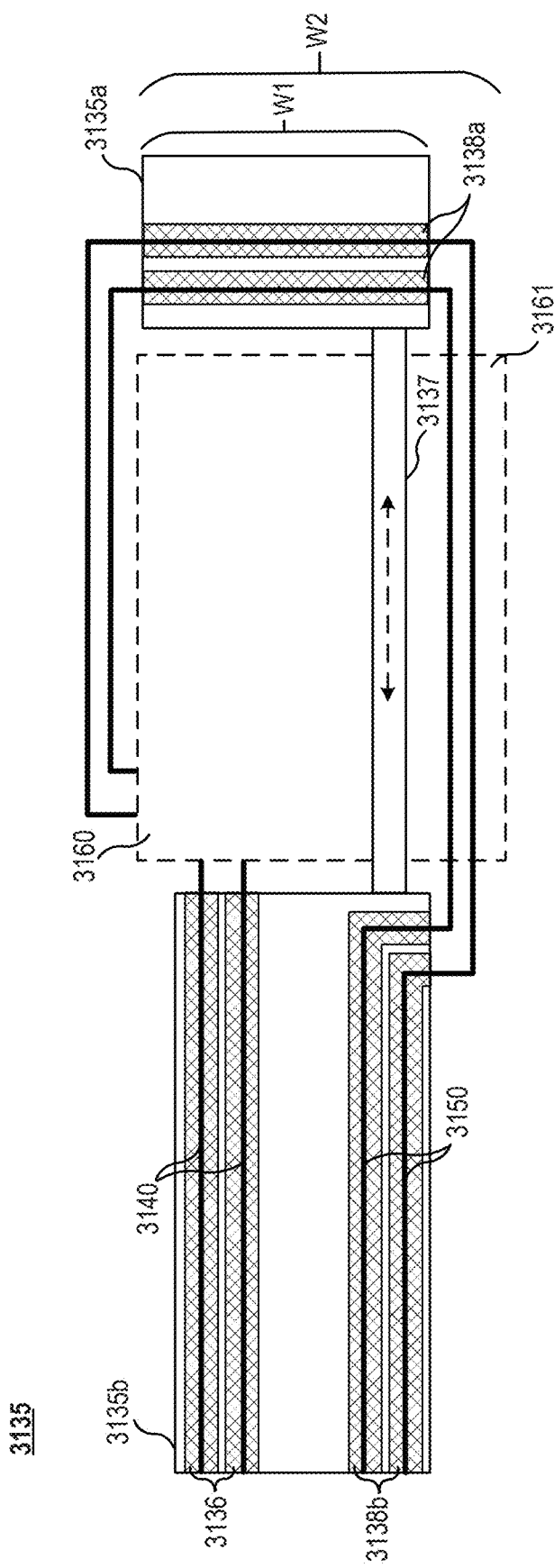
FIG. 40 is a schematic diagram of an implant holder including a proximal portion and a distal portion joined by a connector therebetween, according to embodiments.

FIG. 40 is a schematic diagram of an implant holder 3135, according to embodiments. In some embodiments, the implant holder 3135 may be structurally and/or functionally similar to the implant holder 335, 835, and therefore, certain details of the implant holder 3135 are not described again with respect to FIG. 40. The implant holder 3135 may include a proximal portion 3135b and a distal portion 3135a joined by a connector 3137 therebetween. The implant holder 3135 may be configured to receive an implant 3160 between the proximal portion 3135b and the distal portion 3135a. In some embodiments, a front side of the proximal portion 3135b may include an engagement surface (e.g., an atrial plate stabilizing holder) configured to receive at least an atrial arm of the implant 3160. In some embodiments, a first portion of the implant 3160 may be disposed om the engagement surface and a second portion of the implant (e.g., the leaflet enhancer) may be disposed between the proximal portion 3135b and the distal portion 3135a. In some embodiments, a back side of the implant holder 3135 opposite the front side may define an opening extending from the front side to the back side and disposed between the distal portion 3135a and the proximal portion 3135b. In some embodiments, a portion of the implant 3160 may be disposed in the opening such that a back side of the implant extends beyond (e.g., laterally beyond) the connector and/or the back side of the implant holder 3135.

The proximal portion 3135b of the implant holder 3135 may include one or more atrial channels 3136 through which one or more atrial tethers 3140 may extend. The atrial channel(s) 3136 may define an opening at or near the engagement surface of the proximal portion 3135b such that the atrial tether(s) 3140 can be coupled to the atrial arm of the implant 3160. The proximal portion 3135b may further include a first ventricular channel or a first set of ventricular channels 3138b through which one or more ventricular tethers 3150 may extend. The first set of ventricular channels 3138b may define openings in the proximal portion 3135b such that the ventricular tether(s) 3150 can extend distal to the proximal portion 3135b and into a second ventricular channel or a second set of ventricular channels 3138a in the distal portion 3135a. The second set of ventricular channels 3138a may receive the ventricular tether(s) 3150 through a first set of openings on the backside of the distal portion 3135a (e.g., proximate to a central member of the implant 3160) and a second set of openings on the front side of the distal portion 3135a (e.g., near the arms of the implant 3160) such that the ventricular tether(s) 3150 can extend proximally from the distal portion 3135a and couple to a ventricular arm of the implant 3160.

In contrast to some implementations of the implant holder (e.g., implant holder 835), implant holder 3135 can have a separate proximal portion 3135b and distal portion 3135a (e.g., "the open back design") such that the tethers are not constrained in the material of the implant holder 3135. Therefore, the implant holder 3135 reduces friction on the atrial tether(s) 3140 and ventricular tether(s) 3150 and reduces difficulty in manipulating the tethers from the proximal end of the delivery system. A closed back design may require a sharper bend on the tethers, and therefore, may impart more strain on the tethers.

The open back design of implant holder 3135 may also improve ease of flushing out the atrial channel(s) 3136 and ventricular channel(s) 3138a, 3138b (e.g., due to the reduced length and reduced circuitry of the channel pathways) and reduces the likelihood of blood clots forming in the atrial and ventricular channels 3140, 3150, which can restrict the tethers from being pulled out from a proximal end of the delivery system to release the implant 3160. In some embodiments, the open back design may enable easier flushing of fluid (e.g., saline) to remove bodily fluid (e.g., blood) and/or air from the atrial and ventricular channels 3140, 3150. In the body, if blood pressure is higher than system, blood will flow into the device through the atrial and ventricular channels 3140, 3150; therefore, the atrial and ventricular channels 3140, 3150 should be flushed intermittently or continuously. In some embodiments, flushing can occur periodically with a predefined time interval. In some embodiments, flushing may be continuous. In some embodiments, flushing can occur in response to a measurement from a sensor (e.g., a measurement of blood pressure in the body, a measurement of the presence of blood in a lumen of the device, etc.). In some embodiments, flushing may occur in response to actuation by a user as needed.

The implant holder 3135 with the open back design may improve localization of the implant 3160 during implantation. For example, the implant holder 835 with the closed back design may appear as one structure during imaging (e.g., ultrasound), and therefore, distinguishing between the implant 3160 and the implant holder 835 may be difficult for a user. The implant holder 3135 with the open back design may appear as two separate or distinct portions with a gap or other visual demarcation therebetween when imaging such that the implant 3160 can be discernible from the implant holder 3135 during the procedure. In some embodiments, the proximal portion 3135b and the distal portion 3135a may be used as imaging landmarks (e.g., provide an axis) to help the user maneuver the distal end of the implant delivery system, and specifically the implant 3160, in the desired orientation relative to the heart valve.

In some embodiments, the implant holder 3135 with the open back design may enable easier assessment of whether the implant 3160 is an appropriate size. For example, without the closed back, the implant holder 3135 fills less of the native gap during the implantation process and the implant 3160 can bias more toward the back of the implant holder 3135 (e.g., laterally in the body), whereas the implant holder 835 with the closed back would fill more of the native gap. In some embodiments, the implant 3160 may extend beyond the connector 3137 in a lateral direction (e.g., a direction perpendicular to the longitudinal axis of the distal end of the implant delivery system) such that a maximum width of the distal end of the implant delivery system is defined by the implant 3160. In some embodiments, the implant holder 3135 may include a pair of connectors (e.g., hypotubes), and the implant 3160 may be configured to extend through a space between the connectors towards (or beyond) the back side of the implant 3160. The backside 3161 of the implant 3160 may extend beyond the connector 3137. In other words, the implant holder 3135 may have a first width W1 (or cross-sectional area), and the implant 3160 may have a second width W2 (or cross-sectional area) greater than the first width W1 such that the maximum width of the distal end of the implant delivery system is defined by the second width. In some embodiments, the implant 3160 and the implant holder 3135 may be collectively configured to be delivered into the native valve gap (e.g., the orifice defined by the valve), and when the implant 3160 and implant holder 3135 are disposed in that gap, a maximum dimension (e.g., cross-sectional area, perimeter, or the like) in a direction spanning the gap between the leaflets is defined by the implant 3160. In other words, the implant holder 3135 and implant 3160 collectively define a maximum dimension (e.g., width in the direction spanning the gap between the leaflet), and that maximum dimension is limited by and/or defined by the implant 3160.

Because of the implant 3160 spanning wider (e.g., laterally) than the implant holder 3135, the user may not need to (1) clamp the implant 3160 to the leaflet, (2) loosen (e.g., apply slack to) the atrial and/or ventricular tethers and/or (3) move the distal end of the implant delivery system away from the implant 3160 in order to assess the effectiveness of the implant 3160. Therefore, the open back design may enable the user to assess whether the implant 3160 is addressing valve regurgitation without attaching the implant 3160 to the native leaflet. Instead, the distal end of the implant delivery system can remain in place while the user assesses whether the implant 3160 is treating the regurgitation. With the open back design, when the implant 3160 in the implant holder 3135 (e.g., with the tether(s) taut) is disposed in the opening of the heart valve, the implant 3160 in the implant holder 3135 may occupy a cross-sectional area that is equal to a cross-sectional area of the implant 3160 detached from the implant delivery system. Therefore, with the open back design, the user can more accurately assess whether the implant 3160 is the appropriate size.

In embodiments with the open back design, a method of implantation may include positioning the implant in an opening defined by the heart valve without capturing the free end of the native heart valve leaflet between the pair of arms of the implant; determining a level of valve regurgitation when the implant is positioned in the opening defined by the heart valve, after determining the level of valve regurgitation, transitioning the implant from its closed position to its open position; and transitioning the implant from the open position towards its closed position to clamp the free end of the native leaflet between the pair of arms.

In some embodiments, the distal portion 3135*a* of the implant holder and the proximal portion of the implant holder 3135*b* may be configured to move relative to one another. For example, the connector 3137 may be slidable, retractable, moveable, etc. In some embodiments, the connector 3137 may be one or more hypotubes with an adjustable length. In some embodiments, the distal portion 3135*a* of the implant holder 3135 may be configured to move away from the proximal portion 3135*b* to accommodate a larger implant, for example, and move toward the proximal portion 3135*b* to accommodate a smaller implant. In some embodiments, the connector 3137 may extend from the implant holder 3135 proximally through the catheter system and to the proximal end of the delivery system (e.g., the handle assembly). In some embodiments, the connector 3137 may be adjustable from the proximal end of the delivery system.

In some embodiments, a length of the connector 3137 may be adjustable intra-procedure. For example, the implant holder 3135 may be shortened during a turn toward the valve to reduce likelihood of the distal end of the delivery system colliding with any heart anatomy. In some embodiments, once the sharp turn into the heart is completed, the implant holder 3135 may be lengthened such that the implant 3160 is closer to the native valve leaflets. In some embodiments, the distal portion 3135*a* of the implant holder 3135 may be extended distally to transition the implant 3160 to the open configuration rather than or in addition to pulling the ventricular tether(s) 3150. In some embodiments, controlling a position of the distal portion 3135*a* of the implant holder 3160 may improve controllability of opening the implant 3160. For example, a distance of the distal portion 3135*a* may be controlled incrementally with fine precision. In some embodiments, the ventricular tether(s) 3140 may be tensioned to transition the implant 3160 to the open configuration. In some embodiments, movement of the distal portion 3135*a* may also allow the user to detangle the distal end of the delivery system from the chords below the leaflets.

In some embodiments, after the implant 3160 has been attached to the leaflet, the distal portion 3135*a* and the proximal portion 3135*b* may be moved away from one another to assess whether regurgitation has been improved in addition to or instead of applying slack to the atrial tether(s) 3140 and ventricular tether(s) 3150. In some embodiments, the implant holder 3135 may include a material that improves visibility for imaging (e.g., a transparent or semi-transparent material). For example, the implant holder may include a polymer such as polyetherimide (e.g., ULTEM™). In some embodiments, the connector 3137 may be formed from or include any suitable biocompatible, fluorogenic and echogenic such as, for example, stainless steel, nitinol, etc. In some embodiments, the implant 3160 may be monolithically constructed, while in some embodiments, the implant 3160 may be formed of separate components and then coupled together. In some such embodiments, for example, the distal portion 3135*a*, the proximal portion 3135*b*, and the connector 3237 may all be formed separately and then coupled together via any suitable means (e.g., the proximal portion 3135*b* being coupled to the distal portion 3135*a* via the connector 3237)

FIGS. 41A-41D shows an implant holder 3235 extending distal to a delivery catheter 3220, the implant holder 3235 including a proximal portion 3235*b* and a distal portion 3235*a* adjoined by a connector 3237, according to embodiments. In some embodiments, the implant holder 3235 may be structurally and/or functionally similar to the implant holder 335, 835, 3135, and therefore, certain details of the implant holder 3135 are not described again with respect to FIGS. 41A-41D. As shown, the distal portion 3235*a* and the proximal portion 3235*b* define space therebetween configured to receive the implant 3260. The proximal portion 3235*a* defines one or more atrial channels 3236 through which one or more atrial tethers extend and a first or first set of ventricular channels 3238*b* through which one or more ventricular tethers 3250 extend. In some embodiments, the proximal portion 3235*a* includes an engagement portion 3239 configured to receive an atrial arm 3262 of the implant 3260. The ventricular tether(s) 3150 may extend from the proximal portion 3235*b*, outside of the implant holder 3235, and into a second or second set of ventricular channels 3238*a*. The ventricular tether(s) 3150 may extend from the distal portion 3235*a* to a proximal end of the ventricular arm 3264, as shown. In some embodiments, the connector 3237 may include one or more hypotubes extending from the proximal portion 3135b to the distal portion 3135a. In some embodiments, the connector 3237 may include a pair of hypotubes.

FIGS. 42A-42F and FIG. 44 graphical and flowchart representations, respectively, of a method of reducing heart valve regurgitation using an implant. The method can be applicable to any of the implant delivery systems and implants described herein. As shown, method 4600 may optionally include selecting an implant from a plurality of implants 4608. For example, a plurality of implants corresponding to a variety of potential patients may be provided, and a physician may select an implant that may be appropriately sized for a patient's parameters (e.g., age, gender, type of heart valve, size of heart valve, severity of regurgitation, etc.). The implant may be releasably coupled to a delivery device (e.g., the implant holder) in the delivery configuration, as described previously. The method 4600 may further include advancing the implant in the delivery configuration to a heart valve using the implant delivery system at 4610, as can be seen in FIG. 42A. The heart valve may include the mitral valve, tricuspid valve, aortic valve, pulmonary valve, or portions thereof (e.g., leaflet, chordae tendineae, annulus). As shown, a distal end of the implant delivery system navigates from the atrium, through the mitral valve, and into the ventricle, as shown in FIG. 42B.

Once positioned near the valve, the first and second arms of the implant may be separated at 4612. The first and second arms may be separated using one or more elongate members that extend through the implant delivery system and a respective portion of the implant (e.g., one or more of the arms). For example, the physician may manipulate an actuator (e.g., press a button, pull a trigger) of the implant delivery system to apply a tensile force to the one or more elongate members (e.g., pulls a suture). The one or more elongate members may be coupled to the first and/or second arms such that the applied tensile force may overcome the biasing force of the central member that connects to each of the first and second arms. The tensile force may be of a magnitude sufficient to achieve a separation angle such that the implant may receive heart valve tissue between the first and second arms. The first arm may be positioned on a first side of the heart valve and the second arm may be positioned on a second side of the heart valve at 4620, as shown in FIG. 42C-42D. In some variations, the first segment or arm may be coupled to a leaflet surface on the first side, such as an atrial surface of a mitral valve leaflet. The second segment or arm may be coupled to a leaflet surface on the second side, such as a ventricular surface of the mitral valve leaflet. In further variations, the first and second segments or arms may each be coupled to sides of the tricuspid valve, aortic valve, and/or pulmonary valve.

In some embodiments, a position of the first arm and the second arm relative to one another may be determined using visualization markers on the first arm and the second arm. For example, at least one visualization marker (e.g., radiopaque marker) may be coupled to each of the first and second arms such that a physician may indirectly observe the configuration (e.g., open or closed) of the implant via a suitable imaging modality.

Upon a determination that a placement of the implant is acceptable, at least one of the first and second arms may be released to couple the implant to one or more of a native leaflet and chordae tendineae of the heart valve at 4630. The implant may be coupled to the heart valve tissue via (i) the compressive force generated by the central member and applied by the first and second arms and/or (ii) the friction force generated by the friction elements thereof. In some variations, the compressive and/or friction force may correspond to a pull-out force. The pull-out force may comprise the force (e.g., a tensile force acting along a longitudinal dimension of the implant) required to move the implant without first separating the first and second segments or arms. Unintended movement (e.g., movement without first separating the first and second segments or arms) of the implant while one or more of the compressive and friction forces may be applied by the implant to heart valve tissue may be referred to as dehiscence. In some variations, the compressive and friction forces may, alone or in combination, be multiples greater than the pull-out force, such as about 2 times greater to about 100 times greater, including about 5 times greater, about 10 times greater, about 20 times greater, about 30 times greater, about 40 times greater, or about 50 times greater.

The implant may optionally be repositioned relative to the heart valve at 4640. Repositioning the implant may comprise separating the first and second arms, which may be achieved by applying a tensile force to the one or more elongate members routed through one or more of the first and second arms. Separating the arms may non-destructively (e.g., atraumatically) decouple the arms, including the friction elements, from the heart valve tissue such that the implant may move without scraping or otherwise damaging the heart valve tissue. The implant may then be moved to a second position, which may be observed and/or confirmed via the visualization markers previously described. The second position may be at a different location of the same heart valve to which the implant was previously coupled or, in some variations, may be a location on a different heart valve. With the arms still separated, the implant may receive heart valve tissue associated with the second position. The arms may then be released to recouple the implant to the heart valve. Recoupling the implant may comprise applying the same or similar friction and compressive forces as were applied during the first coupling. The implant may be repeatedly repositioned until the implant is appropriately positioned to effectively treat a cardiac condition, such as heart valve regurgitation. The elongate members routed through the implant may be cut or otherwise decoupled from the implant such that the elongate members and/or delivery device may be retracted from the patient, as can be seen in FIGS. 42E. Optionally, in some variations, a valve replacement procedure (e.g., transcatheter mitral valve replacement) may be performed on the same heart valve coupled by the implant. For example, the valve replacement procedure may be performed to the same heart valve coupled by the implant without removing the coupled implant before, during, or after the procedure.

Figure 43B:
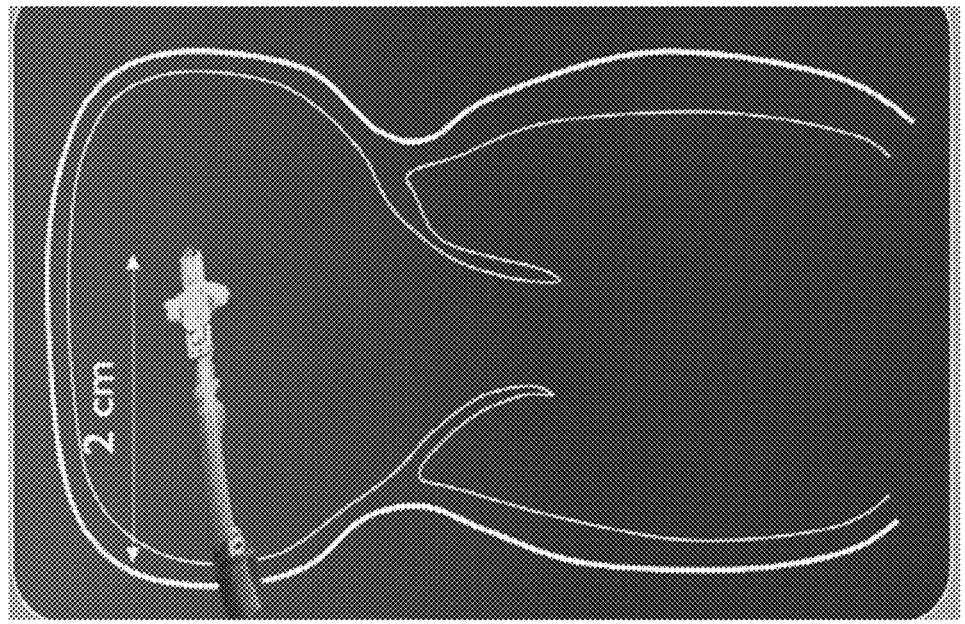
FIGS. 43A-43D illustrate a method for delivery an implant to a heart valve using an implant delivery system to treat heart valve regurgitation, according to embodiments.
Figure 43A:
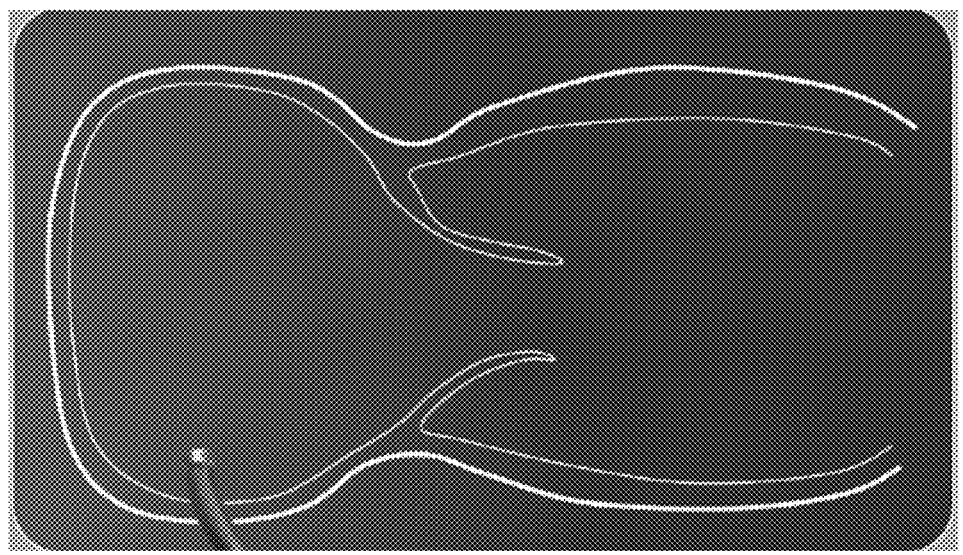
Figure 43D:
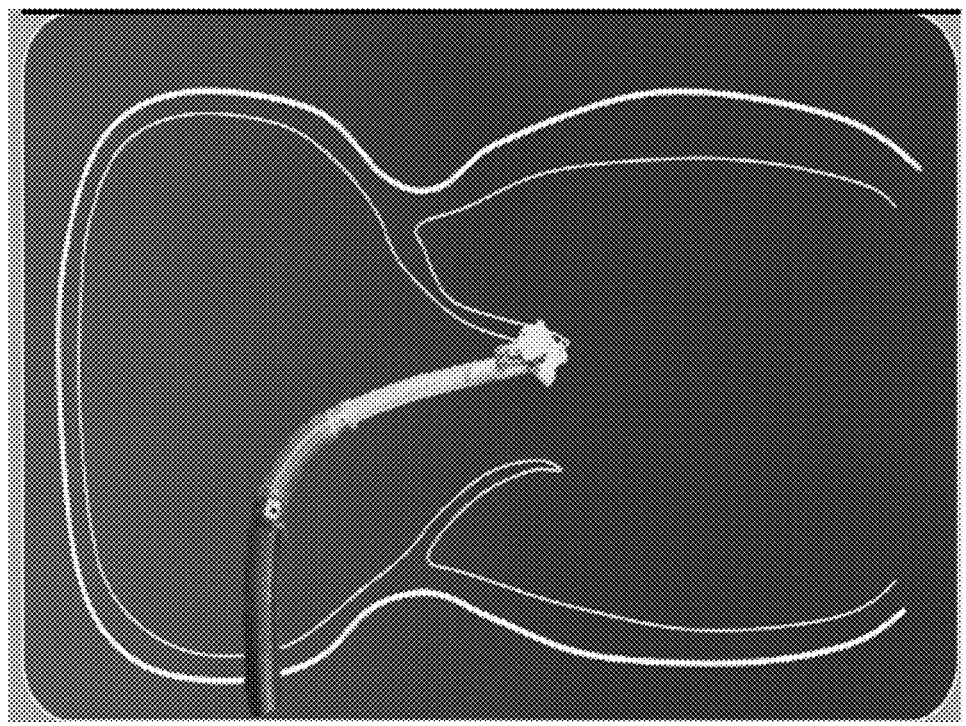
Figure 43C:
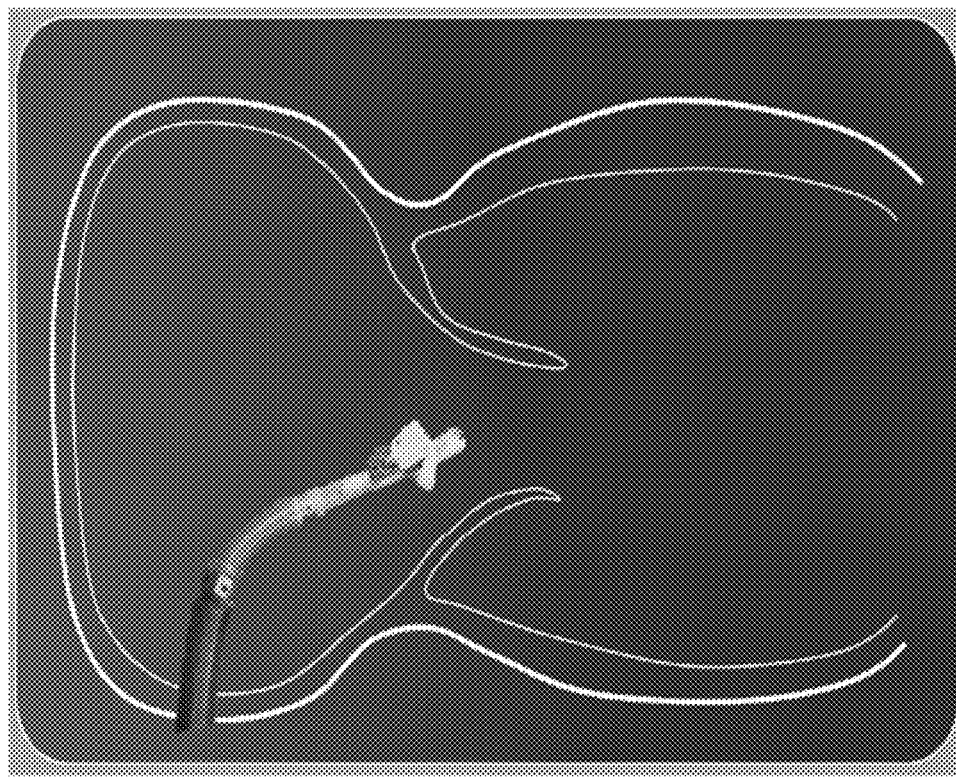
Figure 44:
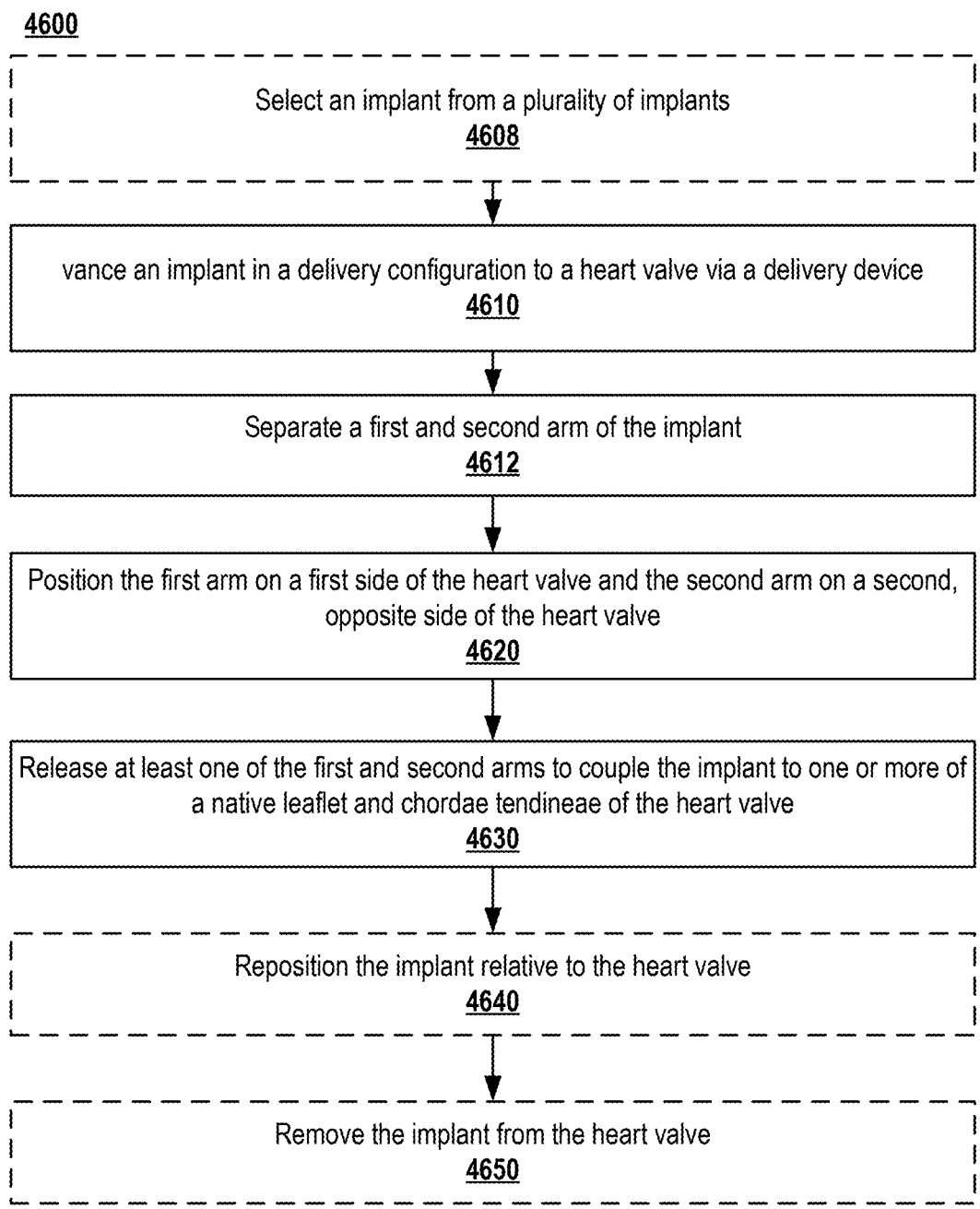
FIG. 44 is a flow chart for an example method of delivering an implant to treat heart valve regurgitation, according to embodiments.

In further variations, more than one implant may be coupled to the heart valve, as illustrated in FIG. 42F. For example, a first implant may be coupled to A1, a second implant may be coupled to P2, and a third implant may be coupled to A3. More than one treatment site may be treated to maximize the efficacy of the implants described herein. That is, a plurality of implants may be required to effectively reduce heart valve regurgitation. The plurality of implants may be implanted during the same surgical procedure, such that the same delivery device may be advanced to insert an implant, retracted, and subsequently advanced to insert an additional implant, or may be implanted during different surgical procedures. In some variations, the implant may optionally be removed from the heart valve at 4650. Similar to the steps described previously, the first and second arms may be separated via a tensile force applied to one or more elongate members routed through one or more of the first and second arms. The implant may then be recoupled to the delivery device such that the delivery device and implant may be removed from the patient's body FIGS. 43A-43D illustrate a method for delivering an implant to a heart valve using an implant delivery system to treat heart valve regurgitation, according to embodiments. The method can be applicable to any of the implant delivery systems and implants described herein. A distal end of the guide catheter is advanced through the inferior vena cava into the right atrium and across the atrial septum into the left atrium, as shown in FIG. 43A. The delivery catheter and the implant catheter including the implant coupled thereto can be advanced through the guide catheter and advanced further into the left atrium (e.g., approximately 2 cm) into the left atrium, as shown in FIG. 43B. The delivery catheter and the implant catheter are steered toward the mitral valve, as shown in FIG. 43C. As shown in FIG. 43D, the implant catheter can be further advanced distally to position the implant relative to a leaflet of the mitral valve. The implant can then be disposed around a portion of the leaflet of the mitral valve, and the effectiveness of the implant for treating heart valve regurgitation can be tested before fully deploying the implant and removing the catheters from the heart.

Figure 45:
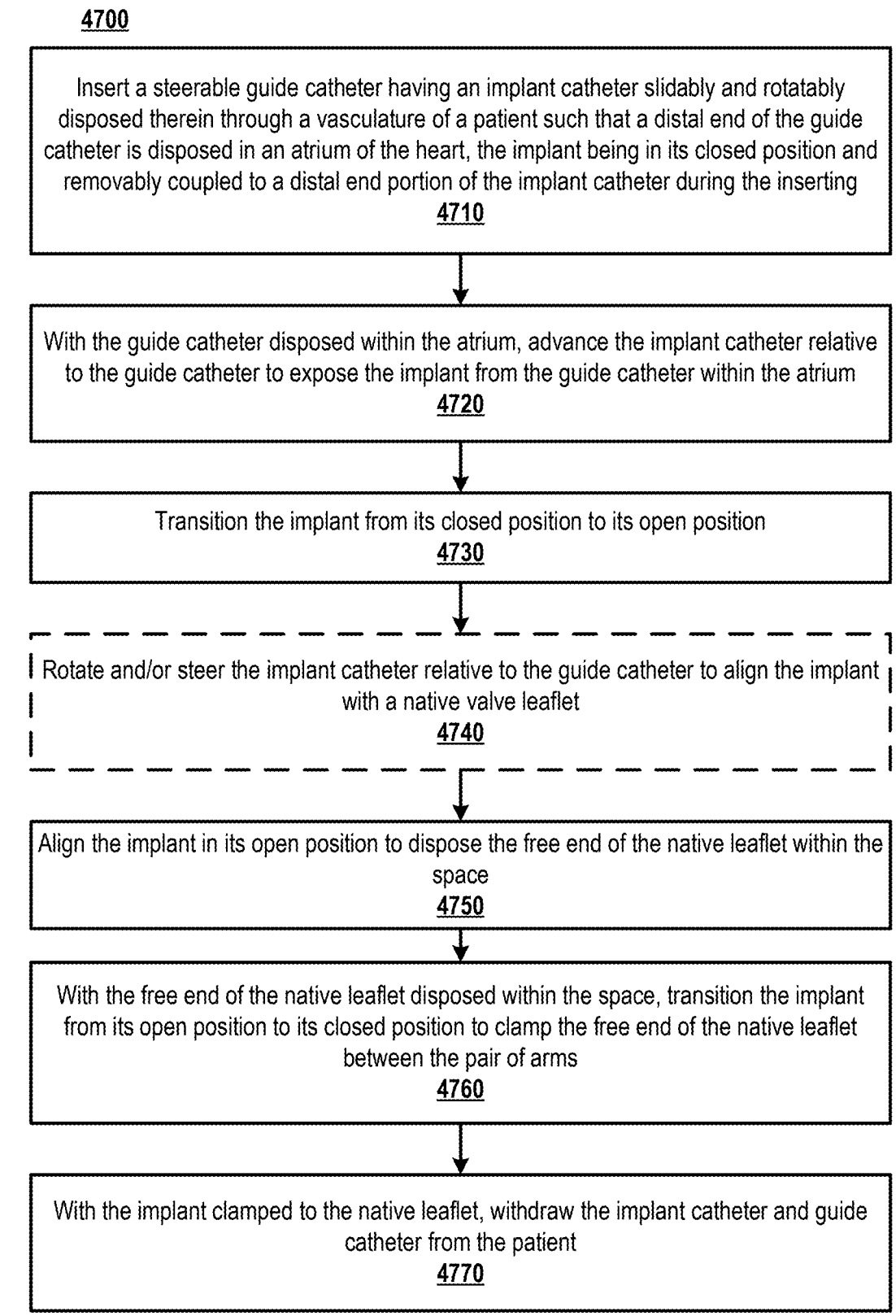
FIG. 45 is a flow chart diagram showing an example method for delivering an implant to reduce heart valve regurgitation, according to embodiments.

FIG. 45 is a flow chart diagram showing an example method for delivering an implant to reduce heart valve regurgitation, according to embodiments. The method can be applicable to any of the implant delivery systems and implants described herein. The method includes inserting a steerable guide catheter having an implant catheter slidably and rotatably disposed therein through a vasculature of a patient such that a distal end of the guide catheter is disposed in an atrium of the heart, the implant being in its closed position and removably coupled to a distal end portion of the implant catheter during the inserting, at 4710. At 4720, with the guide catheter disposed within the atrium, the implant catheter may be advanced relative to the guide catheter to expose the implant from the guide catheter within the atrium. The implant can then be transitioned from a closed position to an open position, at 4730. At 4740, the method 4700 may optionally include rotating and/or steering (or deflecting) the implant catheter relative to the guide catheter to align the implant with a native valve leaflet. At 4750, the implant can be aligned in its open position to dispose the free end of the native leaflet within a space defined by the implant. For example, the implant can be opened such that a portion of heart tissue is positioned between the pair of arms of the implant. With the free end of the native leaflet disposed within the space defined by the implant, the implant can be transitioned from the open position to the closed position to clamp the free end of the native leaflet between the pair of arms, at 4760. With the implant clamped to the native leaflet, the implant catheter and guide catheter can be withdrawn from the patient at 4770. In some embodiments, withdrawing the guide catheter from the patient includes decoupling the elongate members (e.g., the atrial tether(s) and ventricular tether(s)) from the implant by pulling the atrial tethers and ventricular tethers from a proximal end of the implant delivery system. For example, a portion of each of the atrial tether and ventricular tether near a distal end of the implant delivery system may be severed or unlooped and each of the atrial tethers and ventricular tethers may be pulled proximally from the proximal end of the implant delivery system. In some embodiments, the implant catheter can be withdrawn proximally into a lumen of the guide catheter, and the guide catheter with the implant catheter disposed therein can be withdrawn from the heart.

FIG. 46 is a flow chart for an example method of manufacture of an implant, according to embodiments. As shown, the implant, including the implant body and plates described herein, may be cut from a substantially flat sheet of material and subsequently folded, rolled, and/or bent into a 3-dimensional shape 4810. The initially flat configuration of the implant may facilitate faster and more affordable manufacturing. For example, the substantially flat sheet may be cut via laser cutting, waterjet cutting, plasma cutting, and/or handheld tin snips according to a pre-determined design of the implant. The pre-determined design of the implant may correspond to parameters associated with potential patients. Accordingly, a plurality of designs may be generated that correspond to a variety of patients. The cut-out implant body, which may still be flat, may then be further processed to eliminate any sharp edges via, for example, sanding, brushing, and/or deburring 4820. Eliminating sharp edges may prevent damaging tissue when advancing to or otherwise placing the implant at a treatment location and/or coupling the implant to heart valve tissue. The still-flat cut-out may then be set into a pre-set multi-dimensional configuration (e.g., the first configuration) described above 4830. In some embodiments, the implant body may be heat treated in order to be shape set. The flat sheet may comprise a thickness that may facilitate the manufacturing steps described (e.g., cutting, bending), such as about 50 microns to about 500 microns (including all values and sub-ranges therein). In some variations, the flat sheet may have a thickness of about 250 microns. Furthermore, the material used to form the implant body may be a pliable material to facilitate performing the manufacturing steps described. For example, the material may be a metal (e.g., nitinol, titanium, aluminum, gold, silver, alloys thereof) or a plastic (e.g., polypropylene, polyvinyl chloride, polyethylene, polyurethane). The material may further be determined by the shape-setting, shape-memory and/or super-elastic properties thereof. For example, the implant described herein may be capable of returning to the pre-set configuration after elastic deformation. In this way, the implant may advantageously return to the desired shape after being released from the delivery device or, for example, after impingement from a native leaflet. In some embodiments, the first plate and the second plate may be set into a predetermined configuration at 4840. In some variations, the first plate may be attached to the first arm of the implant body 4850. Similarly, the second plate may be attached to the second arm of the implant body 4860. In yet further variations, at least one visualization marker may be attached to the first arm (e.g., via welding) 4870. Similarly, at least one visualization marker may be attached to the second arm (e.g., via welding) 4880. Then, at least one cover may be attached to the implant body 4890. In some variations, a first cover may be coupled to the first arm, second arm, and/or central member, and a second cover may be coupled to the support members extending from the first arm.

EXAMPLES

The following examples are offered to illustrate, but not to limit, the claimed invention.

Example 1: Pull-Out Force

A device as described herein was coupled to an anterior leaflet or a posterior leaflet in 5 pig mitral valves to evaluate the force required for dehiscence and/or pull-out. Dehiscence was defined as motion of the implant by at least 2 mm from its implanted position. Pull-out was defined as complete removal of the implant from the leaflet. Graded weights were suspended from the implant with a non-extensible suture until dehiscence and/or pull-out occurred. The average weight at which the implant moved from its implanted location by 2 mm was 500 g, which corresponds to 4.9N force. None of the tested configurations led to pull out of the implant. Accordingly, the force required to remove the implant was significantly higher than real physiological conditions the implant may experience.

Example 2: Compressive Force

A device as described herein was tested to measure the compressive force imposed on mitral valve tissue by the two segments or arms. A custom made load cell setup was designed to measure the compressive force that the implant imposes on native mitral valve leaflets of different thicknesses. The implant imposed a minimum of 200 mN compressive force, which increased linearly as leaflet thickness increased. Upon performing theoretical calculations of the hemodynamic forces imposed by blood flow and transmitral pressure, the measured force was 40× greater than the calculated force associated with dehiscence. Accordingly, the compressive force imposed by the implant on the native mitral valve was sufficient for firm attachment without any dehiscence.

Example 3: Patient Populations

Three clinically relevant valve pathologies were studied—atrial FMR (aFMR), where the primary contributor to loss of valve coaptation is severe annular dilatation (seen in patients with chronic atrial fibrillation); ischemic FMR (iFMR), where the contributor to loss of valve coaptation is annular dilatation combined with focal displacement of the postero-medial papillary muscle due to an underlying postero-lateral or inferior myocardial infarction; dilated cardiomyopathy FMR (dFMR), where the contributor to loss of valve coaptation is annular dilatation combined with displacement of both papillary muscles due to concentric dilatation of the left ventricle from various etiologies. A left heart simulator was used. Pig mitral valves were mounted into this simulator, with the annulus mounted into a system that enables dilatation, and the papillary muscles mounted onto a system that allows for spatial displacement/relocation. The simulator was then used to induce aFMR, iFMR or dFMR. Mitral valve hemodynamics were measured with calibrated pressure transducers, and flow was measured with calibrated electromagnetic flow probes. At baseline, which is the valve in its healthy/non-diseased configuration, regurgitant fraction was 0%. With the implant deployed onto the healthy/non diseased valve, the regurgitant fraction was 1.03±0.86%, which is negligible. In the atrial FMR condition (aFMR), significant rise in regurgitation fraction was observed with annular dilatation, at 14.78±3.10%. With the implant deployed, aFMR was significantly reduced to 6.79±1.89% (p=0.001). In the ischemic FMR condition (iFMR), the regurgitant fraction before the repair was 20.52±2% and was reduced with use of the implant to 6.63±2.15% (p<0.0001). In the dilated cardiomyopathy FMR condition (dFMR), the regurgitant fraction before the repair was 21.93±7.2%, which was significantly reduced by use of the implant to 7.12±2.8%. The results are figuratively depicted in FIG. 16. Accordingly, Quantitative measurement of mitral regurgitation in different clinically relevant anatomical states that cause FMR demonstrate that the implant can very effectively treat aFMR, iFMR, and dFMR.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications and anatomy (e.g., intracranial and extracranial vascular structure) for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within 10% of the recited value. For example, in some instances, "about 100 [units]" may mean within 10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The specific examples and descriptions herein are exemplary in nature and embodiments may be developed by those skilled in the art based on the material taught herein without departing from the scope of the present invention.

The invention claimed is:

1. A system, comprising:
    an implant configured to be coupled to a native heart valve leaflet of a heart of a patient to reduce valve regurgitation, the implant including (1) an atrial arm and a ventricular arm collectively movable between a closed position and an open position and defining a space sufficient to capture a free end of the native leaflet between the atrial arm and the ventricular arm, and (2) a leaflet enhancer;

an implant catheter including an implant holder at a distal end thereof, the implant holder including a distal portion and a proximal portion collectively defining an opening therebetween the proximal portion and the distal portion connected by a connector extending across a portion of the opening, the front side of the implant holder including an engagement surface, a first portion of the implant configured to be disposed in the opening between the distal and the proximal portion, a second portion of the implant configured to abut the engagement surface, the proximal portion of the implant holder defining a pair of atrial channels configured to slidably receive an atrial tether, the atrial tether configured to be removably coupled to the atrial arm of the implant, the proximal portion of the implant holder defining a first pair of ventricular channels configured to slidably receive a first portion of a ventricular tether, the distal portion of the implant holder defining a second pair of ventricular channels separate from the first pair of ventricular channels and configured to slidably receive a second portion of the ventricular tether such that the ventricular tether extends through the first pair of ventricular channels, outside of the implant holder, and through the second pair of ventricular channels, the ventricular tether configured to be removably coupled to the ventricular arm of the implant.

2. The system of claim 1, wherein a portion of the leaflet enhancer is configured to extend laterally beyond the connector and a perimeter defined by the implant holder.

3. The system of claim 2, wherein the leaflet enhancer is deformable such that the portion of the leaflet enhancer can extend beyond the connector.

4. The system of claim 1, wherein tension applied to a proximal portion of the atrial tether moves the atrial arm of the implant toward the engagement surface.

5. The system of claim 4, wherein tension is released from the proximal portion of the ventricular tether to move the ventricular arm of the implant closer to the atrial arm of the implant, thereby transitioning the implant from the open position towards the closed position.

6. The system of claim 1, wherein tension applied to a proximal portion of the ventricular tether moves the ventricular arm of the implant away from the atrial arm of the implant, thereby transitioning the implant towards the open position.

7. The system of claim 1, wherein the distal portion of the implant holder includes an atraumatic distal end.

8. The system of claim 1, wherein the pair of atrial channels include a pair of atrial openings in the proximal portion of the implant holder, the first pair of ventricular channels include a first pair of ventricular openings in the proximal portion of the implant holder, the second pair of ventricular channels include a second pair of ventricular openings on a back side of the distal portion of the implant holder and a third pair of ventricular openings on a front side of the distal portion of the implant holder.

9. The system of claim 1, wherein the pair of atrial channels and the first pair of ventricular channels are configured to receive a flushing fluid from a fluid source to prevent blood clots from forming therein.

10. The system of claim 1, wherein the connector includes one or more hypotubes.

11. The system of claim 1, wherein the atrial arm of the implant includes an atrial suture loop disposed thereon and the ventricular arm of the implant includes a ventricular suture loop disposed thereon, the atrial tether configured to be routed through the atrial suture loop to operably couple to the atrial tether to the atrial arm and the ventricular tether configured to be routed through the ventricular suture loop to operably couple the ventricular tether to the ventricular arm.

12. The system of claim 1, wherein the implant holder includes a transparent material.

13. The system of claim 1, wherein a distance between the proximal end and the distal end of the implant holder is adjustable.

14. A system, comprising:
an implant configured to be to delivered to a native heart valve leaflet of a heart of a patient to reduce valve regurgitation through a gap within the native heart valve, the implant including (1) an atrial arm and a ventricular arm collectively movable between a closed position and an open position and defining a space sufficient to capture a free end of the native leaflet B between the atrial arm and the ventricular arm, the ventricular arm being configured to move laterally relative to the atrial arm to define the space; and (2) a leaflet enhancer an implant catheter including an implant holder at a distal end thereof, the implant holder configured to hold the implant to form a distal assembly, the implant holder defining a pair of atrial channels configured to slidably receive an atrial tether, the atrial tether configured to be removably coupled to the atrial arm of the implant, the implant holder defining a first pair of ventricular channels and a second pair of ventricular channels separate from the first pair of ventricular channels, the first pair of ventricular channels and the second pair of ventricular channels configured to slidably receive a ventricular tether, the ventricular tether configured to be removably coupled to the ventricular arm of the implant, a maximum lateral dimension of the distal assembly being defined by the implant when the implant is in the closed position.

15. The system of claim 14, wherein tension applied to a proximal portion of the ventricular tether moves the ventricular arm of the implant away from the atrial arm of the implant, thereby transitioning the implant towards the open position, tension released from the proximal portion of the ventricular tether moves the ventricular arm of the implant closer to the atrial arm of the implant, thereby transitioning the implant from the open position towards the closed position.

16. The system of claim 14, wherein the implant catheter is configured to be manipulated to position the implant, when the implant is coupled to the implant catheter in the closed position, near the gap within the native heart valve leaflet such that a level of regurgitation can be determined by performing at least one of fluoroscopy imaging or echocardiography.

17. The system of claim 14, wherein a level of valve regurgitation can be determined when the implant is positioned near the gap within the native heart valve leaflet without capturing the free end of the native leaflet between the atrial arm and the ventricular arm.

18. The system of claim 14, wherein the implant holder includes a distal portion and proximal portion separate from the distal portion, the distal portion and the proximal portion defining an opening therebetween and connected by a connector extending across the opening, a portion of the implant configured to be disposed in the opening.

19. The system of claim 18, wherein the portion of the implant configured to be disposed in the opening is a first portion, a front side of the proximal portion of the implant holder includes an engagement surface, a second portion of the implant configured to abut the engagement surface.

20. The system of claim 18, wherein a portion of the leaflet enhancer is configured to extend beyond the connector and a perimeter defined by the implant holder so that the maximum lateral dimension of the leaflet enhancer is greater than a maximum lateral dimension of the implant holder.

21. The system of claim 20, wherein the leaflet enhancer is deformable such that the portion of the leaflet enhancer can extend beyond the connector.

22. The system of claim 18, wherein the connector includes one or more hypotubes.

23. The system of claim 14, wherein the implant holder includes a transparent material.

24. A method of coupling an implant to a native heart valve leaflet of a heart valve of a patient to reduce valve regurgitation, the implant including (1) a pair of arms movable between an at-rest closed position and a biased open position, the pair of arms in the biased open position defining a space therebetween sufficient to capture a free end of the native leaflet between the pair of arms, and (2) a leaflet enhancer, the method comprising:
  positioning the implant in an opening defined by the heart valve without capturing the free end of the native heart valve leaflet between the pair of arms;
  determining a level of valve regurgitation when the implant is positioned in the opening defined by the heart valve;
  after determining the level of valve regurgitation, transitioning the implant from its closed position to the biased open position; and
  transitioning the implant from the biased open position towards its closed position to clamp the free end of the native leaflet between the pair of arms.

25. The method of claim 24, wherein the method further comprises:
  inserting a steerable guide catheter having an implant catheter slidably and rotatably disposed therein through a vasculature of the patient such that a distal end of the guide catheter is disposed in an atrium of the heart, the implant being in its closed position and removably coupled to a distal end portion of the implant catheter during the inserting; and
  with the guide catheter disposed within the atrium, advancing the implant catheter relative to the guide catheter to expose the implant within the atrium.

26. The method of claim 25, wherein a cross-sectional area of the leaflet enhancer is greater than or equal to a distal end portion of the implant catheter such that the level of valve regurgitation can be determined without capturing the free end of the native leaflet between the pair of arms.

27. The method of claim 25, wherein the implant catheter includes an implant holder disposed on a distal end thereof and configured to hold the implant, the implant holder including:
  a distal portion and a proximal portion collectively defining an opening therebetween extending from a front side of the implant holder to a back side of the implant holder, the proximal portion and the distal portion connected by a connector extending across the opening, a portion of the implant configured to be disposed in the opening between the distal portion and the proximal portion.

28. The method of claim 27, wherein determining the level of valve regurgitation includes performing fluoroscopy imaging, the implant being discernable from the implant holder when the fluoroscopy imaging is performed.

29. The method of claim 24, wherein the determining the level of valve regurgitation includes performing at least one of fluoroscopy imaging of the heart or echocardiography while the implant is positioned in the opening defined by the heart valve.

30. The method of claim 24, wherein the pair of arms includes a first arm and a second arm and the implant catheter includes a first tether coupled to the first arm and a second tether coupled to the second arm.

31. The method of claim 30, wherein tension is not removed from the first tether and the second tether during the determining the level of valve regurgitation.

\* \* \* \* \*